United States Patent
Suh et al.

(10) Patent No.: US 11,588,116 B2
(45) Date of Patent: Feb. 21, 2023

(54) ORGANIC LIGHT EMITTING DEVICE

(71) Applicant: LG CHEM, LTD., Seoul (KR)

(72) Inventors: Sang Duk Suh, Daejeon (KR); Min Woo Jung, Daejeon (KR); Jungha Lee, Daejeon (KR); Su Jin Han, Daejeon (KR); Seulchan Park, Daejeon (KR); Sunghyun Hwang, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 60 days.

(21) Appl. No.: 17/624,921

(22) PCT Filed: Feb. 23, 2021

(86) PCT No.: PCT/KR2021/002270
§ 371 (c)(1),
(2) Date: Jan. 5, 2022

(87) PCT Pub. No.: WO2021/182775
PCT Pub. Date: Sep. 16, 2021

(65) Prior Publication Data
US 2022/0310936 A1  Sep. 29, 2022

(30) Foreign Application Priority Data

Mar. 11, 2020  (KR) .................... 10-2020-0030233

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/86* (2013.01); *C07D 405/14* (2013.01);
(Continued)

(58) Field of Classification Search
CPC ................ C07D 251/22; C07D 209/86; C07D 405/14; C07D 487/04; H01L 51/0072;
(Continued)

(56) References Cited

U.S. PATENT DOCUMENTS 9,496,506 B2  11/2016  Lecloux et al.
9,893,290 B2  2/2018  Min et al.
(Continued)

FOREIGN PATENT DOCUMENTS

CN  101414665 A  4/2009
CN  103204846  7/2013
(Continued)

OTHER PUBLICATIONS

Tsuji et al., "The hydrogen/deuterium isotope effect of the host material on the lifetime of organic light-emitting diodes," Chemical Communications 50(94): 14870-14872 (2014).

*Primary Examiner* — Vu A Nguyen
(74) *Attorney, Agent, or Firm* — Dentons US LLP

(57) ABSTRACT

Provided is an organic light-emitting device comprising an anode, a cathode, and a light-emitting layer provided between the anode and the cathode, wherein the light-emitting layer comprises a first compound of Chemical Formula 1 and a second compound of Chemical Formula 2:
(Continued)

<Chemical Formula 1>

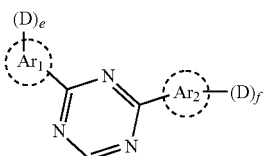

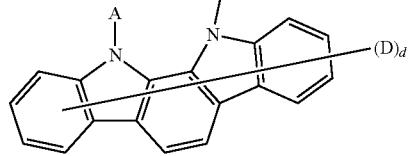

<Chemical Formula 2>

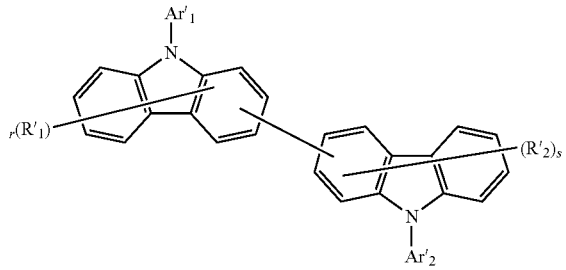

wherein:

A is Chemical Formula 1a or 1b:

<Chemical Formula 1a>

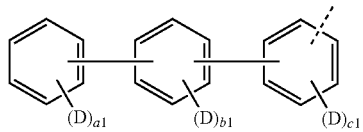

<Chemical Formula 1b>

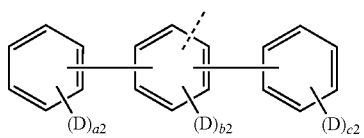

$Ar_1$ and $Ar_2$ are each independently a $C_{6-60}$ aromatic ring or a $C_{2-60}$ heteroaromatic ring, and $Ar_1$ and $Ar_2$ are unsubstituted, or substituted with $C_{1-60}$ alkyl, $C_{6-60}$ aryl, or $C_{2-60}$ heteroaryl;

$Ar'_1$ and $Ar'_2$ are each independently substituted or unsubstituted $C_{6-60}$ aryl or substituted or unsubstituted $C_{2-60}$ heteroaryl;

provided that a1+b1+c1+d+e+f is 1 or more; or a2+b2+c2+d+e+f is 1 or more;

$R'_1$ and $R'_2$ are each independently hydrogen, deuterium, $C_{1-60}$ alkyl, $C_{6-60}$ aryl, or $C_{2-60}$ heteroaryl; and r and s are each independently 0 to 7.

12 Claims, 1 Drawing Sheet

(51) Int. Cl.
C07D 209/86 (2006.01)
C07D 405/14 (2006.01)
C07D 487/04 (2006.01)
C09K 11/06 (2006.01)

(52) U.S. Cl.
CPC ............ *C07D 487/04* (2013.01); *C09K 11/06* (2013.01); *H01L 51/0052* (2013.01); *H01L 51/0067* (2013.01); *H01L 51/0073* (2013.01); *H01L 51/0074* (2013.01); *C07B 2200/05* (2013.01); *C09K 2211/1018* (2013.01); *H01L 51/5012* (2013.01); *H01L 2251/5384* (2013.01); *H01L 2251/552* (2013.01)

(58) Field of Classification Search
CPC ............ H01L 51/0073; H01L 51/0074; H01L 51/5012; H01L 2251/5384; C07B 2200/05
See application file for complete search history.

(56) References Cited

U.S. PATENT DOCUMENTS

| | | | |
|---|---|---|---|
| 11,189,802 B2 * | 11/2021 | Ogawa | ............... H01L 51/0072 |
| 2004/0251816 A1 | 12/2004 | Leo et al. | |
| 2012/0040482 A1 | 2/2012 | Ushikubo et al. | |
| 2012/0175598 A1 | 7/2012 | Balaganesan et al. | |
| 2013/0037784 A1 | 2/2013 | Yamamoto et al. | |
| 2013/0134406 A1 | 5/2013 | Ushikubo et al. | |
| 2013/0140544 A1 | 6/2013 | Lecloux et al. | |
| 2015/0001488 A1 | 1/2015 | Min et al. | |
| 2016/0130194 A1 | 5/2016 | Howard, Jr. et al. | |
| 2016/0163995 A1 | 6/2016 | Kang et al. | |
| 2016/0301012 A1 | 10/2016 | Han et al. | |
| 2016/0308138 A1 | 10/2016 | Kim et al. | |
| 2016/0351822 A1 | 12/2016 | Lee et al. | |
| 2017/0117486 A1 | 4/2017 | Cho et al. | |
| 2018/0083202 A1 | 3/2018 | Kim et al. | |
| 2018/0090690 A1 | 3/2018 | Kim et al. | |
| 2018/0114918 A1 | 4/2018 | Han et al. | |
| 2018/0339967 A1 | 11/2018 | Kim et al. | |
| 2019/0140193 A1 | 5/2019 | Dyatkin et al. | |
| 2020/0176688 A1 | 6/2020 | Cho et al. | |
| 2020/0373497 A1 | 11/2020 | Jang et al. | |
| 2021/0143340 A1 | 5/2021 | Ogawa et al. | |
| 2022/0006022 A1 * | 1/2022 | Suh | ....................... C07D 487/04 |

FOREIGN PATENT DOCUMENTS

| | | |
|---|---|---|
| EP | 3246326 A1 | 11/2017 |
| EP | 3618132 A1 | 3/2020 |
| EP | 3862355 A1 | 8/2021 |
| JP | 2016-111346 | 6/2016 |
| KR | 10-2000-0051826 | 8/2000 |
| KR | 10-2014-0124654 | 10/2014 |
| KR | 10-2015-0030511 | 3/2015 |
| KR | 10-2016-0069934 | 6/2016 |
| KR | 10-2017-0084048 | 7/2017 |
| KR | 10-2018-0137772 | 12/2018 |

(56) References Cited

FOREIGN PATENT DOCUMENTS

| | | |
|---|---|---|
| KR | 10-2054806 | 12/2019 |
| KR | 10-2020-0002885 | 1/2020 |
| WO | 2003-012890 A2 | 2/2003 |
| WO | 2015-111848 | 7/2015 |
| WO | 2015-156449 | 10/2015 |
| WO | 2016-171356 | 10/2016 |
| WO | 2017-104946 | 6/2017 |
| WO | 2017-135510 | 8/2017 |
| WO | 2018-173598 | 9/2018 |
| WO | 2018-198844 | 11/2018 |
| WO | 2019-066304 A2 | 4/2019 |
| WO | 2021-025328 A1 | 2/2021 |

\* cited by examiner

【FIG. 1】
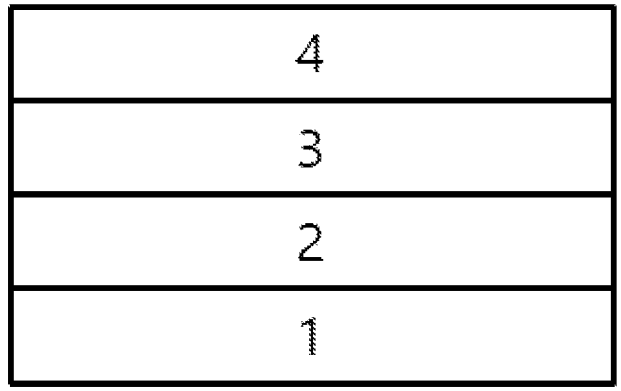
【FIG. 2】
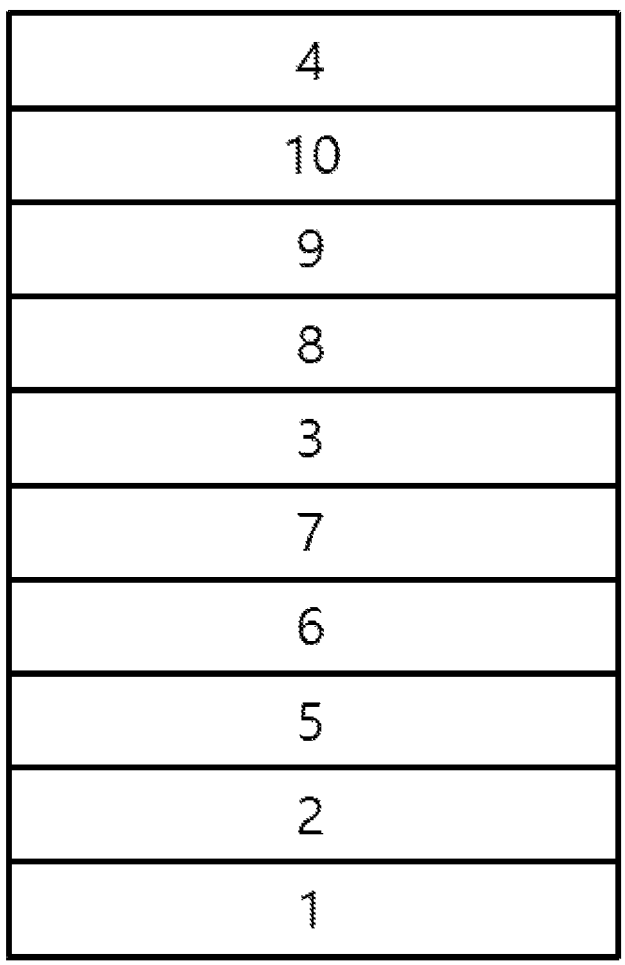

ORGANIC LIGHT EMITTING DEVICE

CROSS-REFERENCE TO RELATED APPLICATION(S)

This application is a National Stage Application of International Application No. PCT/KR2021/002270 filed on Feb. 23, 2021, which claims the benefit of Korean Patent Application No. 10-2020-0030233 filed on Mar. 11, 2020 in the Korean Intellectual Property Office, the disclosures of which are incorporated herein by reference in their entirety.

TECHNICAL FIELD

The present disclosure relates to an organic light emitting device.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 0001) Korean Unexamined Patent Publication No. 10-2000-0051826

BRIEF DESCRIPTION

Technical Problem

The present disclosure relates to an organic light emitting device.

Technical Solution

In the present disclosure, there is provided the following organic light emitting device, comprising:
an anode;
a cathode provided to face the anode; and
a light emitting layer provided between the anode and the cathode;

wherein the light emitting layer comprises a first compound of the following Chemical Formula 1 and a second compound of the following Chemical Formula 2:

<Chemical Formula 1> wherein in Chemical Formula 1:
A is the following Chemical Formula 1a or 1 b:

[Chemical Formula 1a]

[Chemical Formula 1b]

wherein in Chemical Formulae 1a and 1b:
a1, a2 and c2 are each independently an integer of 0 to 5;
b1 and c1 are each independently an integer of 0 to 4;
b2 is an integer of 0 to 3;
$Ar_1$ and $Ar_2$ are each independently a $C_{6-60}$ aromatic ring or a $C_{2-60}$ heteroaromatic ring containing at least one heteroatom of N, O and S,
wherein, $Ar_1$ and $Ar_2$ are unsubstituted, or substituted with at least one substituent selected from the group consisting of $C_{1-60}$ alkyl, $C_{6-60}$ aryl, and $C_{2-60}$ heteroaryl containing at least one heteroatom of N, O and S;
D is deuterium; and
d, e and f are each independently an integer of 0 to 10,
provided that a1+b1+c1+d+e+f is 1 or more; or a2+b2+c2+d+e+f is 1 or more;

<Chemical Formula 2>

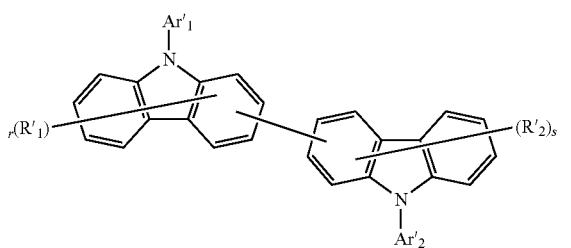

wherein in Chemical Formula 2:

Ar'1 and Ar'2 are each independently substituted or unsubstituted $C_{6-60}$ aryl or substituted or unsubstituted $C_{2-60}$ heteroaryl containing at least one heteroatom of N, O and S;

R'$_1$ and R'$_2$ are each independently hydrogen, deuterium, $C_{1-60}$ alkyl, $C_{6-60}$ aryl, or $C_{2-60}$ heteroaryl containing at least one heteroatom of N, O and S;

r and s are each independently an integer of 0 to 7; and when each of r and s is 2 or more, the substituents in parentheses are the same as or different from each other.

Advantageous Effects

The above-described organic light emitting device can improve efficiency, driving voltage, and/or lifespan characteristics by including two kinds of host compounds in the light emitting layer.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, an electron blocking layer 7, a light emitting layer 3, a hole blocking layer 8, an electron transport layer 9, an electron injection layer 10, and a cathode 4.

DETAILED DESCRIPTION

Hereinafter, embodiments of the present disclosure will be described in more detail to facilitate understanding of the invention.

As used herein, the notation 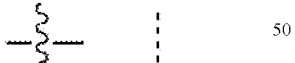, or means a bond linked to another substituent group, and D means deuterium.

As used herein, the term "substituted or unsubstituted" means being unsubstituted or substituted with one or more substituents selected from the group consisting of deuterium, a halogen group, a nitrile group, a nitro group, a hydroxyl group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O and S atoms, or being unsubstituted or substituted with a substituent in which two or more substituents of the above-exemplified substituents are connected. For example, "a substituent in which two or more substituents are connected" can be a biphenyl group. Namely, a biphenyl group can be an aryl group, or it can also be interpreted as a substituent in which two phenyl groups are connected.

In the present disclosure, the carbon number of a carbonyl group is not particularly limited, but is preferably 1 to 40. Specifically, the carbonyl group can be a group having the following structural formulae, but is not limited thereto:

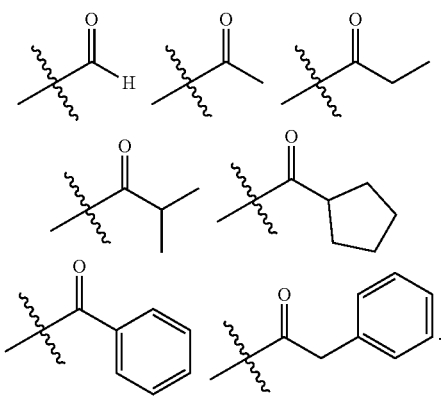

In the present disclosure, an ester group can have a structure in which oxygen of the ester group is substituted by a straight-chain, branched-chain, or cyclic alkyl group having 1 to 25 carbon atoms, or an aryl group having 6 to 25 carbon atoms. Specifically, the ester group can be a group having the following structural formulae, but is not limited thereto:

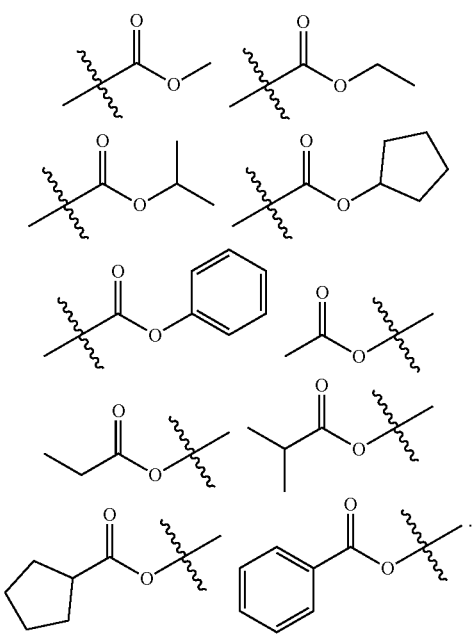

In the present disclosure, the carbon number of an imide group is not particularly limited, but is preferably 1 to 25.

Specifically, the imide group can be a group having the following structural formulae, but is not limited thereto:

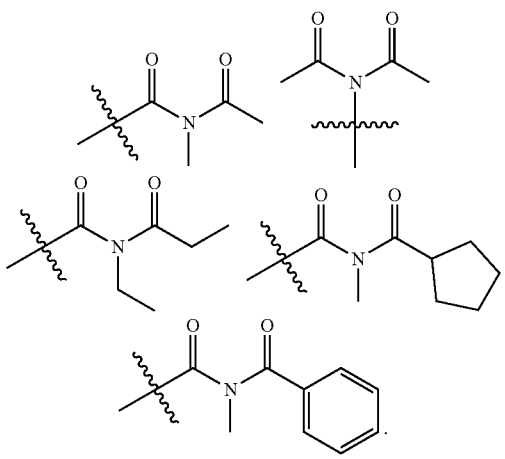

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, a phenylboron group and the like, but is not limited thereto.

In the present disclosure, examples of a halogen group include fluorine, chlorine, bromine, or iodine.

In the present disclosure, the alkyl group can be straight-chain, or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylhexyl, 4-methylhexyl, 5-methylhexyl, and the like, but are not limited thereto.

In the present disclosure, the alkenyl group can be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, adamantyl and the like, but are not limited thereto.

In the present disclosure, an aryl group is not particularly limited, but the carbon number thereof is preferably 6 to 60, and it can be a monocyclic aryl group or a polycyclic aryl group. According to one embodiment, the carbon number of the aryl group is 6 to 30. According to one embodiment, the carbon number of the aryl group is 6 to 20. The monocyclic aryl group includes a phenyl group, a biphenyl group, a terphenyl group and the like, but is not limited thereto. The polycyclic aryl group includes a naphthyl group, an anthracenyl group, a phenanthryl group, a pyrenyl group, a perylenyl group, a chrysenyl group, a fluorenyl group or the like, but is not limited thereto.

In the present disclosure, a fluorenyl group can be substituted, and two substituents can be bonded to each other to form a spiro structure. In the case where the fluorenyl group is substituted,

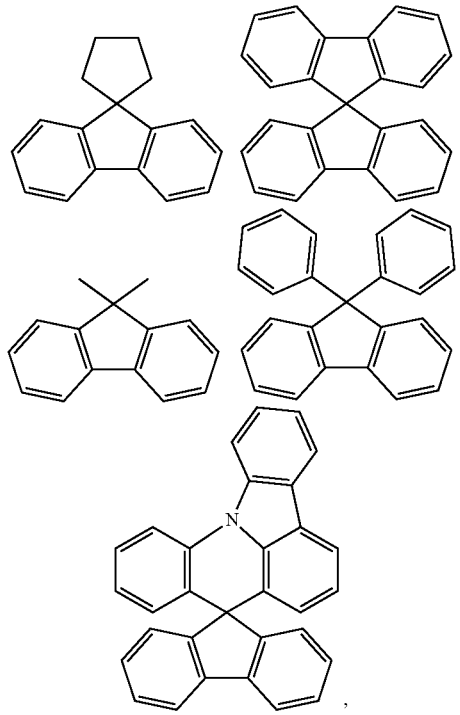

and the like can be formed. However, the structure is not limited thereto.

In the present disclosure, a heteroaryl group is a heterocyclic group containing at least one heteroatom of N, O and S as a heterogeneous element, and the carbon number thereof is not particularly limited, but is preferably 2 to 60. Examples of the heteroaryl include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

As used herein, the term "aromatic ring" is understood to include not only a condensed monocyclic or condensed polycyclic ring in which the entire molecule has aromaticity while containing only carbon as a ring-forming atom, but also a condensed polycyclic ring formed by connecting a plurality of condensed monocyclic rings such as a fluorene ring to adjacent substituents. At this time, the carbon number of the aromatic ring is 6 to 60, 6 to 30, or 6 to 20, but is not limited thereto. In addition, the aromatic ring can be a benzene ring, a naphthalene ring, an anthracene ring, a phenanthrene ring, a pyrene ring, a fluorene ring, but is not limited thereto.

As used herein, the term "heterocyclic ring" means a hetero-condensed monocyclic or hetero-condensed polycyclic ring in which the entire molecule has aromaticity or does not have aromaticity, while including at least one heteroatom of O, N, and S other than carbon as a ring-forming atom. The carbon number of the hetero ring is 2 to 60, 2 to 30, or 2 to 20, but is not limited thereto. In addition, the hetero ring can be a benzofuran ring, a benzothiophene ring, a dibenzofuran ring, a dibenzothiophene ring, or the like, but is not limited thereto.

In the present disclosure, the aryl group in the aralkyl group, the aralkenyl group, the alkylaryl group, the arylamine group and the arylsilyl group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine group can apply the aforementioned description of the heteroaryl group. In the present disclosure, the alkenyl group in the aralkenyl group is the same as the aforementioned examples of the alkenyl group. In the present disclosure, the aforementioned description of the aryl group can be applied except that the arylene is a divalent group. In the present disclosure, the aforementioned description of the heteroaryl group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heteroaryl group can be applied, except that the heterocycle is not a monovalent group but formed by combining two substituent groups.

As used herein, the term "deuterated or substituted with deuterium" means that at least one available hydrogen in each Chemical Formula is substituted with deuterium. Specifically, "substituted with deuterium" in the definition of each Chemical Formula or substituent means that at least one or more positions at which hydrogen can be bonded in the molecule are substituted with deuterium. More specifically, it means that at least 10% of the available hydrogen is substituted with deuterium. For example, at least 20%, at least 30%, at least 40%, at least 50%, at least 60%, at least 70%, at least 80%, at least 90%, or 100% are deuterated in each Chemical Formula.

There is provided an organic light emitting device including an anode; a cathode provided to face the anode; and a light emitting layer provided between the anode and the cathode; wherein the light emitting layer includes a first compound of Chemical Formula 1 and a second compound of Chemical Formula 2:

The organic light emitting device according to the present disclosure includes two kinds of compounds having a specific structure as host materials in the light emitting layer, thereby improving efficiency, driving voltage, and/or lifespan characteristics of the organic light emitting device.

Hereinafter, the present invention will be described in detail for each configuration.

Anode and Cathode

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides such as $ZnO:Al$ or $SnO_2:Sb$; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

Hole Injection Layer

The organic light emitting device according to the present disclosure can include a hole injection layer between an anode and a hole transport layer to be described later, if necessary.

The hole injection layer is located on the anode to inject holes from the anode, and includes a hole injection material. The hole injection material is preferably a compound which can transport holes, and thus has an effect of injecting holes at the anode and an excellent effect of injecting holes for the light emitting layer or the light emitting material, prevents excitons produced in the light emitting layer from moving to an electron injection layer or an electron injection material, and is excellent in forming a thin film. It is preferred that HOMO (highest occupied molecular orbital) of the hole injection material is between the work function of the anode material and the HOMO of a peripheral organic material layer.

Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based conductive polymer, and the like, but are not limited thereto.

Hole Transport Layer

The organic light emitting device according to the present disclosure can include a hole transport layer between an anode and a light emitting layer. The hole transport layer is a layer which receives holes from the anode or the hole injection layer formed on the anode and transports holes to the light emitting layer, and includes a hole transport material. As the hole transport material, a material capable of receiving holes from an anode or a hole injection layer and transporting them to a light emitting layer, and having a large mobility for the holes is suitable. Specific examples thereof include an arylamine-based organic material, a conductive polymer, a block copolymer in which a conjugate portion and a non-conjugate portion are present together, and the like, but are not limited thereto.

Electron Blocking Layer

The organic light emitting device according to the present disclosure can include an electron blocking layer between a hole transport layer and a light emitting layer, if necessary. The electron blocking layer means a layer which is formed on the hole transport layer, is preferably provided in contact with the light emitting layer, and thus serves to control hole mobility, to prevent excessive movement of electrons, and to increase the probability of hole-electron bonding, thereby improving the efficiency of the organic light emitting device. The electron blocking layer includes an electron blocking material, and an arylamine-based organic material can be used as an example of the electron blocking material, but is not limited thereto.

Light Emitting Layer

The organic light emitting device according to the present disclosure can include a light emitting layer between an anode and a cathode, and the light emitting layer includes the first compound and the second compound as host materials. Specifically, the first compound functions as an N-type host material having an electron transport ability superior to a hole transport ability, and the second compound functions as a P-type host material having a hole transport ability superior to an electron transport ability, thereby maintaining the ratio of holes to electrons in the light emitting layer. Accordingly, excitons can emit light evenly throughout the light emitting layer, so that the light emitting efficiency and lifespan characteristics of the organic light emitting device can be simultaneously improved.

Hereinafter, the first compound and the second compound will be described.

(First Compound)

The first compound is of Chemical Formula 1. Specifically, it is a compound having a structure in which two N atoms of an indolocarbazole core are substituted with a terphenylyl group and a triazinyl group, respectively. The first compound is characterized by containing at least one deuterium (D).

The terphenylyl group of the first compound can improve amorphous properties of the molecule and at the same time increase the glass transition temperature of the molecule, thereby improving thermal stability. In addition, the triazinyl group of the first compound is excellent in transporting holes, and thus when used in the light emitting layer with the second compound having excellent hole transport ability to be described later, exciplex can be easily formed in the light emitting layer. Moreover, the first compound becomes in a radical anion state when forming the exciplex, and at this time, deuterium (D) contained in the molecule of the first compound lowers vibration energy of the radical anion state. Accordingly, the first compound can have stable energy, and the formed exciplex can also be in a more stable state.

Therefore, the first compound has improved thermal and electrochemical stability compared to i) a compound which does not include deuterium (D) in the same structure and ii) a compound in which a terphenylyl group is not substituted on one of N atoms of an indolocarbazole core, and contributes to the formation of stable exciplex to effectively transfer energy to the dopant. Accordingly, the driving voltage, light emitting efficiency, and lifespan characteristics of the organic light emitting device including the first compound can be improved.

The first compound of Chemical Formula 1 can be the following Chemical Formula 1A or Chemical Formula 1B, depending on structure A.

Specifically, when A in Chemical Formula 1 is Chemical Formula 1a, the first compound can be the following Chemical Formula 1A:

<Chemical Formula 1A>

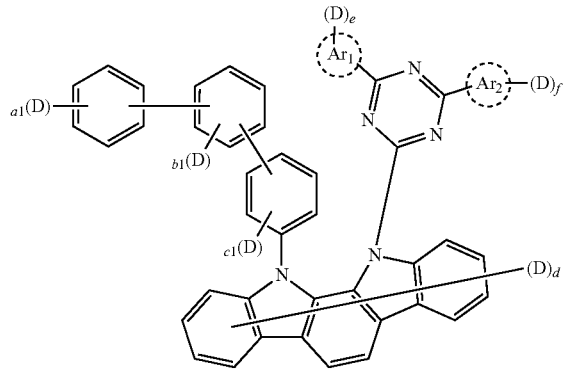

<Chemical Formula 1A> wherein in Chemical Formula 1A:

$Ar_1$, $Ar_2$, a1, b1, c1, d, e, and f are as defined in Chemical Formula 1, provided that a1+b1+c1+d+e+f is 1 or more.

Herein, in Chemical Formula 1A, a1, b1, c1, d, e, and f means the number of substitutions with deuterium (D), wherein a1 is 0, 1, 2, 3, 4, or 5, b1 and c1 are each independently 0, 1, 2, 3, or 4, and d, e, and f are each independently 0, 1, 2, 3, 4, 5, 6, 7, 8, 9, or 10.

More specifically, in Chemical Formula 1A:

$Ar_1$ and $Ar_2$ can each independently be a benzene ring, a biphenyl ring, a terphenyl ring, a fluorene ring, a carbazole ring, or a dibenzothiophenyl ring, wherein $Ar_1$ and $Ar_2$ can be unsubstituted, or substituted with 1 or 2 substituents selected from the group consisting of $C_{1-10}$ alkyl and $C_{6-20}$ aryl;

and a1+b1+c1+d+e+f can be 1 to 43.

For example, in Chemical Formula 1A, $Ar_1$ and $Ar_2$ can each independently be a benzene ring, a biphenyl ring, a terphenyl ring, a fluorene ring, a carbazole ring, or a dibenzothiophenyl ring, wherein $Ar_1$ and $Ar_2$ can be unsubstituted, or substituted with 1 or 2 substituents selected from the group consisting of methyl, ethyl, phenyl and naphthyl, and a1+b1+c1+d+e+f can be 1 to 43.

Alternatively, when A in Chemical Formula 1 is Chemical Formula 1b, the first compound can be the following Chemical Formula 1B:

<Chemical Formula 1B>

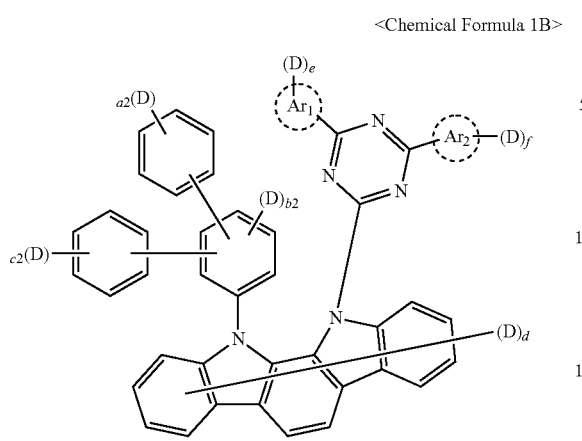

wherein in Chemical Formula 1B:
$Ar_1$, $Ar_2$, a2, b2, c2, d, e, and f are as defined in Chemical Formula 1,
provided that a2+b2+c2+d+e+f is 1 or more.
Herein, in Chemical Formula 1B, a2, b2, c2, d, e, and f means the number of substitutions with deuterium (D), wherein a2 and $C_2$ are each independently 0, 1, 2, 3, 4, or 5, and b2 is 0, 1, 2, or 3, and d, e, and f are each independently 0, 1, 2, 3, 4, 5, 6, 7, 8, 9, or 10.

More specifically, in Chemical Formula 1B,
$Ar_1$ and $Ar_2$ can each independently be a benzene ring, a biphenyl ring, a terphenyl ring, a fluorene ring, a carbazole ring, or a dibenzothiophenyl ring,
wherein $Ar_1$ and $Ar_2$ can be unsubstituted, or substituted with 1 or 2 substituents selected from the group consisting of $C_{1-10}$ alkyl and $C_{6-20}$ aryl, and
a2+b2+c2+d+e+f can be 1 to 43.

For example, in Chemical Formula 1B,
$Ar_1$ and $Ar_2$ can each independently be a benzene ring, a biphenyl ring, a terphenyl ring, a fluorene ring, a carbazole ring, or a dibenzothiophenyl ring,
wherein $Ar_1$ and $Ar_2$ can be unsubstituted, or substituted with 1 or 2 substituents selected from the group consisting of methyl, ethyl, phenyl and naphthyl, and
a2+b2+c2+d+e+f can be 1 to 43.

Alternatively, at least one of $Ar_1$ and $Ar_2$ can be a benzene ring that is unsubstituted, or substituted with 1 or 2 substituents selected from the group consisting of $C_{1-10}$ alkyl and $C_{6-20}$ aryl. When at least one of $Ar_1$ and $Ar_2$ is a benzene ring, it is possible to prevent the deposition temperature from becoming too high due to an excessively large molecular weight, which is preferable in terms of the manufacturing process of the organic light emitting device.

Specifically, Ar can be a benzene ring, and $Ar_2$-$(D)_f$ can be any one selected from the group consisting of the following:

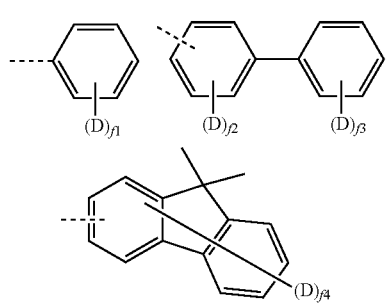

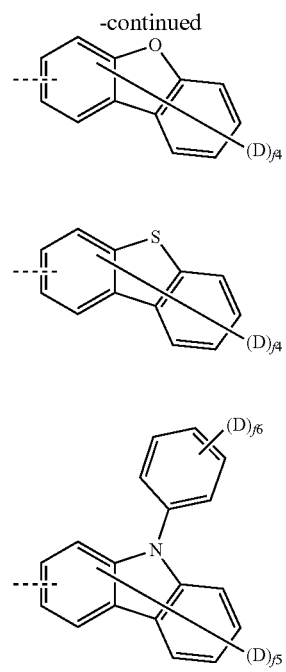

wherein:
f1 is an integer of 0 to 5, that is, 0, 1, 2, 3, 4, or 5,
f2 is an integer of 0 to 4, that is, 0, 1, 2, 3, or 4,
f3 is an integer of 0 to 5, that is, 0, 1, 2, 3, 4, or 5,
f4 is an integer of 0 to 7, that is, 0, 1, 2, 3, 4, 5, 6, or 7,
f5 is an integer of 0 to 7, that is, 0, 1, 2, 3, 4, 5, 6, or 7, and
f6 is an integer of 0 to 5, that is, 0, 1, 2, 3, 4, or 5.

Accordingly, Chemical Formula 1A can be the following Chemical Formula 1A':

<Chemical Formula 1A'>

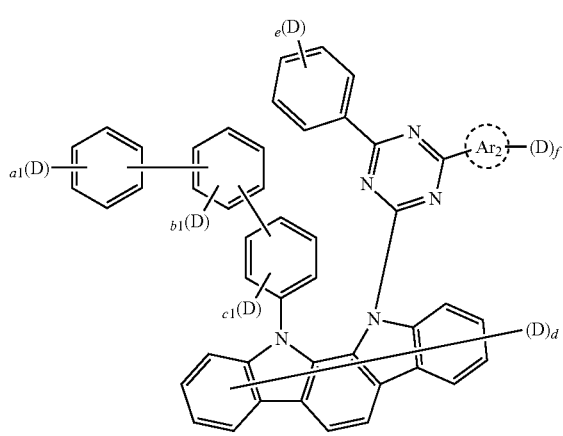

wherein in Chemical Formula 1A':
a1 is an integer of 0 to 5,
b1 and c1 are each independently an integer of 0 to 4,
d is an integer of 0 to 10,
e is an integer of 0 to 5, Ar$_2$-(D)$_f$ is any one selected from the group consisting of the following:

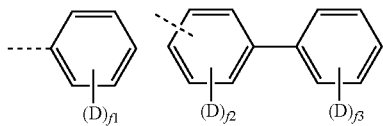
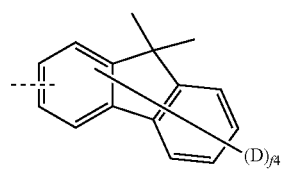
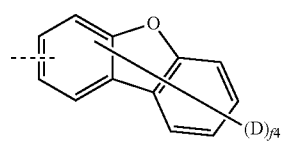
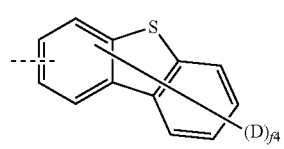
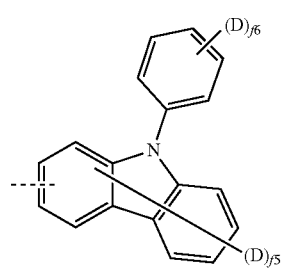

wherein:
f1 is an integer of 0 to 5,
f2 is an integer of 0 to 4,
f3 is an integer of 0 to 5,
f4 is an integer of 0 to 7,
f5 is an integer of 0 to 7,
f6 is an integer of 0 to 5, and
R$_1$ to R$_6$ are deuterium,
provided that a1+b1+c1+d+e+f1 is 1 to 33,
a1+b1+c1+d+e+f2+f3 is 1 to 37,
a1+b1+c1+d+e+f4 is 1 to 35, and
a1+b1+c1+d+e+f5+f6 is 1 to 40.

In addition, Chemical Formula 1B can be the following Chemical Formula 1B':

<Chemical Formula 1B'>

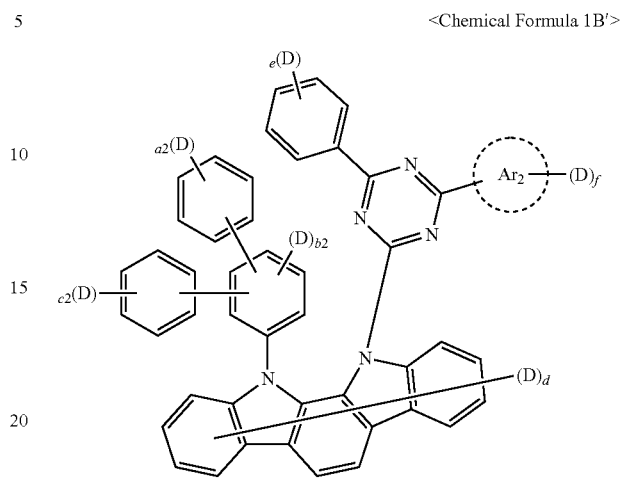

wherein in Chemical Formula 1B':
a2 and c2 are each independently an integer of 0 to 5,
b2 is an integer of 0 to 3,
d is an integer of 0 to 10,
e is an integer of 0 to 5, and
Ar$_2$-(D)$_f$ is any one selected from the group consisting of the following:

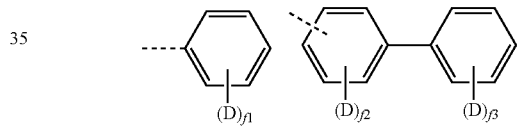
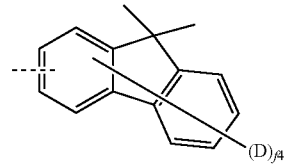
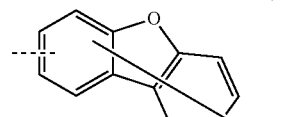
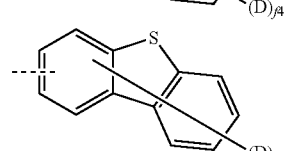
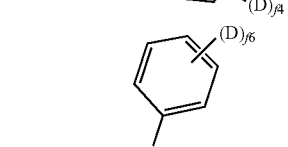
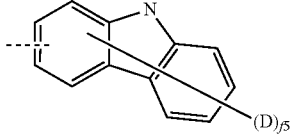

wherein:

f1 is an integer of 0 to 5, f2 is an integer of 0 to 4, f3 is an integer of 0 to 5, f4 is an integer of 0 to 7, f5 is an integer of 0 to 7, and f6 is an integer of 0 to 5, and $R_1$ to $R_6$ are deuterium, provided that a2+b2+c2+d+e+f1 is 1 to 33, a2+b2+c2+d+e+f2+f3 is 1 to 37, a2+b2+c2+d+e+f4 is 1 to 35, and a2+b2+c2+d+e+f5+f6 is 1 to 40.

In addition, in Chemical Formula 1, A can be any one of the following Chemical Formulae 1a-1 to 1a-9 and Chemical Formulae 1b-1 to 1b-6:

1a-1

1a-2

1a-3

1a-4

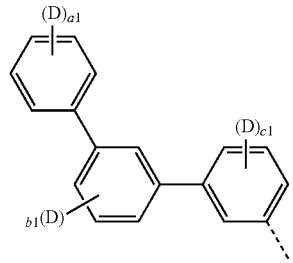

1a-5

1a-6

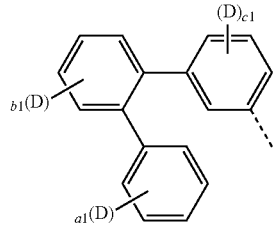

1a-7

1a-8

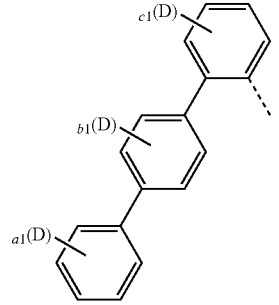

1a-9

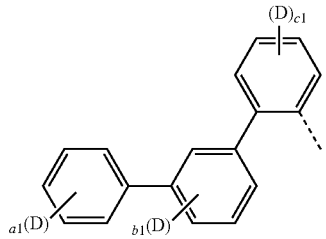

1b-1

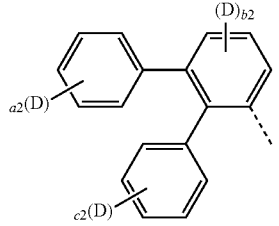

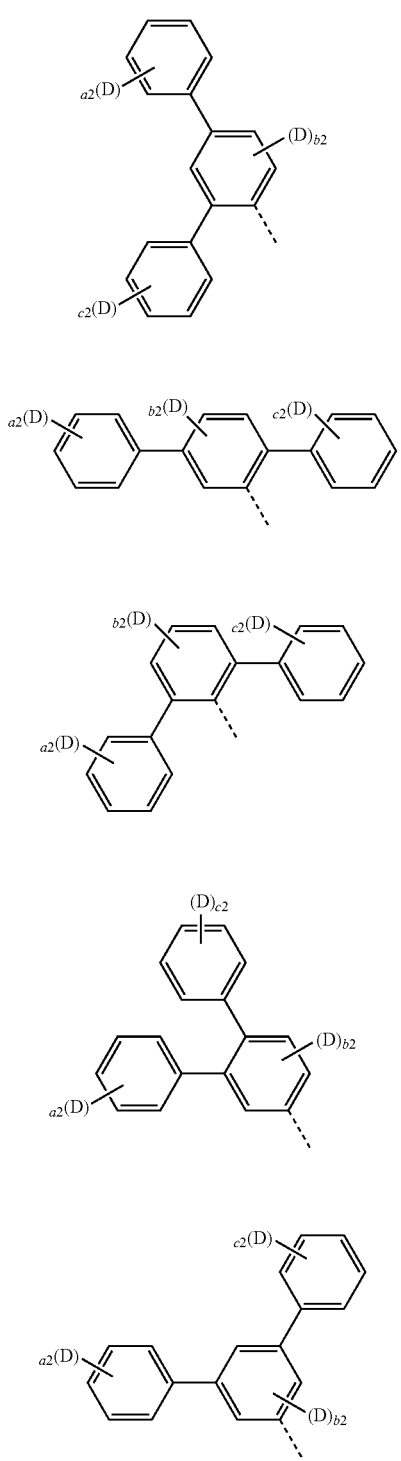
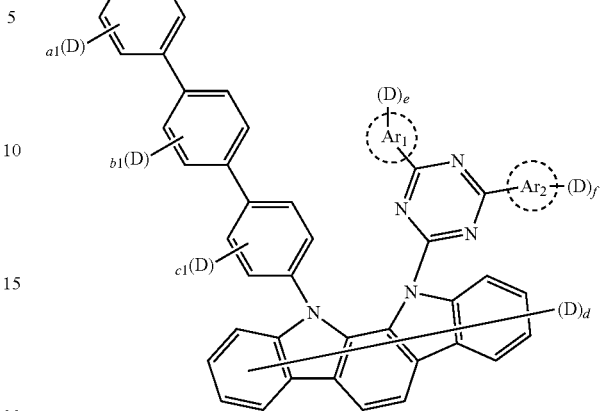
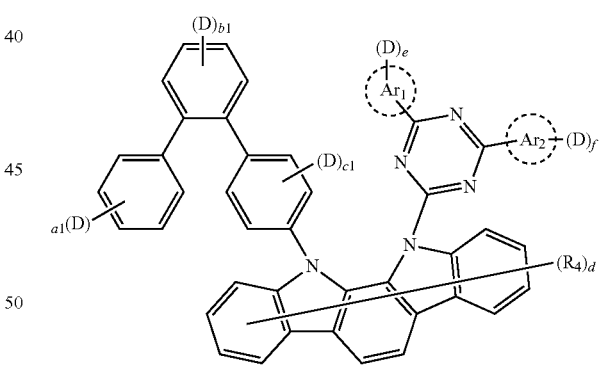
wherein in Chemical Formulae 1a-1 to 1a-9 and Chemical Formulae 1b-1 to 1b-6:
a1, b1, c1, a2, b2, c2, d, e, and f are as defined in Chemical Formula 1.
Accordingly, when A is any one of Chemical Formulae 1a-1 to 1a-9 in Chemical Formula 1, the first compound can be any one of Chemical Formulae 1A-1 to 1A-9:

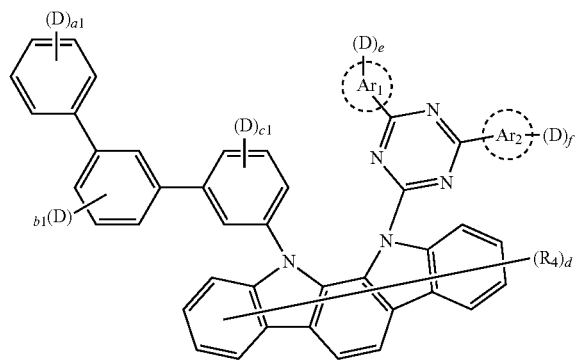
1A-5
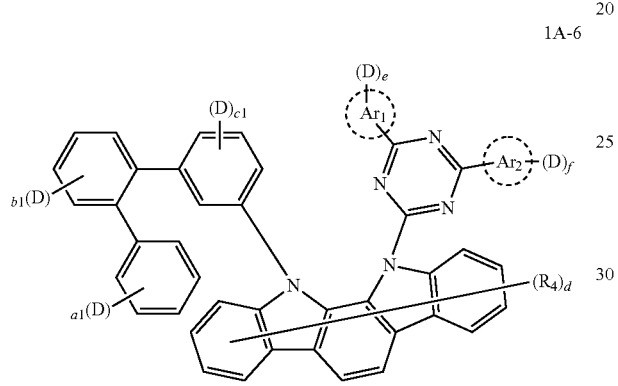
1A-6
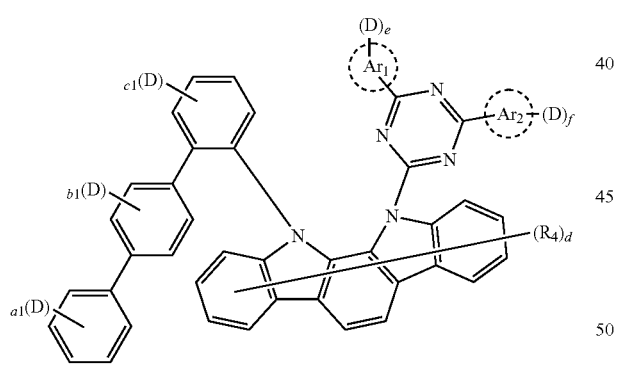
1A-7
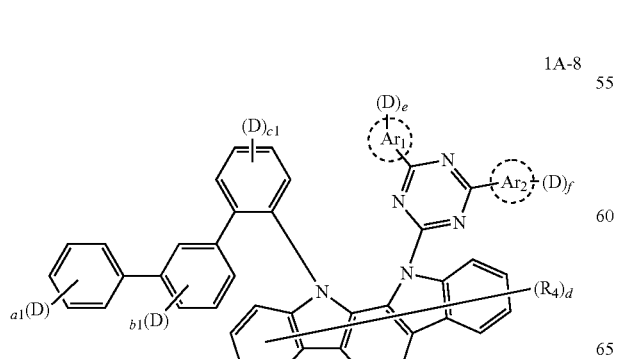
1A-8
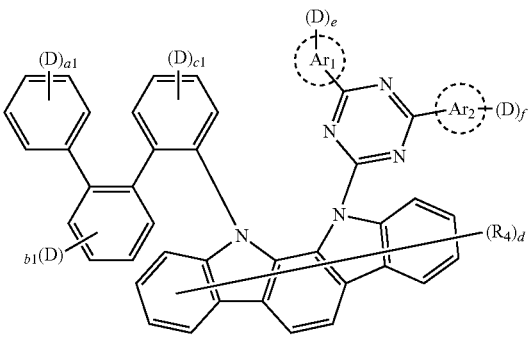
1A-9
wherein in Chemical Formulae 1A-1 to 1A-9:
Ar$_1$, Ar$_2$, a1, b1, c1, d, e and f are as defined in Chemical Formula 1,
provided that a1+b1+c1+d+e+f is 1 to 43.
Alternatively, when A is any one of Chemical Formulae 1b-1 to 1b-6 in Chemical Formula 1, the first compound can be any one of Chemical Formulae 1B-1 to 1B-6:
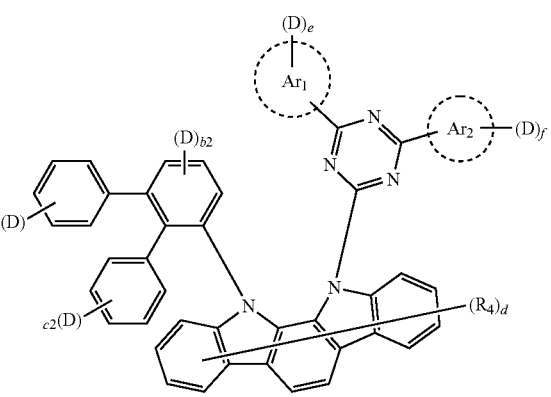
1B-1
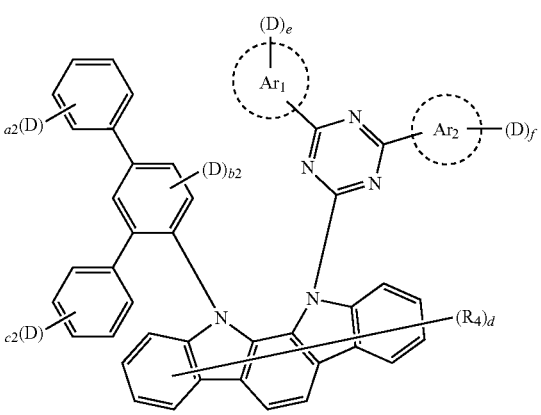
1B-2

-continued
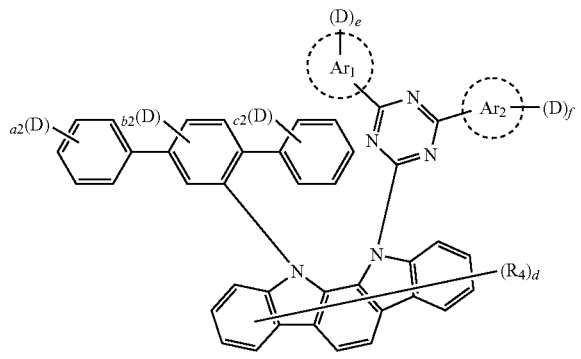
1B-3
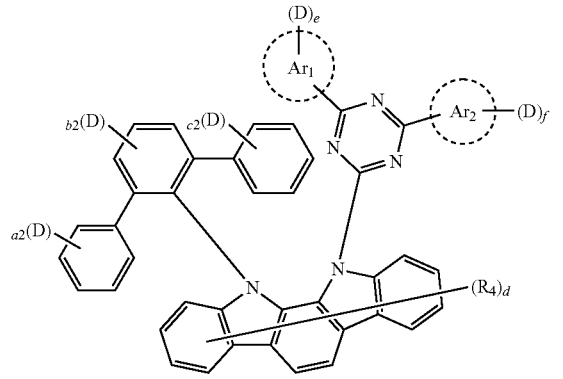
1B-4
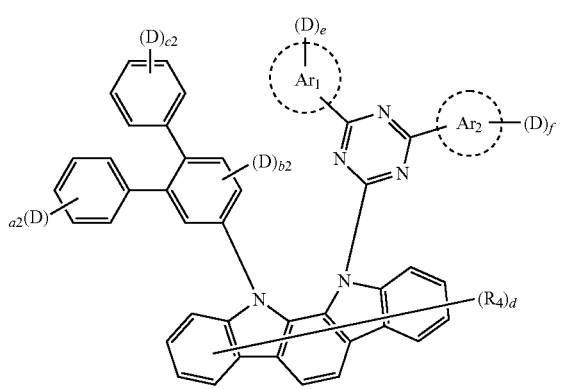
1B-5
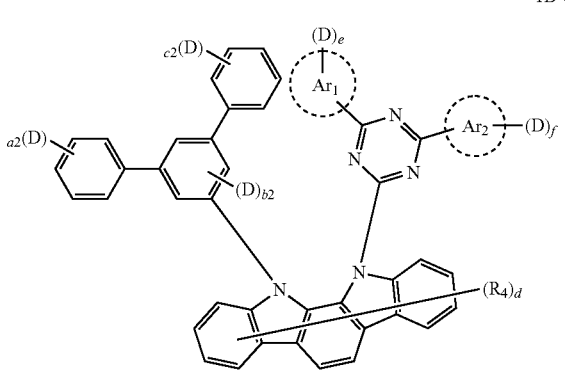
1B-6
wherein in Chemical Formulae 1B-1 to 1B-6:
Ar$_1$, Ar$_2$, a2, b2, c2, d, e, and f are as defined in Chemical Formula 1,
provided that a2+b2+c2+d+e+f is 1 to 43.
Representative examples of the compound of Chemical Formula 1 are as follows:
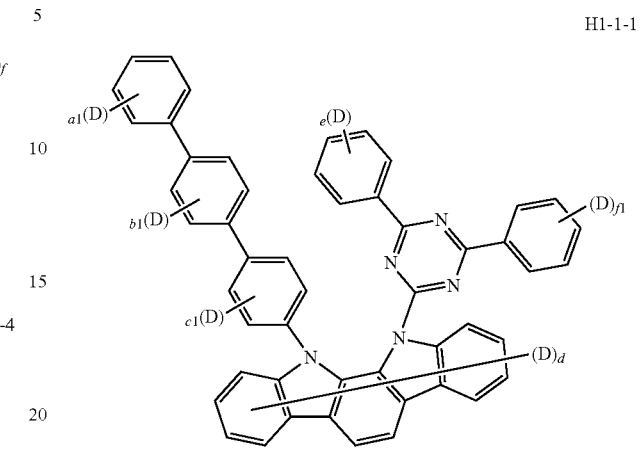
H1-1-1
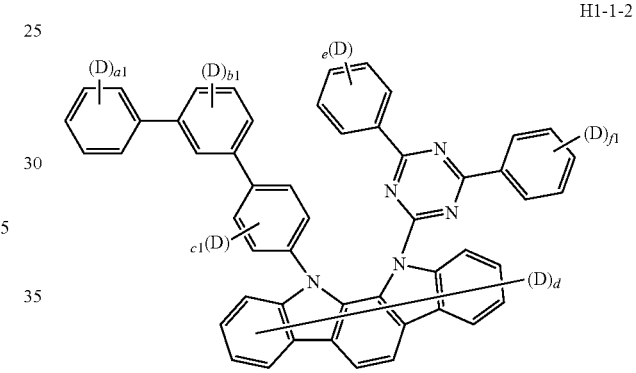
H1-1-2
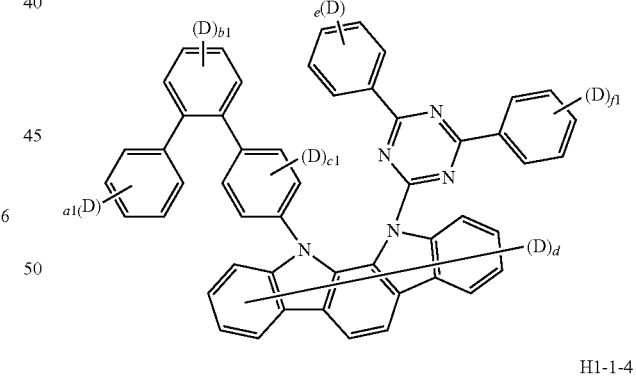
H1-1-3
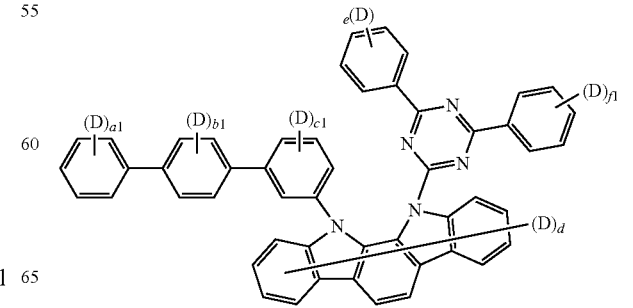
H1-1-4

H1-1-5
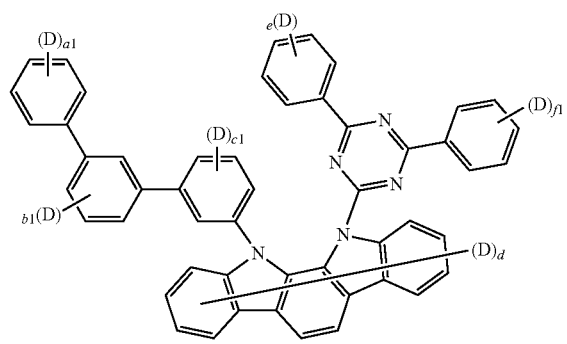
H1-1-6
H1-1-7
H1-1-8
H1-1-9
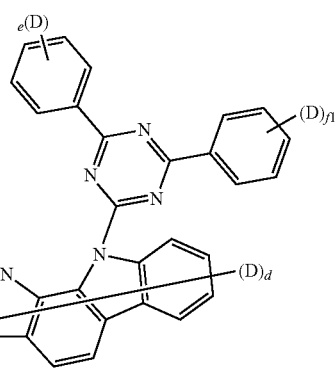
wherein in Chemical Formulae H1-1-1 to H1-1-9:
a1, b1, c1, and d are as defined in Chemical Formula 1, and
e and f1 are each independently an integer of 0 to 5,
provided that a1+b1+c1+d+e+f1 is 1 to 33;
H1-1-10
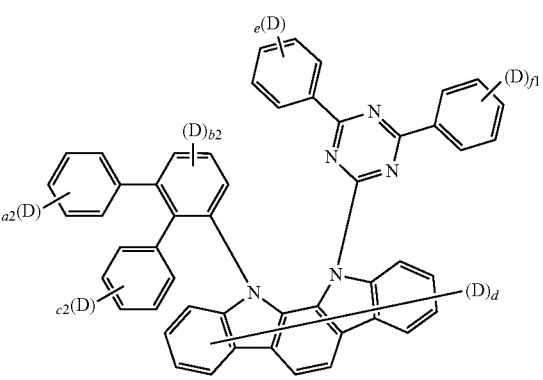
H1-1-11
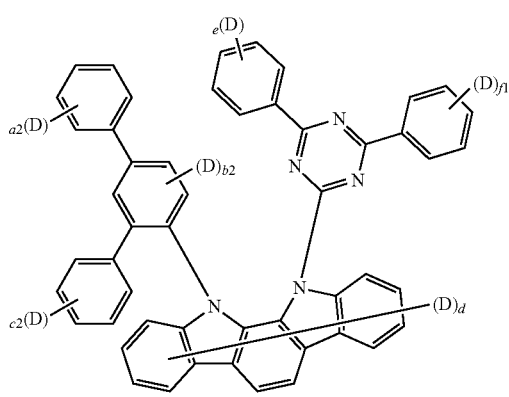

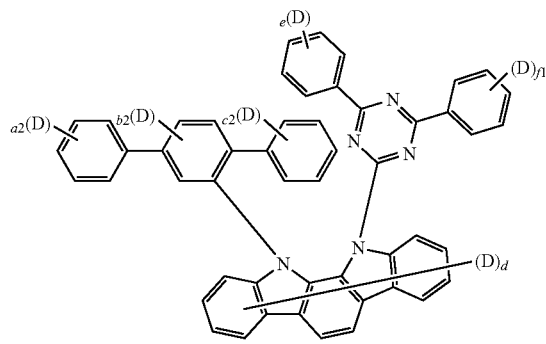
H1-1-12
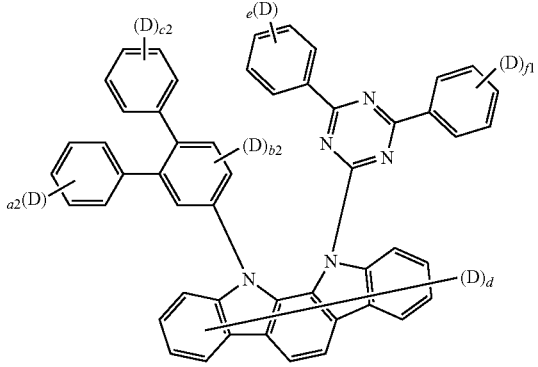
H1-1-14
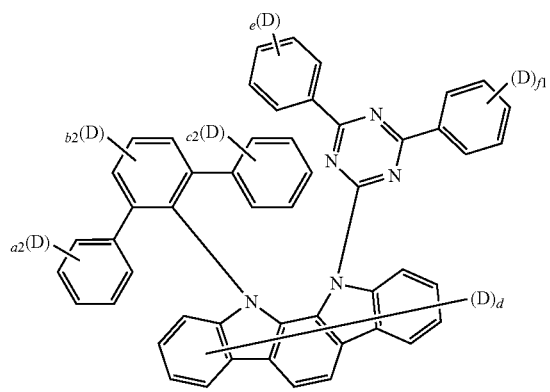
H1-1-13
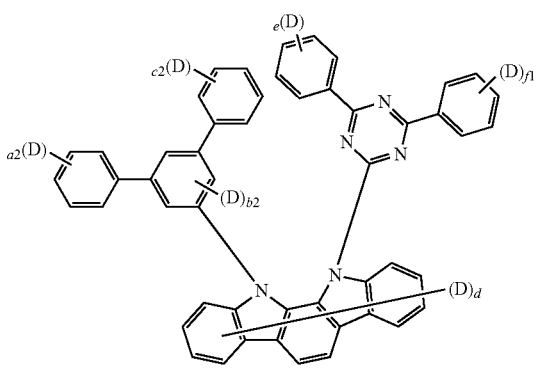
H1-1-15
wherein in Chemical Formulae H1-1-10 to H1-1-15:
a2, b2, c2, and d are as defined in Chemical Formula 1, and
e and f1 are each independently an integer of 0 to 5, provided that a2+b2+c2+d+e+f1 is 1 to 33;
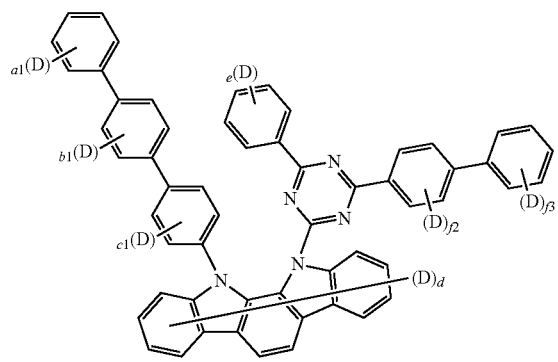
H1-2-1
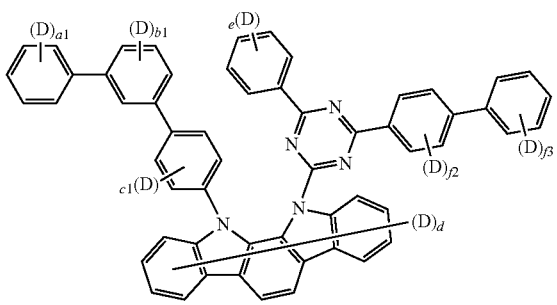
H1-2-2

-continued
H1-2-3
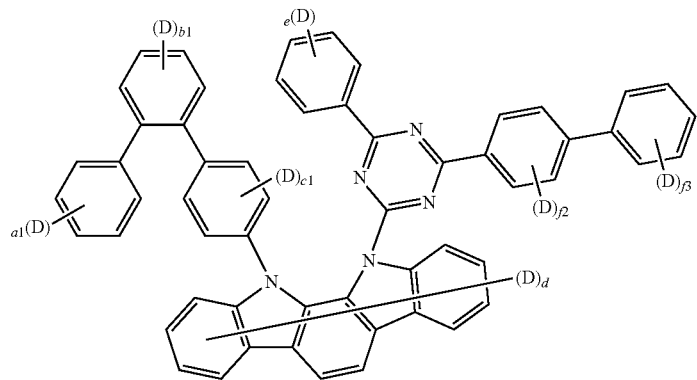
H1-2-4
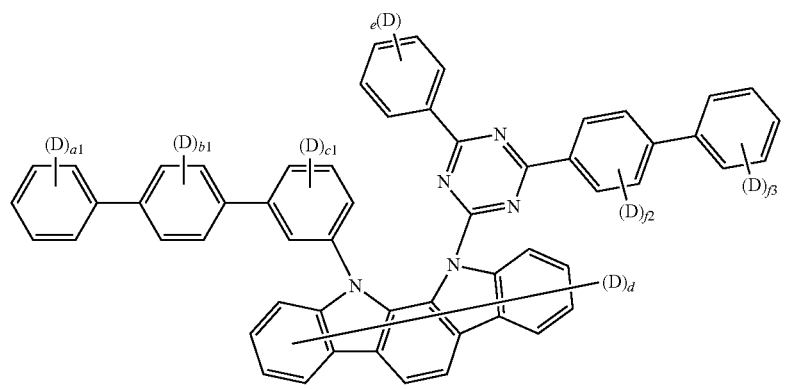
H1-2-5
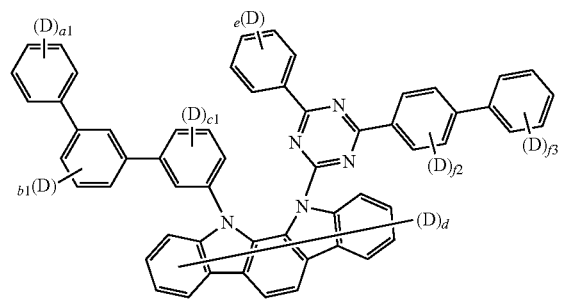
H1-2-6
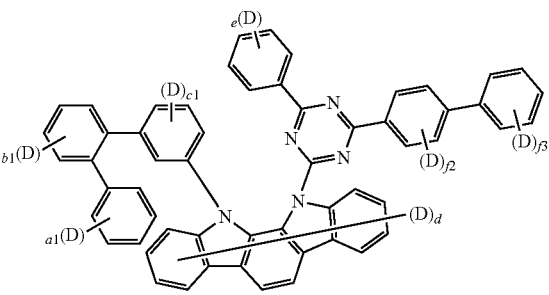
H1-2-7
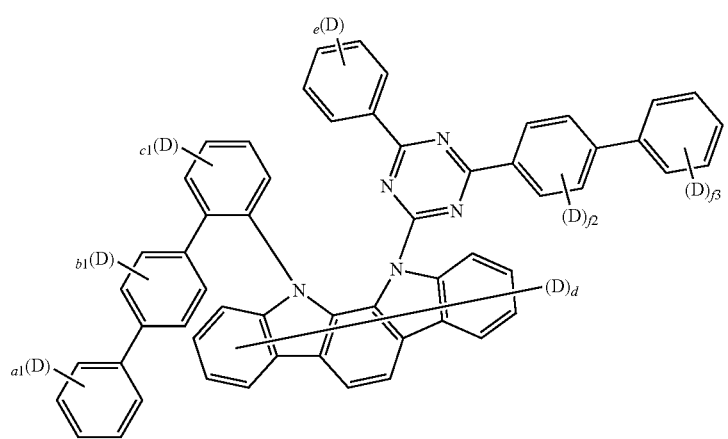

-continued
H1-2-8
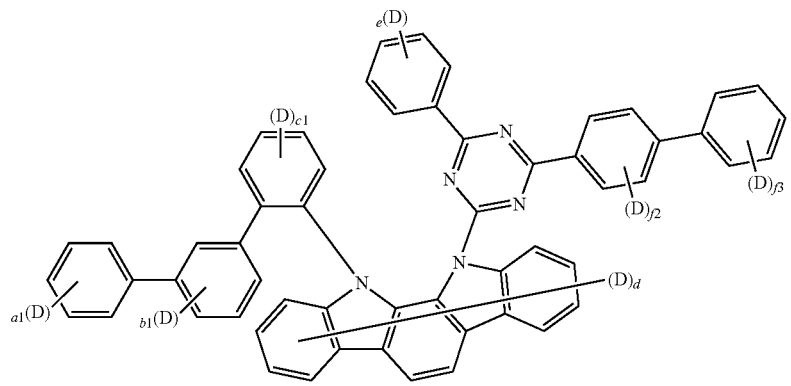
H1-2-9
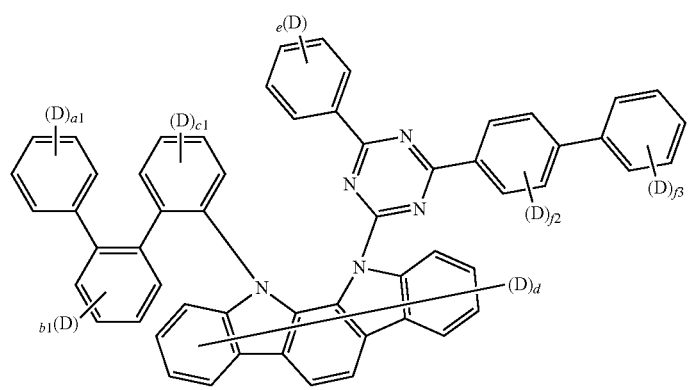
H1-3-1
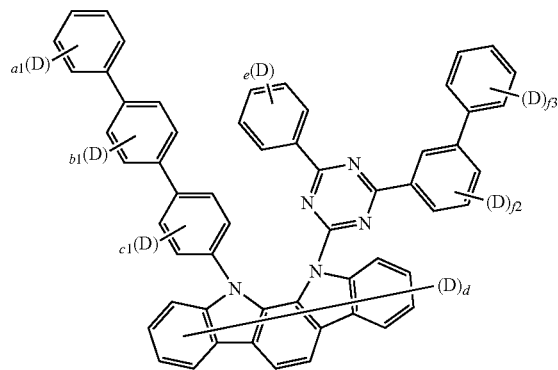
H1-3-2
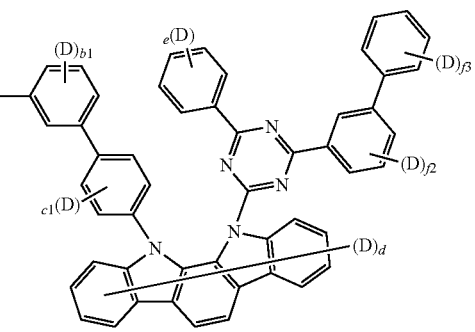
H1-3-3
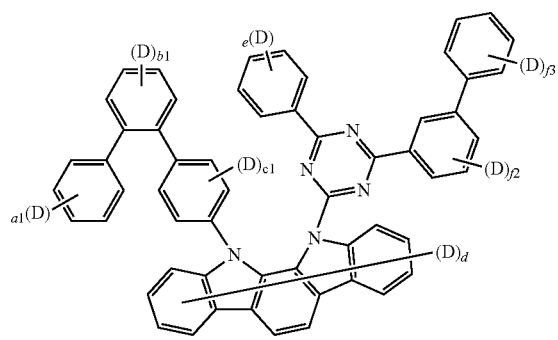
H1-3-4
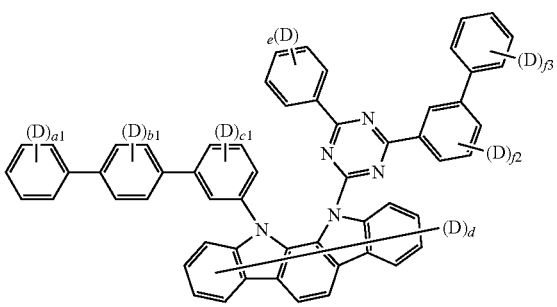

-continued
H1-3-5
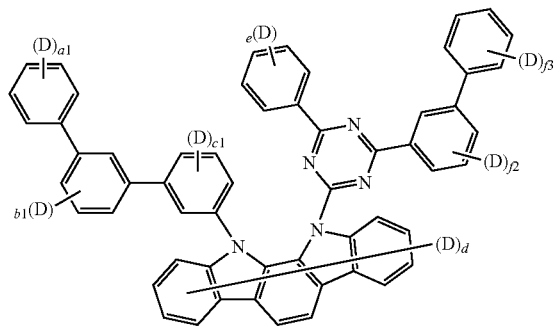
H1-3-6
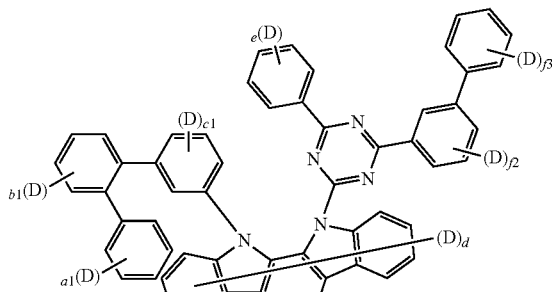
H1-3-7
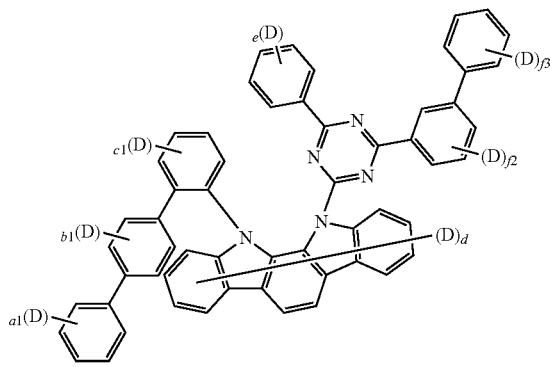
H1-3-8
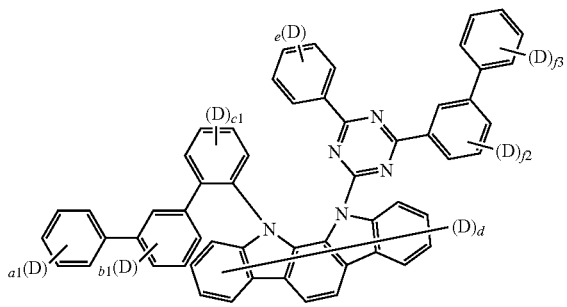
H1-3-9
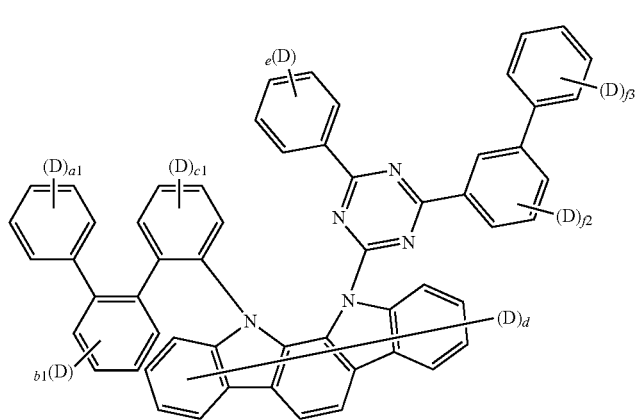

wherein in Chemical Formulae H1-2-1 to H1-2-9 and H1-3-1 to H1-3-9:
a1, b1, c1, and d are as defined in Chemical Formula 1,
e is an integer of 0 to 5,
f2 is an integer of 0 to 4,
f3 is an integer of 0 to 5, and
a1+b1+c1+d+e+f2+f3 is 1 to 37;
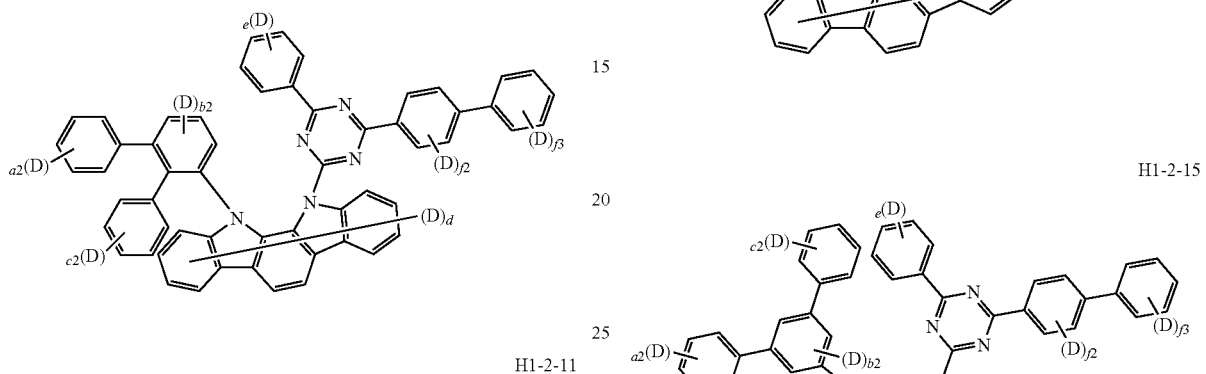
H1-2-10
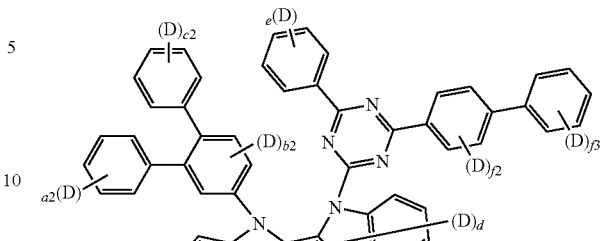
H1-2-14
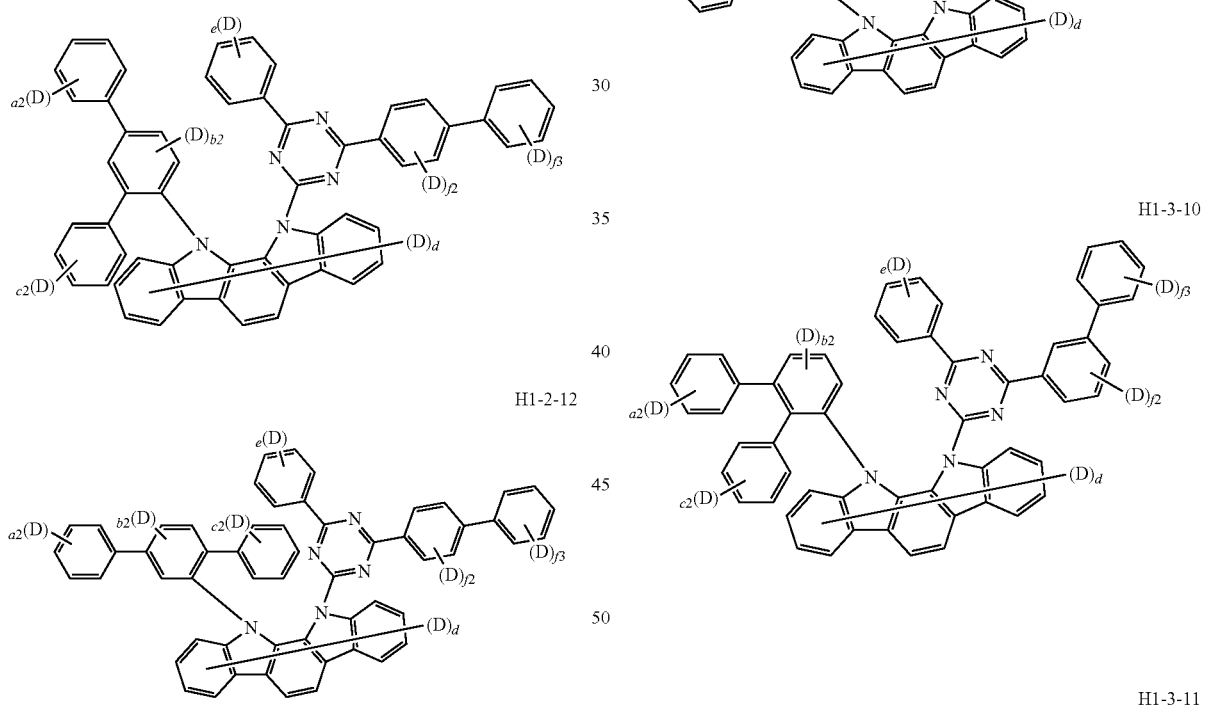
H1-2-11
H1-2-12
H1-2-13
H1-2-15
H1-3-10
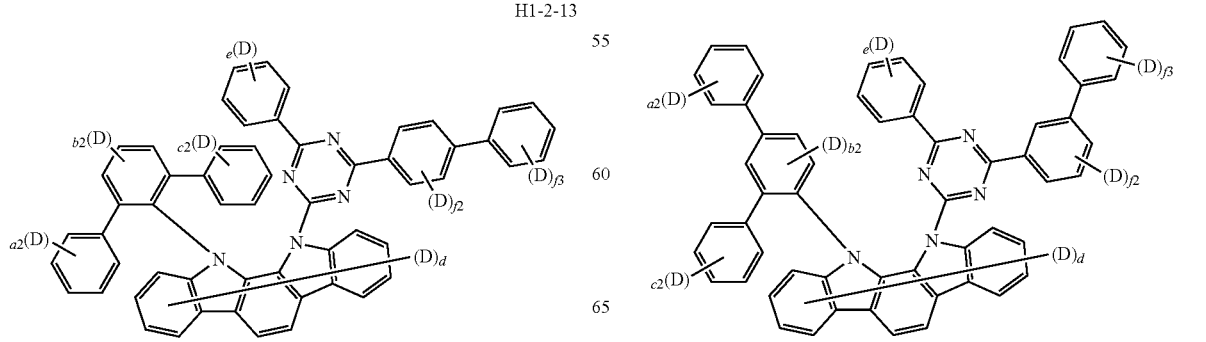
H1-3-11

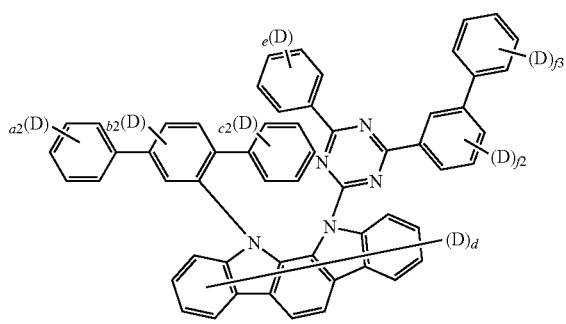
H1-3-12
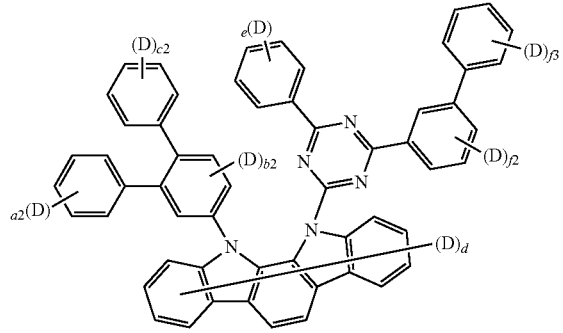
H1-3-14
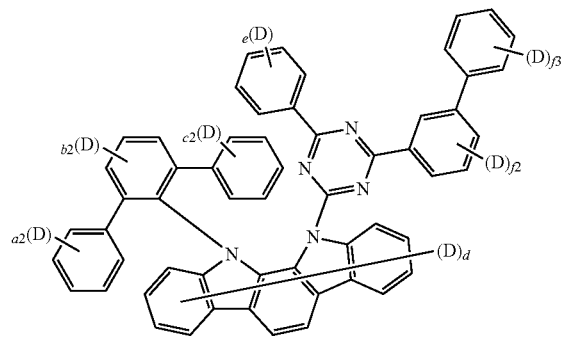
H1-3-13
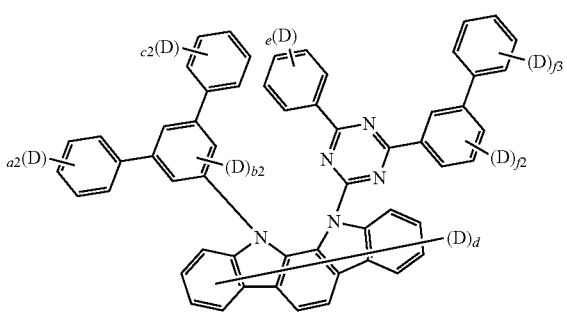
H1-3-15
wherein in Chemical Formulae H1-2-10 to H1-2-15 and H1-3-10 to H1-3-15:
a2, b2, c2, and d are as defined in Chemical Formula 1,
e is an integer of 0 to 5,
f2 is an integer of 0 to 4,
f3 is an integer of 0 to 5, and
a2+b2+c2+d+e+f2+f3 is 1 to 37;
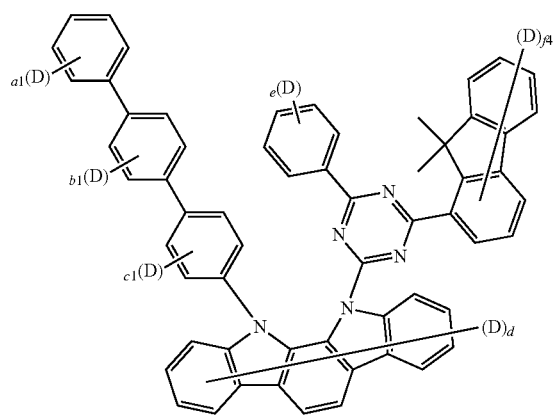
H1-4-1
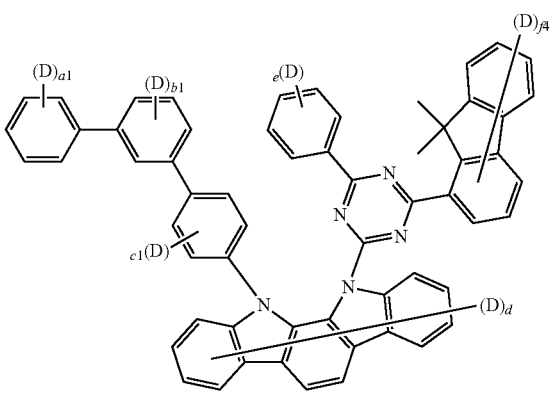
H1-4-2

-continued
H1-4-3
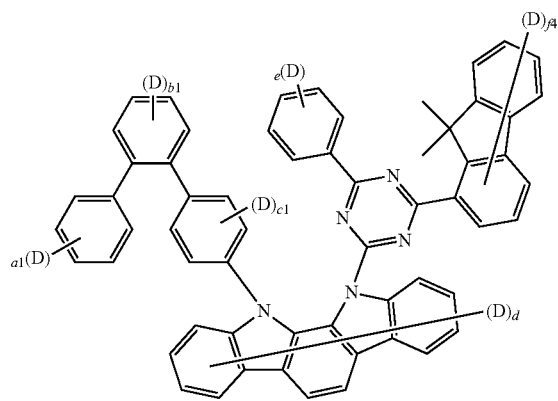
H1-4-4
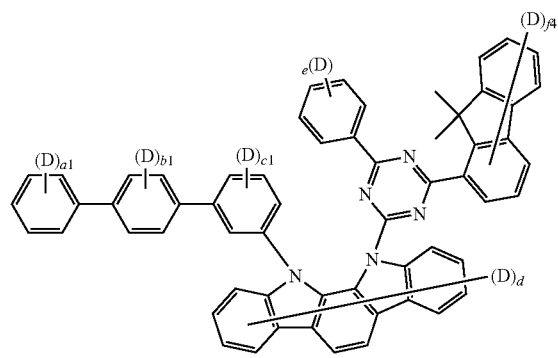
H1-4-5
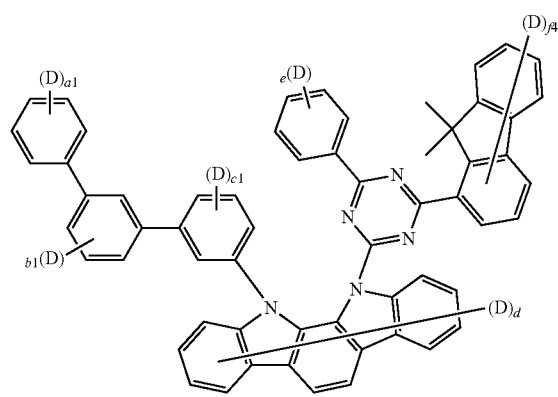
H1-4-6
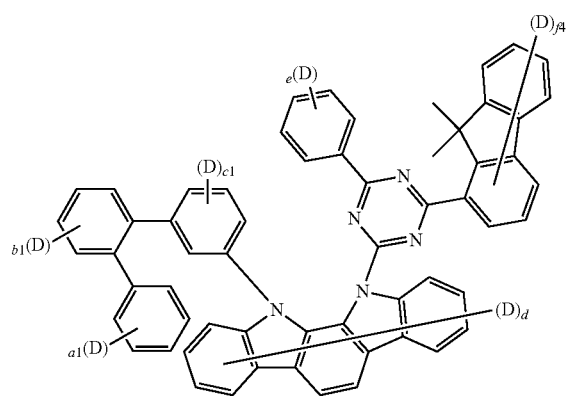
H1-4-7
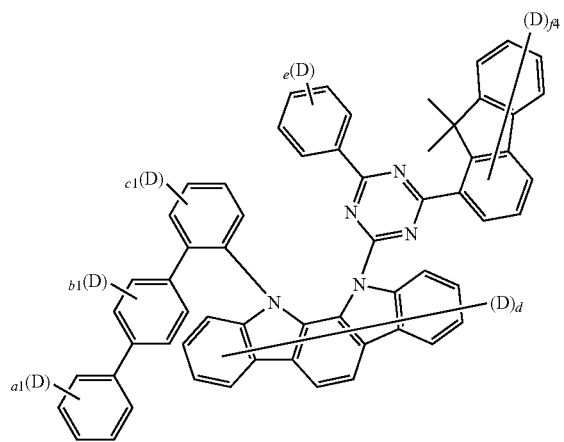
H1-4-8
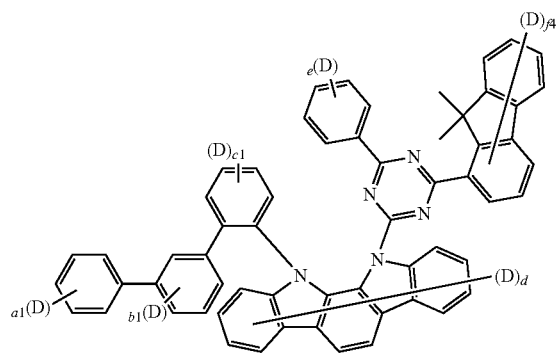

-continued
H1-4-9
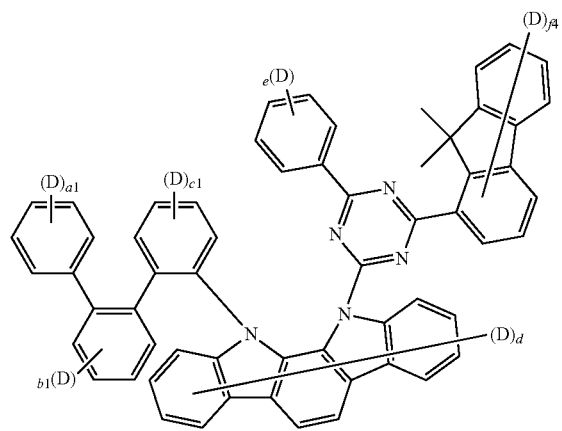
H1-5-1
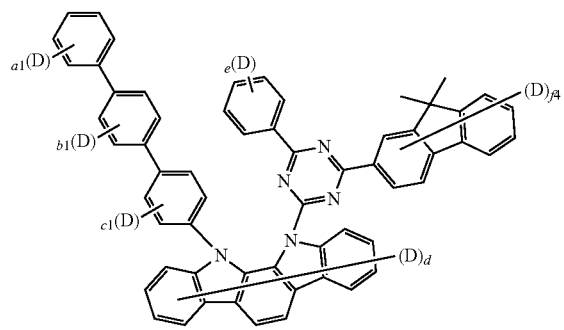
H1-5-2
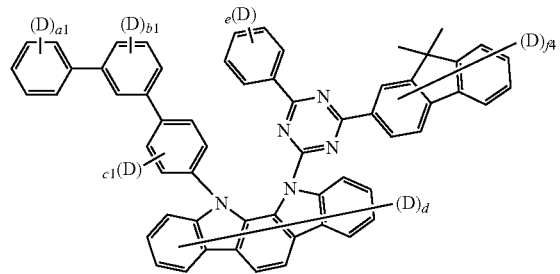
H1-5-3
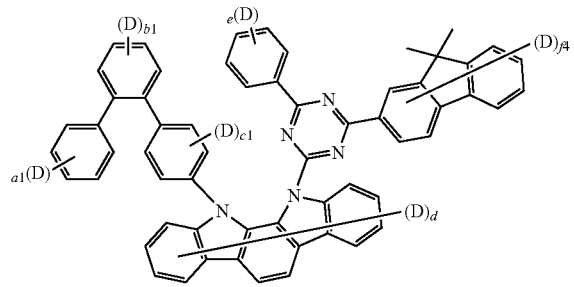
H1-5-4
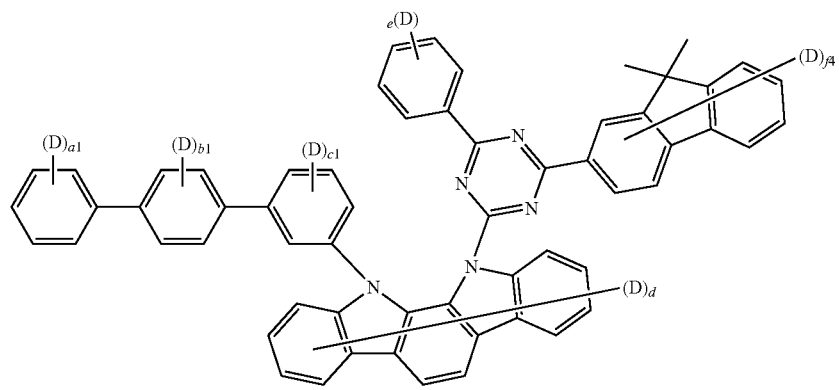
H1-5-5
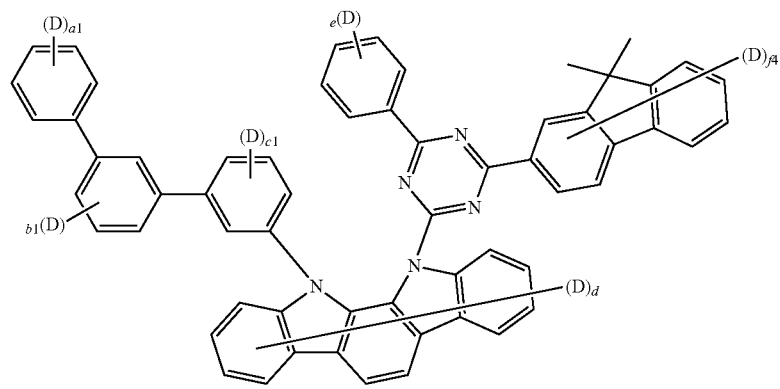

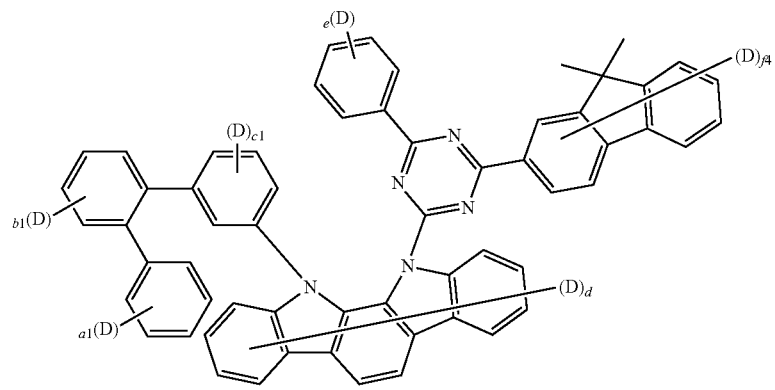
H1-5-6
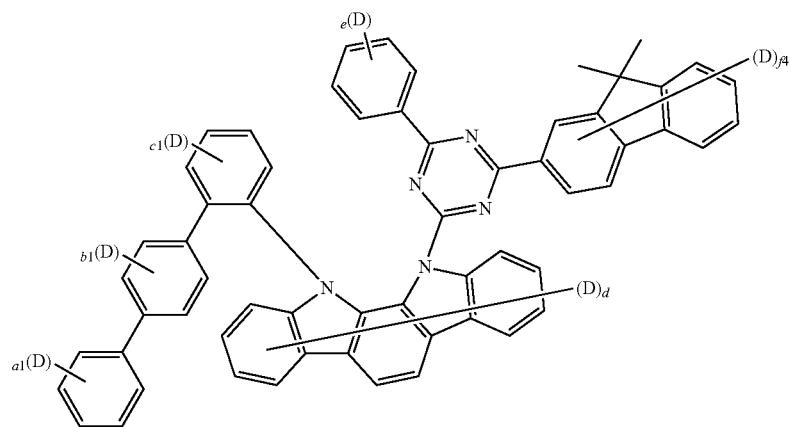
H1-5-7
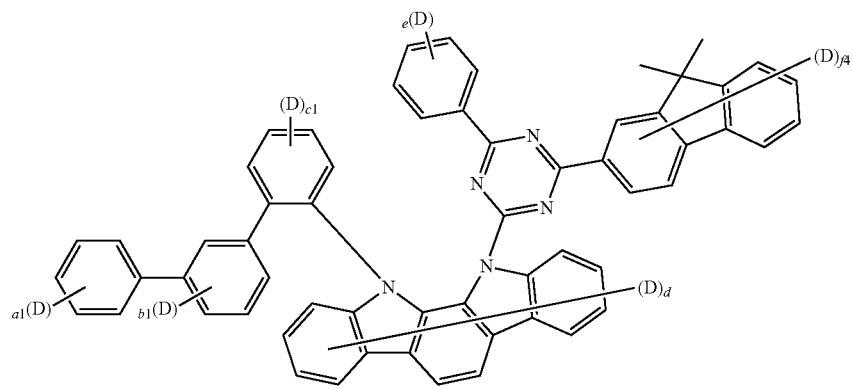
H1-5-8
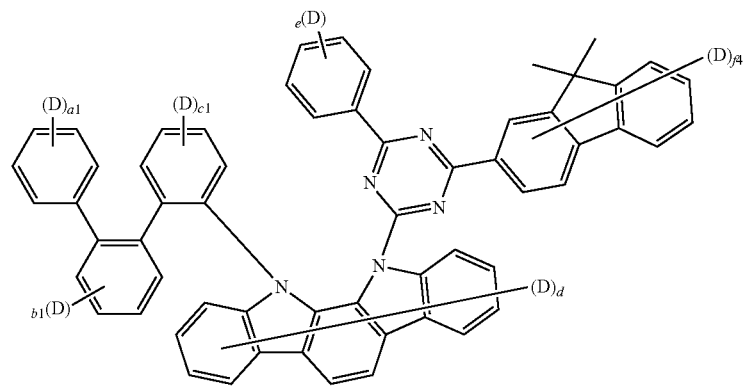
H1-5-9

-continued
H1-6-1
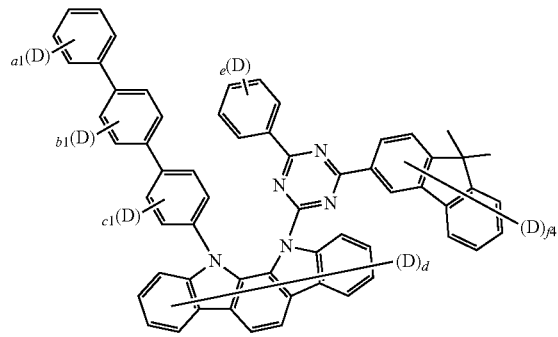
H1-6-2
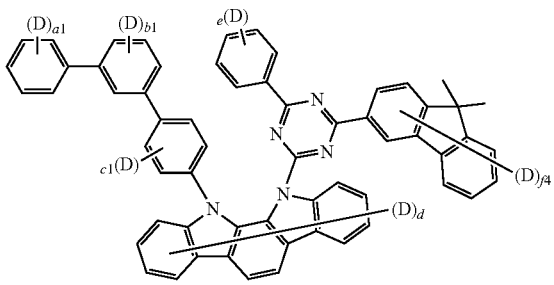
H1-6-3
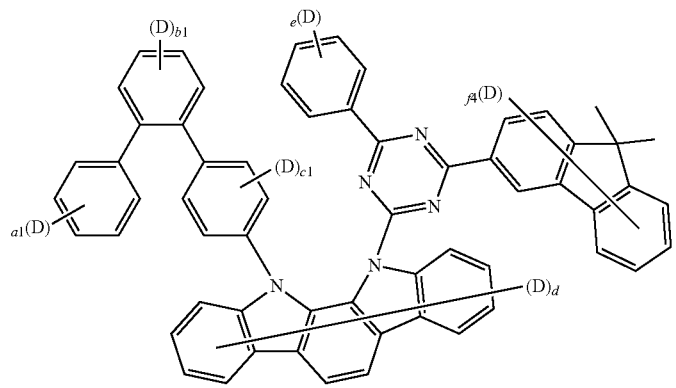
H1-6-4
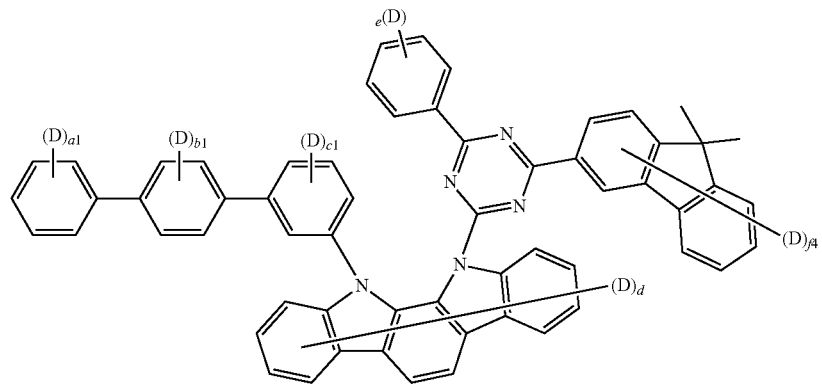
H1-6-5
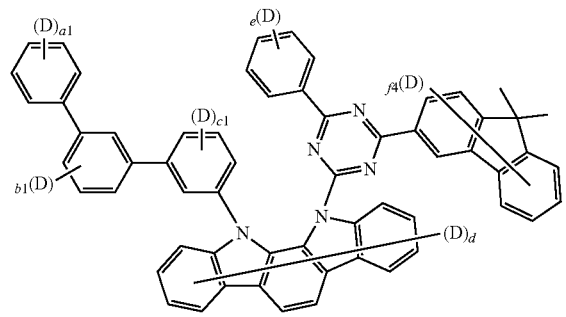
H1-6-6
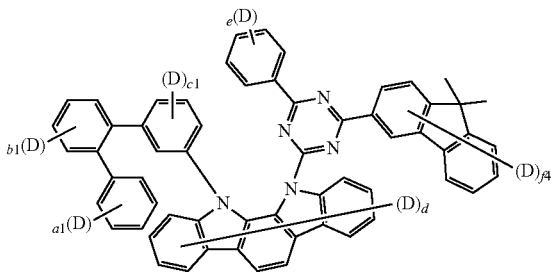

H1-6-7
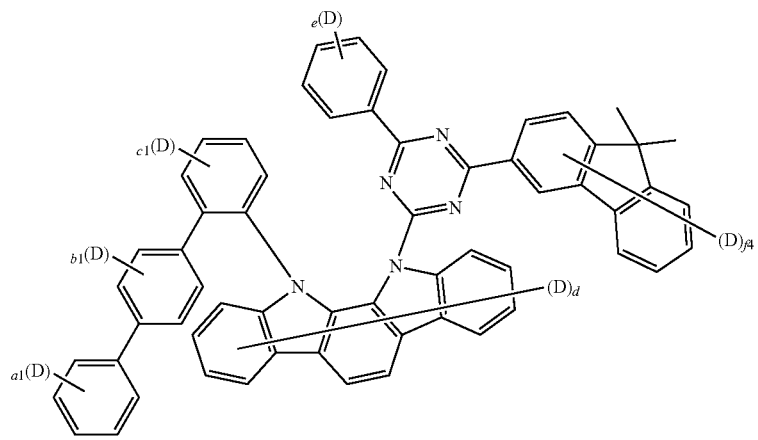
H1-6-8
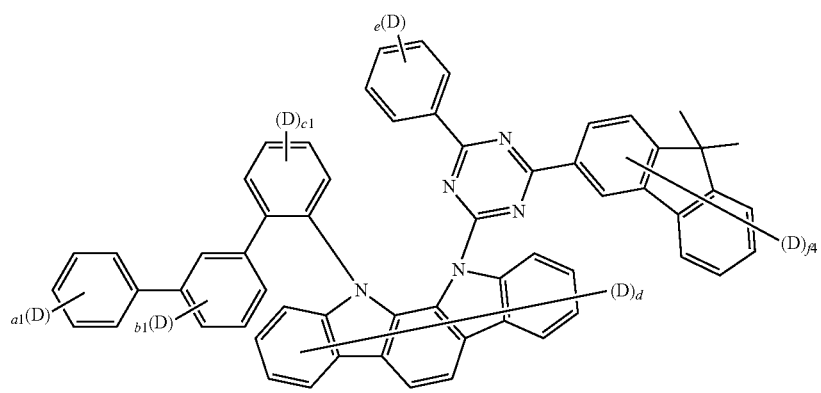
H1-6-9
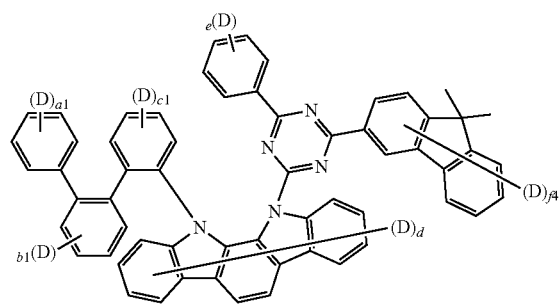
H1-7-1
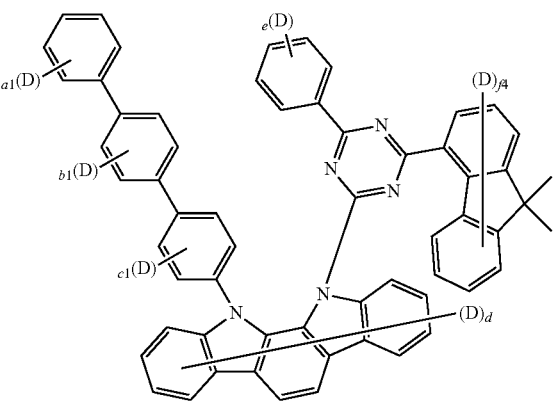
H1-7-2
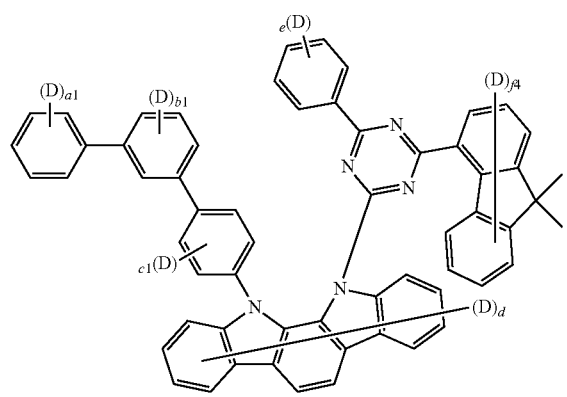
H1-7-3
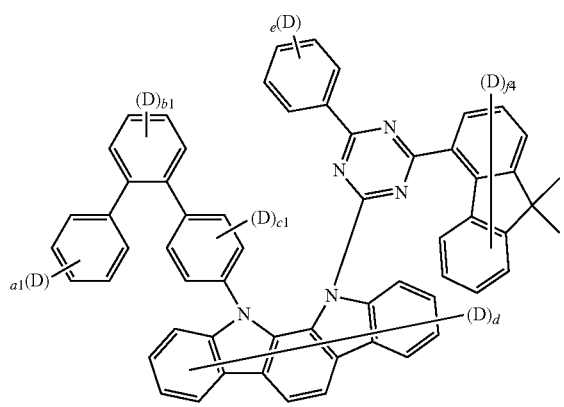

-continued
H1-7-4
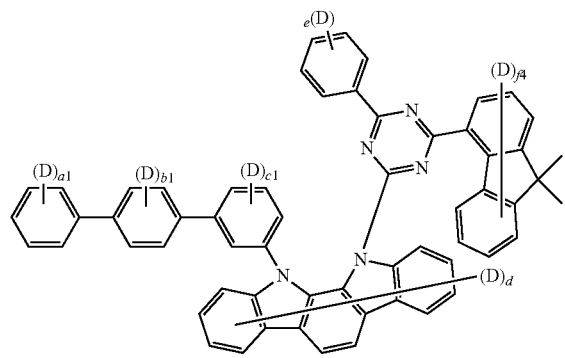
H1-7-5
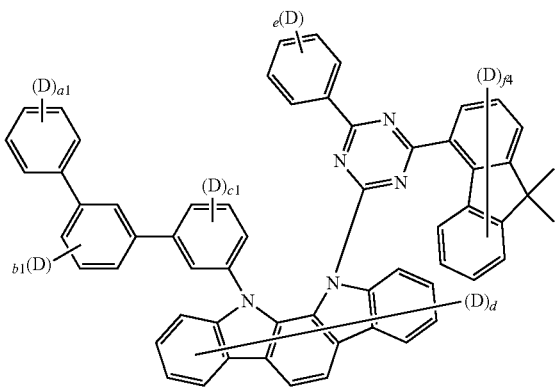
H1-7-6
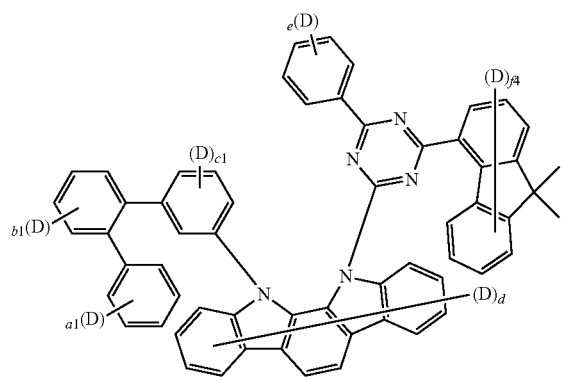
H1-7-7
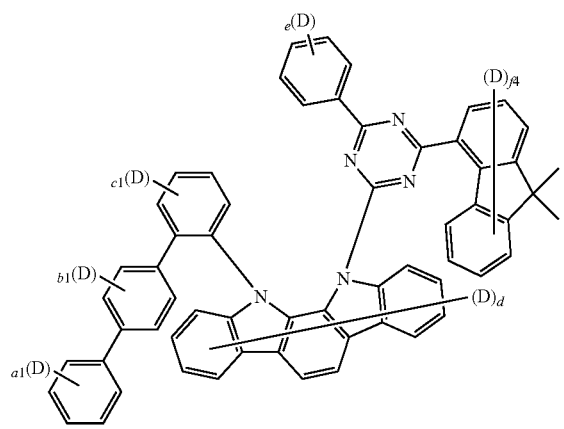
H1-7-8
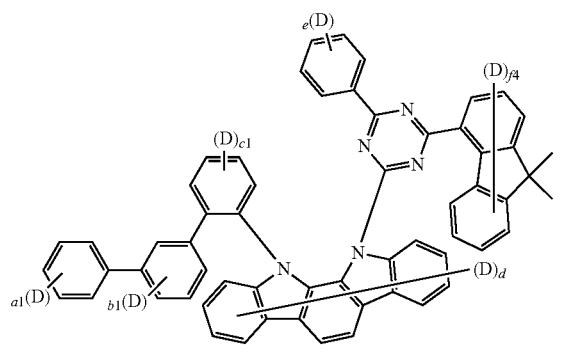
H1-7-9
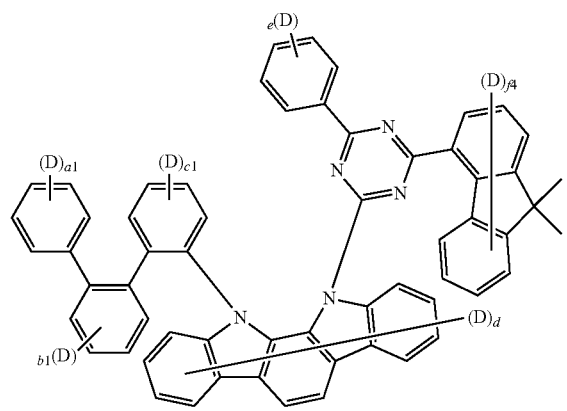

-continued
H1-8-1
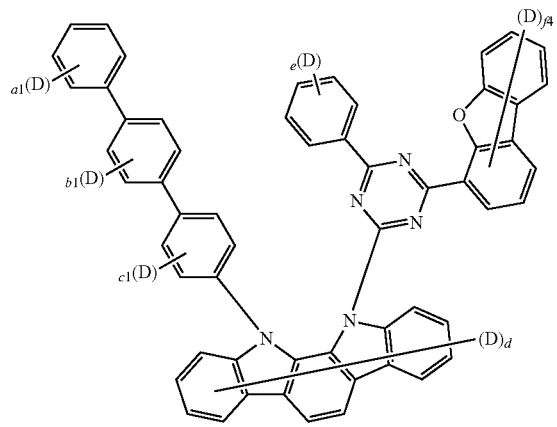
H1-8-2
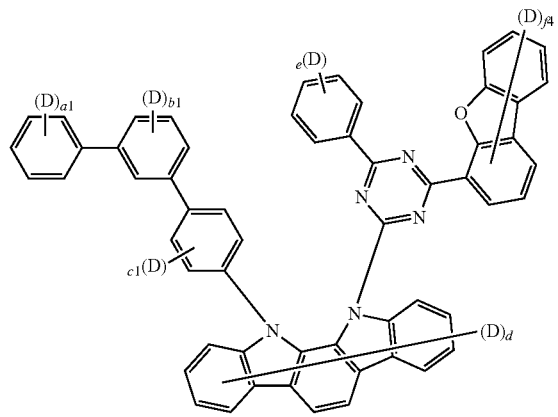
H1-8-3
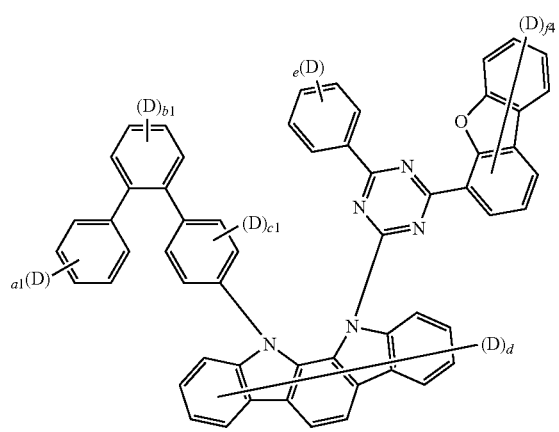
H1-8-4
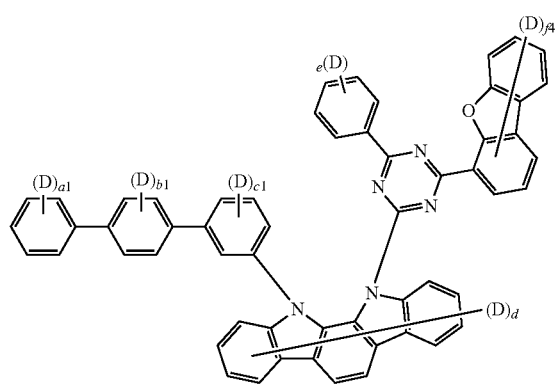
H1-8-5
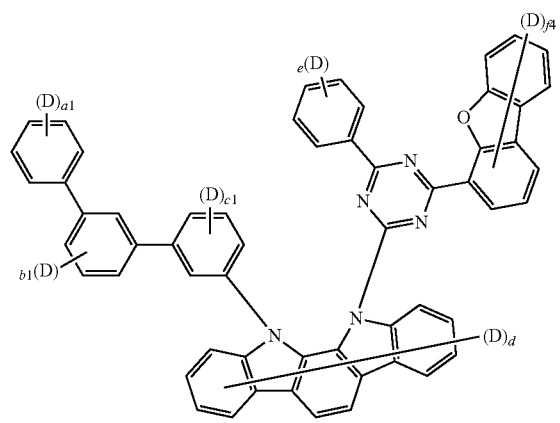
H1-8-6
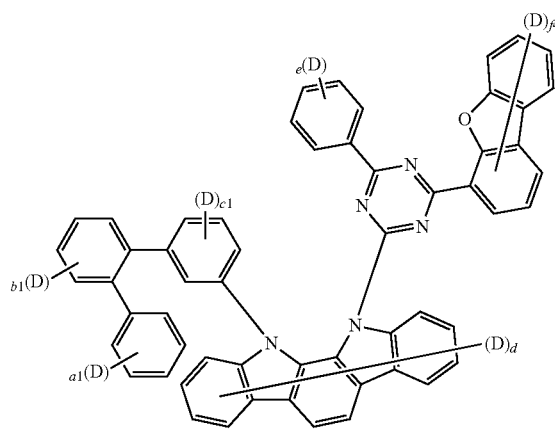

-continued
H1-8-7
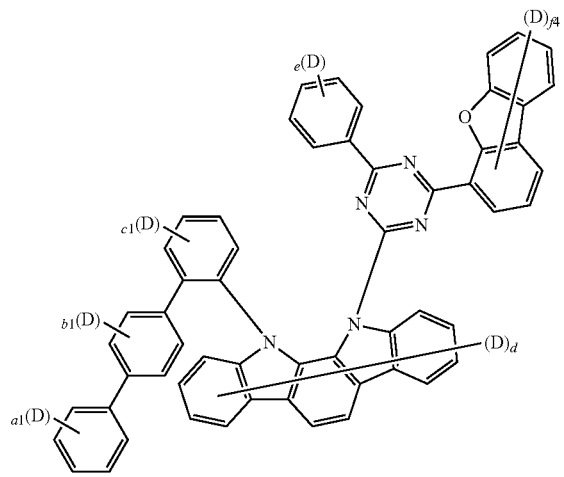
H1-8-8
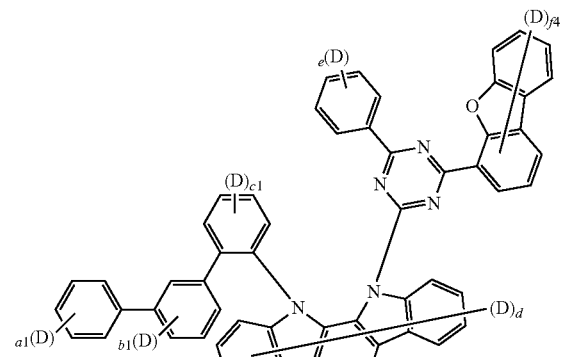
H1-8-9
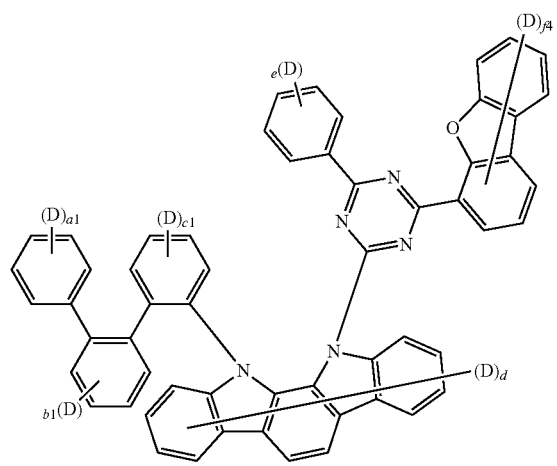
H1-9-1
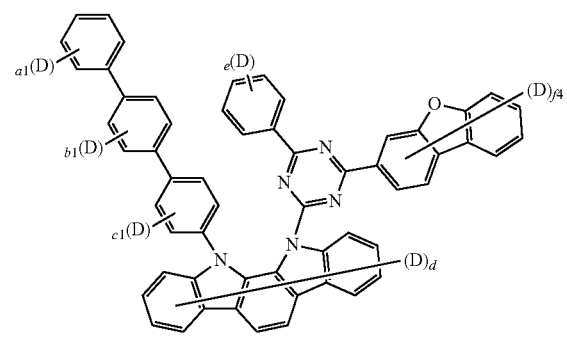
H1-9-2
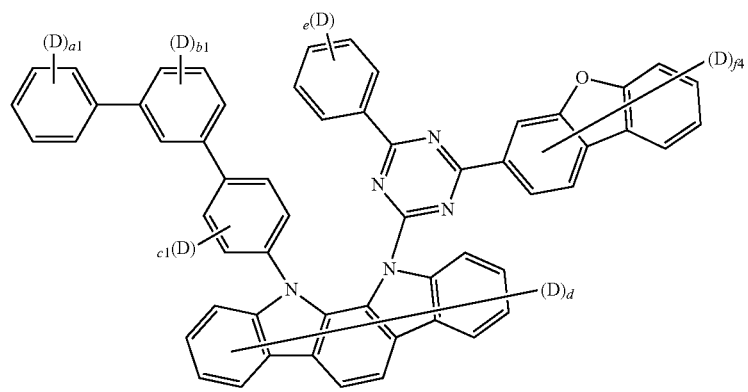

-continued
H1-9-3
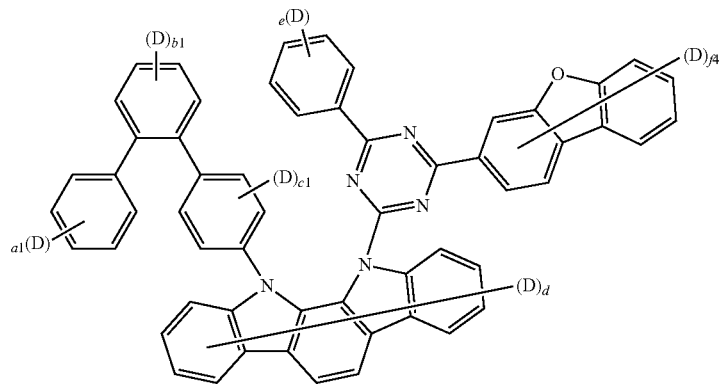
H1-9-4
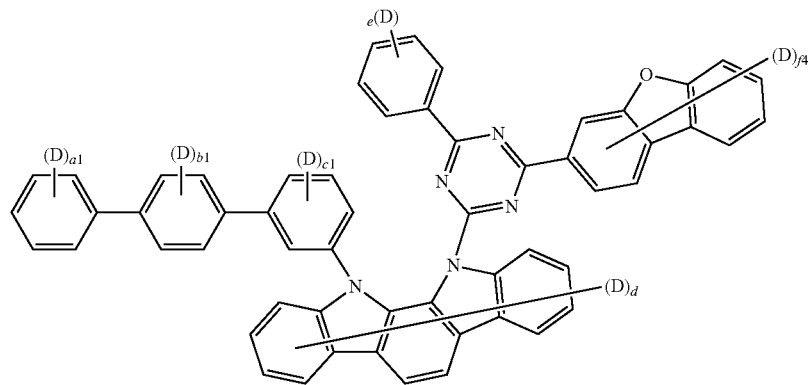
H1-9-5
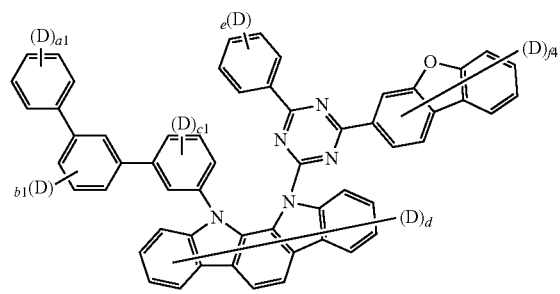
H1-9-6
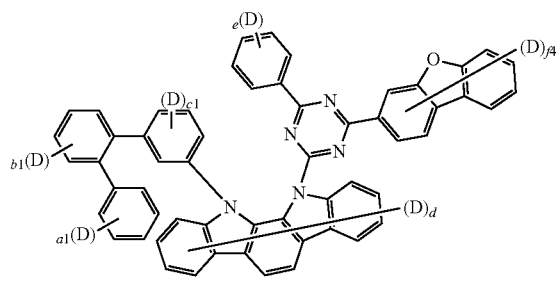
H1-9-7
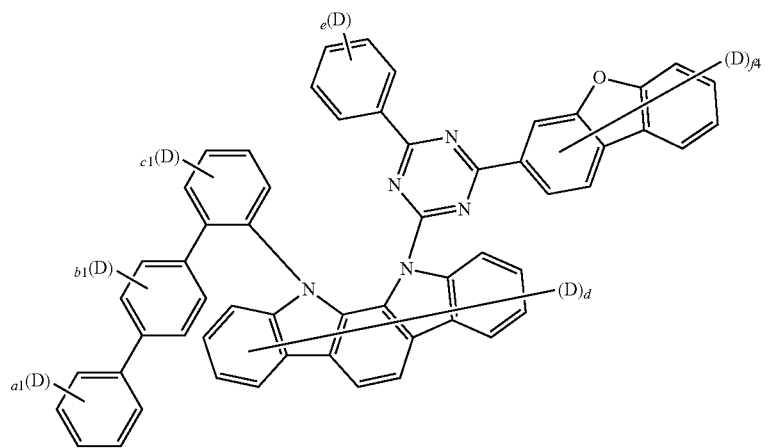

H1-9-8
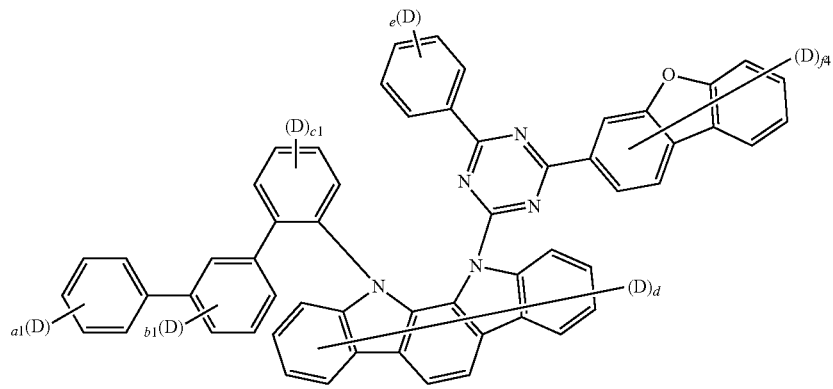
H1-9-9
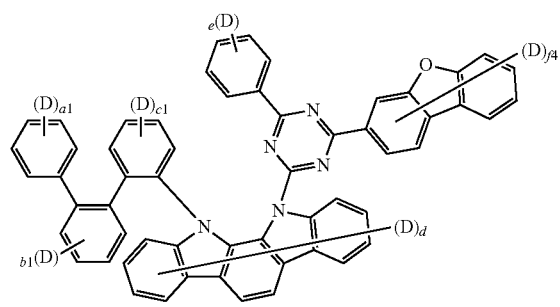
H1-10-1
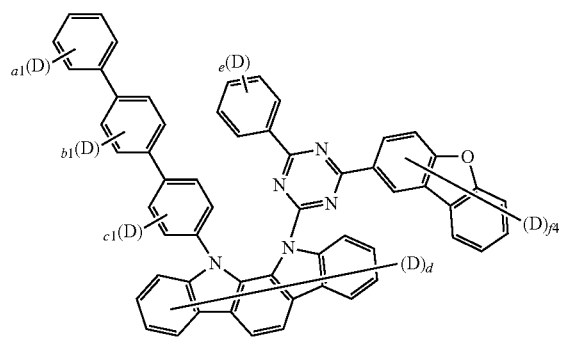
H1-10-2
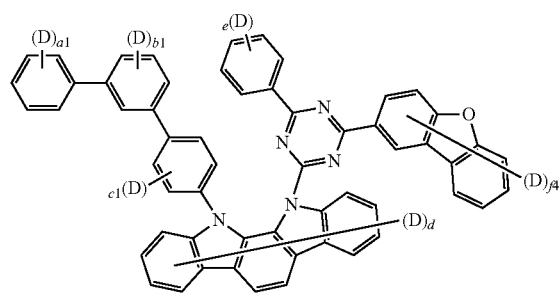
H1-10-3
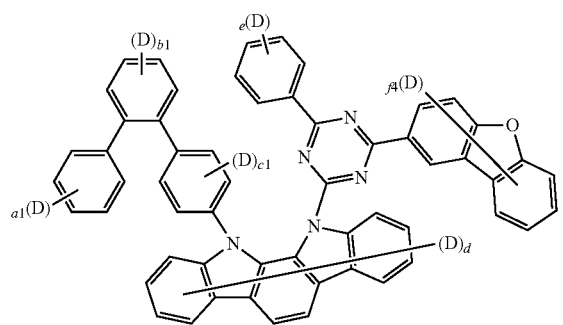
H1-10-4
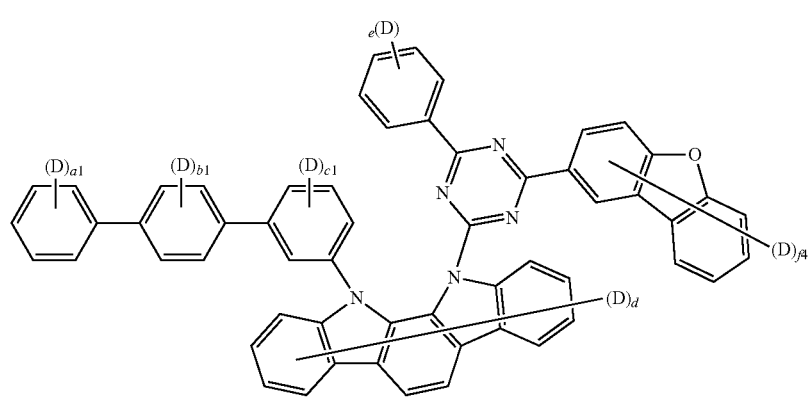

-continued
H1-10-5
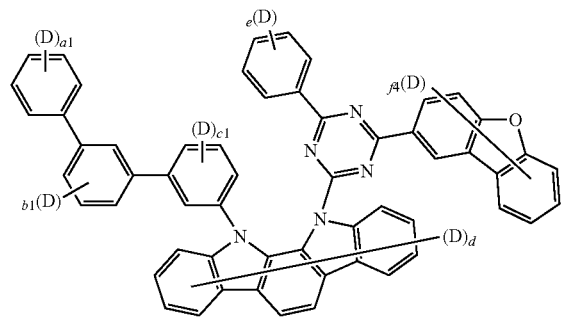
H1-10-6
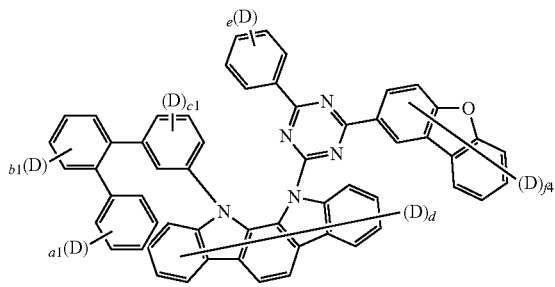
H1-10-7
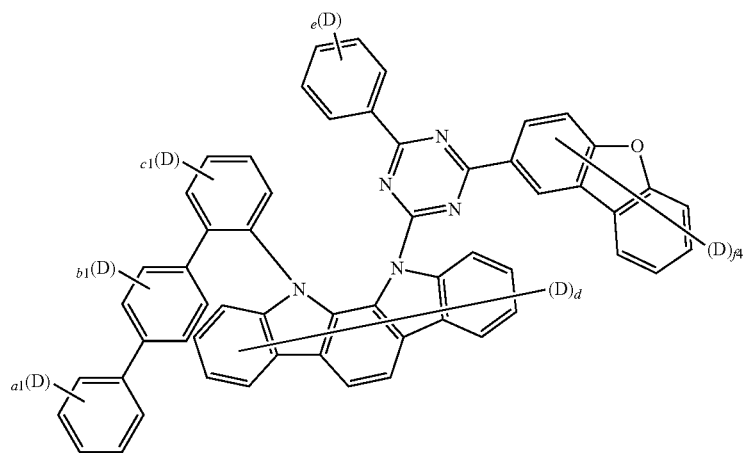
H1-10-8
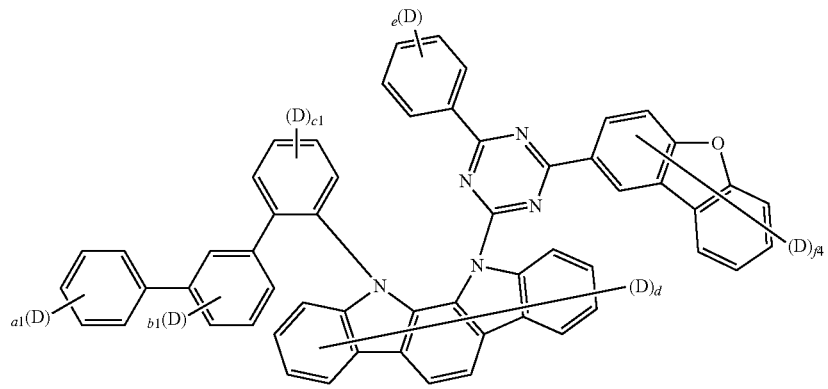
H1-10-9
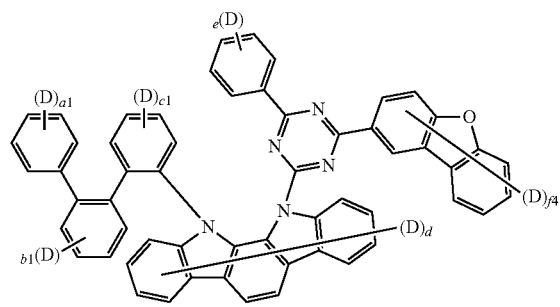
H1-11-1
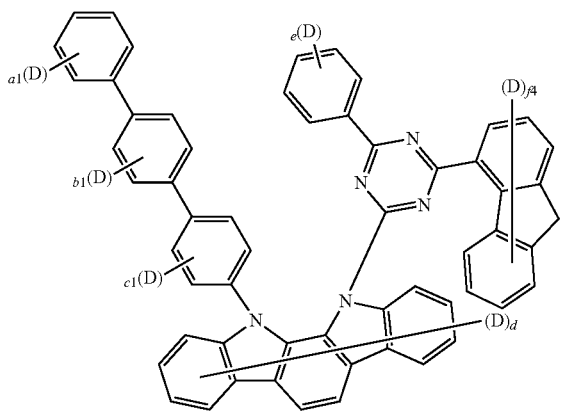

-continued
H1-11-2
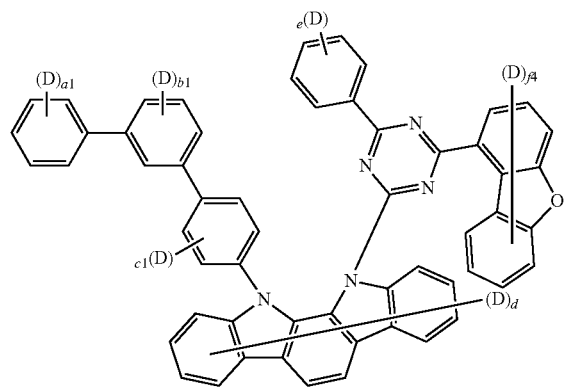
H1-11-3
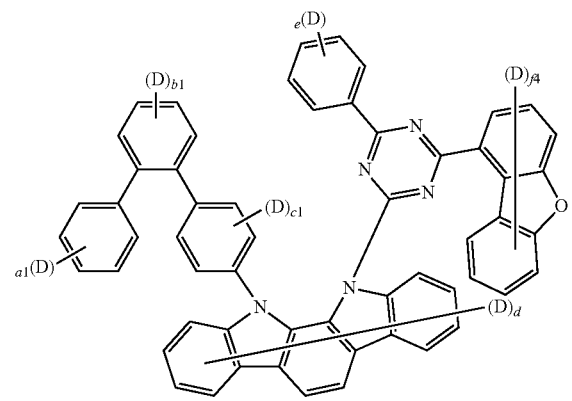
H1-11-4
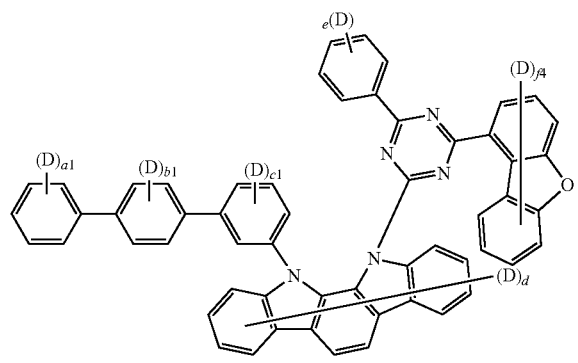
H1-11-5
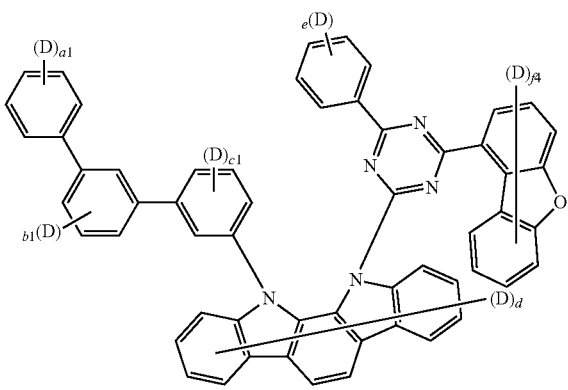
H1-11-6
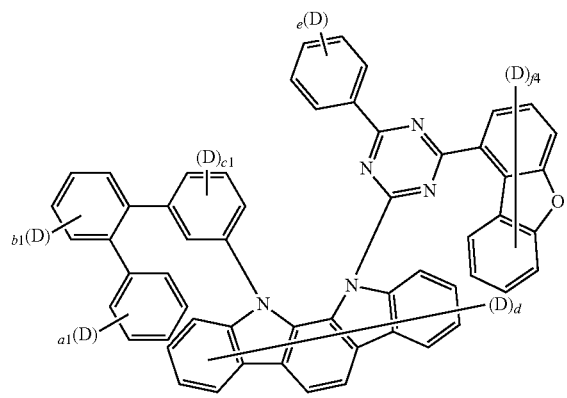
H1-11-7
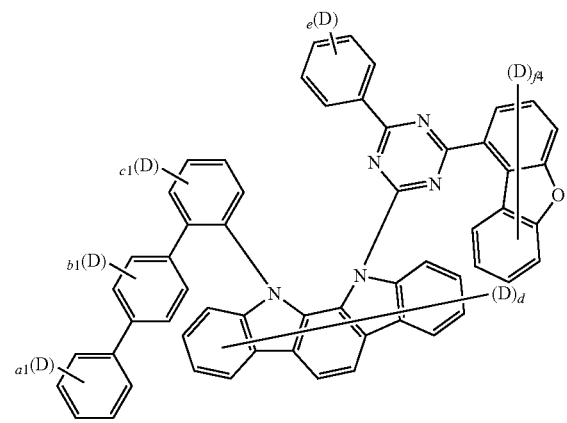

-continued
H1-11-8
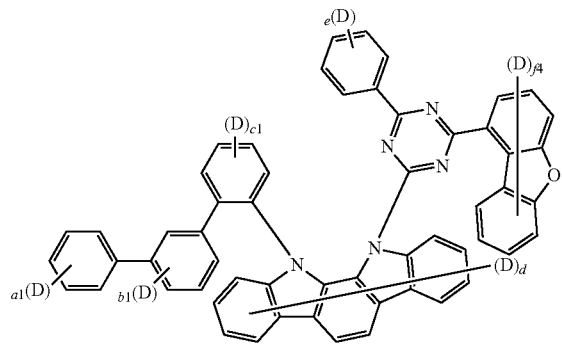
H1-11-9
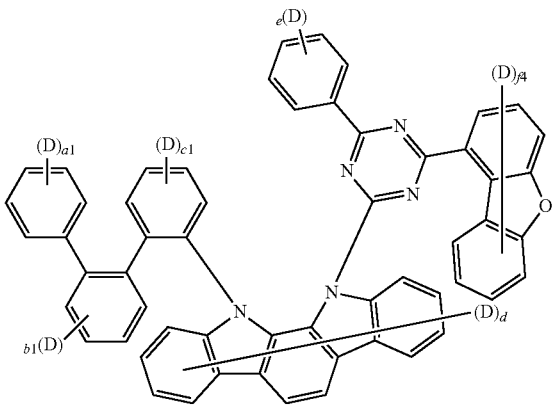
H1-12-1
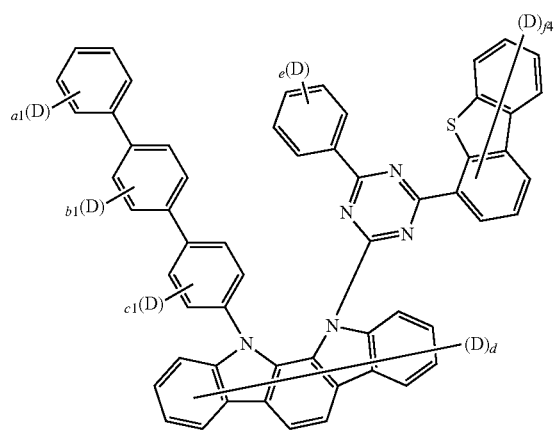
H1-12-2
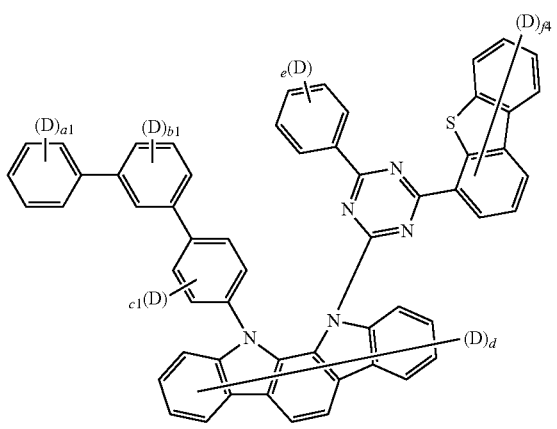
H1-12-3
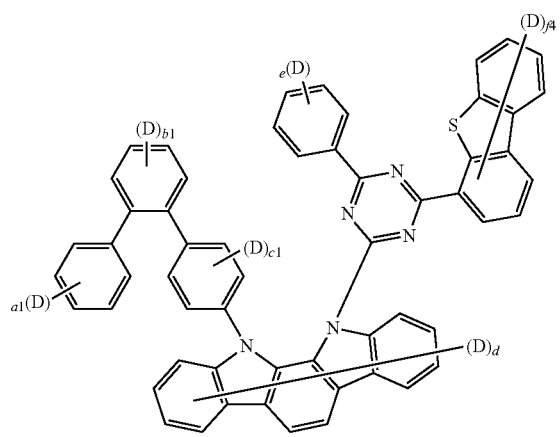
H1-12-4
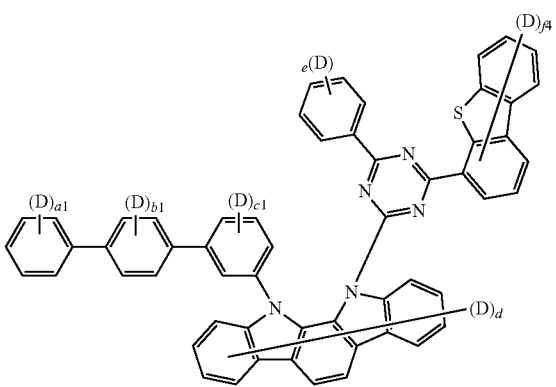

-continued
H1-12-5
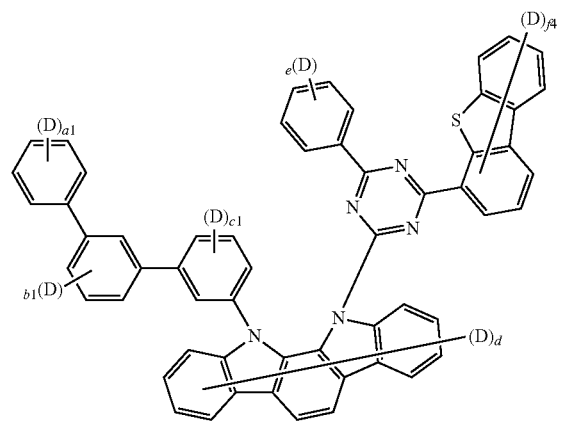
H1-12-6
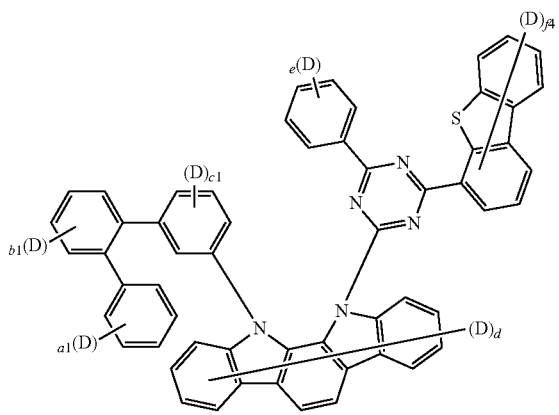
H1-12-7
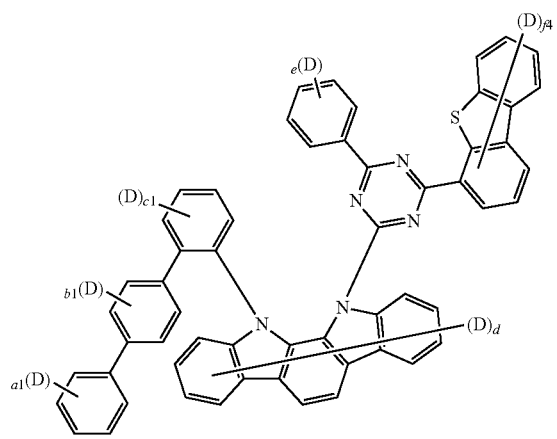
H1-12-8
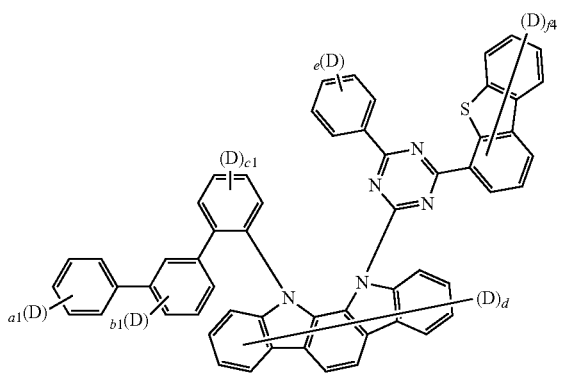
H1-12-9
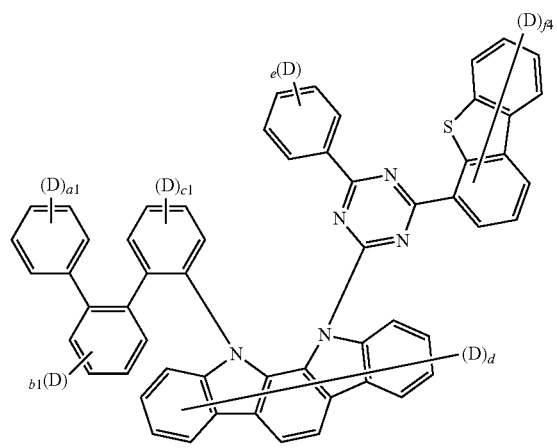
H1-13-1
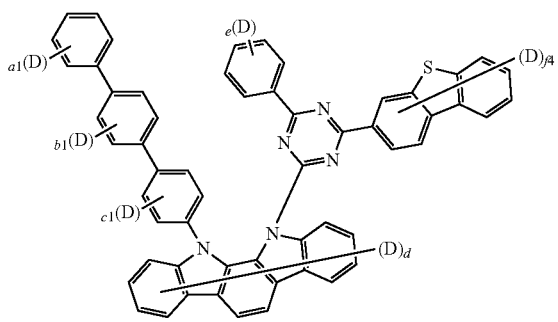

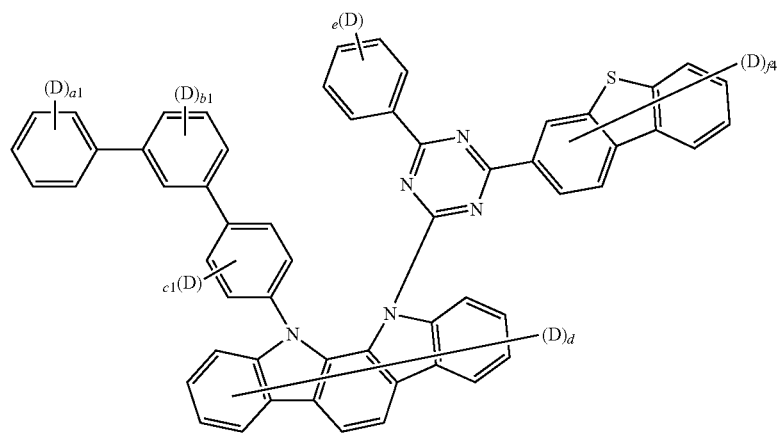
H1-13-2
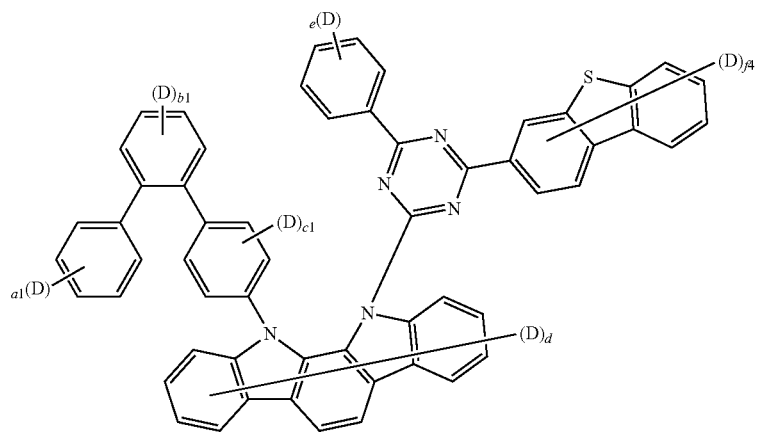
H1-13-3
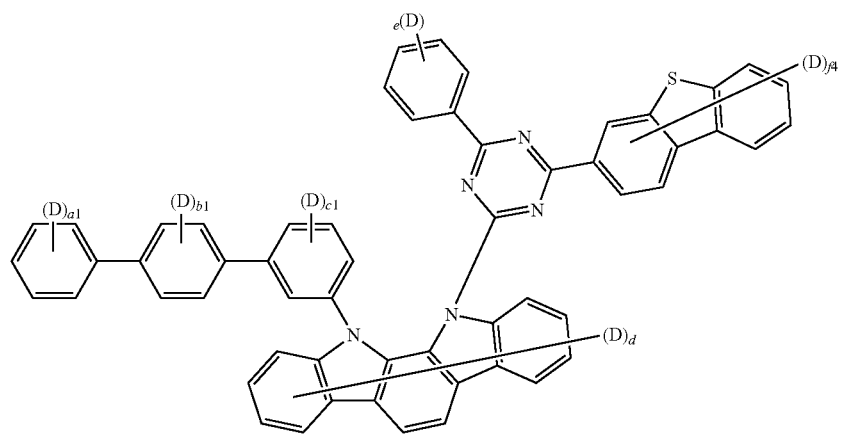
H1-13-4

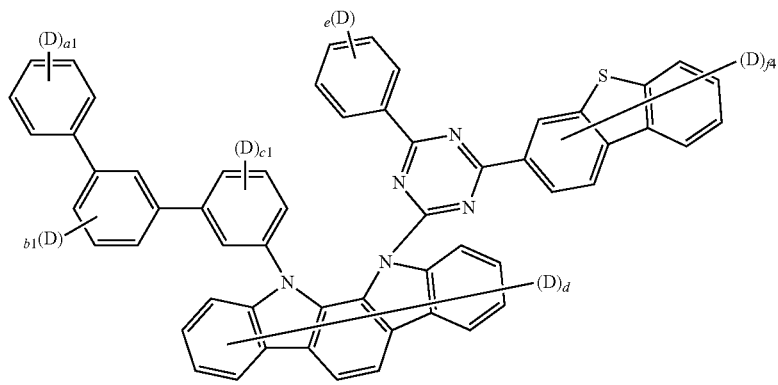
H1-13-5
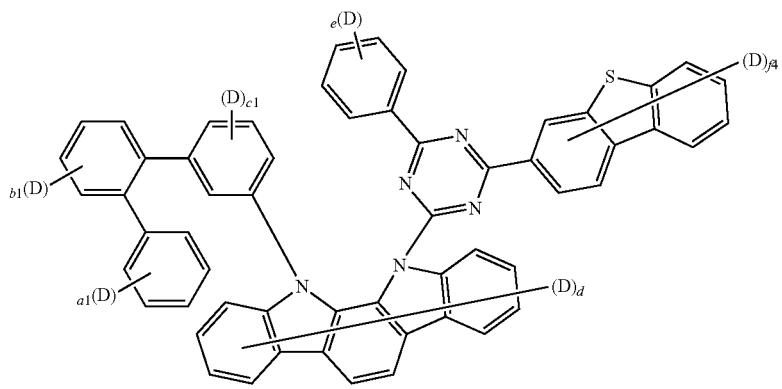
H1-13-6
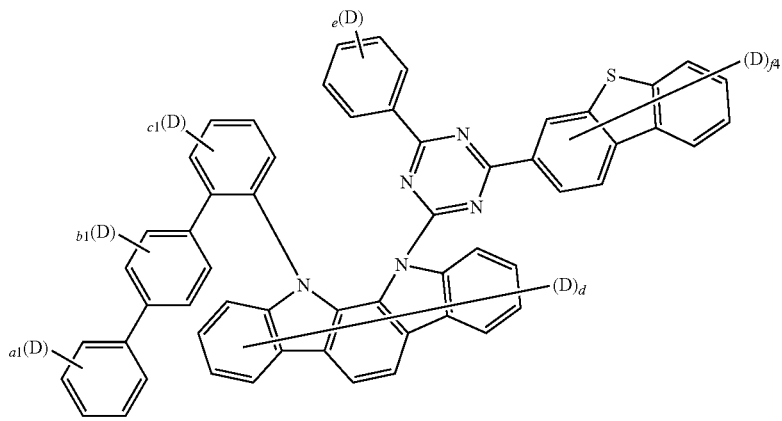
H1-13-7
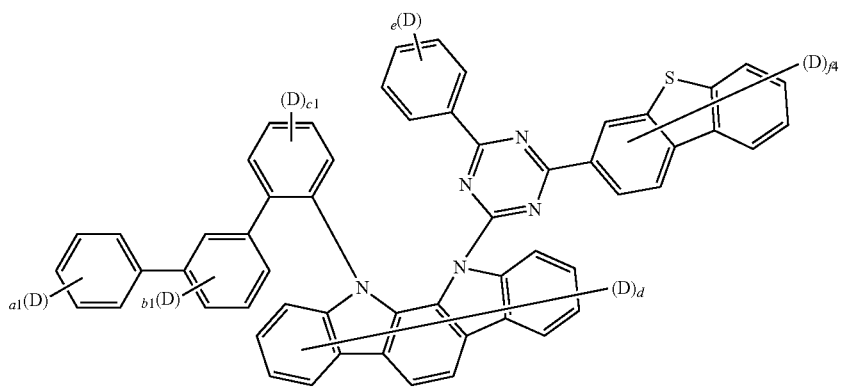
H1-13-8

-continued
H1-13-9
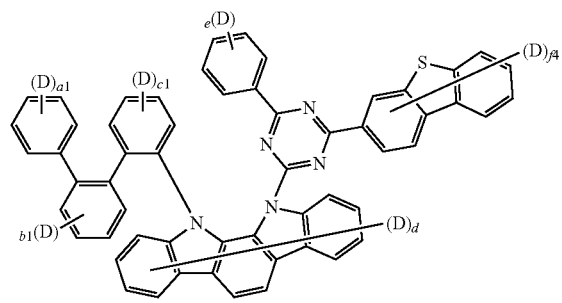
H1-14-1
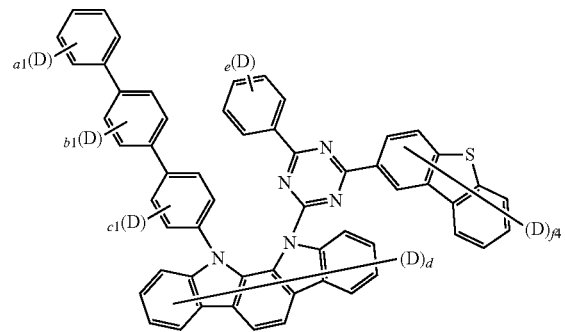
H1-14-2
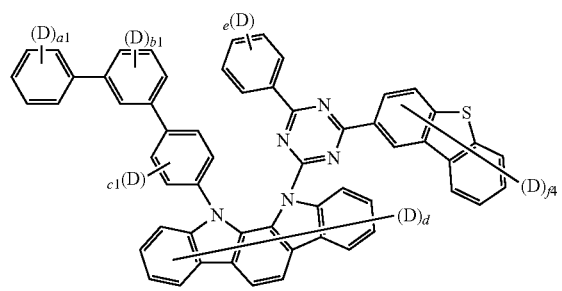
H1-14-3
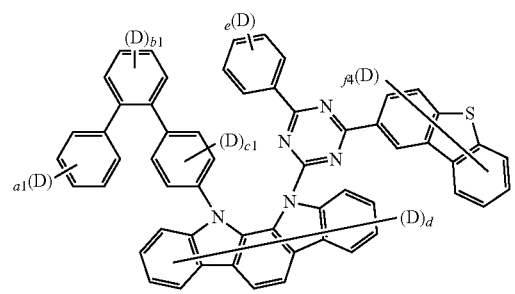
H1-14-4
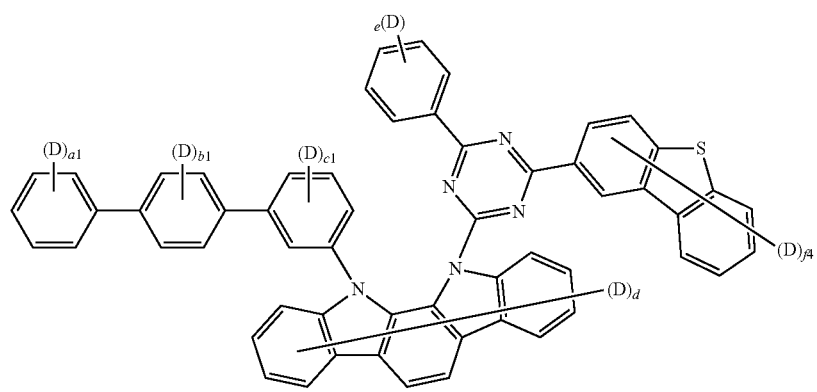
H1-14-5
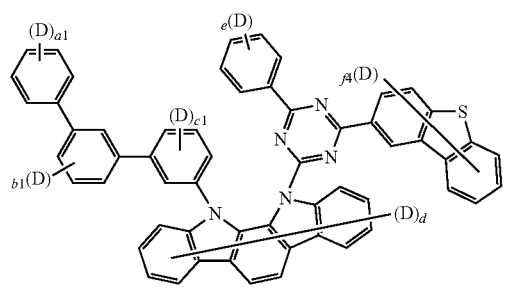
H1-14-6
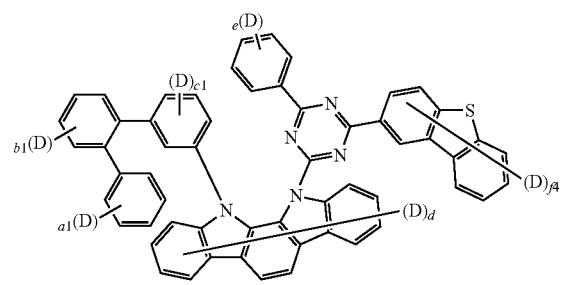

H1-14-7
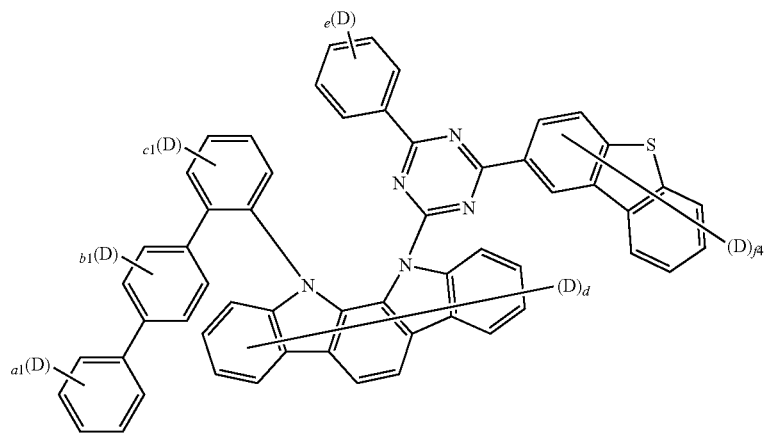
H1-14-8
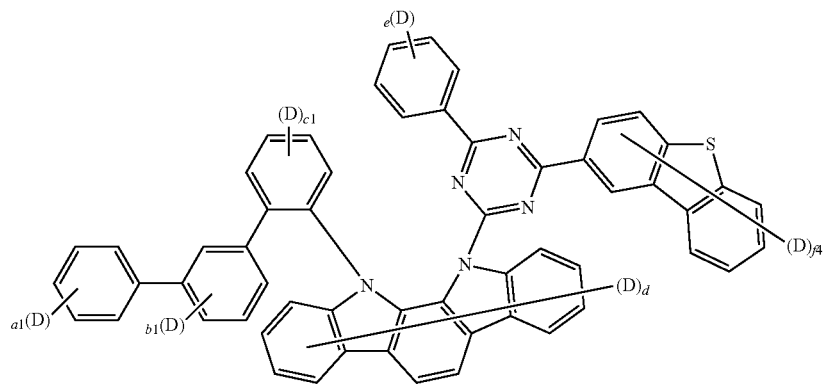
H1-14-9
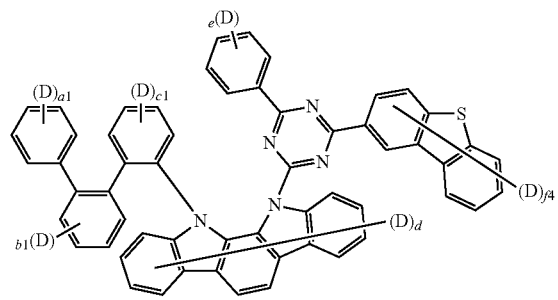
H1-15-1
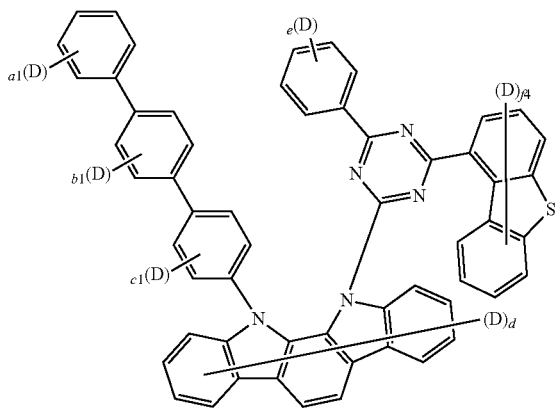

-continued
H1-15-2
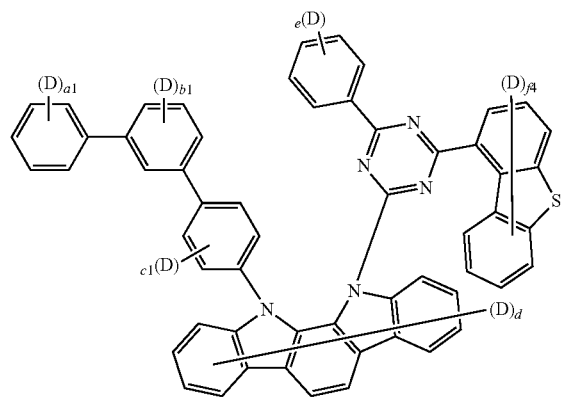
H1-15-3
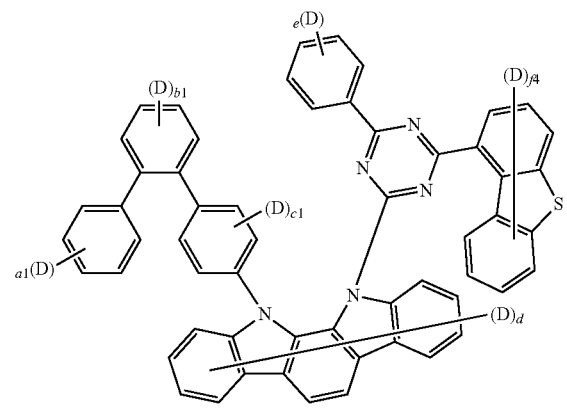
H1-15-4
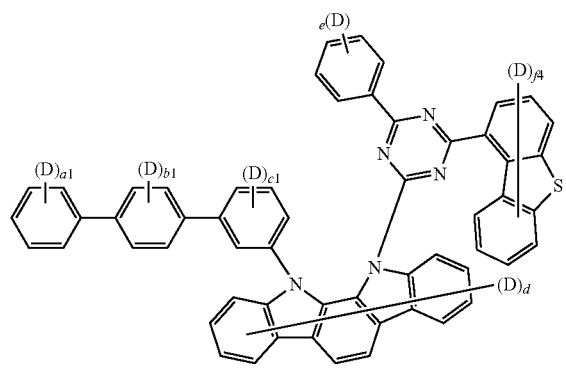
H1-15-5
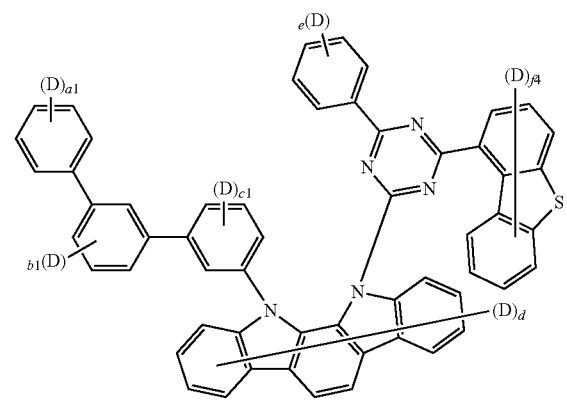
H1-15-6
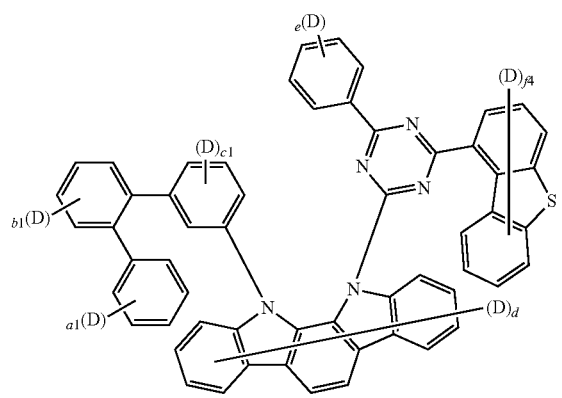
H1-15-7
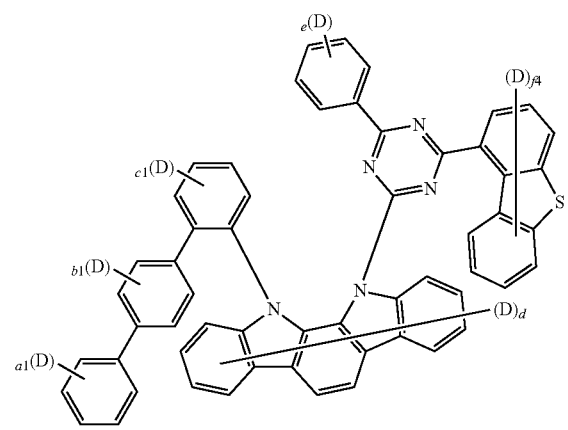

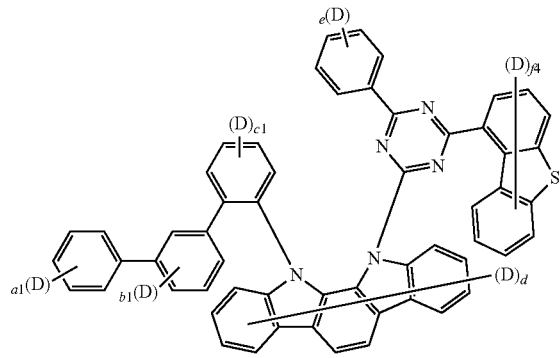
H1-15-8
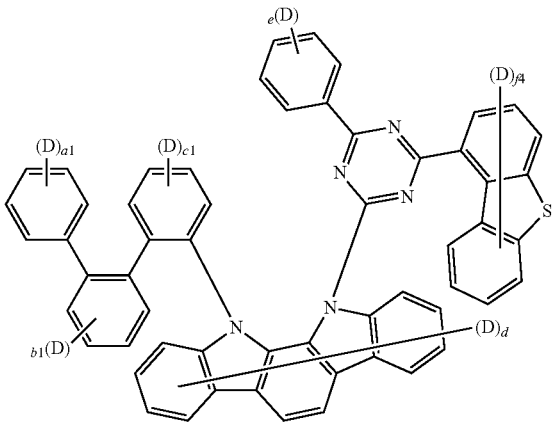
H1-15-9
wherein in Chemical Formulae H1-4-1 to H1-4-9, H1-5-1 to H1-5-9, H1-6-1 to H1-6-9, H1-7-1 to H1-7-9, H1-8-1 to H1-8-9, H1-9-1 to H1-9-9, H1-10-1 to H1-10-9, H1-11-1 to H1-11-9, H1-12-1 to H1-12-9, H1-13-1 to H1-13-9, H1-14-1 to H1-14-9, and H1-15-1 to H1-15-9:
a1, b1, c1, and d are as defined in Chemical Formula 1,
e is an integer of 0 to 5,
f4 is an integer of 0 to 7, and
a1+b1+c1+d+e+f4 is 1 to 35,
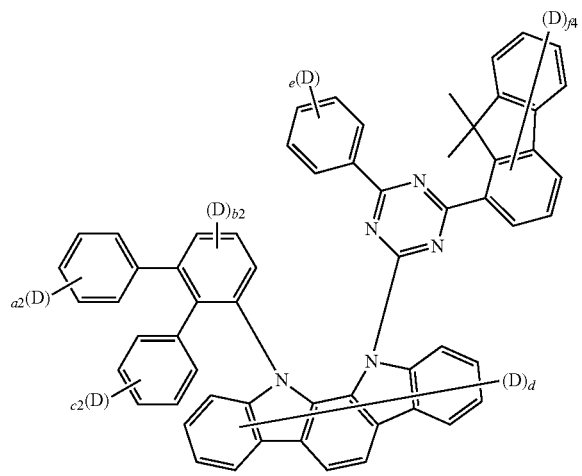
H1-4-10
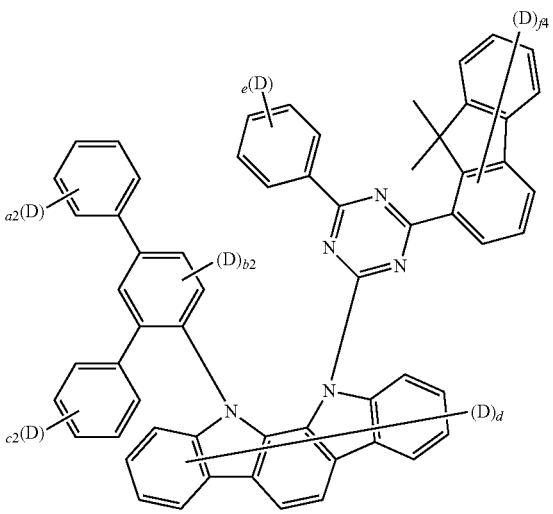
H1-4-11

-continued
H1-4-12
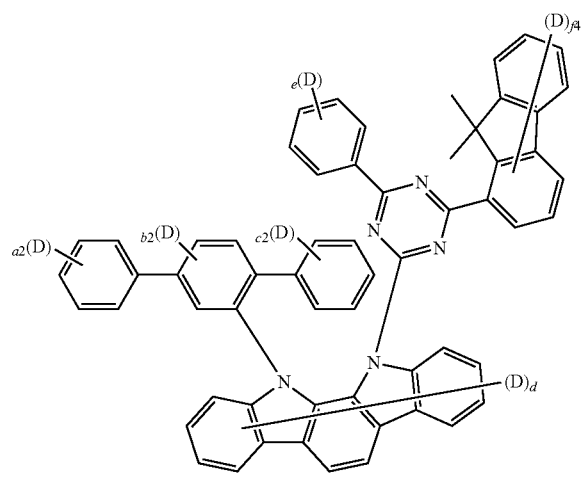
H1-4-13
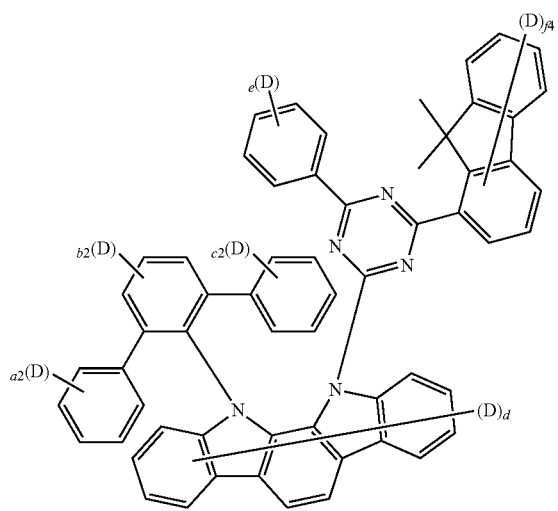
H1-4-14
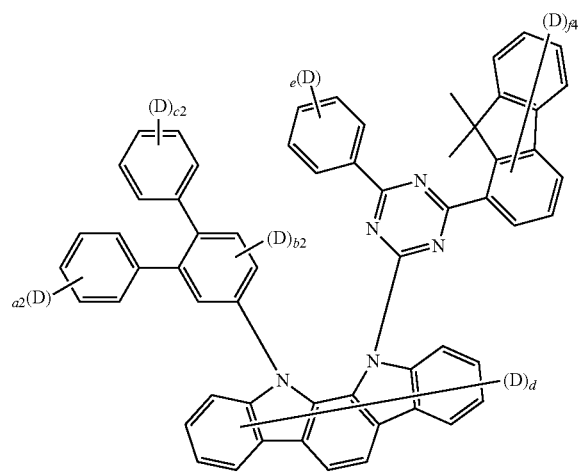
H1-4-15
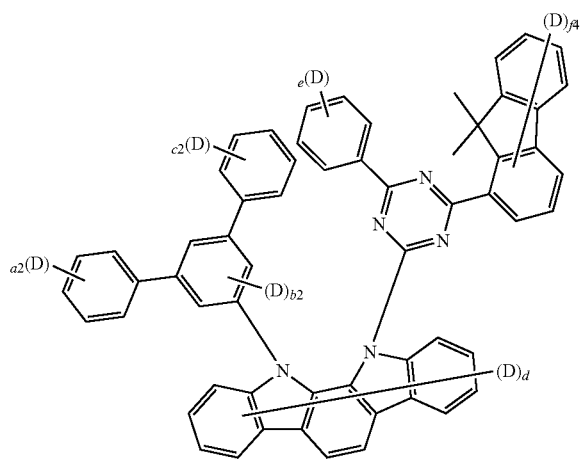
H1-5-10
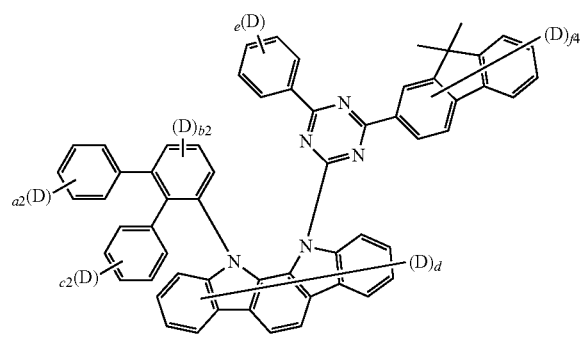
H1-5-11
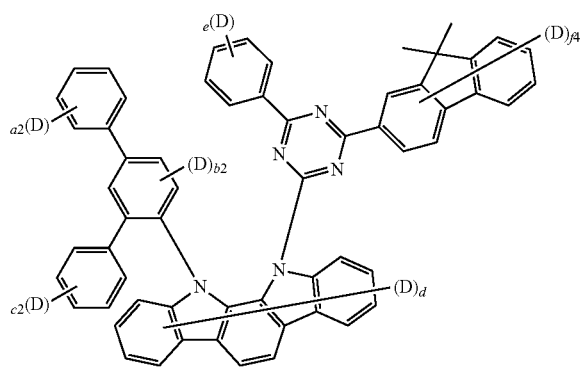

-continued
H1-5-12
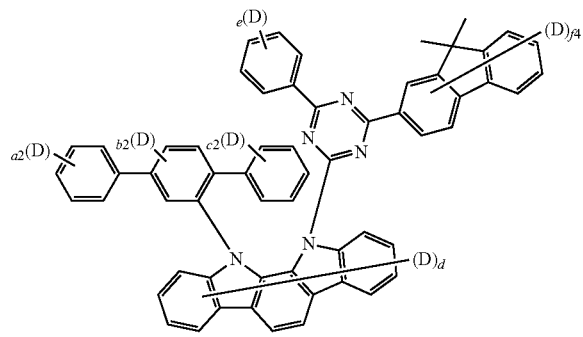
H1-5-13
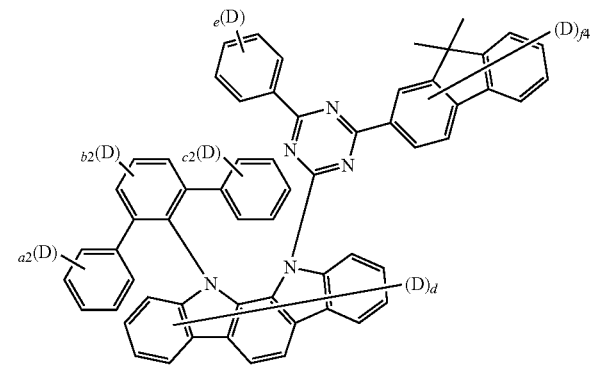
H1-5-14
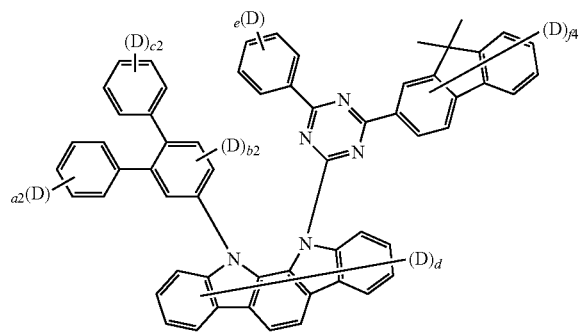
H1-5-9
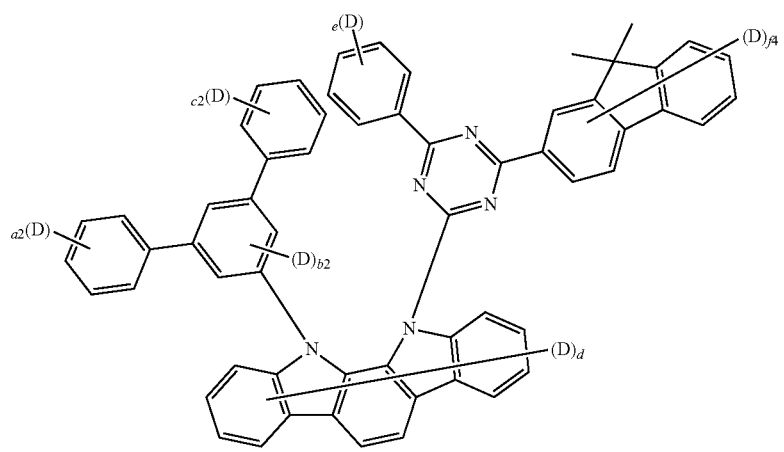
H1-6-10
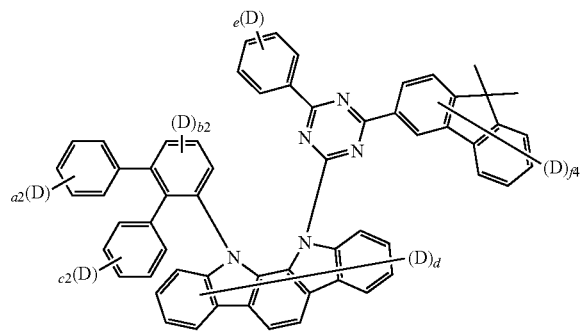
H1-6-11
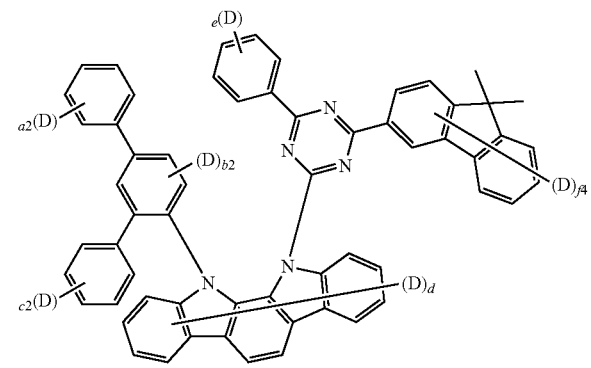

-continued
H1-6-12
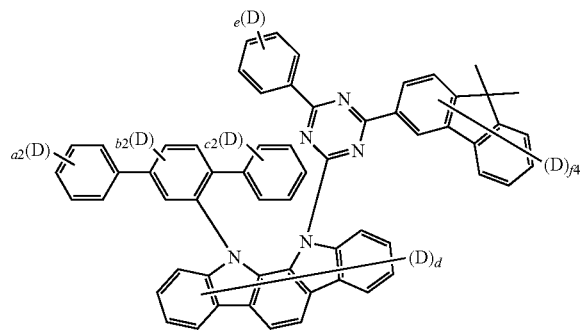
H1-6-13
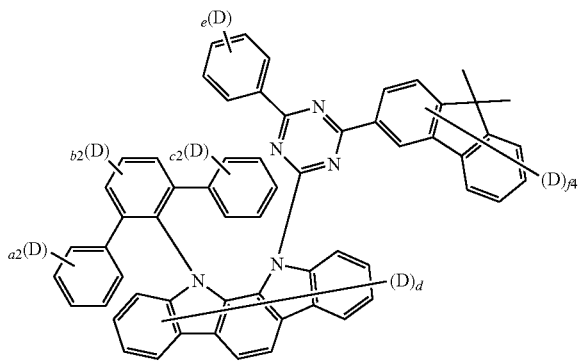
H1-6-14
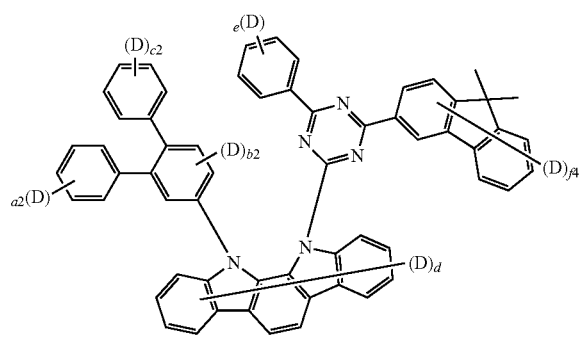
H1-6-15
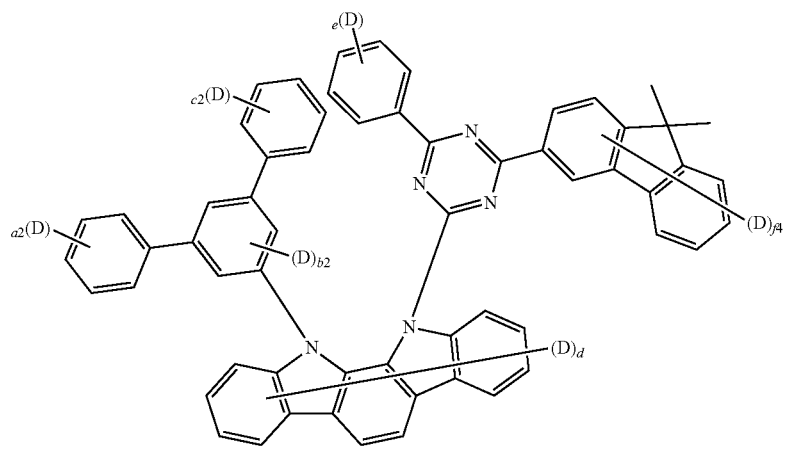
H1-7-10
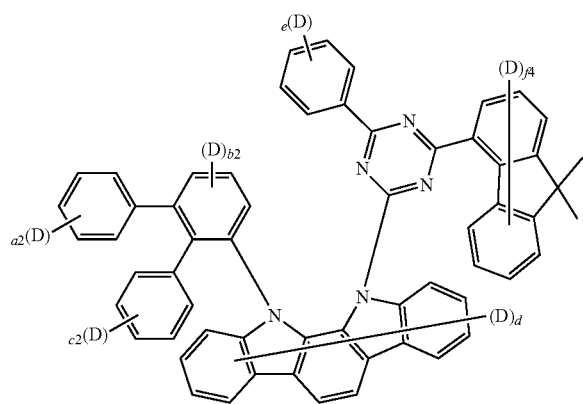
H1-7-11
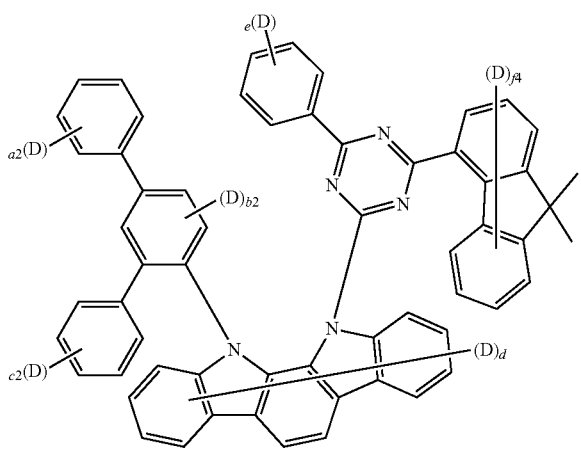

-continued
H1-7-12
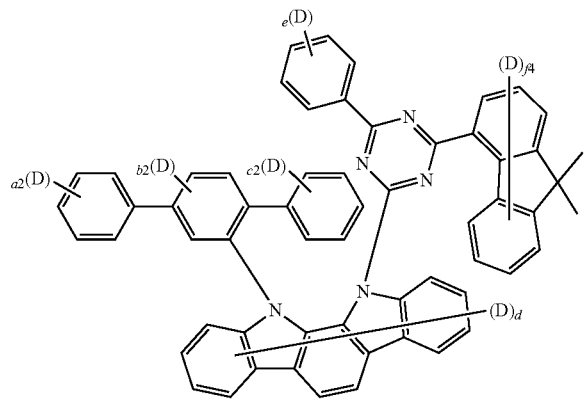
H1-7-13
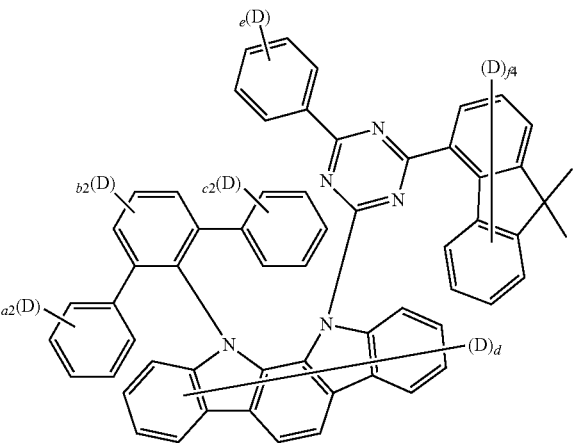
H1-7-14
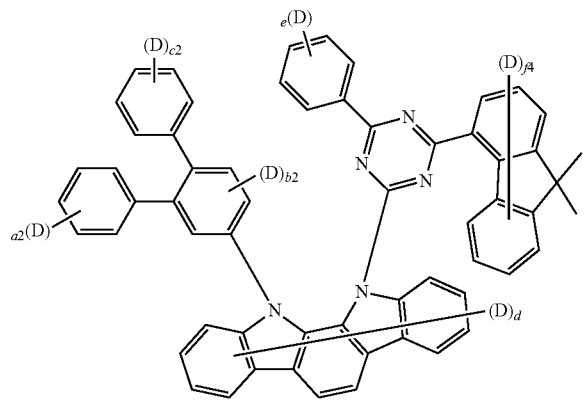
H1-7-15
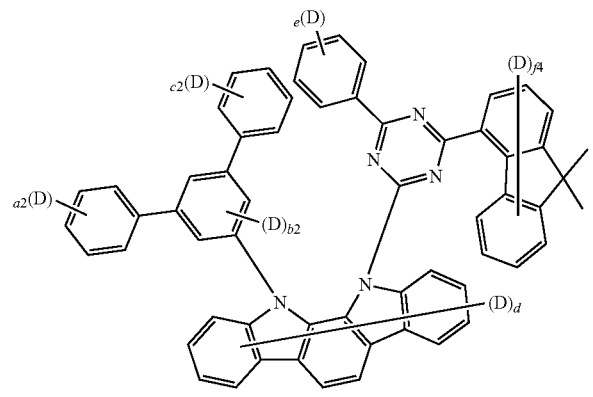
H1-8-10
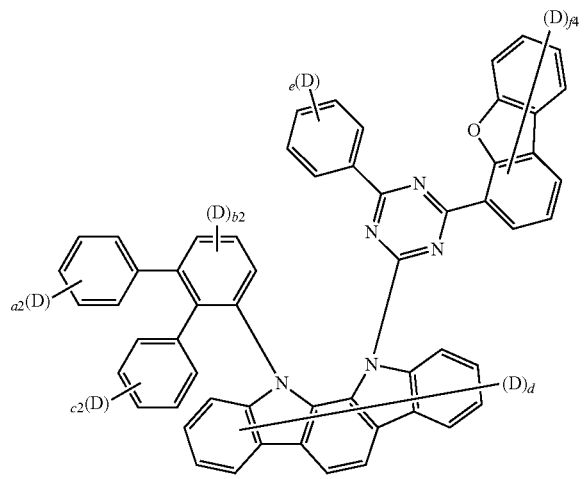
H1-8-11
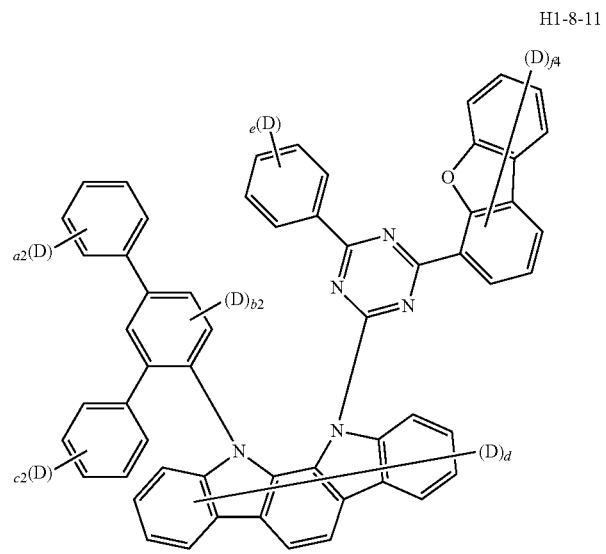

-continued
H1-8-12
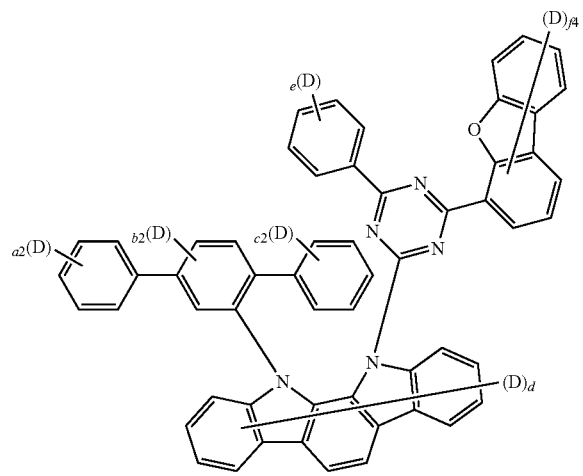
H1-8-13
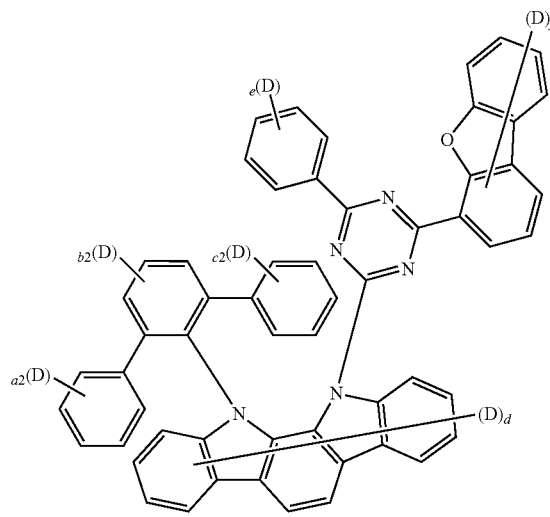
H1-8-14
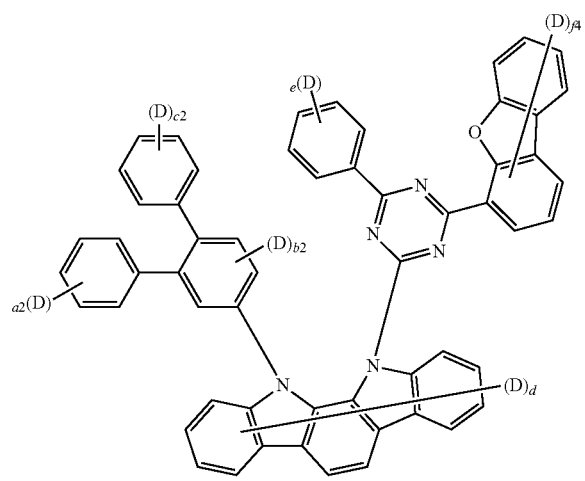
H1-8-15
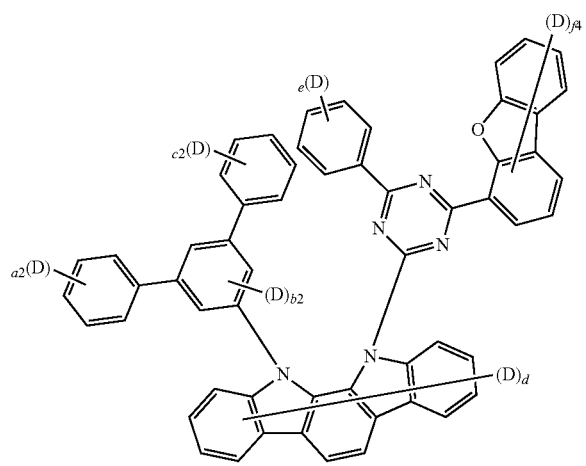
H1-9-10
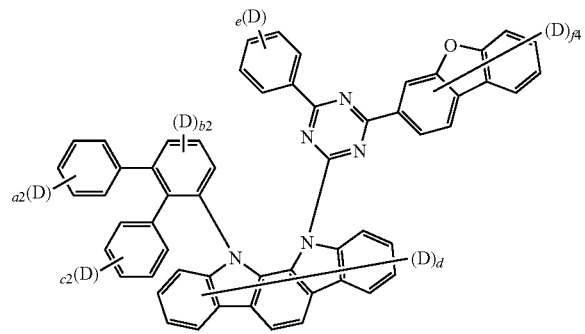
H1-9-11
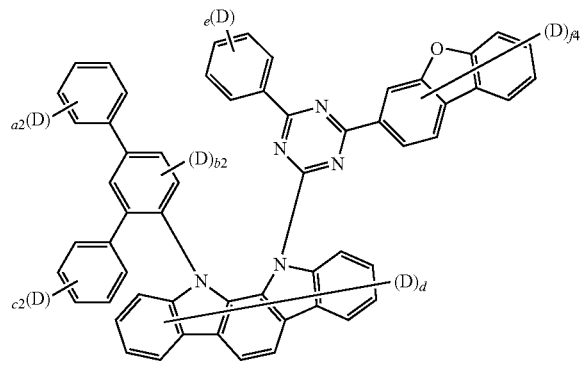

-continued
H1-9-12
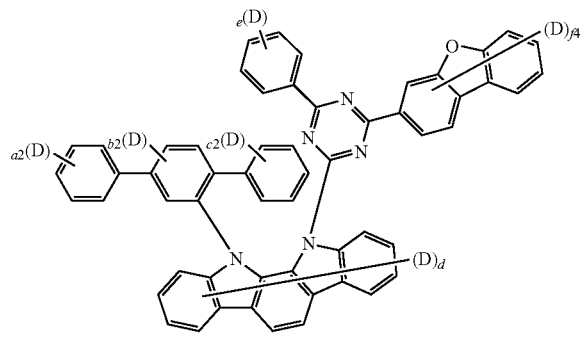
H1-9-13
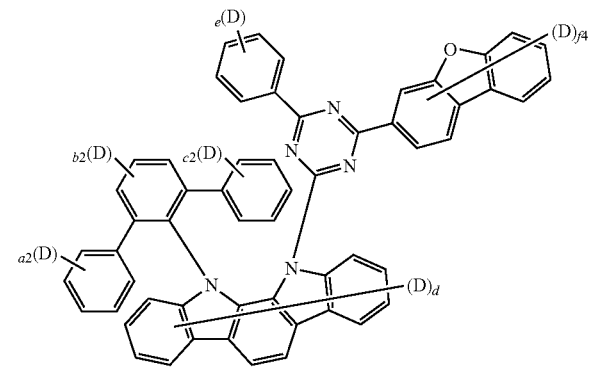
H1-9-14
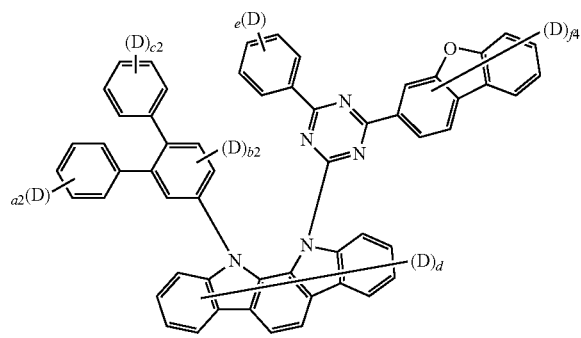
H-9-15
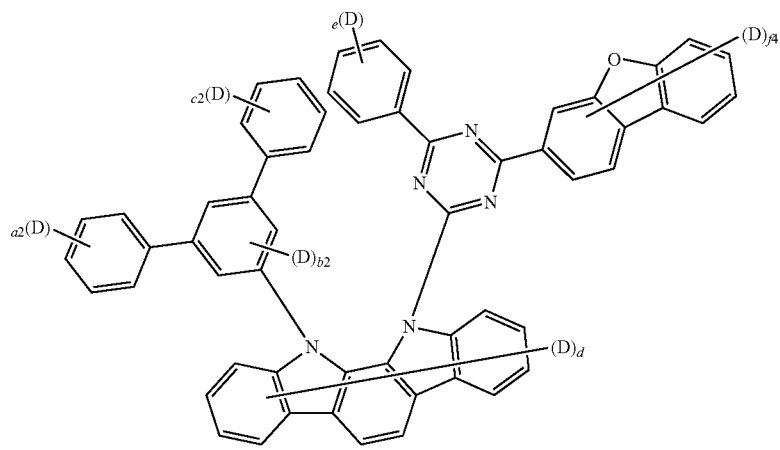
H1-10-10
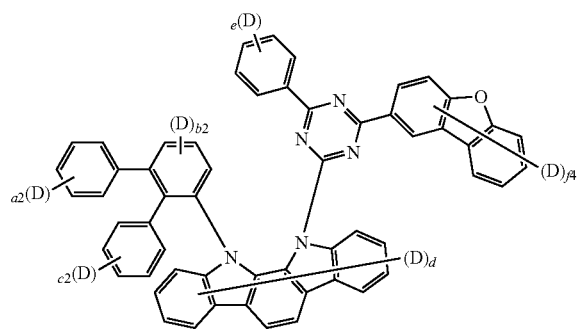
H1-10-11
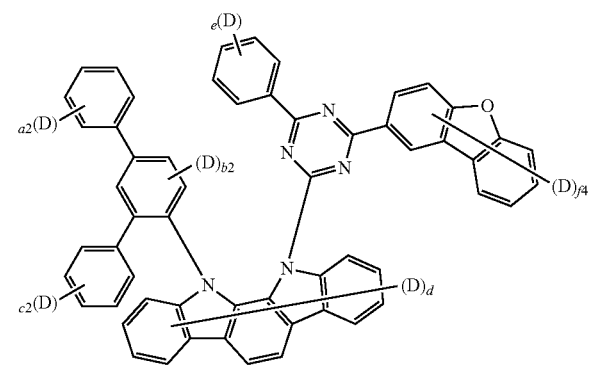

-continued
H1-10-12
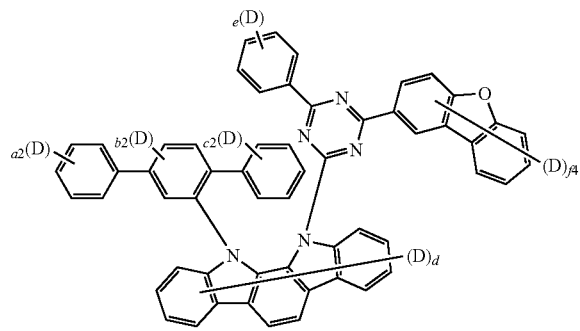
H1-10-13
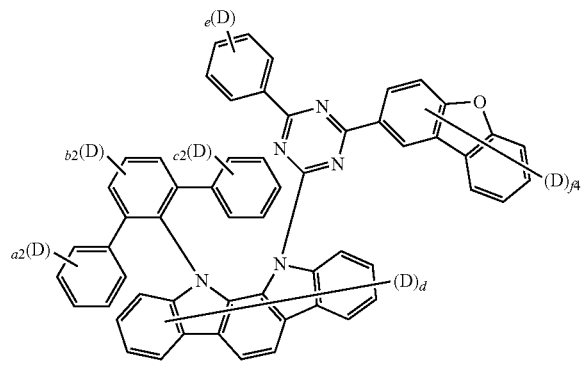
H1-10-14
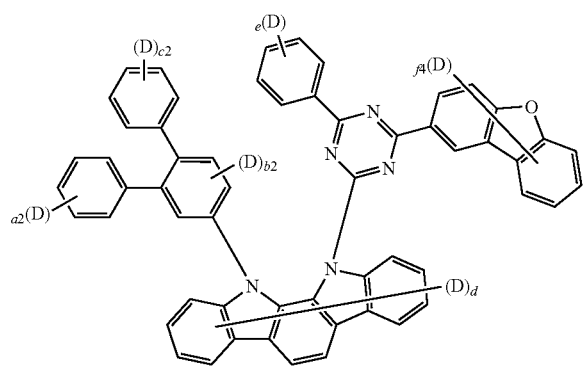
H1-10-15
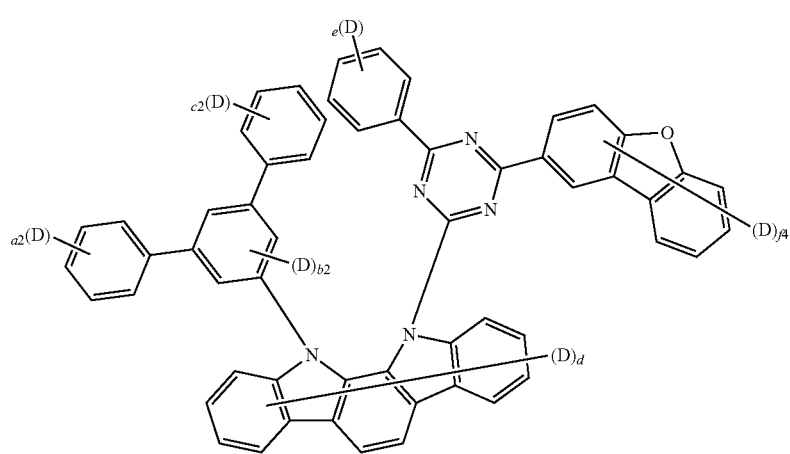

-continued
H1-11-10
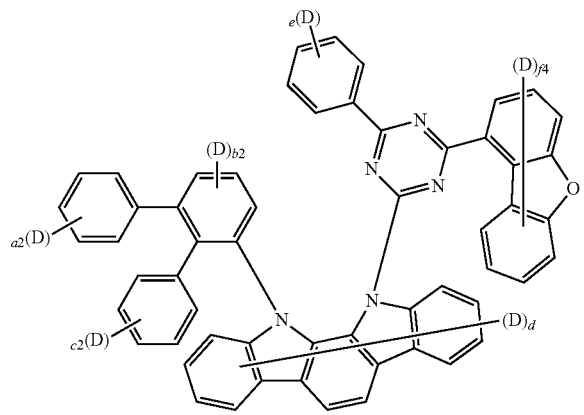
H1-11-11
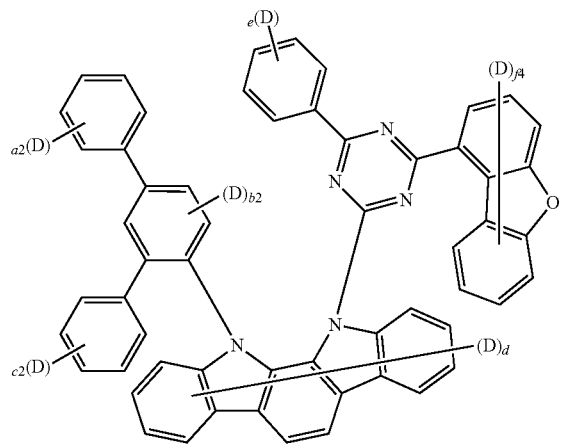
H1-11-12
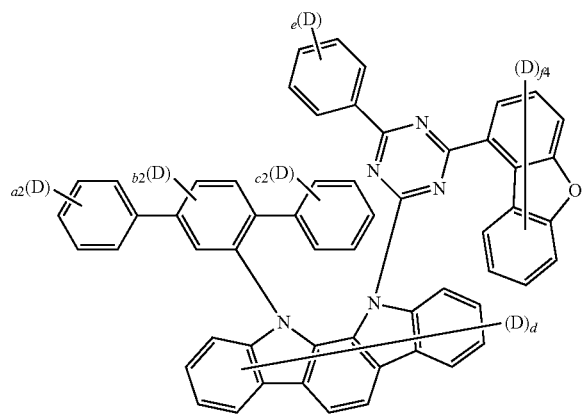
H1-11-13
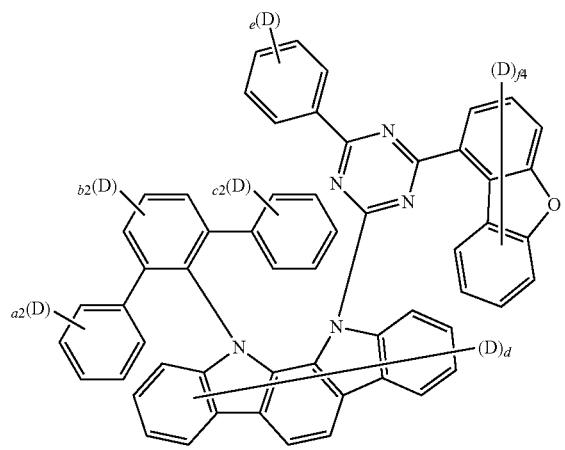
H1-11-14
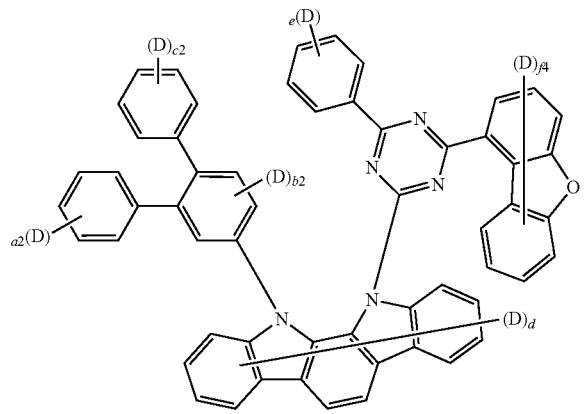
H1-11-15
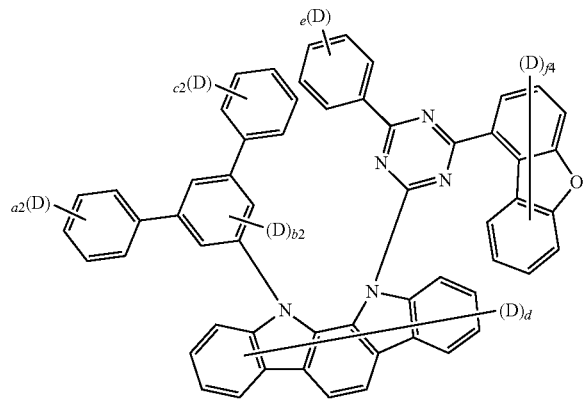

H1-12-10
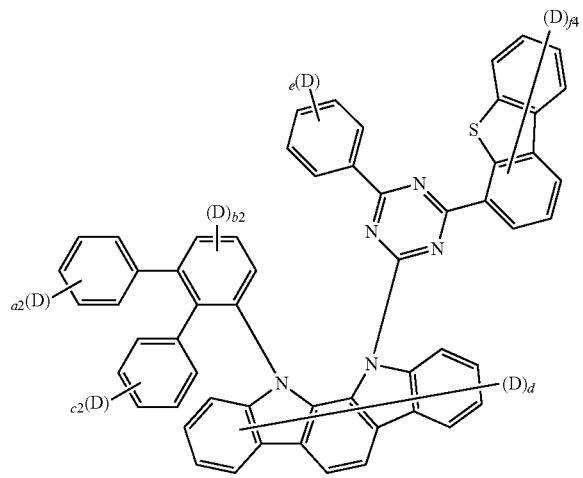
H1-12-11
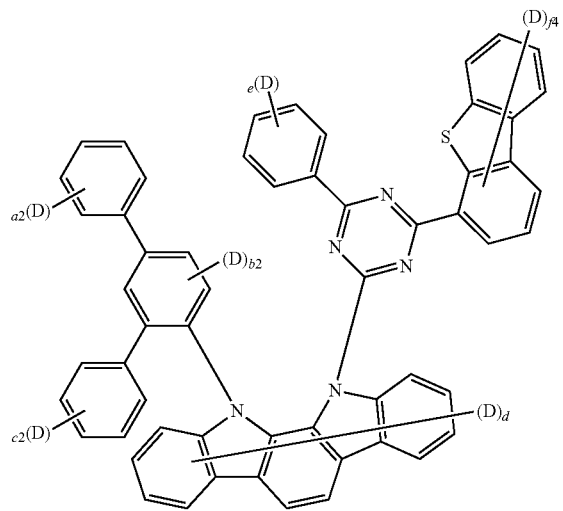
H1-12-12
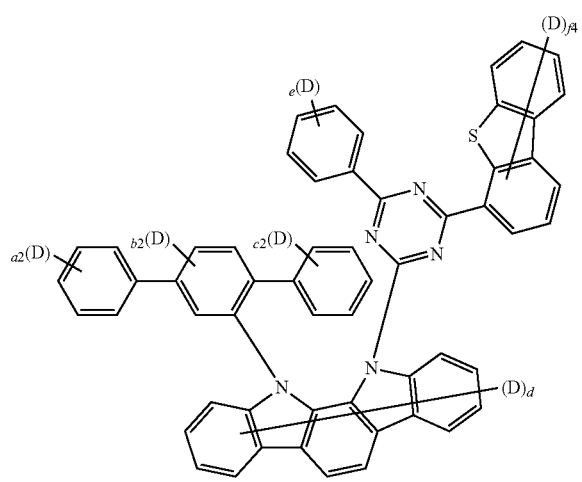
H1-12-13
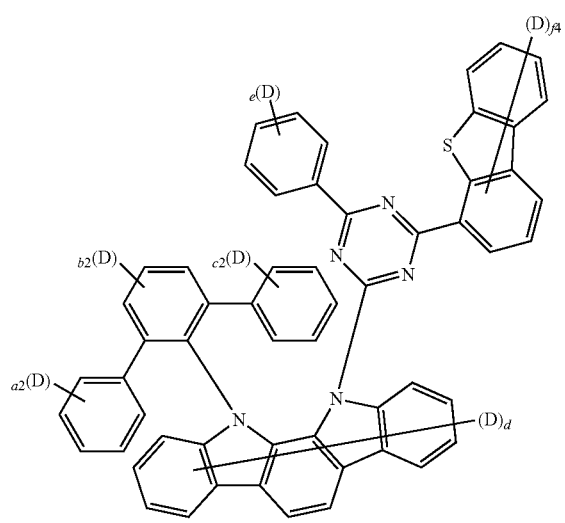
H1-12-14
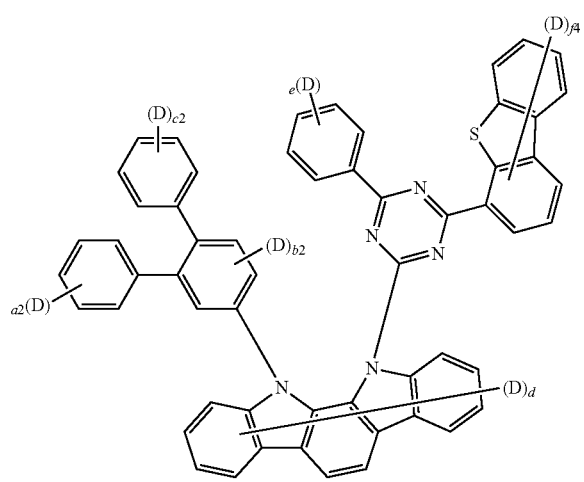
H1-12-15
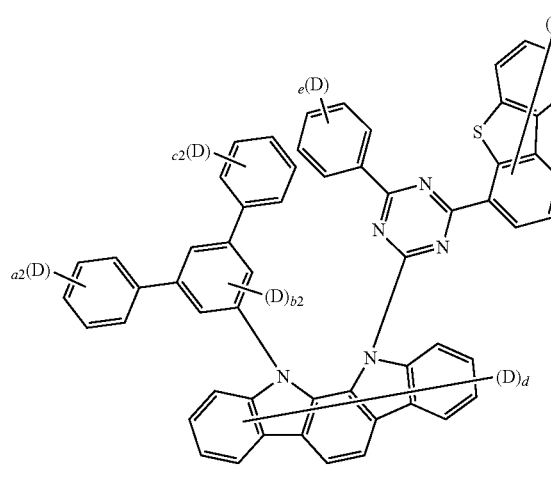

-continued
H1-13-10
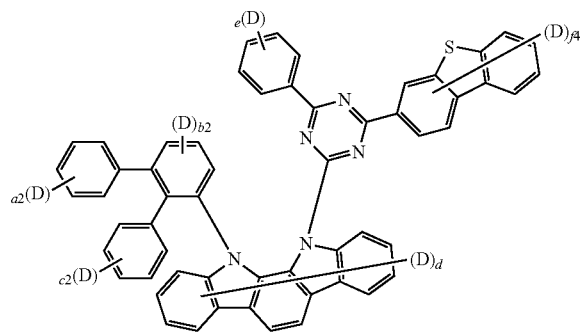
H1-13-11
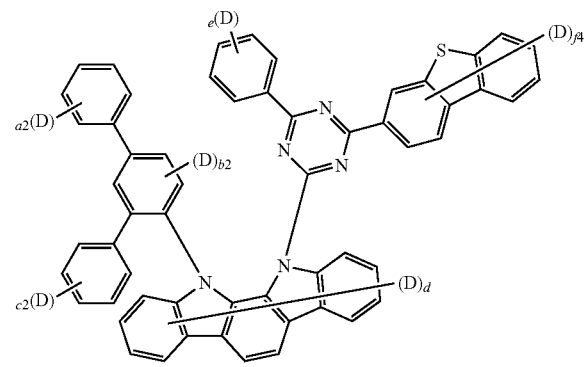
H1-13-12
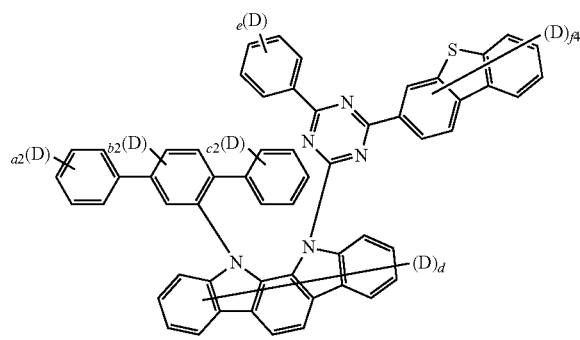
H1-13-13
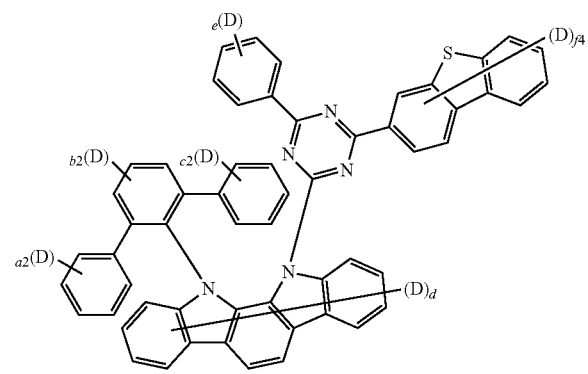
H1-13-14
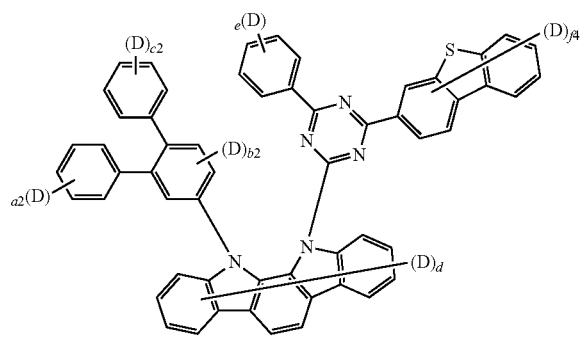
H-13-15
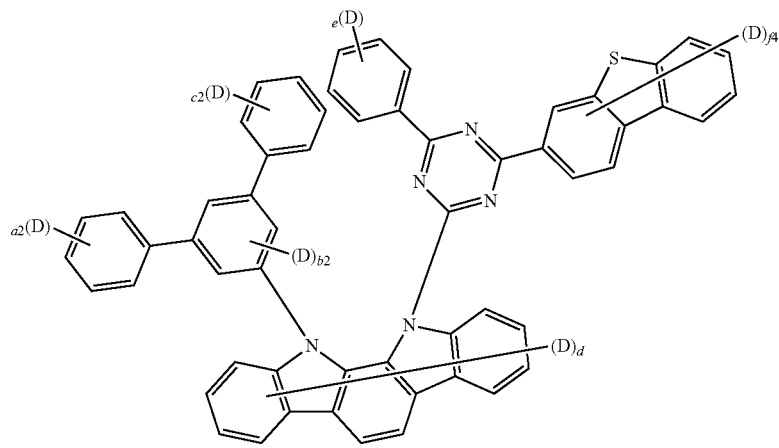

-continued
H1-14-10
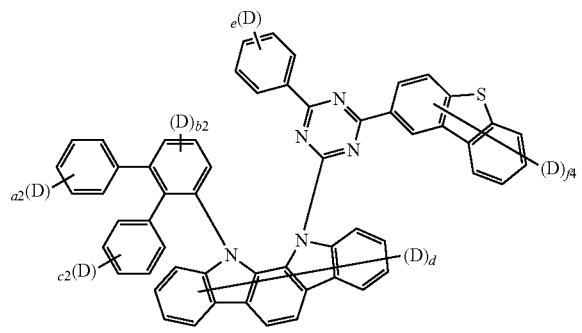
H1-14-11
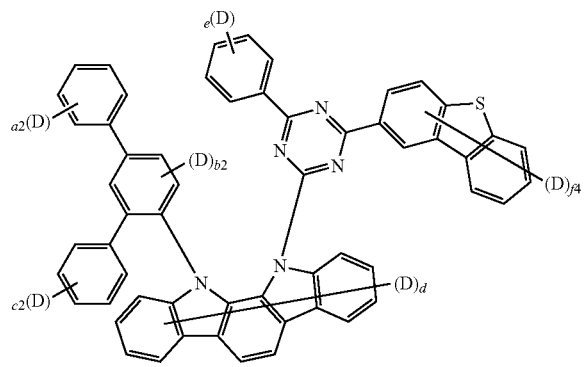
H1-14-12
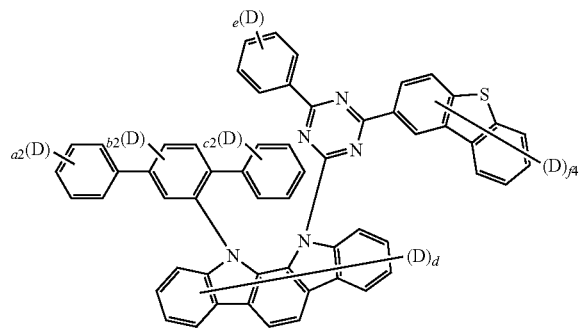
H1-14-13
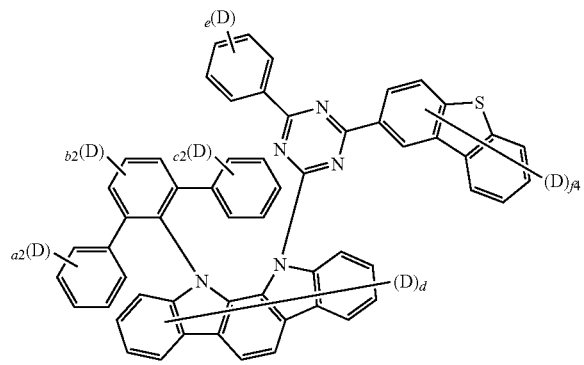
H1-14-14
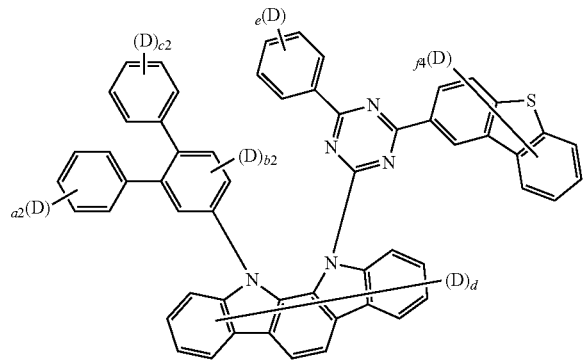
H1-14-15
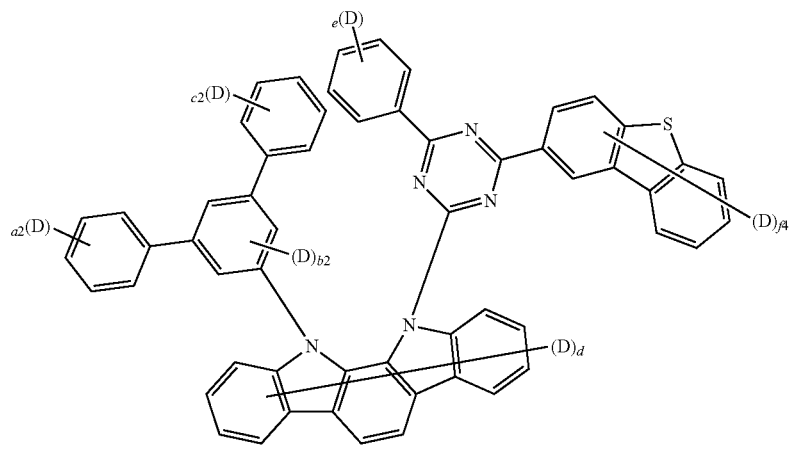

-continued
H1-15-10
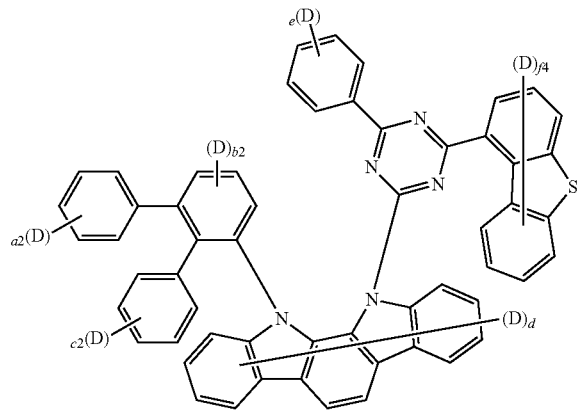
H1-15-11
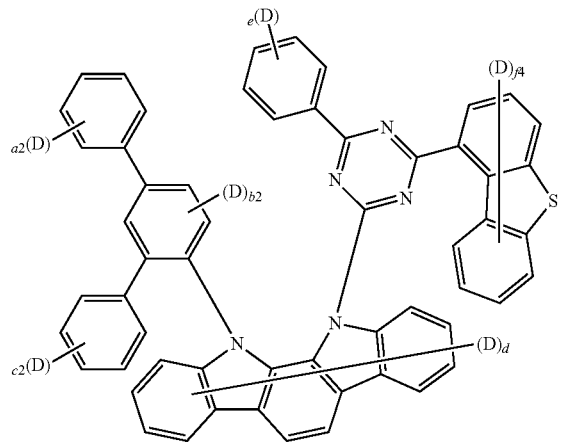
H1-15-12
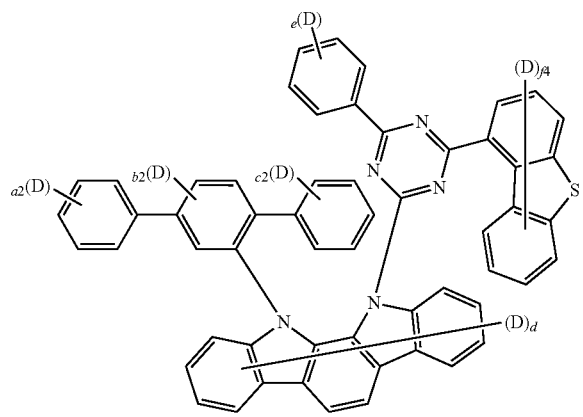
H1-15-13
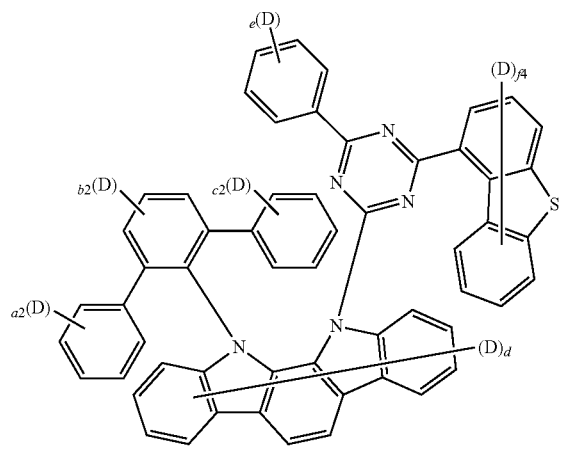
H1-15-14
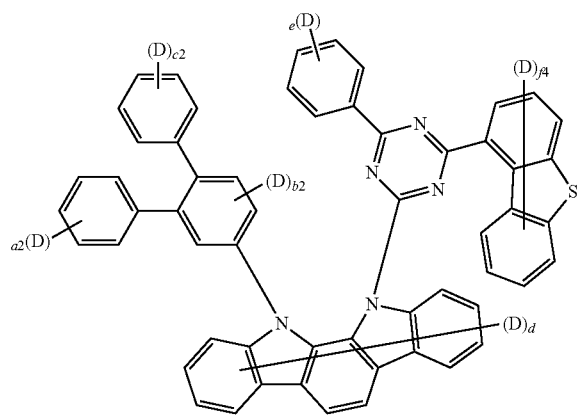
H1-15-15
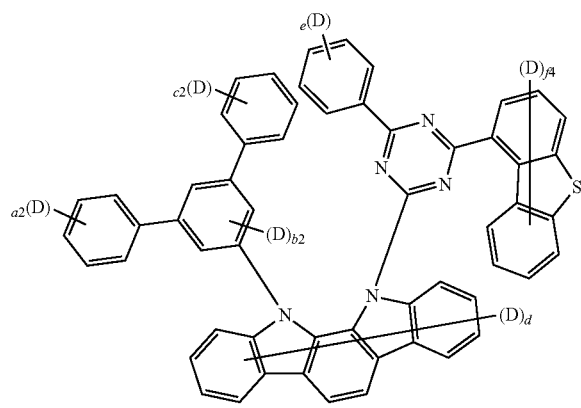

wherein in Chemical Formulae H1-4-10 to H1-4-15, H1-5-10 to H1-5-15, H1-6-10 to H1-6-15, H1-7-10 to H1-7-15, H1-8-10 to H1-8-15, H1-9-10 to H1-9-15, H1-10-10 to H1-10-15, H1-11-10 to H1-11-15, H1-12-10 to H1-12-15, H1-13-10 to H1-13-15, H1-14-10 to H1-14-15, and H1-15-10 to H1-15-15:
a2, b2, c2, and d are as defined in Chemical Formula 1,
e is an integer of 0 to 5,
f4 is an integer of 0 to 7, and
a2+b2+c2+d+e+f4 is 1 to 35;
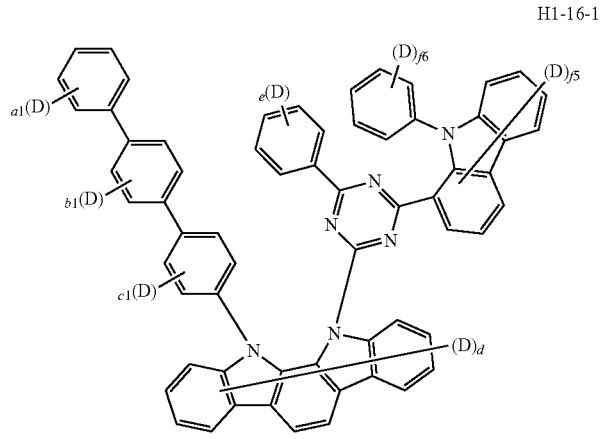
H1-16-1

H1-16-2
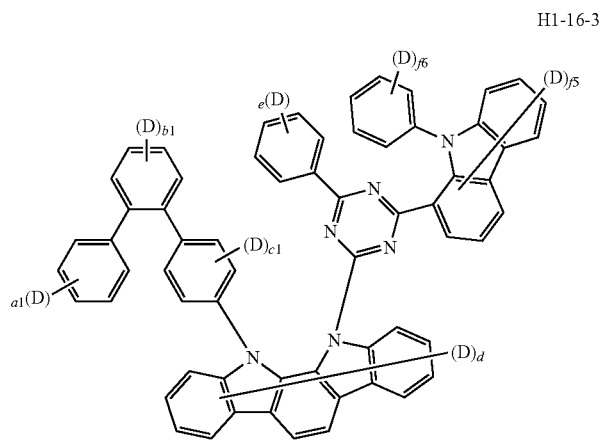
H1-16-3
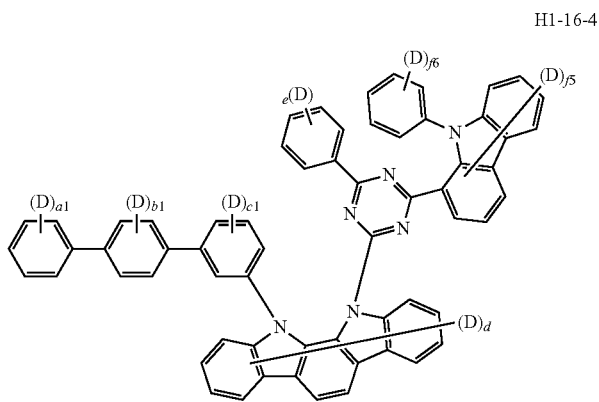
H1-16-4
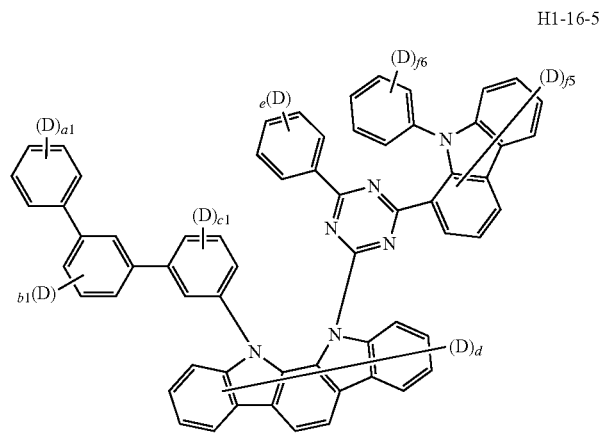
H1-16-5
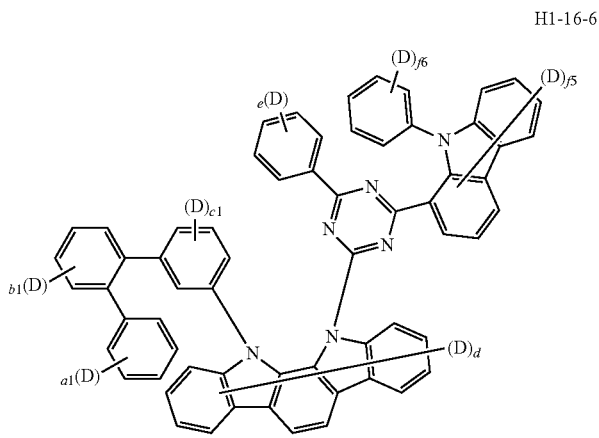
H1-16-6

-continued
H1-16-7
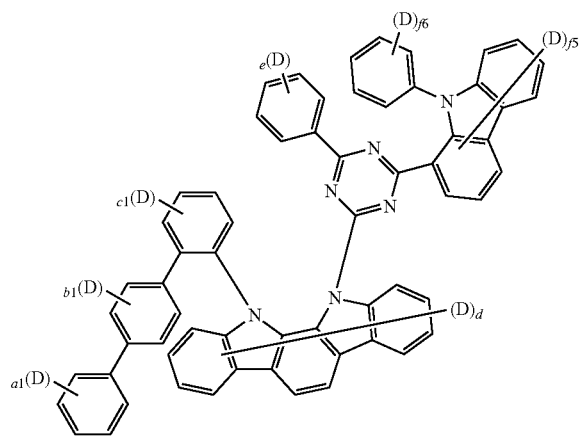
H1-16-8
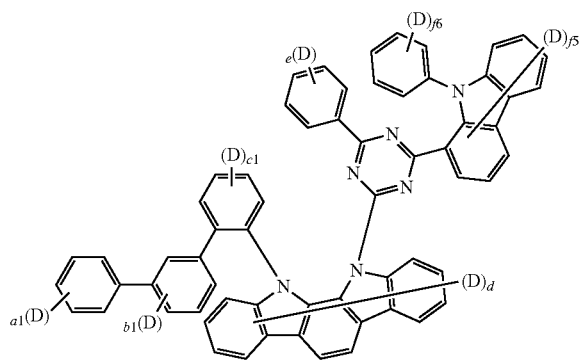
H1-16-9
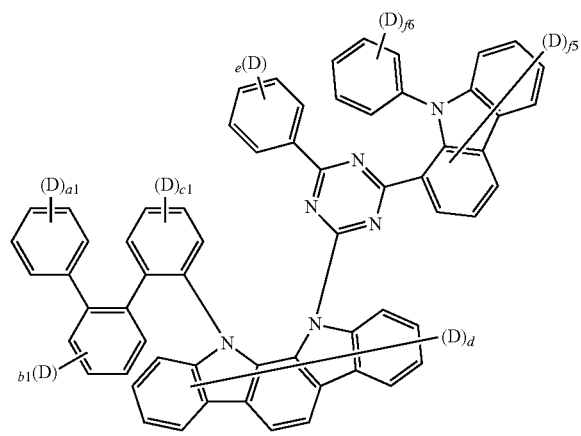
H1-17-1
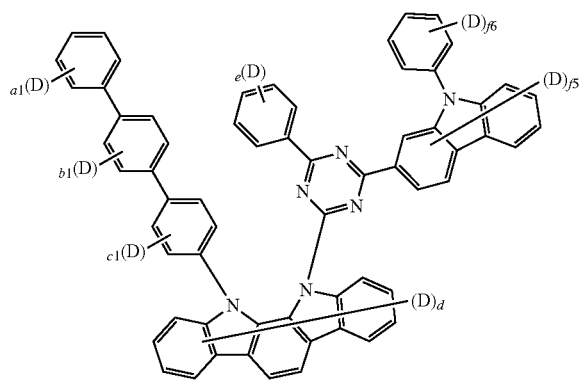
H1-17-2
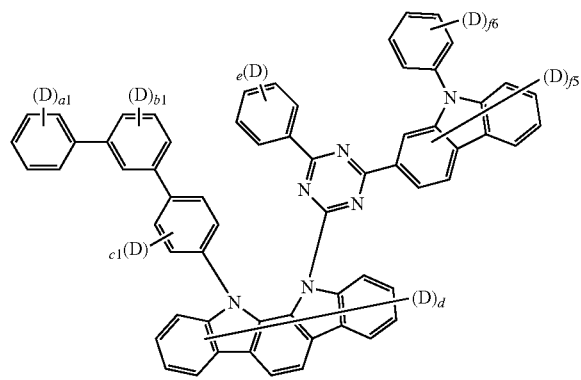
H1-17-3
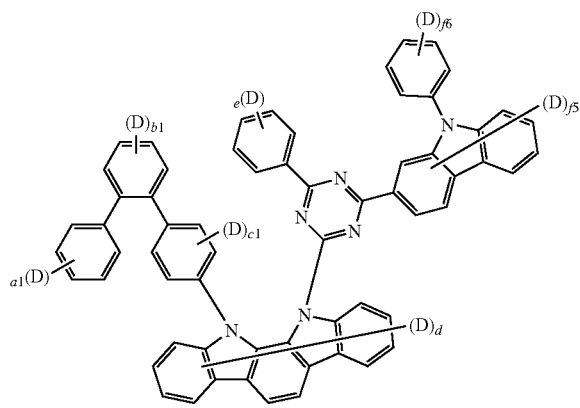

H1-17-4
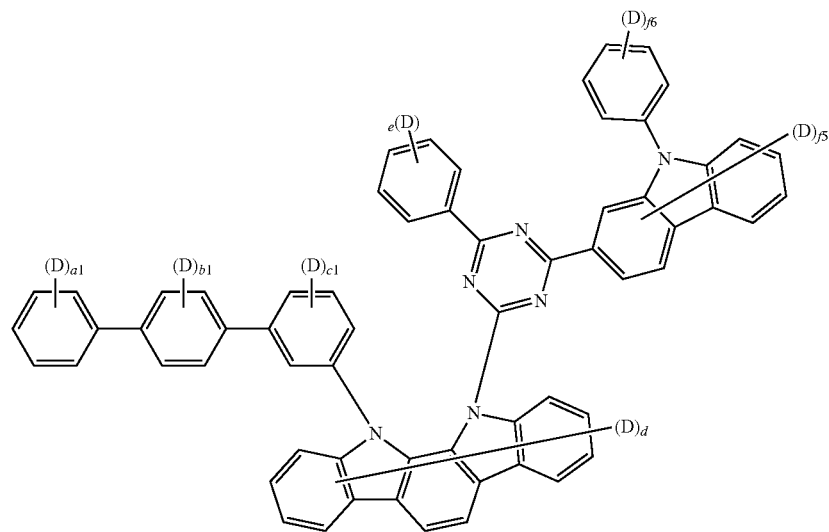
H1-17-5 H1-17-6
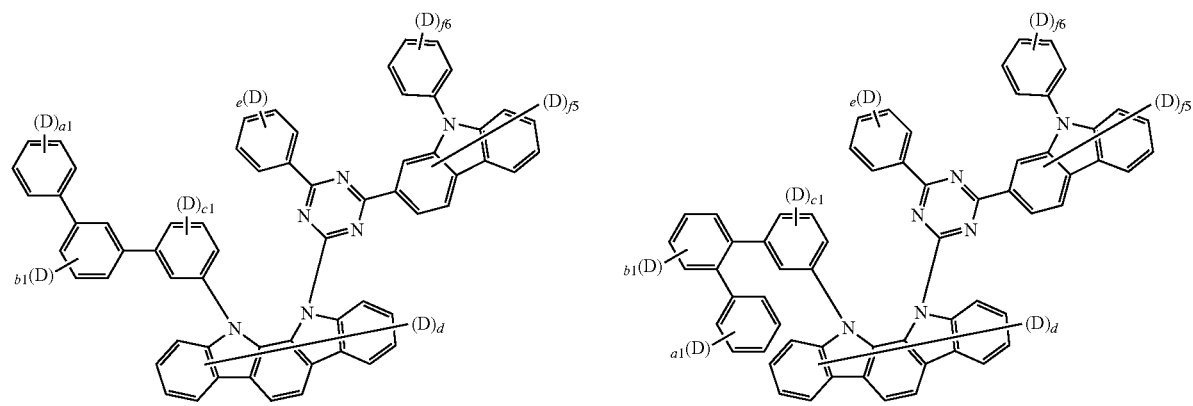
H1-17-7
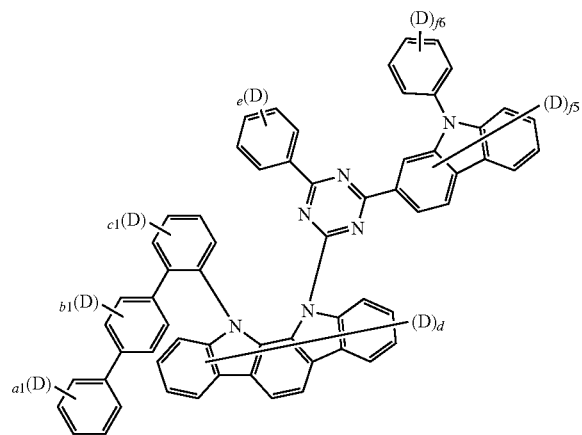

-continued
H1-17-8
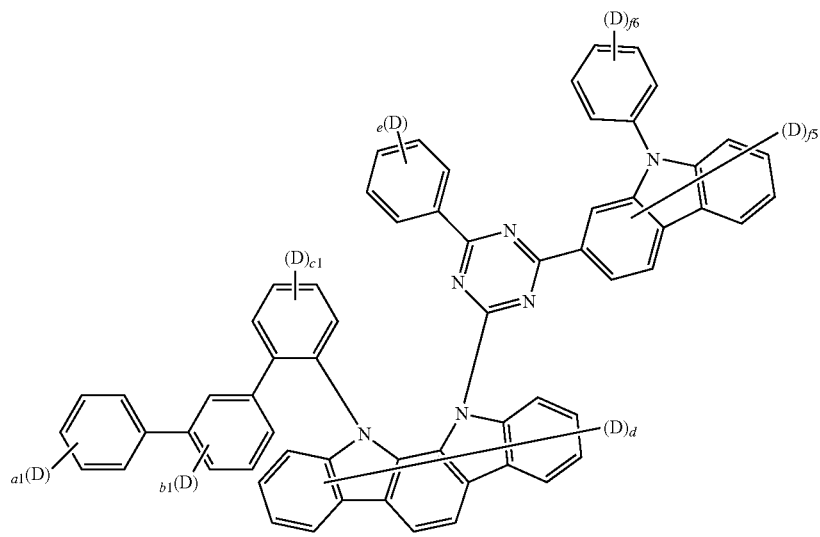
H1-17-9
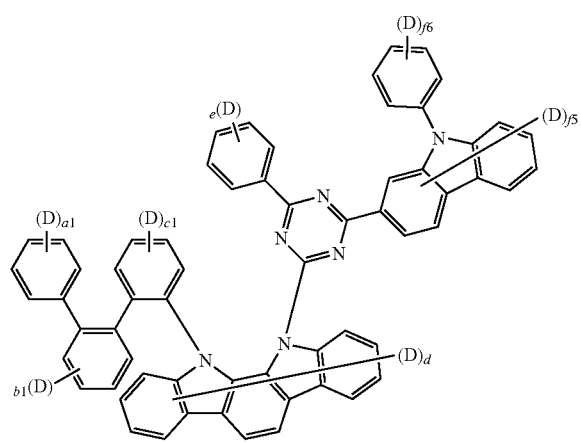
H1-18-1
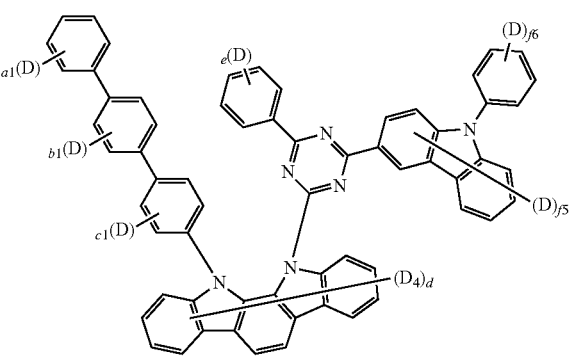
H1-18-2
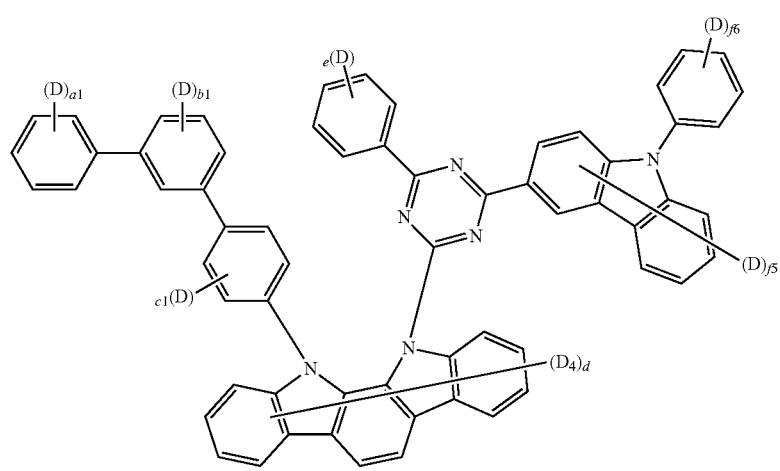

-continued
H1-18-3
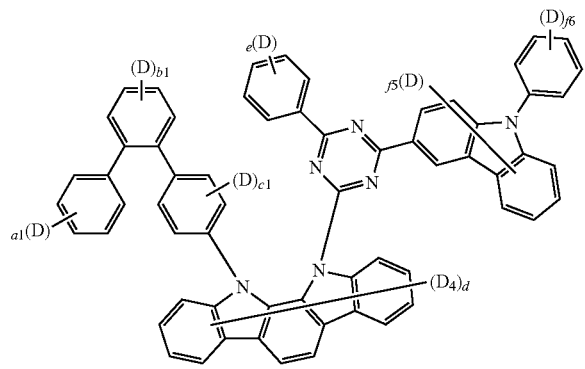
H1-18-4
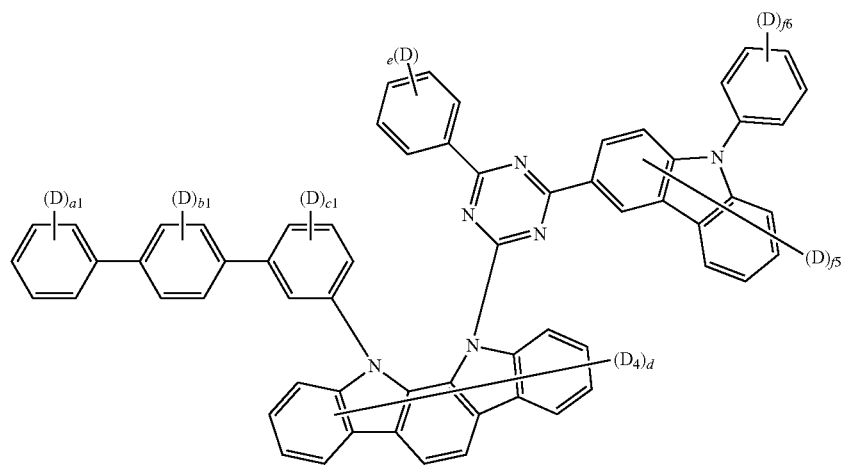
H1-18-5
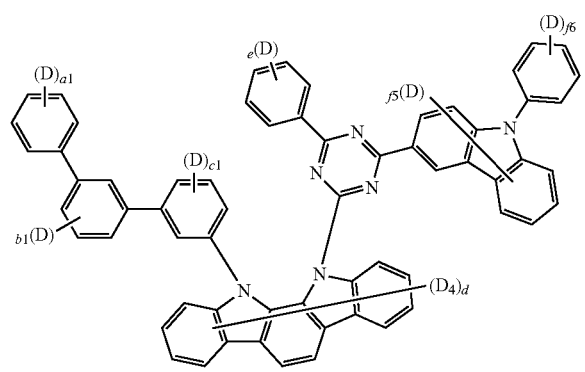
H1-18-6
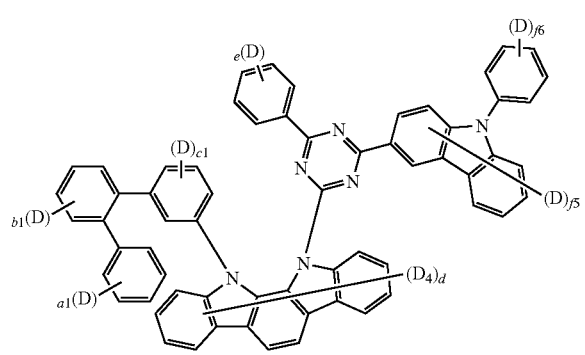
H1-18-7
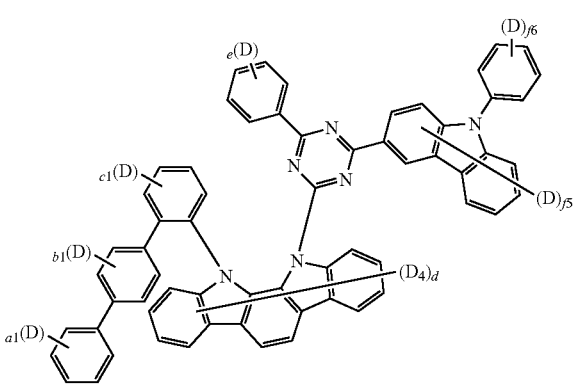

H1-18-8
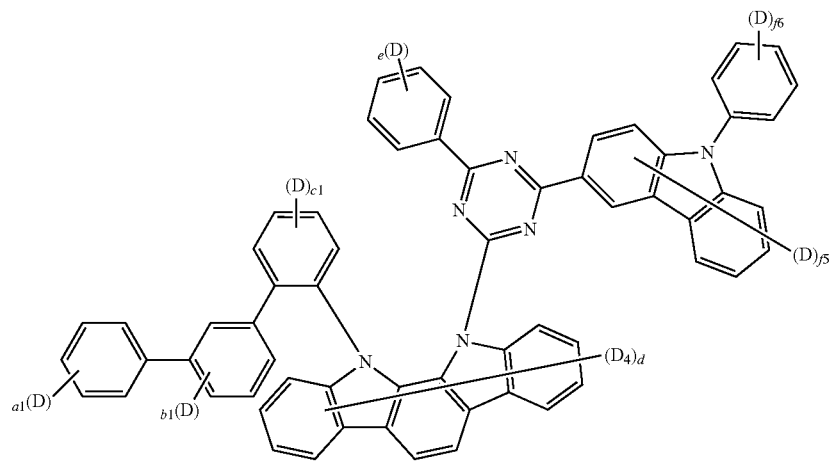
H1-18-9
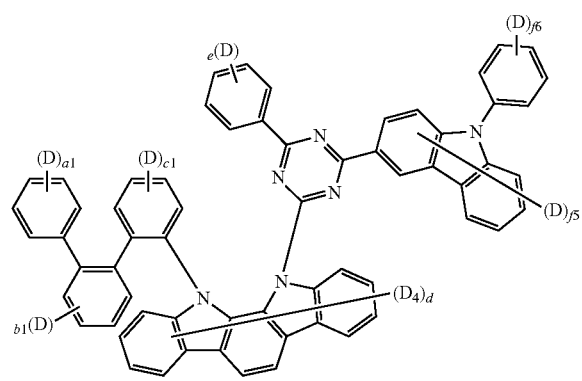
H1-19-1
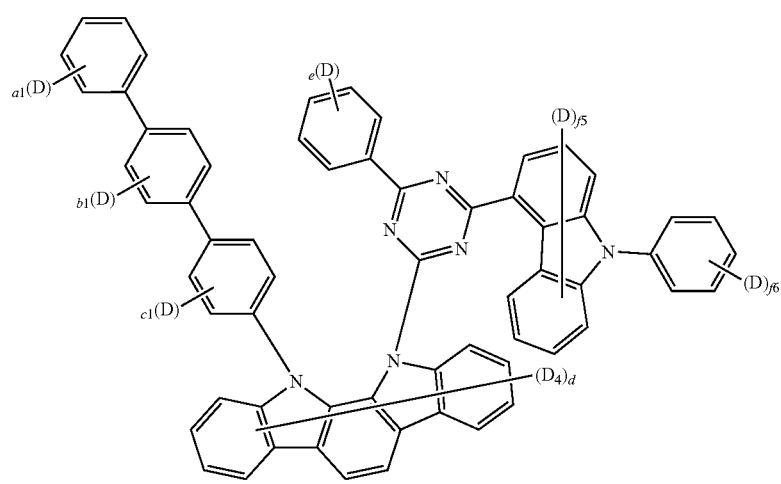

H1-19-2
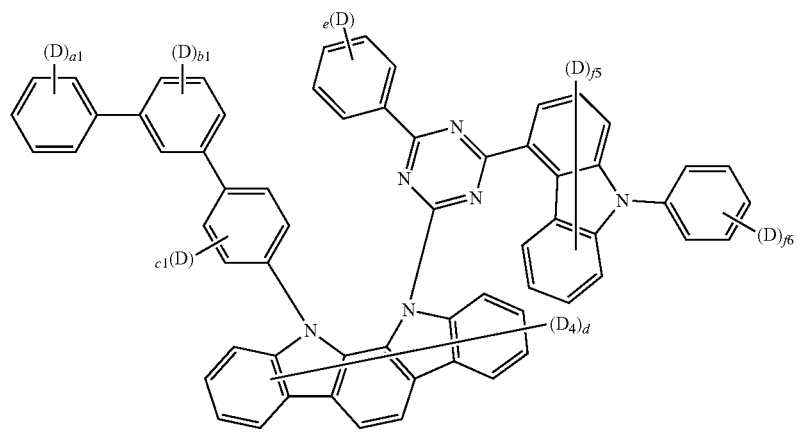
H1-19-3
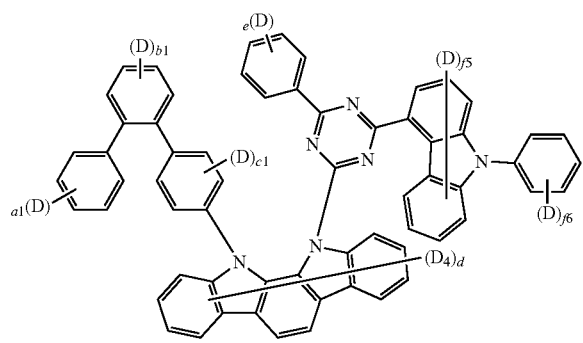
H1-19-4
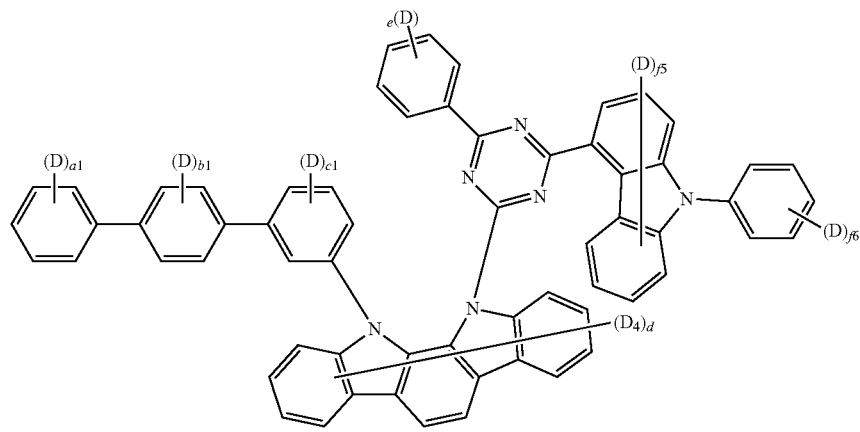
H1-19-5
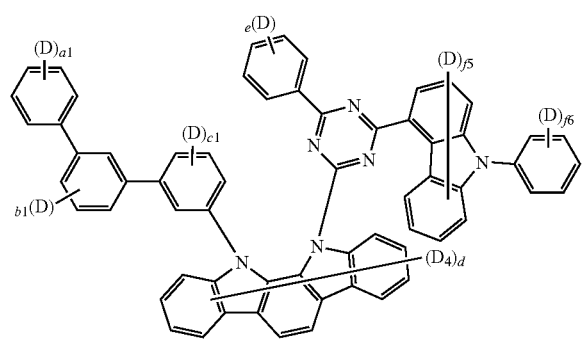
H1-19-6
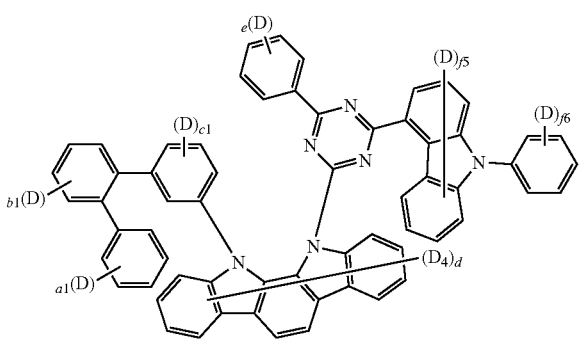

-continued
H1-19-7
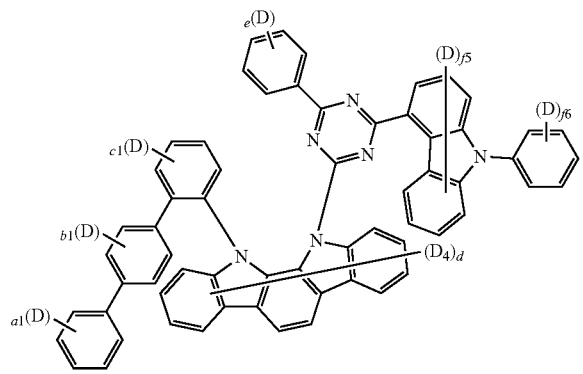
H1-19-8
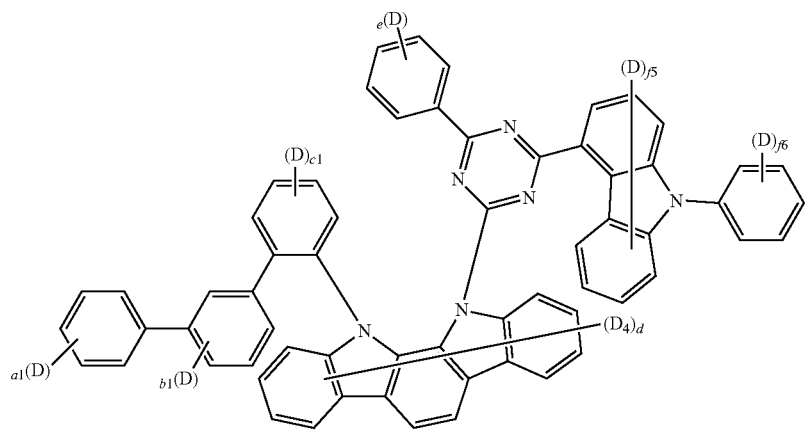
H1-19-9
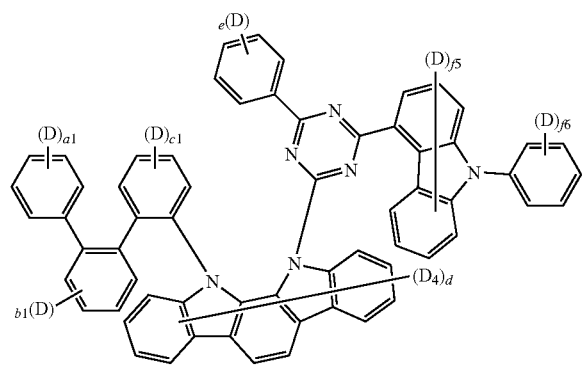

wherein in Chemical Formulae H1-16-1 to H1-16-9, H1-17-1 to H1-17-9, H1-18-1 to H1-18-9, and H1-19-1 to H1-19-9:
a1, b1, c1, and d are as defined in Chemical Formula 1,
e is an integer of 0 to 5,
f5 is an integer of 0 to 7,
f6 is an integer of 0 to 5, and
a1+b1+c1+d+e+f5+f6 is 1 to 40;
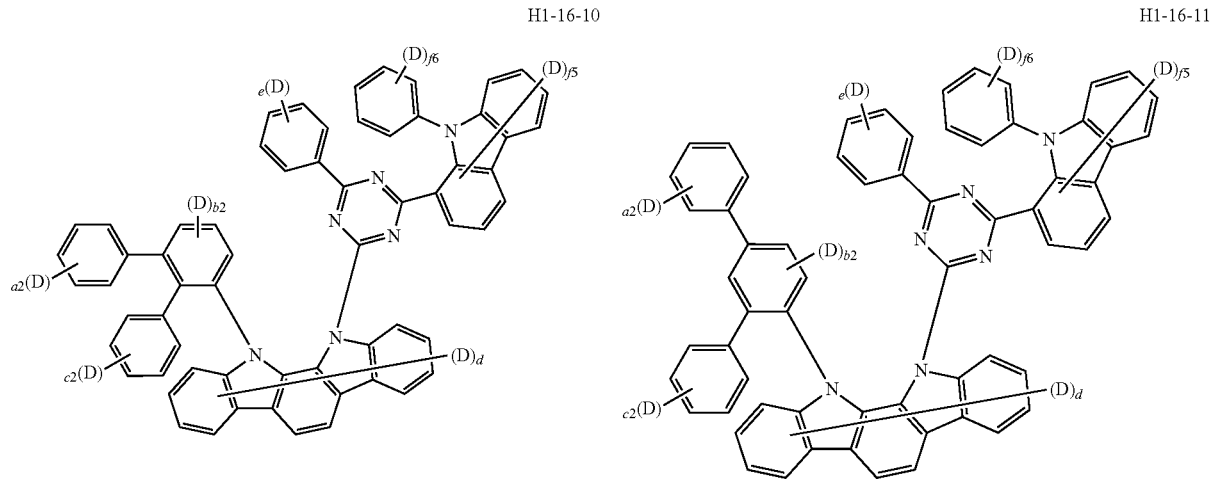
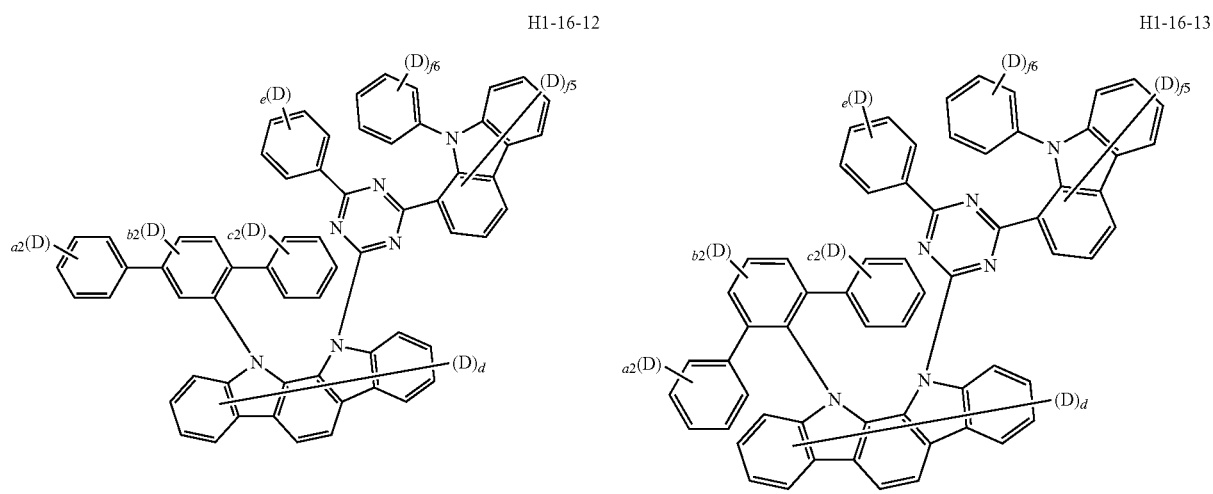
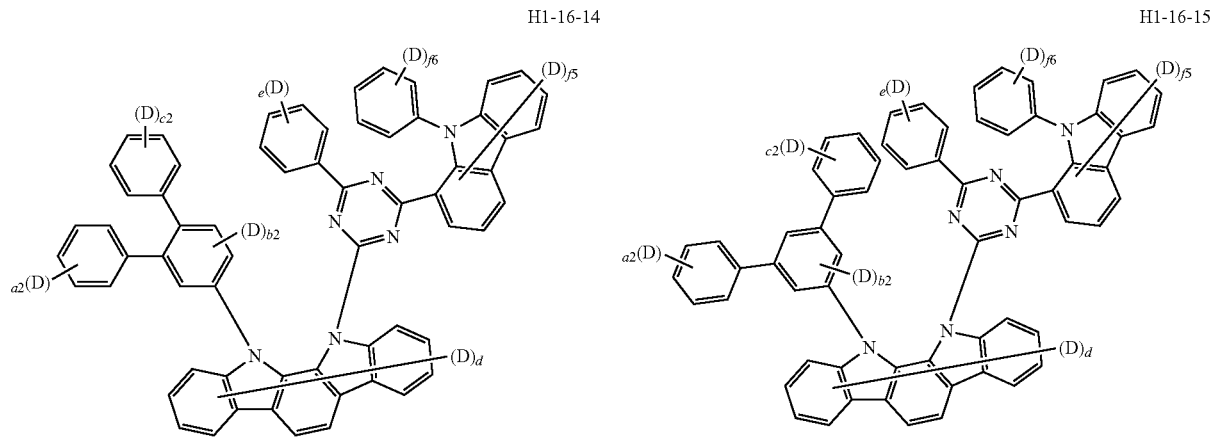

-continued
H1-17-10
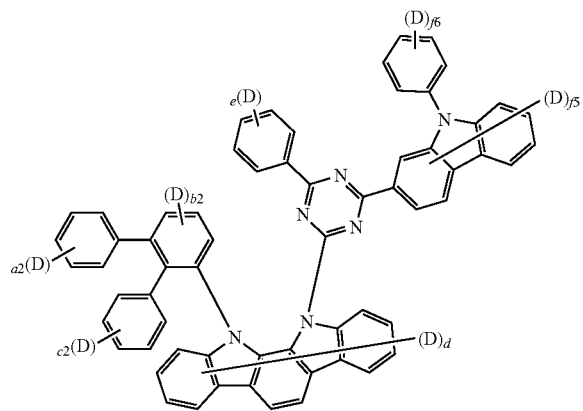
H1-17-11
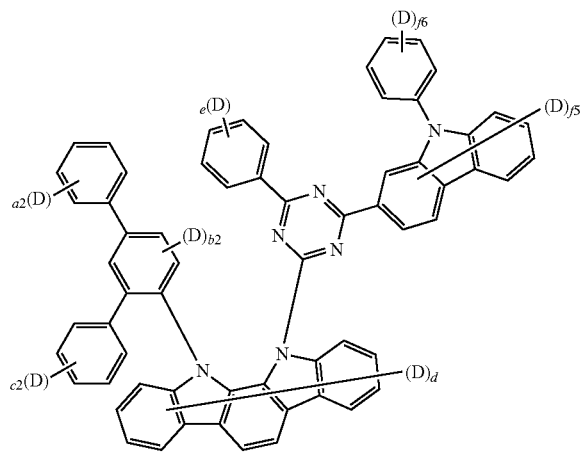
H1-17-12
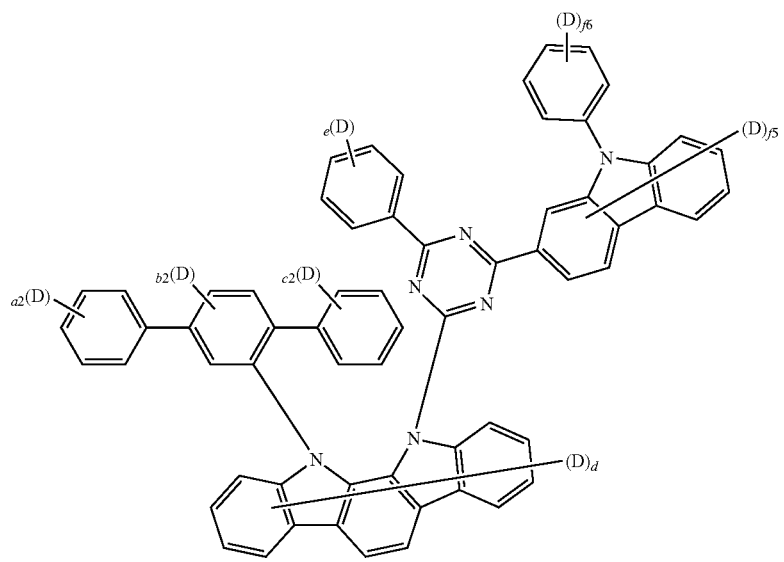
H1-17-13
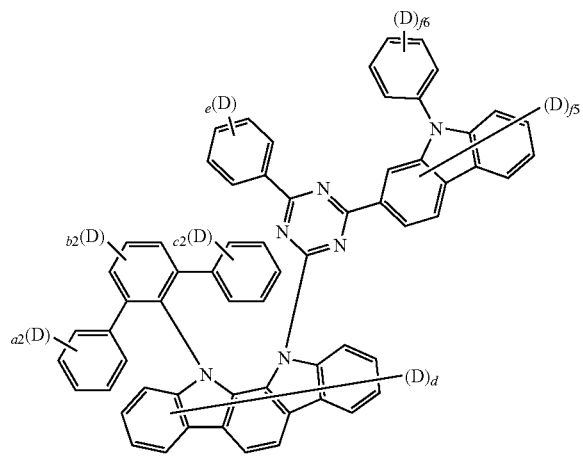

H1-17-14
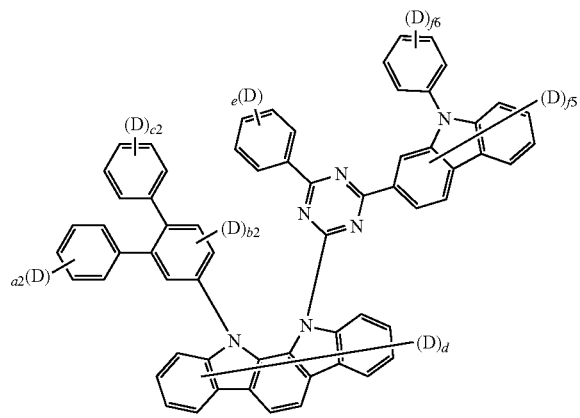
H1-17-15
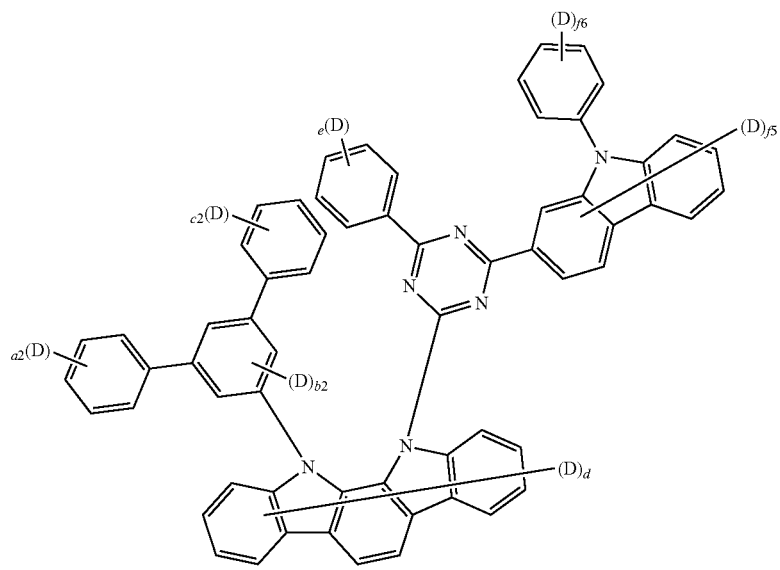
H1-18-10
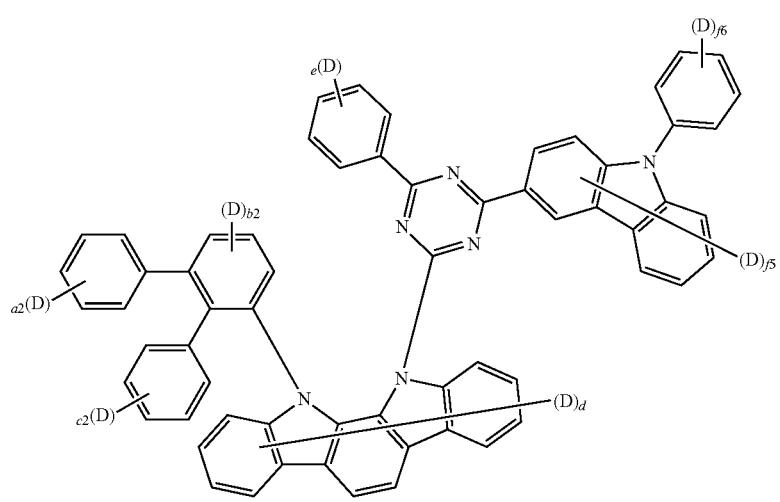

-continued
H1-18-11
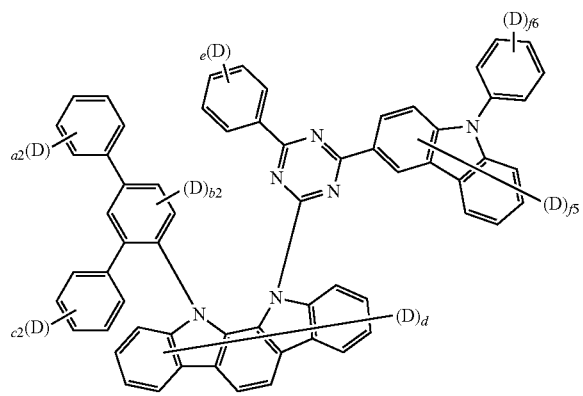
H1-18-12
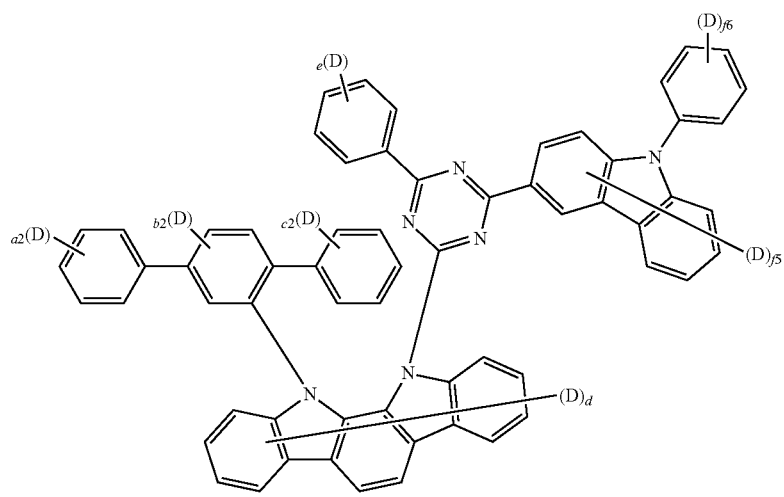
H1-18-13
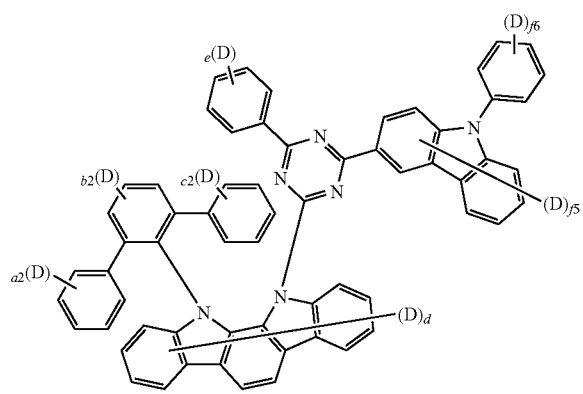

-continued
H1-18-14
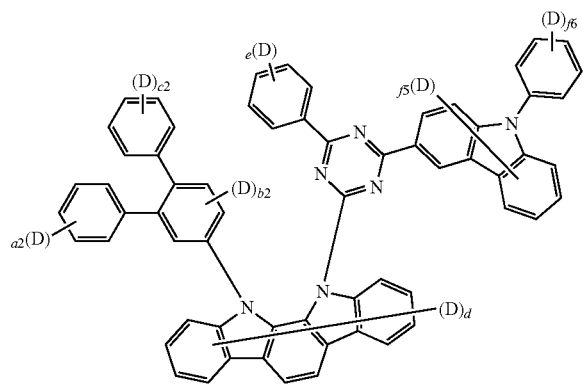
H1-18-15
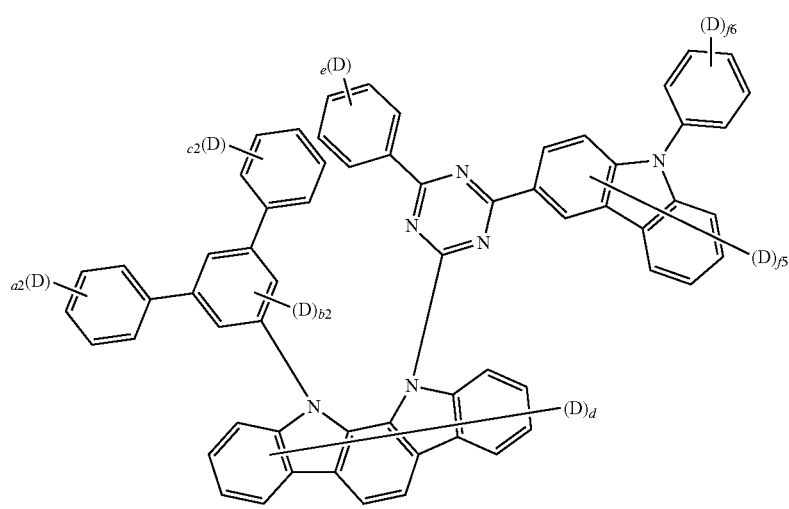
H1-19-10
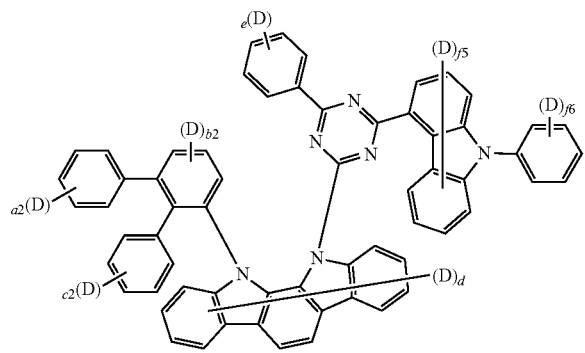
H1-19-11
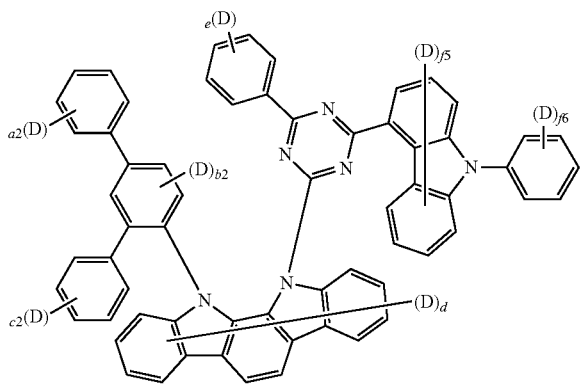

-continued

H1-19-12
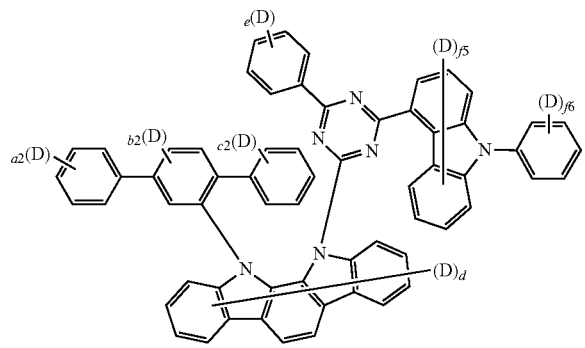

H1-19-13
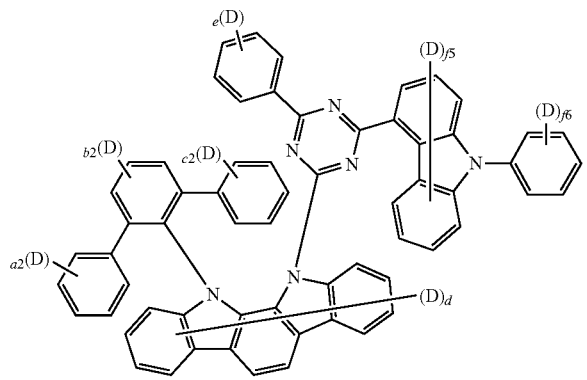

H1-19-14
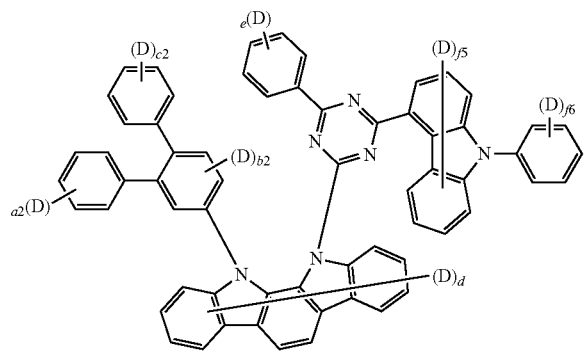

H1-19-15
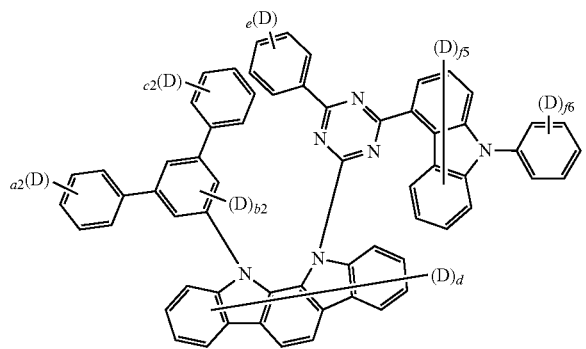

wherein in Chemical Formulae H1-16-10 to H1-16-15, H1-17-10 to H1-17-15, H1-18-10 to H1-18-15, and H1-19-10 to H1-19-15:

a2, b2, c2, and d are as defined in Chemical Formula 1,
e is an integer of 0 to 5,
f5 is an integer of 0 to 7,
f6 is an integer of 0 to 5, and
a2+b2+c2+d+e+f5+f6 is 1 to 40.

Meanwhile, the compound of Chemical Formula 1 can be prepared by, for example, a preparation method as shown in Reaction Scheme 1 below.

<Reaction Scheme 1>

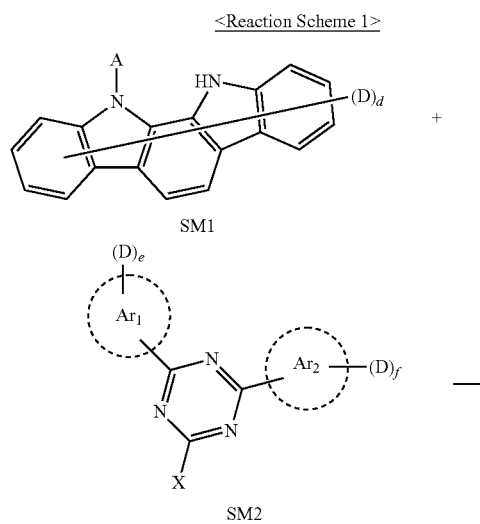

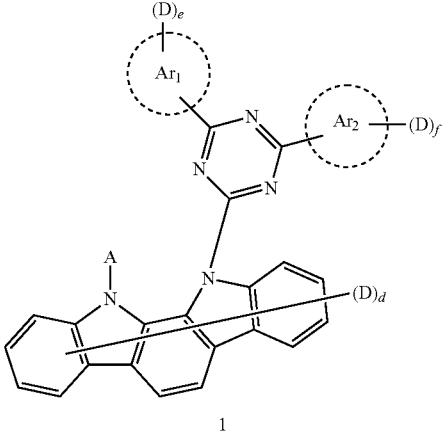

wherein in the Reaction Scheme 1, each X is independently halogen, preferably bromo, or chloro, and the definitions of other substituents are the same as described above.

Specifically, the compound of Chemical Formula 1 is prepared by combining starting materials of SM1 and SM2 through an amine substitution reaction. Such an amine substitution reaction is preferably performed in the presence of a palladium catalyst and a base. In addition, the reactive group for the amine substitution reaction can be appropriately changed, and the method for preparing the compound of Chemical Formula 1 can be more specifically described in Synthesis Examples described below, (Second Compound)

The second compound is the following Chemical Formula 2. Specifically, the second compound has a biscarbazolebased structure, can efficiently transfer holes to a dopant material, and thus can increase the probability of hole-electron recombination in the light emitting layer together with the first compound having excellent electron transport ability.

In Chemical Formula 2, the bonding positions of two carbazole structures are as follows:

<Chemical Formula 2>

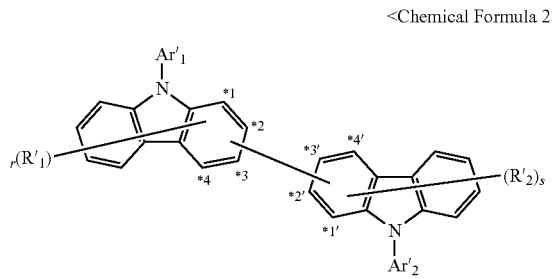

wherein in Chemical Formula 2:

the description of each substituent is the same as described above, and a single bond connecting the two carbazole structures can be connected to one of the carbon at position *1, the carbon at position *2, the carbon at position *3, and the carbon at position *4 of the left carbazole structure, and one of the carbon at position *1', the carbon at position *2', the carbon at position *3', and the carbon at position *4' of the right carbazole structure.

More specifically, the second compound can be a compound in which (carbon at position *1, carbon at position *1'), (carbon at position *2, carbon at position *2'), (carbon at position *3, carbon at position *3'), or (carbon at position *4, carbon at position *4') in the left carbazole structure and the right carbazole structure are linked and bonded to each other.

According to one embodiment, the second compound can be the following Chemical Formula 2' having a structure in which (carbon at position *3 of the left carbazole structure, carbon at position *3' of the right carbazole structure) are bonded to each other:

<Chemical Formula 2'>

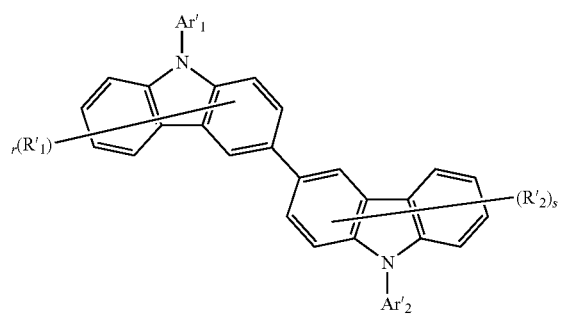

wherein in Chemical Formula 2':

$Ar'_1$, $Ar'_2$, $R'_1$, $R'_2$, r, and s are as defined in Chemical Formula 2.

In addition, in Chemical Formula 2, $Ar'_1$ and $Ar'_2$ can each independently be $C_{6-20}$ aryl, or a $C_{2-20}$ heteroaryl containing at least one heteroatom of N, O and S, wherein $Ar'_1$ can be unsubstituted, or substituted with at least one substituent selected from the group consisting of deuterium and $C_{6-20}$ aryl.

For example, $Ar'_1$ and $Ar'_2$ can each independently be phenyl, biphenylyl, terphenylyl, naphthyl, dibenzofuranyl, or dibenzothiophenyl, wherein $Ar'_1$ can be unsubstituted, or substituted with at least one substituent selected from the group consisting of deuterium and $C_{6-20}$ aryl.

Herein, at least one of $Ar'_1$ and $Ar'_2$ can be phenyl or biphenylyl.

In addition, in Chemical Formula 2, $R'_1$ and $R'_2$ can each independently be hydrogen, deuterium, or $C_{6-20}$ aryl.

For example, $R'_1$ and $R'_2$ can each independently be hydrogen, deuterium, or phenyl, but the present disclosure is not limited thereto.

In addition, r and s, each representing the number of $R'_1$ and $R'_2$, can each independently be 0, 1, 2, 3, 4, 5, 6, or 7.

More specifically, r and s can each independently be 0, 1, or 7.

For example, r+s can be 0 or 1.

Representative examples of the compound of Chemical Formula 2 are as follows:

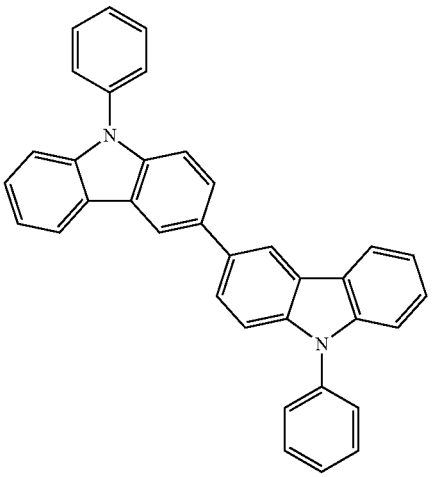

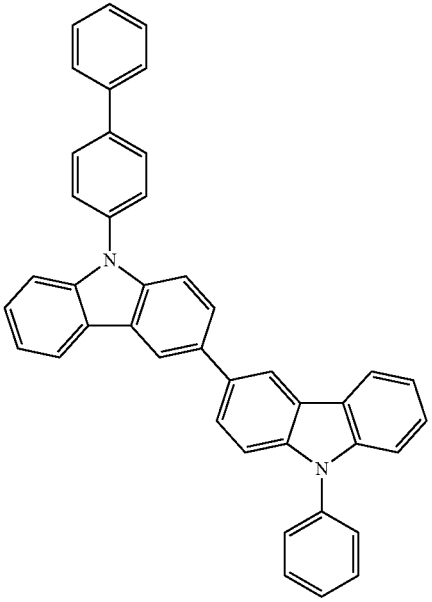

131
-continued
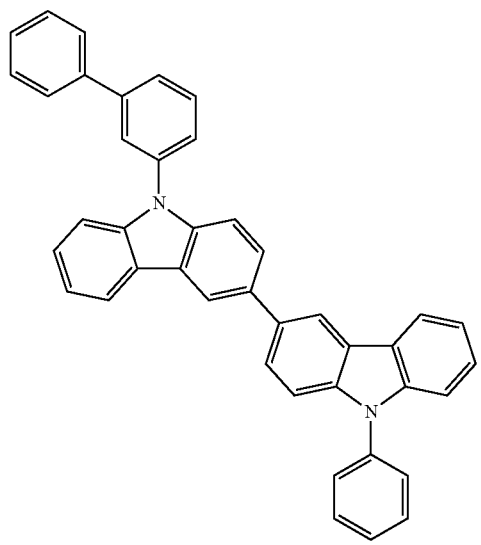
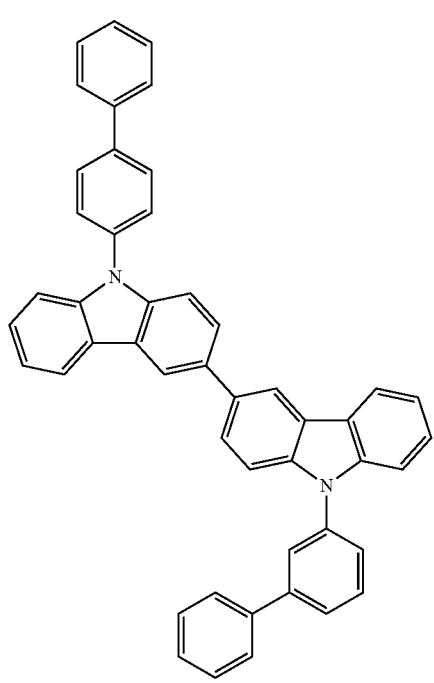
132
-continued
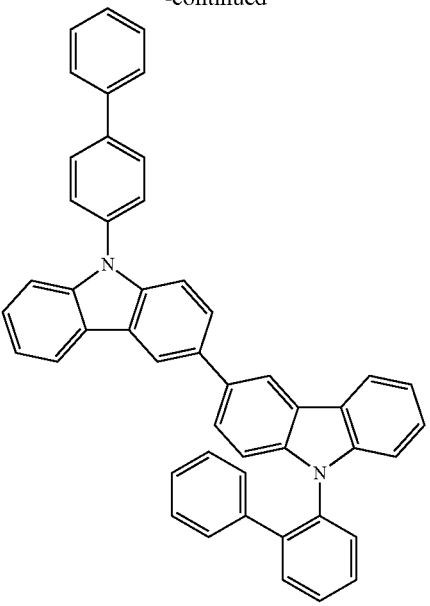
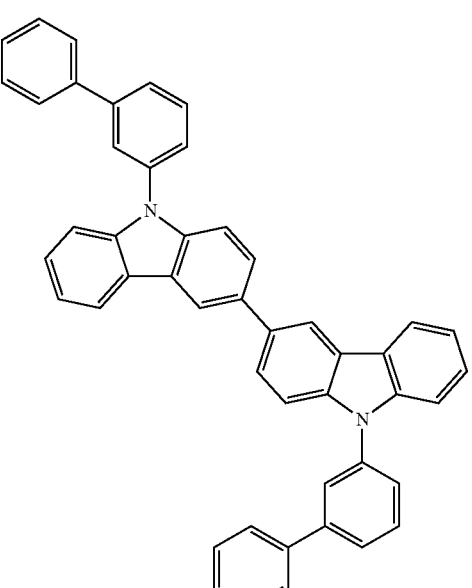
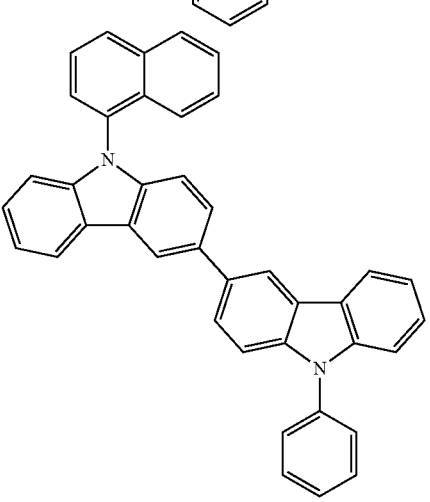

133
-continued
134
-continued
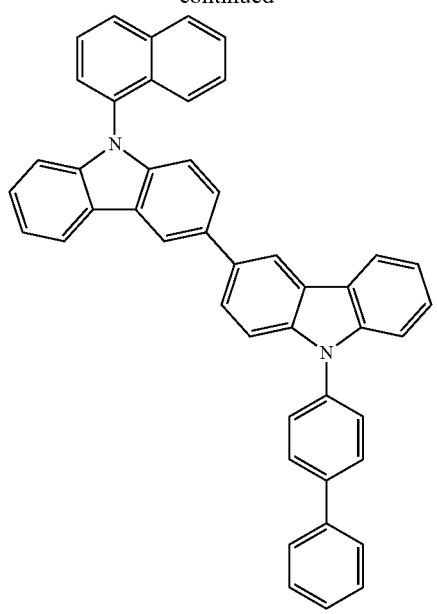
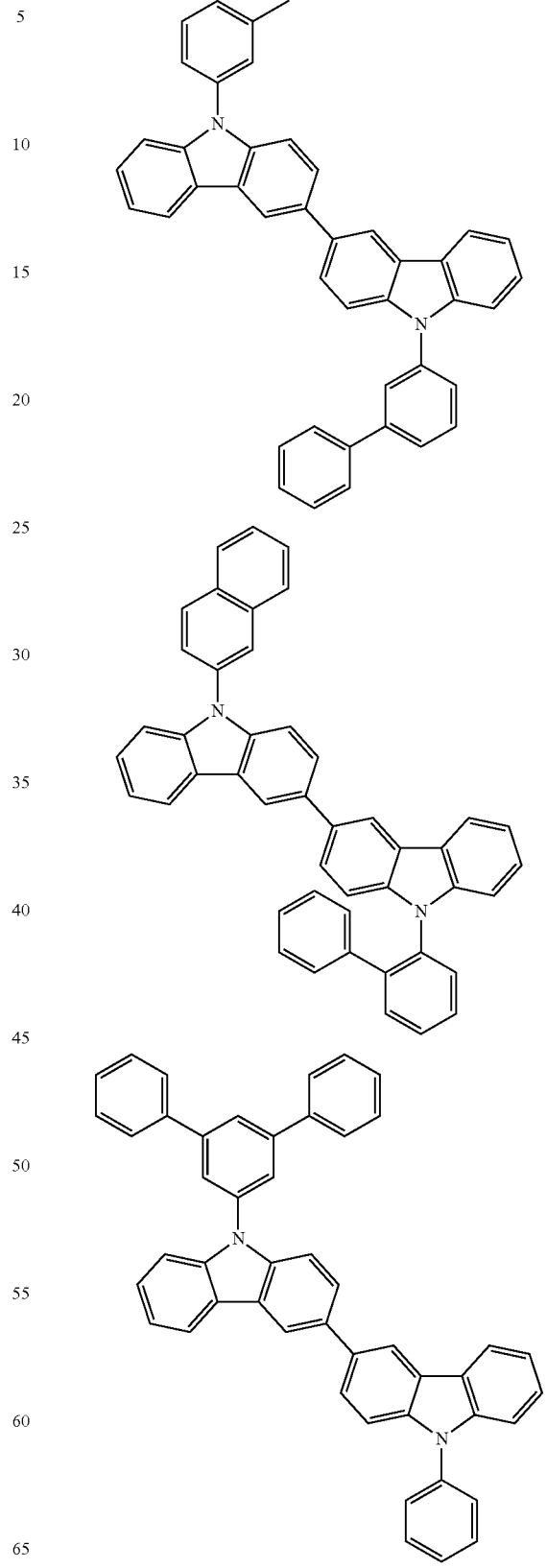
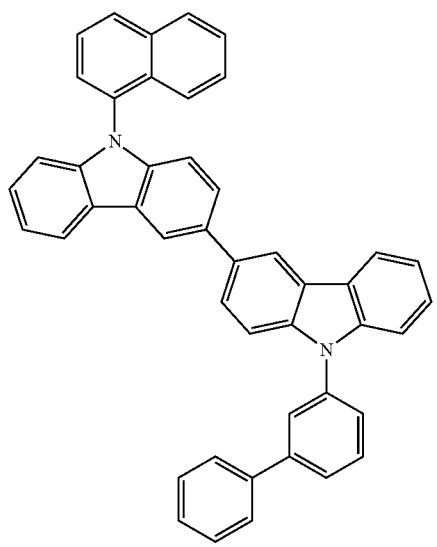

135
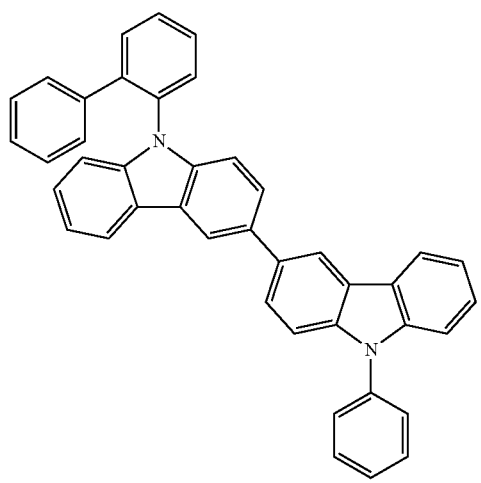
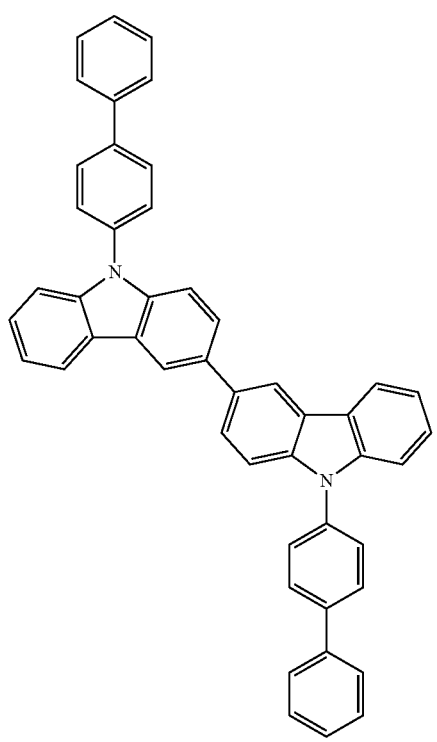
136
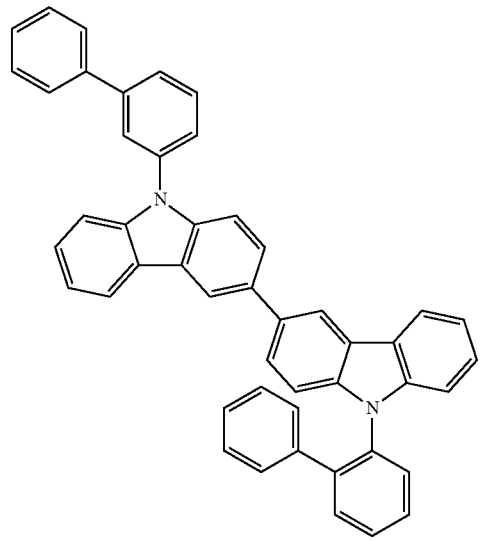
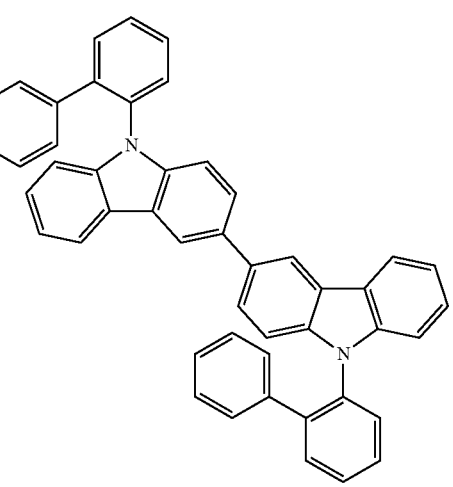
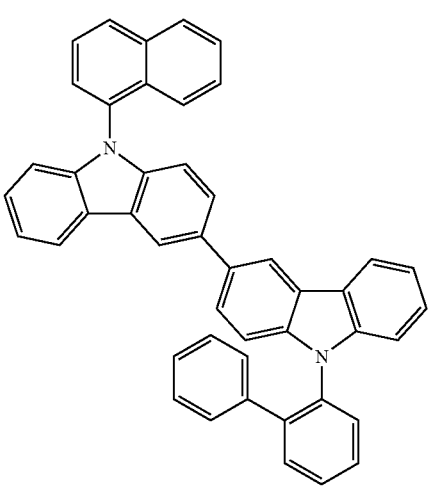

137
-continued
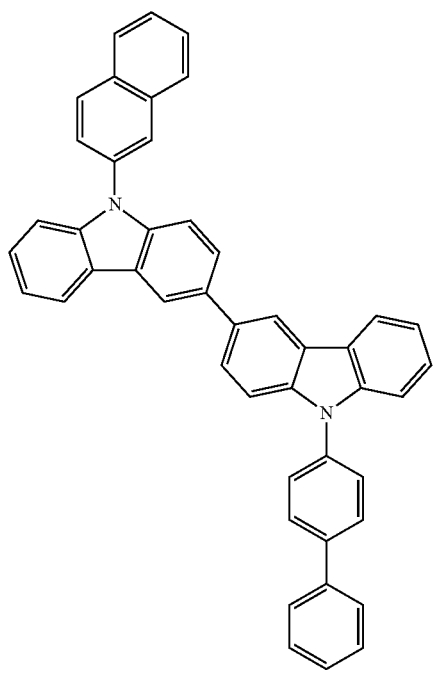
138
-continued
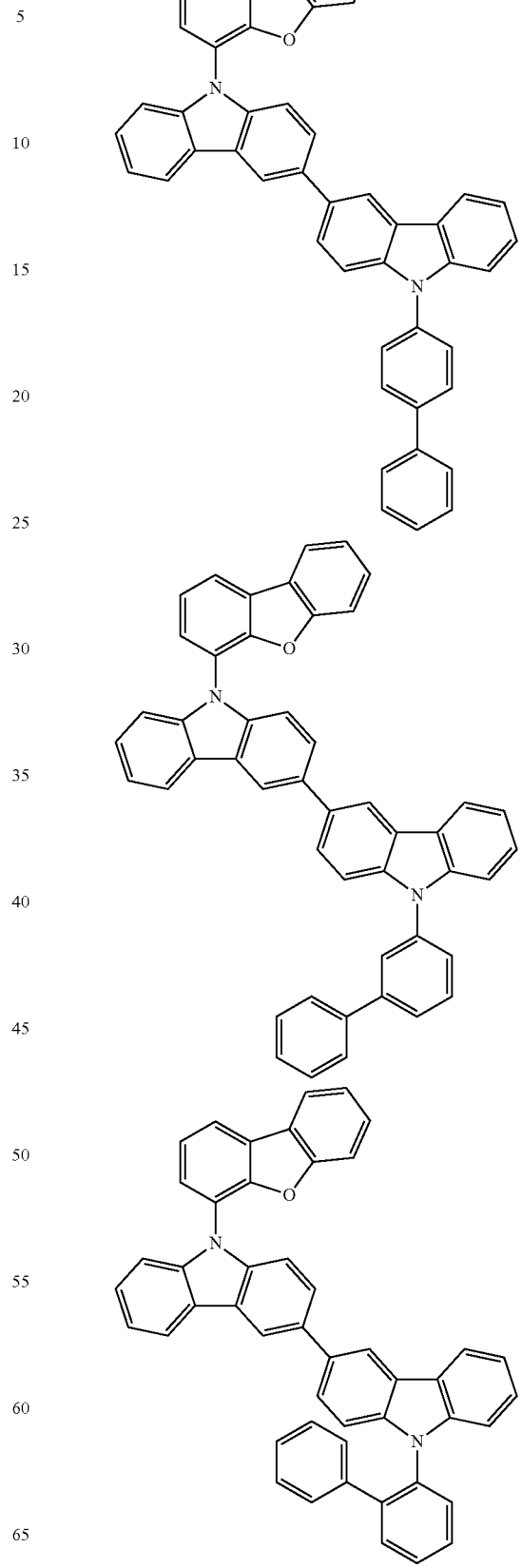
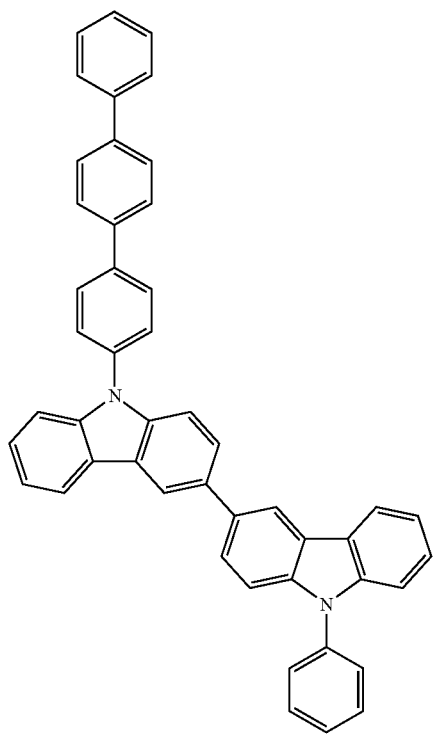

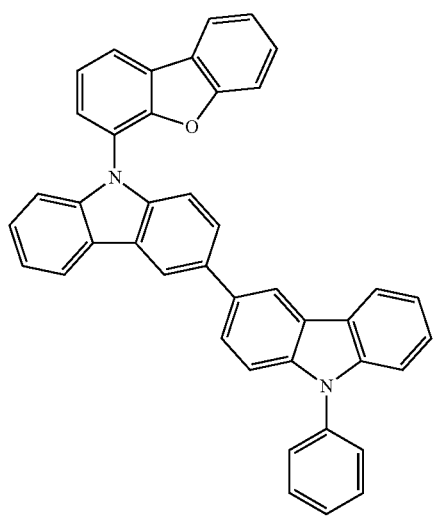
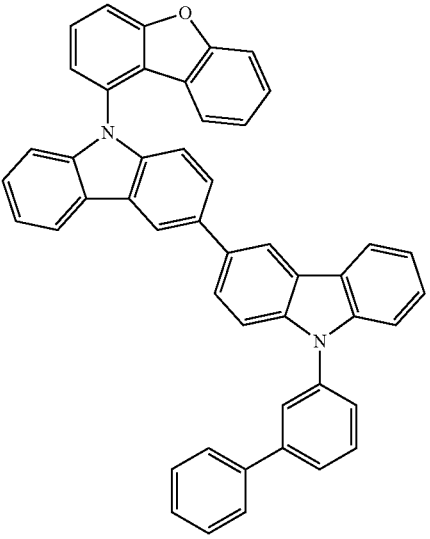
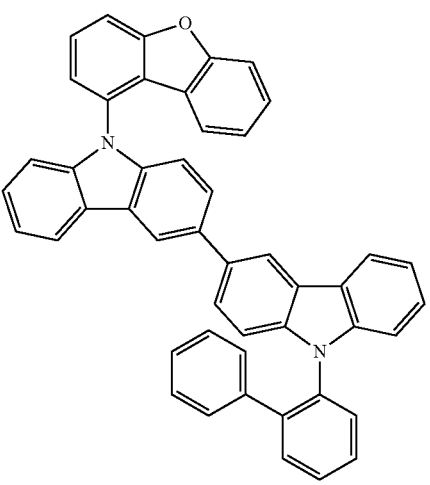
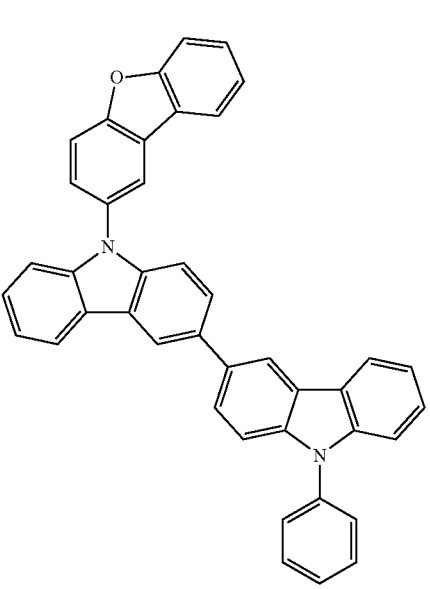

141
-continued
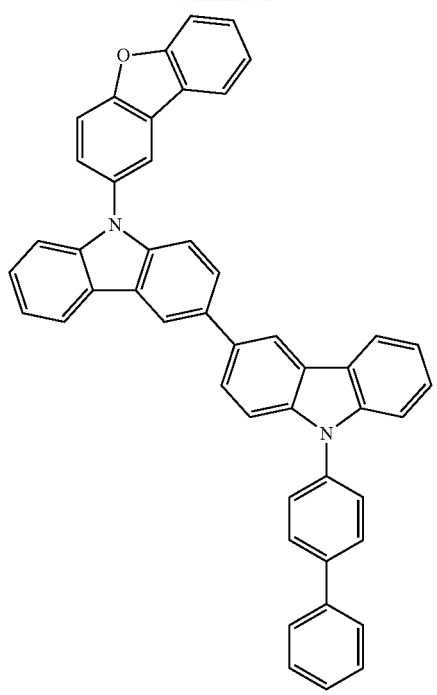
142
-continued
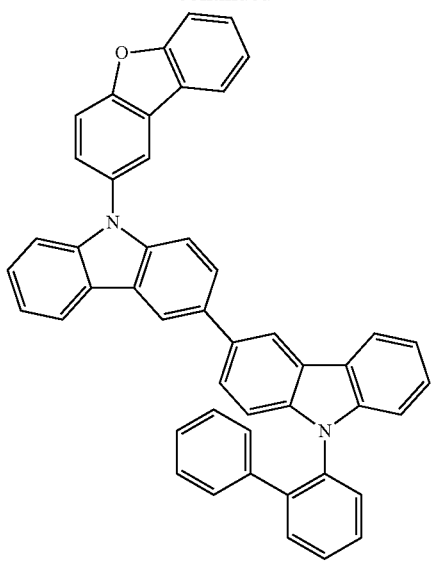
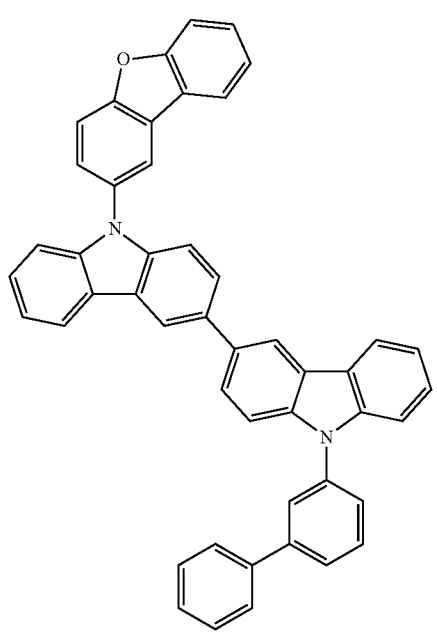
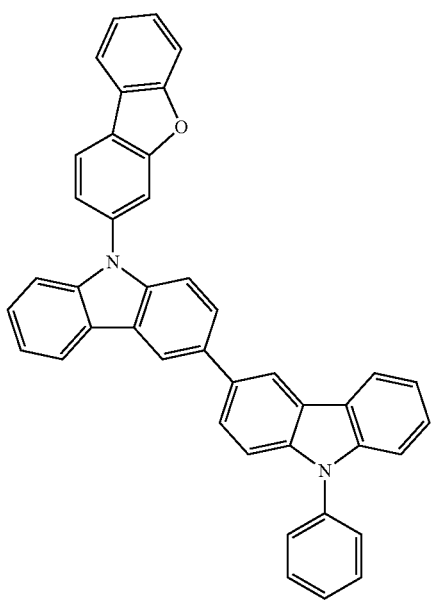

143
-continued
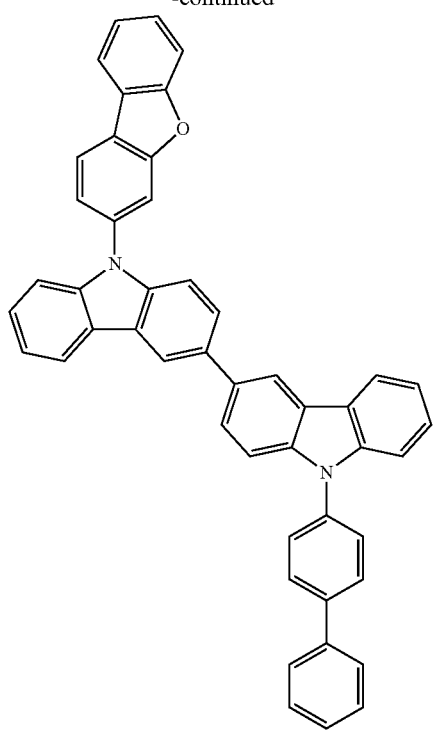
144
-continued
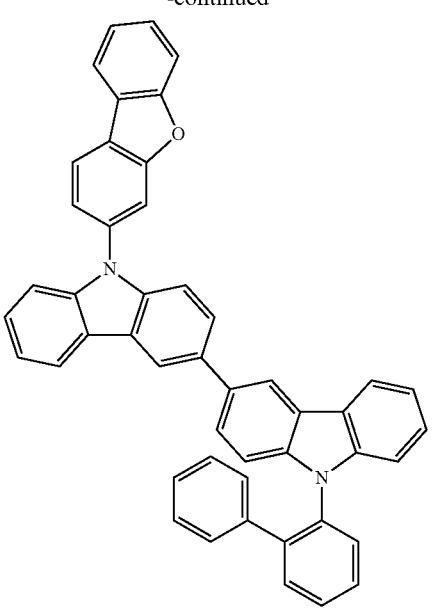

145
-continued
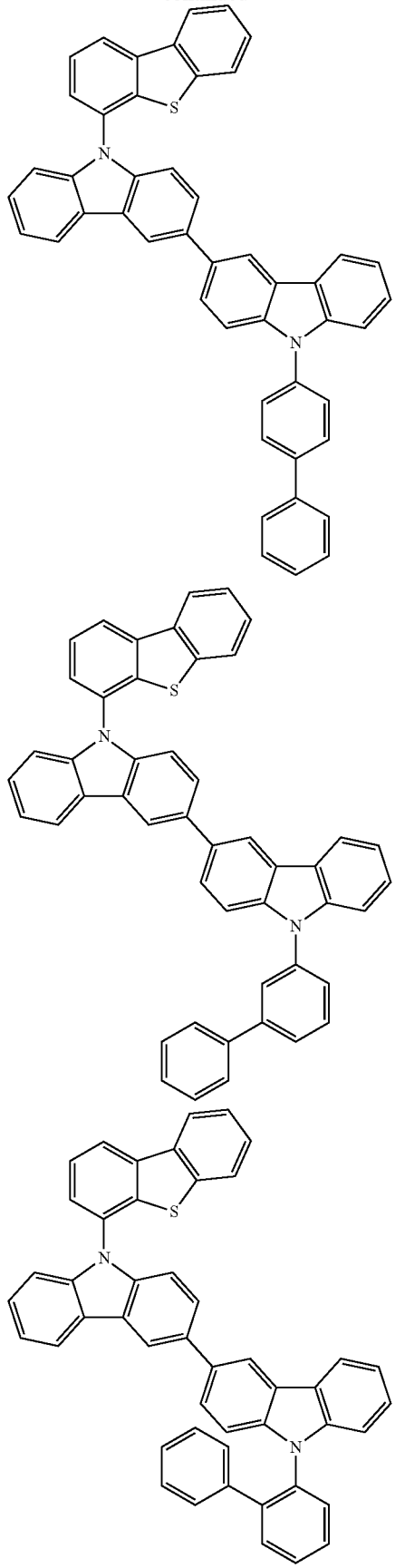
146
-continued
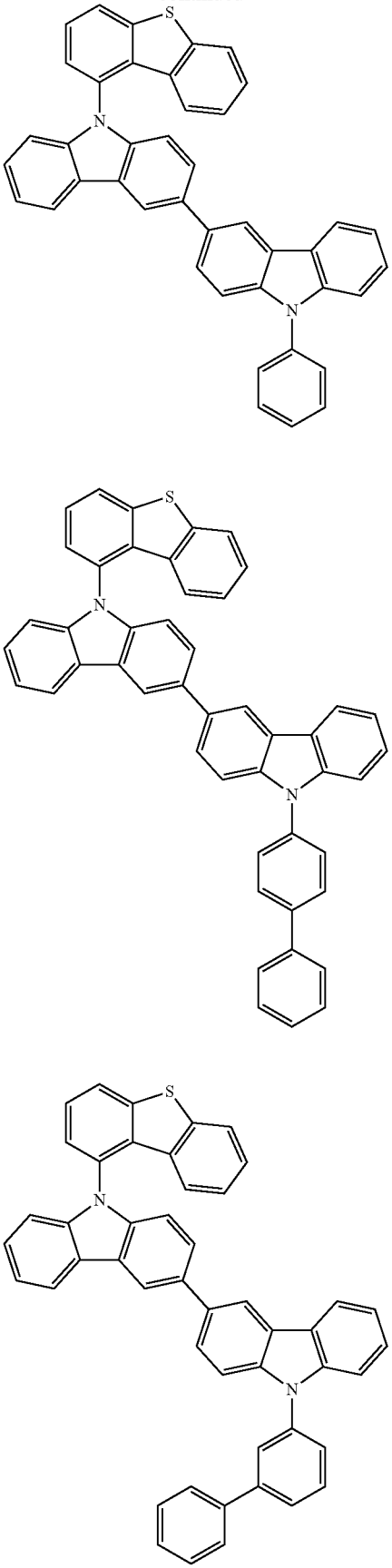

147
-continued
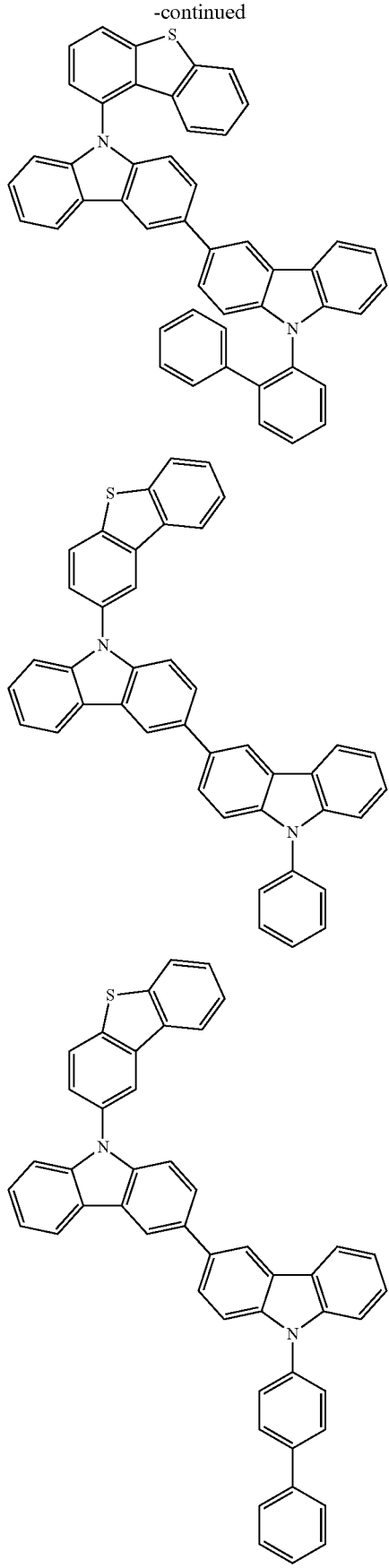
148
-continued
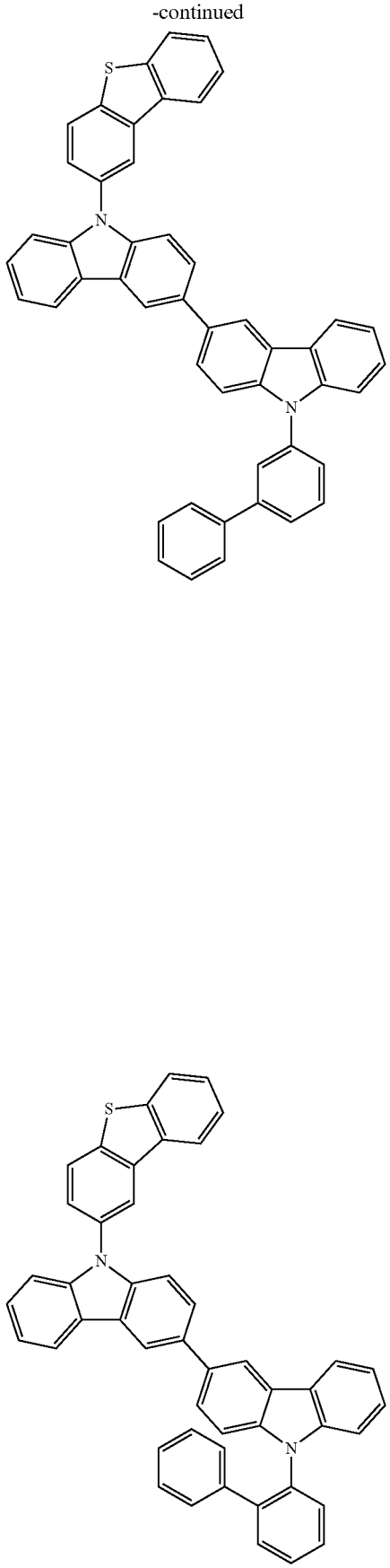

149
-continued
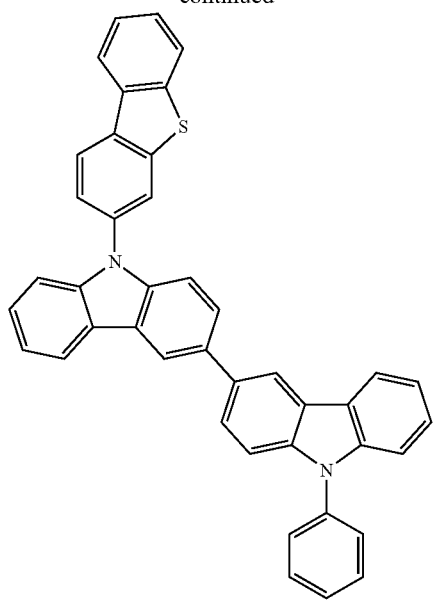
150
-continued
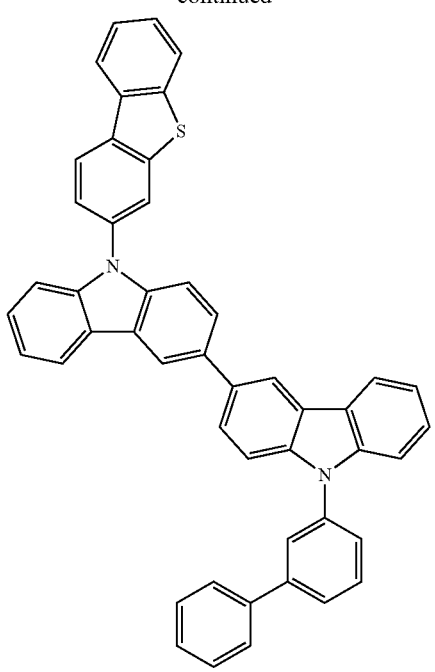
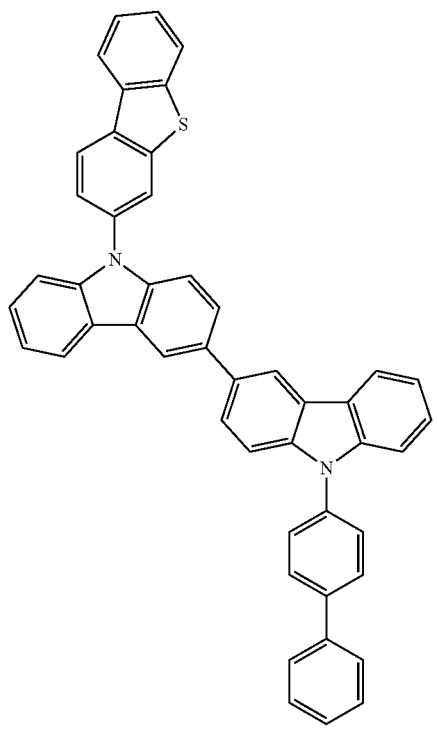
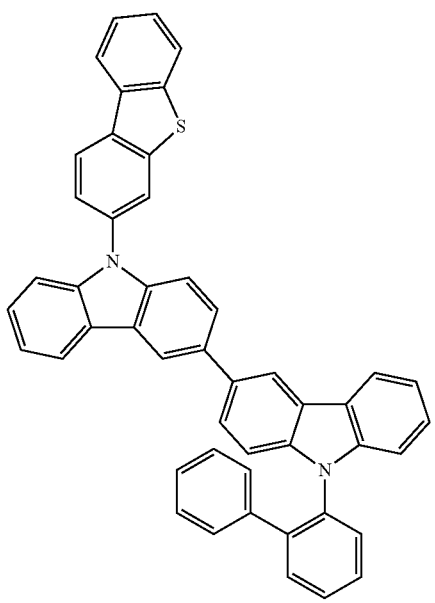

151
-continued
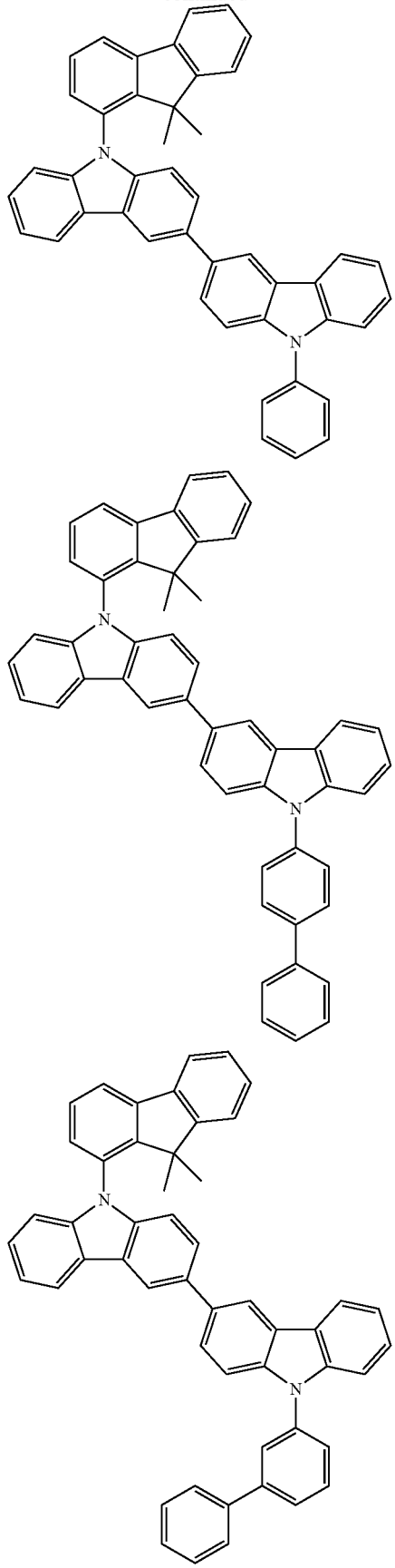
152
-continued
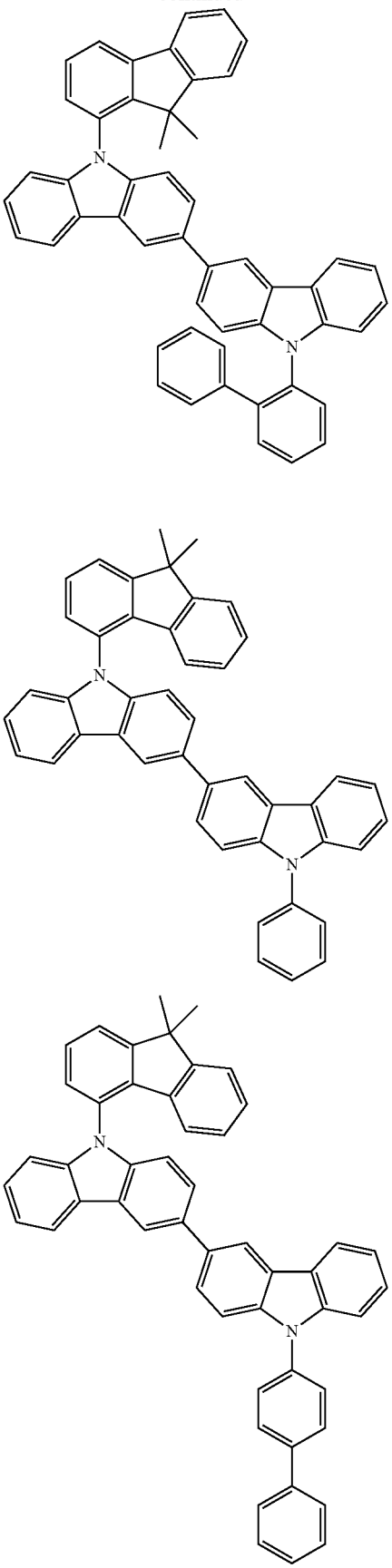

153
-continued
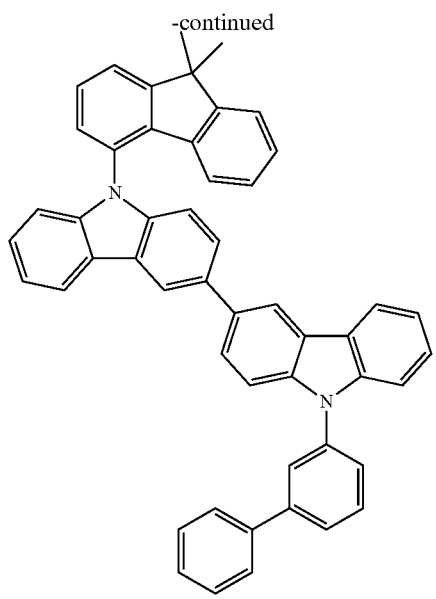
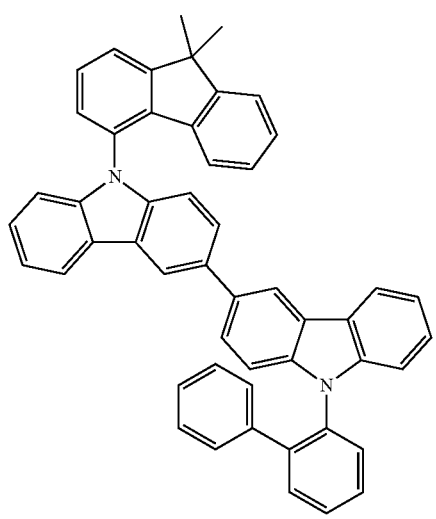
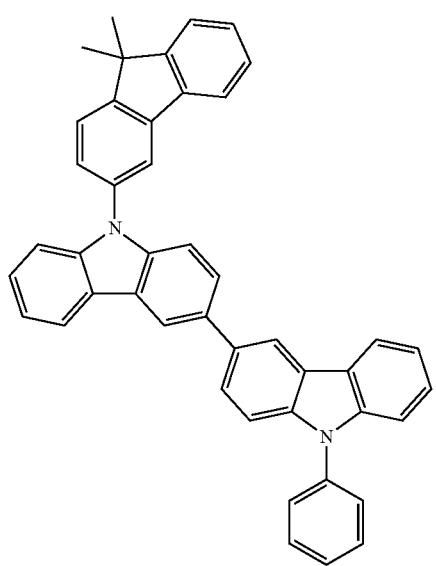
154
-continued
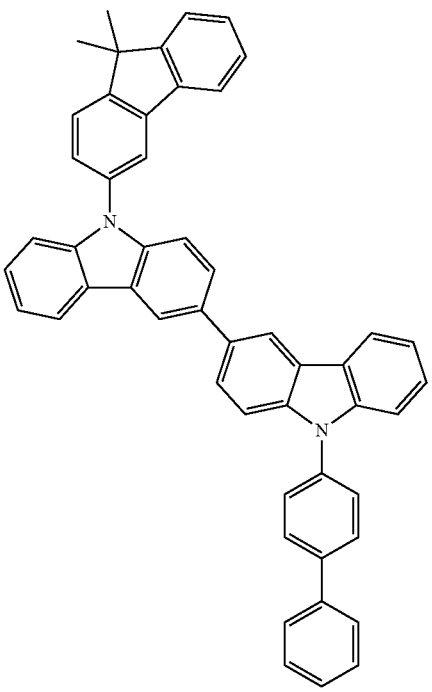
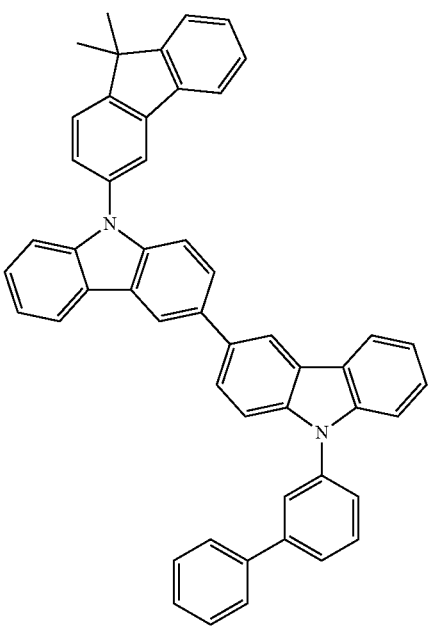

155
-continued
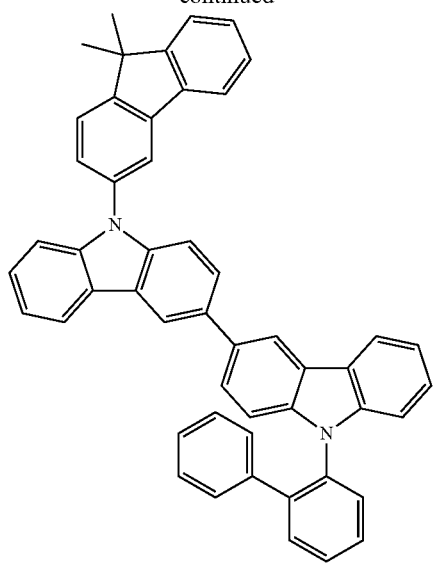
156
-continued
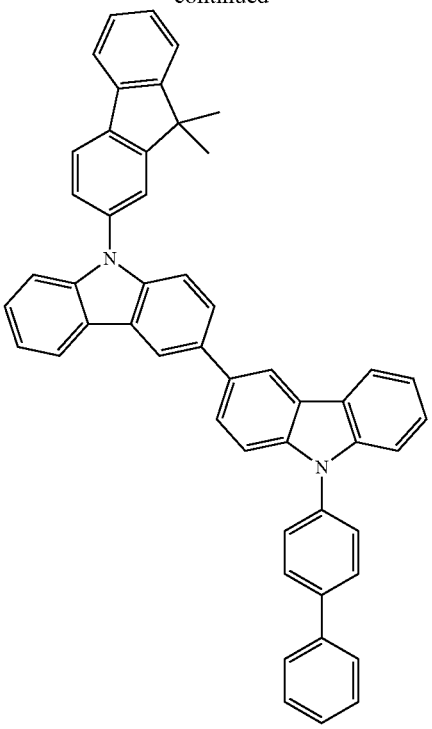
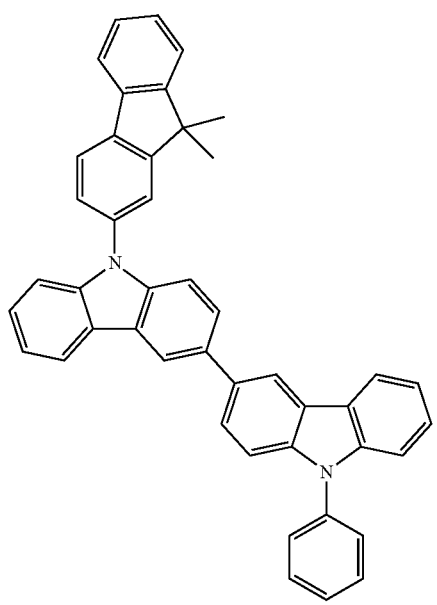
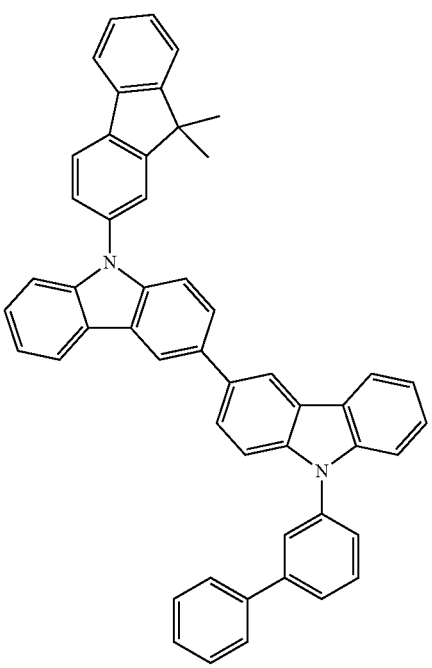

157
-continued
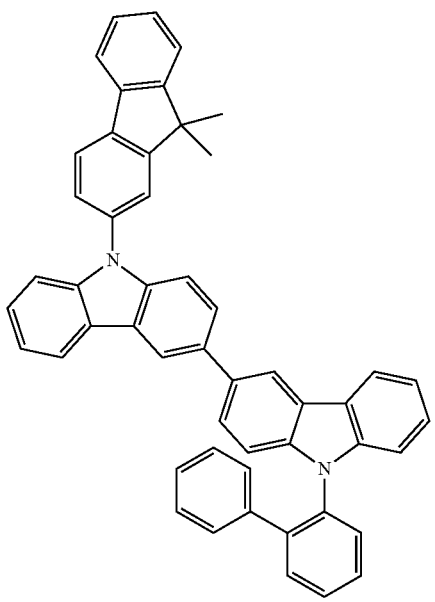
158
-continued
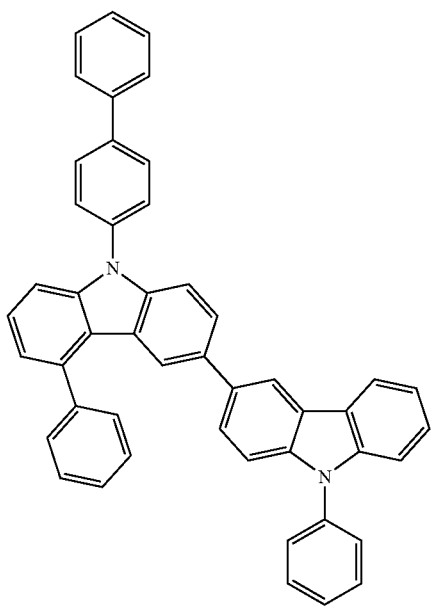
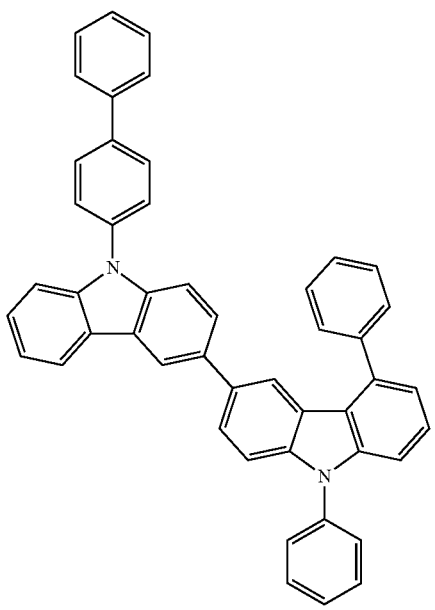
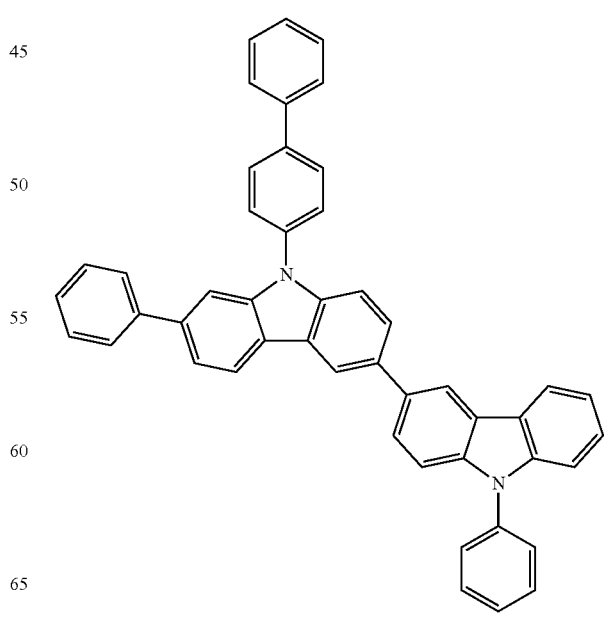

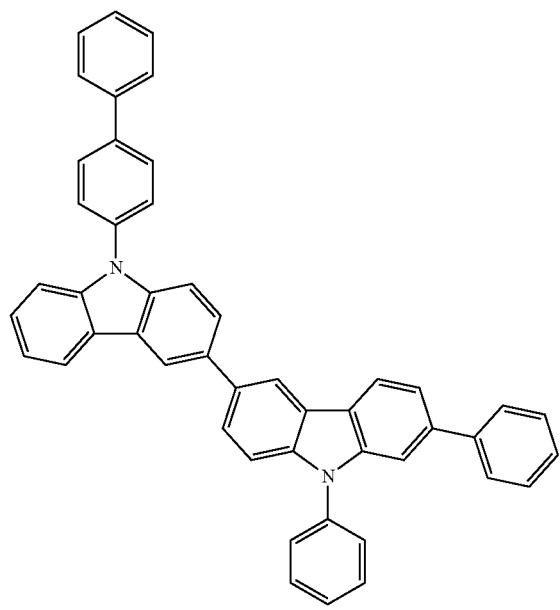
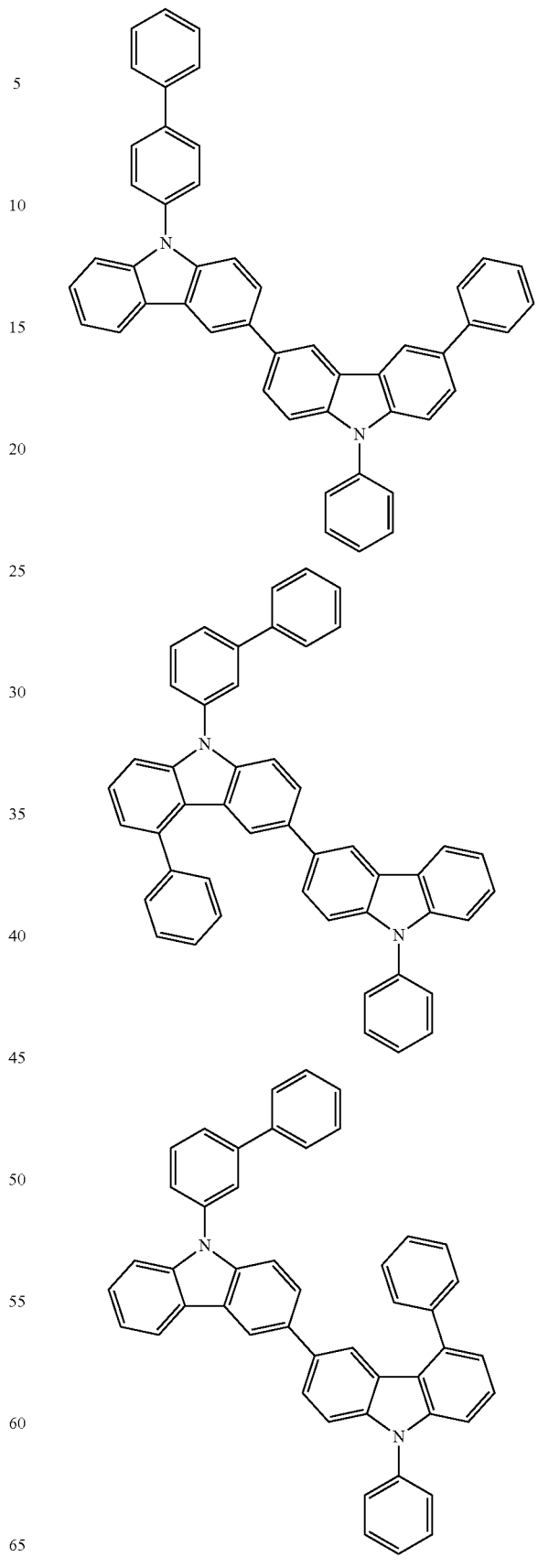

Meanwhile, the compound of Chemical Formula 2 can be prepared by, for example, a preparation method as shown in Reaction Scheme 2 below.

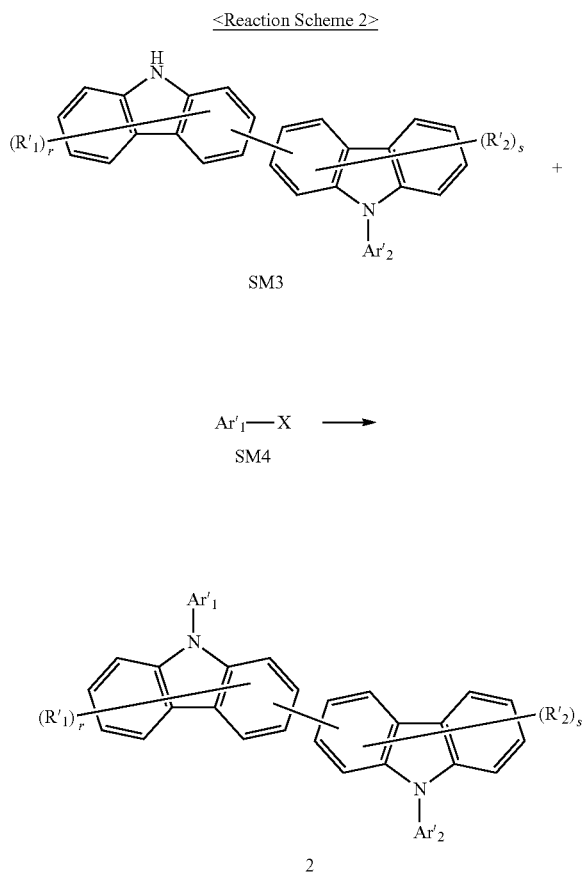

wherein in the Reaction Scheme 2, each X is independently halogen, preferably bromo, or chloro, and the definitions of other substituents are the same as described above.

Specifically, the compound of Chemical Formula 2 is prepared by combining starting materials of SM3 and SM4 through an amine substitution reaction. Such an amine substitution reaction is preferably performed in the presence of a palladium catalyst and a base. In addition, the reactive group for the amine substitution reaction can be appropriately changed, and the method for preparing the compound of Chemical Formula 2 can be more specifically described in Synthesis Examples described below, In addition, the first compound and the second compound, which are two kinds of host materials, can be included in the light emitting layer in a weight ratio of 10:90 to 90:10. More specifically, the first compound and the second compound can be included in the light emitting layer in a weight ratio of 10:90 to 50:50, or 20:80 to 50:50. At this time, the first compound and the second compound can be included in the light emitting layer in a weight ratio of 30:70 so that an exciplex is stably formed in the light emitting layer.

Meanwhile, the light emitting layer can further include a dopant material other than the two kinds of host materials. Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

Hole Blocking Layer

The organic light emitting device according to the present disclosure can include a hole blocking layer, if necessary, between a light emitting layer and an electron transport layer to be described later. The hole blocking layer means a layer which is formed on the light emitting layer, is preferably provided in contact with the light emitting layer, and thus serves to control electron mobility, to prevent excessive movement of holes, and to increase the probability of hole-electron bonding, thereby improving the efficiency of the organic light emitting device. The hole blocking layer includes a hole blocking material, and as an example of such a hole blocking material, compounds having introduced electron attracting groups, such as azine-based derivatives including triazine; triazole derivatives; oxadiazole derivatives; phenanthroline derivatives; phosphine oxide derivatives can be used, but is not limited thereto.

Electron Transport Layer

The electron transport layer is formed between the light emitting layer and a cathode, and receives electrons from an electron injection layer and transports electrons to a light emitting layer. The electron transport layer includes an electron transport material, and the electron transport material is suitably a material which can receive electrons well from a cathode and transport the electrons to a light emitting layer, and has a large mobility for electrons.

Specific examples of the electron injection and transport material include: an Al complex of 8-hydroxyquinoline; a complex including $Alq_3$; an organic radical compound; a hydroxyflavone-metal complex; a triazine derivative, and the like, but are not limited thereto. Alternatively, it can be used together with fluorenone, anthraquinodimethane, diphenoquinone, thiopyran dioxide, oxazole, oxadiazole, triazole, imidazole, perylenetetracarboxylic acid, fluorenylidene methane, anthrone, or derivatives thereof, a metal complex compound, a nitrogen-containing 5-membered ring derivative, or the like, but are not limited thereto.

Electron Injection Layer

The organic light emitting device according to the present disclosure can include an electron injection layer between an electron transport layer and a cathode, if necessary.

The electron injection layer is located between the electron transport layer and a cathode, and injects electrons from the cathode. The electron injection layer includes an electron injection material, and a material capable of transporting electrons, having an excellent effect of injecting electrons to a light emitting layer or a light emitting material, and excellent in forming a thin film is suitable.

Specific examples of the electron injection material include ytterbium (Yb), LiF, NaCl, CsF, $Li_2O$, BaO, fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)-gallium, bis(10-hydroxybenzo[h]quinolinato) beryllium, bis(10-hydroxybenzo-[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)-aluminum, bis(2-methyl-8-quinolinato)(2-naphtholato)gallium, and the like, but are not limited thereto.

Organic Light Emitting Device

A structure of the organic light emitting device according to the present disclosure is illustrated in FIG. 1. FIG. 1 shows an example of an organic light emitting device including a substrate 1, an anode 2, a light emitting layer 3, and a cathode 4. In such a structure, the first compound and the second compound can be included in the light emitting layer.

FIG. 2 shows an example of an organic light emitting device including a substrate 1, an anode 2, a hole injection layer 5, a hole transport layer 6, an electron blocking layer 7, a light emitting layer 3, a hole blocking layer 8, an electron transport layer 9, an electron injection layer 10, and a cathode 4. In such a structure, the first compound and the second compound can be included in the light emitting layer.

The organic light emitting device according to the present disclosure can be manufactured by sequentially laminating the above-mentioned components. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming the above-mentioned respective layers thereon, and then depositing a material that can be used as the cathode thereon. In addition to such a method, the organic light emitting device can be manufactured by sequentially depositing a cathode material, an organic material layer and an anode material on a substrate. Further, the light emitting layer can be formed using the host and the dopant by a solution coating method as well as a vacuum deposition method. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

Meanwhile, the organic light emitting device according to the present disclosure can be a front side emission type, a backside emission type, or a double-sided emission type according to the used material.

The preparation of the organic light emitting device will be described in detail in the following examples. However, these examples are presented for illustrative purposes only, and are not intended to limit the scope of the present disclosure.

Preparation Example: Synthesis of Compound

Preparation Example 1-1: Synthesis of Compound 1-1

Step 1) Synthesis of Compound 1-1-a

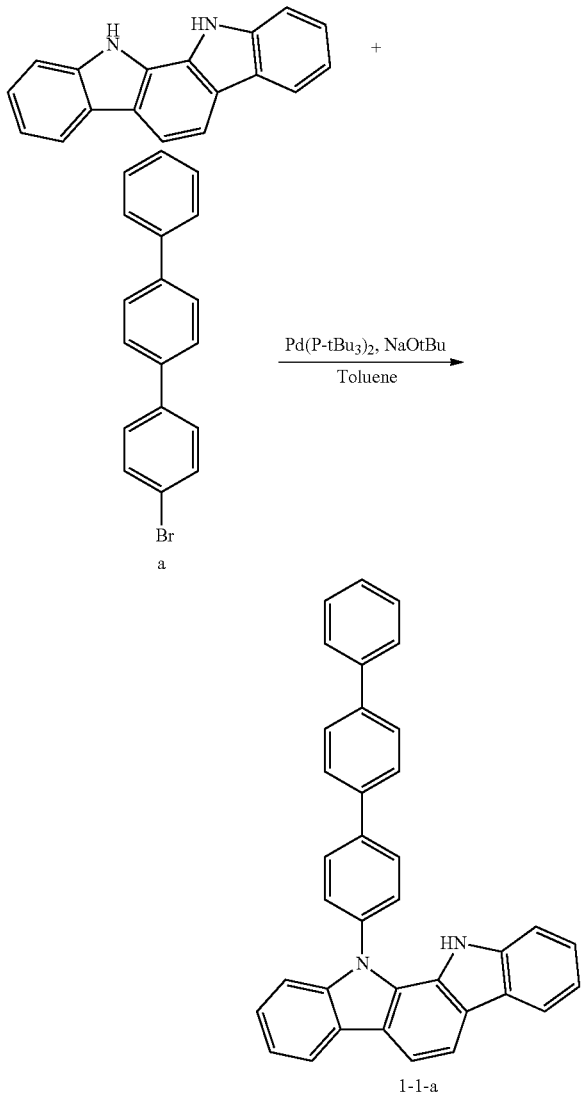

11,12-dihydroindolo[2,3-a]carbazole (15.0 g, 58.5 mmol) and Compound a (19.9 g, 64.4 mmol) were added to 300 ml of toluene under a nitrogen atmosphere, and the mixture was stirred and refluxed. Then, sodium tert-butoxide (8.4 g, 87.8 mmol) and bis(tri-tert-butylphosphine)palladium(0) (0.9 g, 1.8 mmol) were added thereto. After 9 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 20.7 g (yield 73%) of Compound 1-1-a.

MS[M+H]$^+$=486

Step 2) Synthesis of Compound 1-1

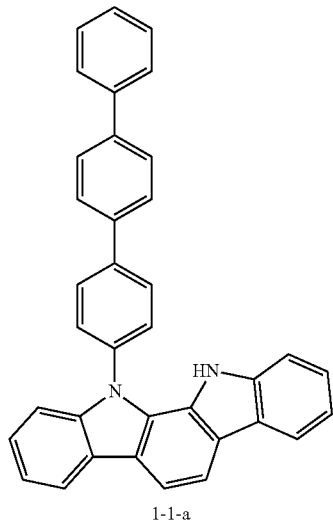

1-1-a

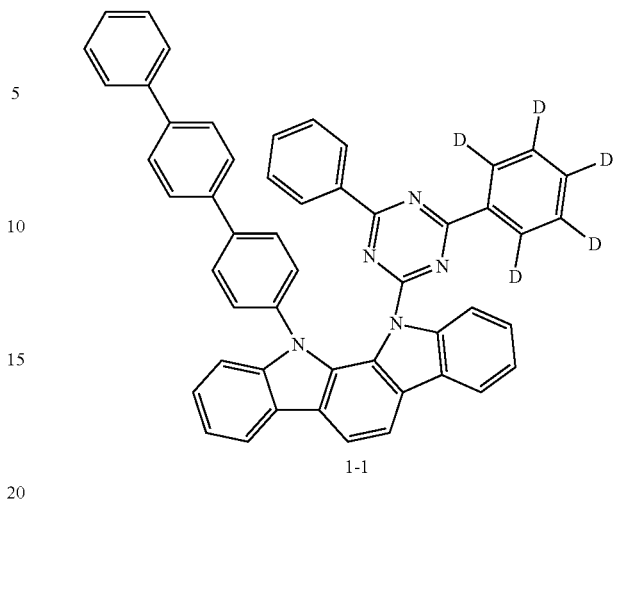

1-1

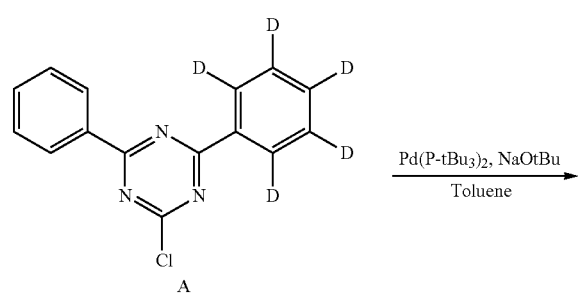

Compound 1-1-a (15.0 g, 31.0 mmol) and Intermediate A (9.3 g, 34.0 mmol) were added to 300 ml of toluene under a nitrogen atmosphere, and the mixture was stirred and refluxed. Then, sodium tert-butoxide (4.5 g, 46.4 mmol) and bis(tri-tert-butylphosphine)palladium(0) (0.5 g, 0.9 mmol) were added thereto. After 8 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography, and then 9.1 g (yield 41%) of Compound 1-1 was prepared through sublimation purification.

MS[M+H]$^+$=722

Preparation Example 1-2: Synthesis of Compound 1-2

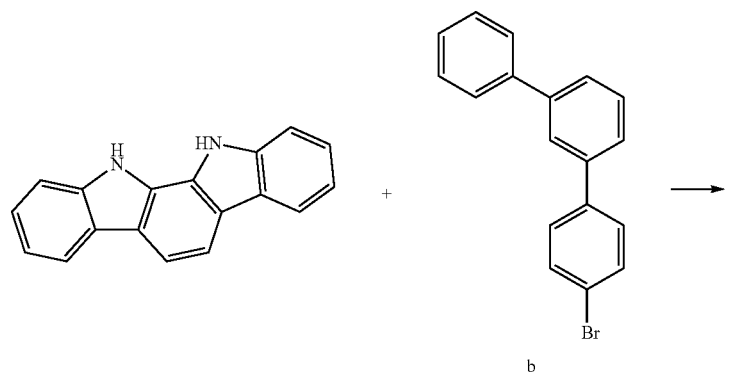

b

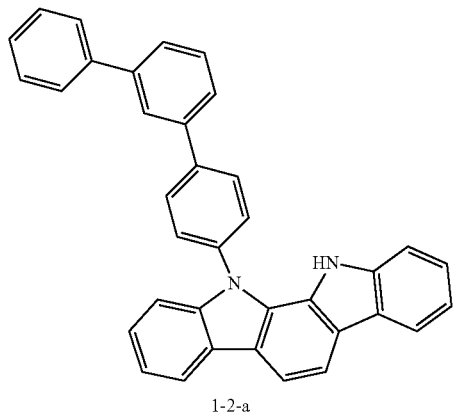
1-2-a
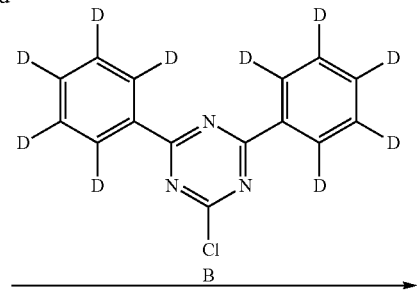
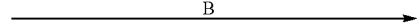
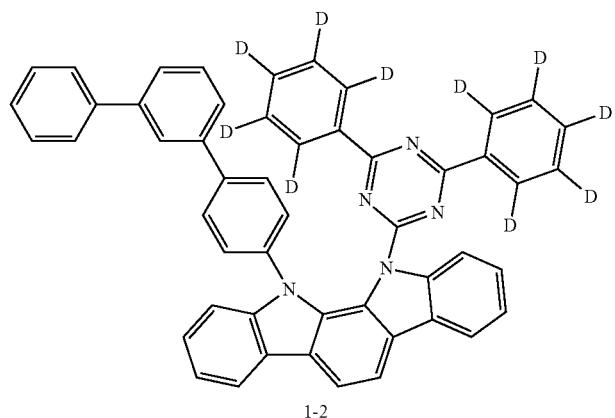
1-2
Compound 1-2 was prepared in the same manner as in the preparation method of Compound 1-1, except that Compound a was changed to Compound b and Intermediate A was changed to Intermediate B in Preparation Example 1-1.
MS[M+H]$^+$=727
Preparation Example 1-3: Synthesis of Compound 1-3
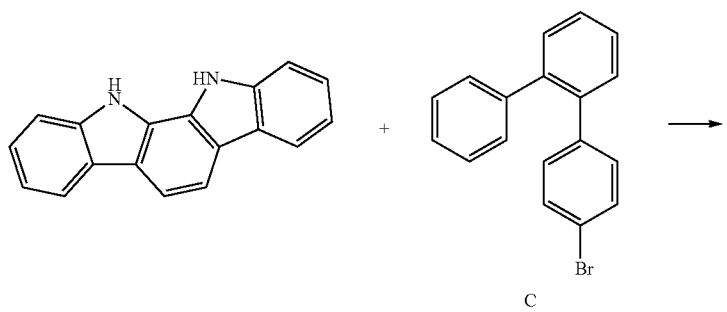
C

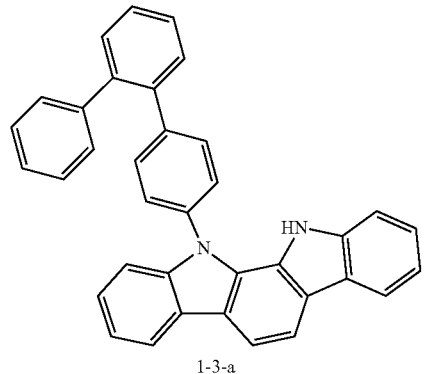
1-3-a
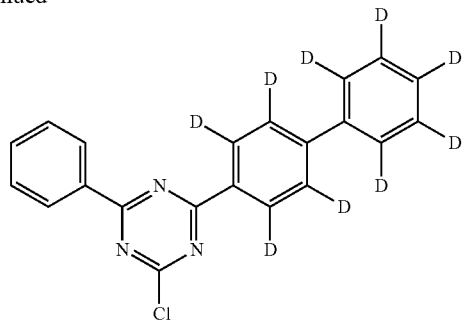
C
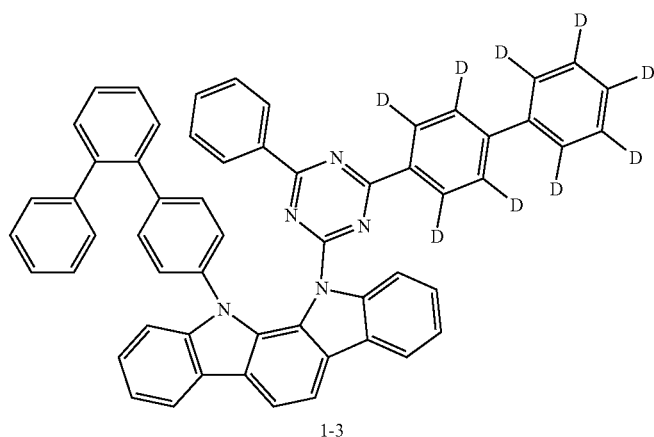
1-3
Compound 1-3 was prepared in the same manner as in the preparation method of Compound 1-1, except that Compound a was changed to Compound c and Intermediate A was changed to Intermediate C in Preparation Example 1-1.
MS[M+H]$^+$=802
Preparation Example 1-4: Synthesis of Compound 1-4
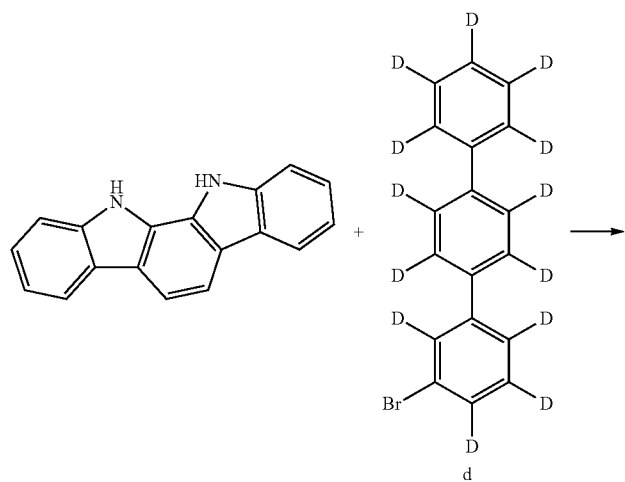
d -continued
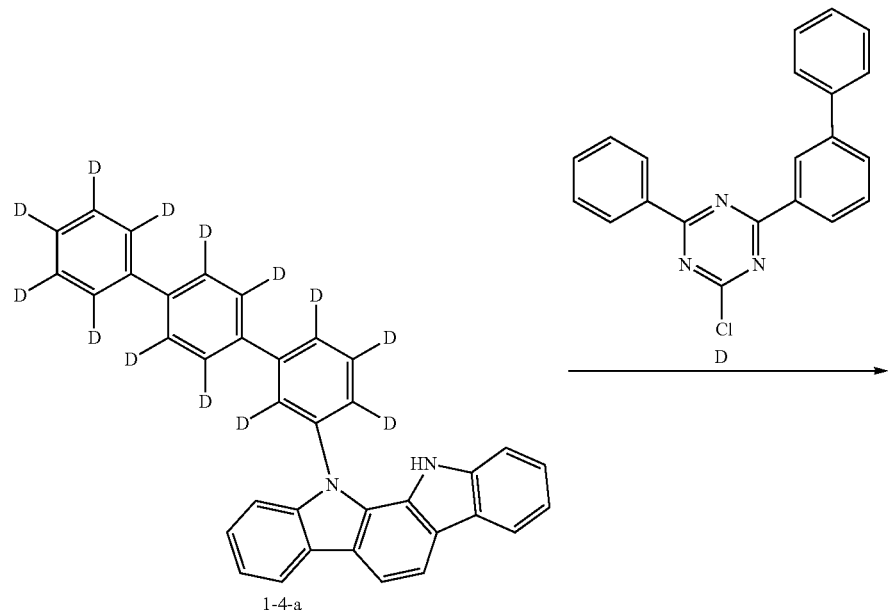
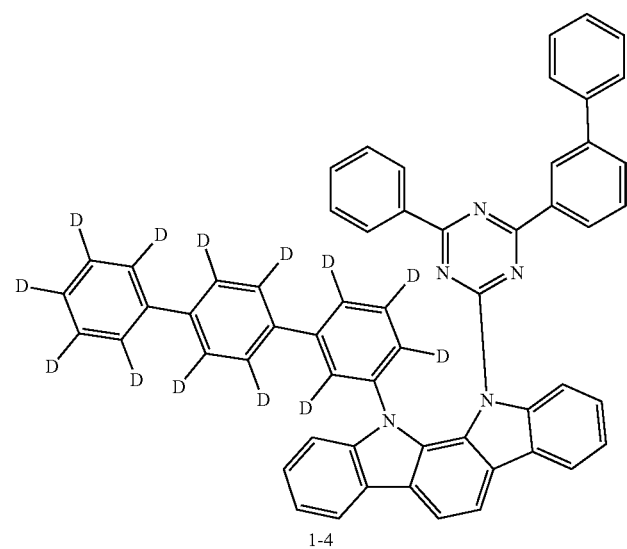

Compound 1-4 was prepared in the same manner as in the preparation method of Compound 1-1, except that Compound a was changed to Compound d and Intermediate A was changed to Intermediate D in Preparation Example 1-1.
MS[M+H]$^+$=806
Preparation Example 1-5: Synthesis of Compound 1-5
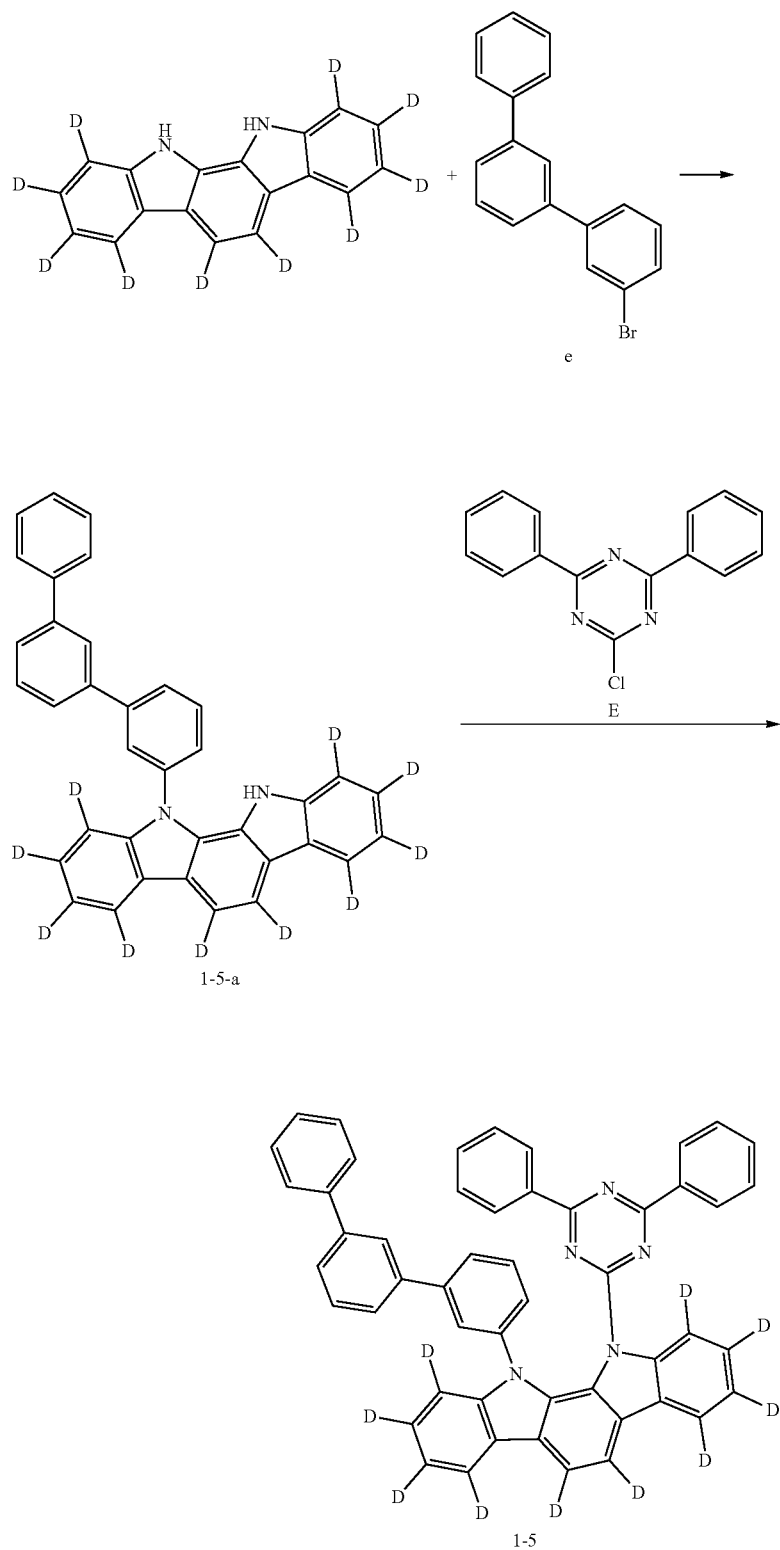

Compound 1-5 was prepared in the same manner as in the preparation method of Compound 1-1, except that Compound a was changed to Compound e and Intermediate A was changed to Intermediate E in Preparation Example 1-1.
MS[M+H]$^+$=727
Preparation Example 1-6: Synthesis of Compound 1-6
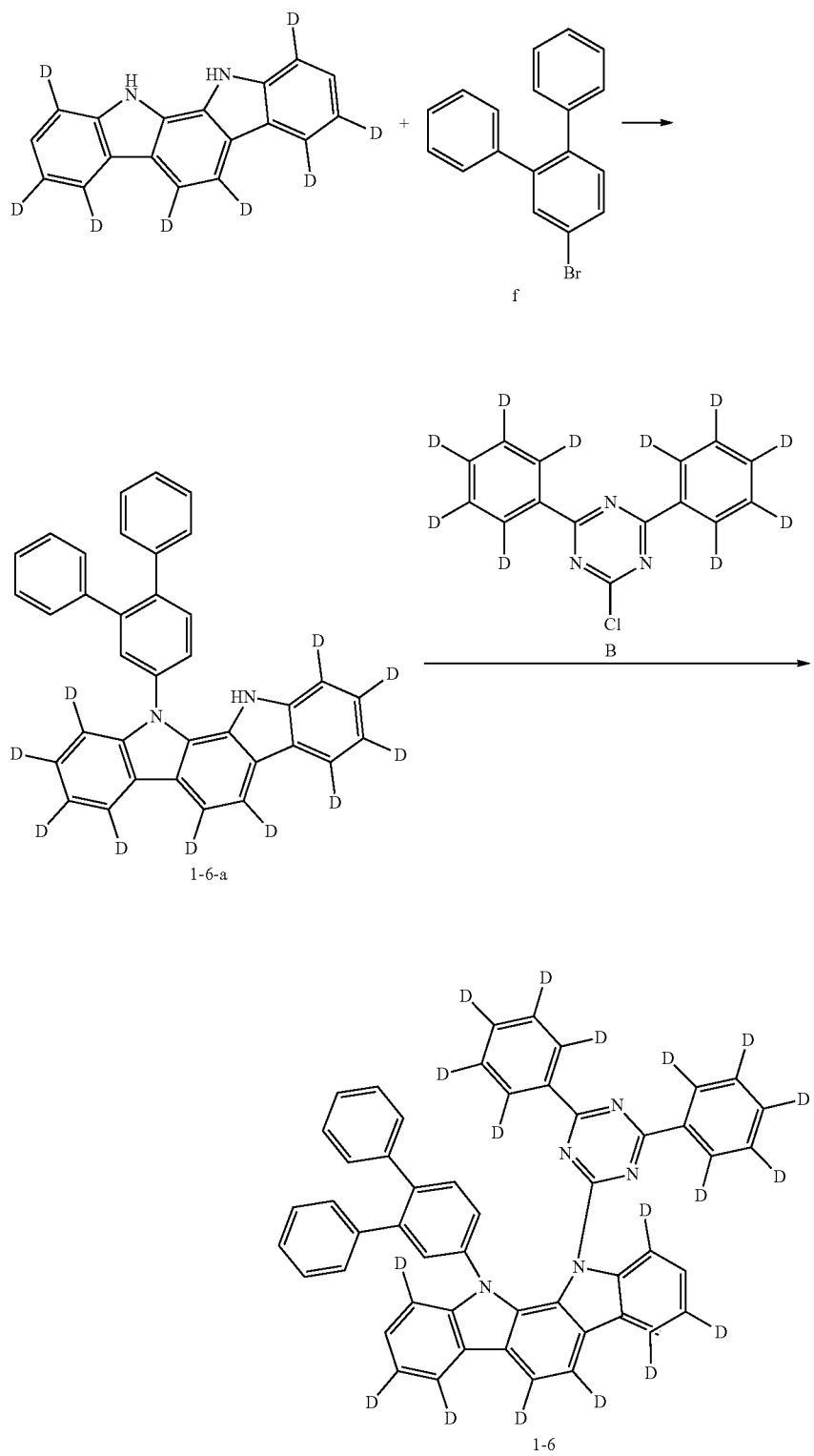

Compound 1-6 was prepared in the same manner as in the preparation method of Compound 1-1, except that Compound a was changed to Compound f and Intermediate A was changed to Intermediate B in Preparation Example 1-1.
MS[M+H]$^+$=735
Preparation Example 1-7: Synthesis of Compound 1-7
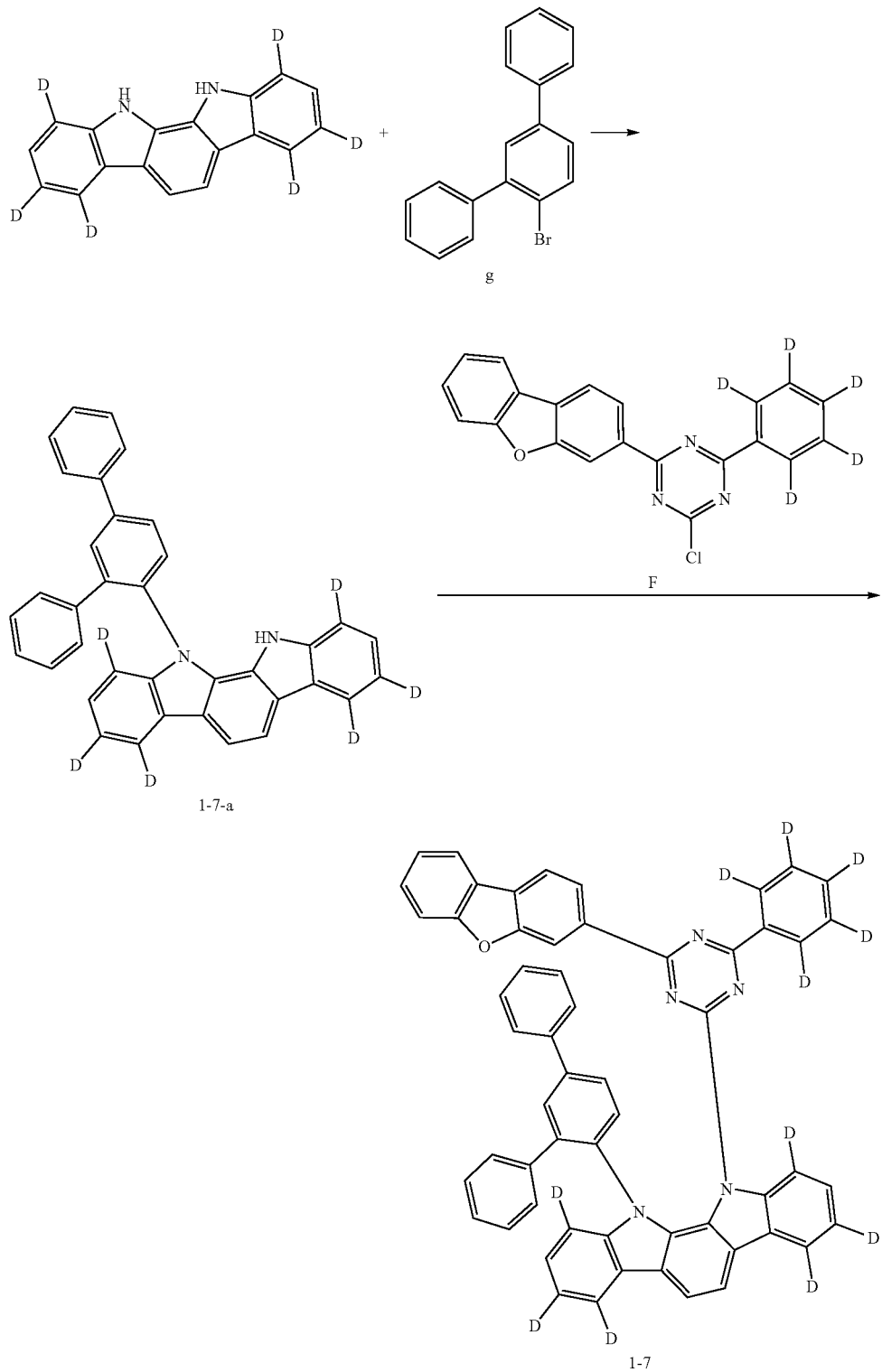

Compound 1-7 was prepared in the same manner as in the preparation method of Compound 1-1, except that Compound a was changed to Compound g and Intermediate A was changed to Intermediate F in Preparation Example 1-1.
MS[M+H]$^+$=818
Preparation Example 1-8: Synthesis of Compound 1-8
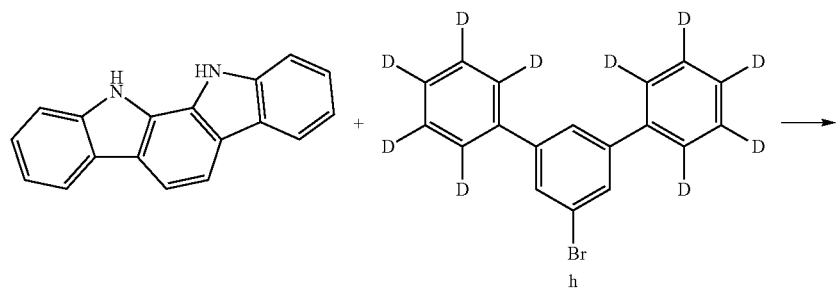
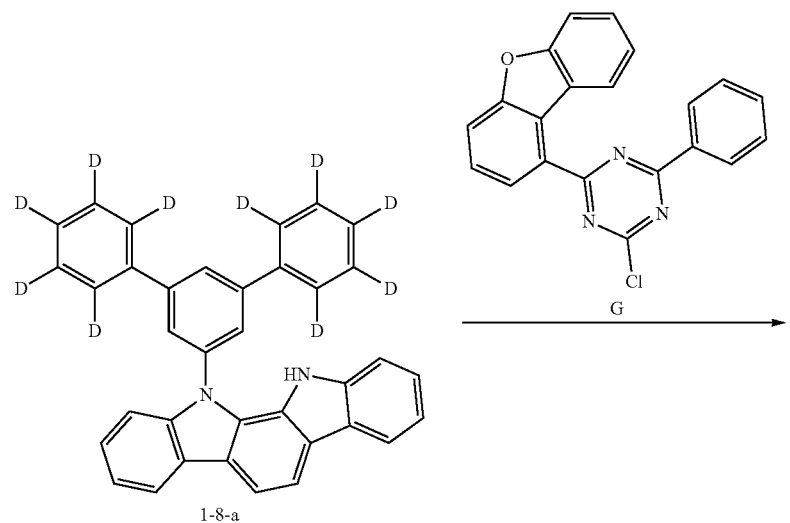
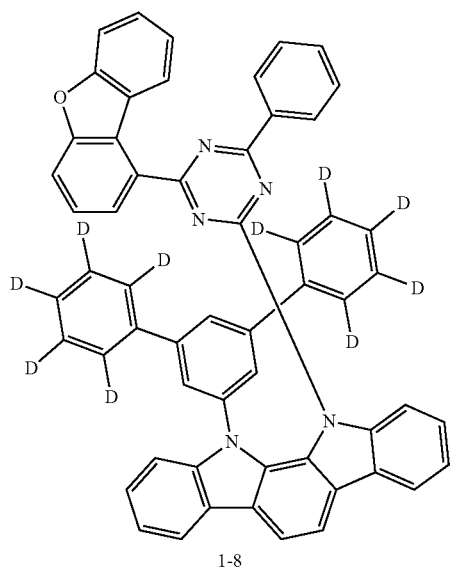

Compound 1-8 was prepared in the same manner as in the preparation method of Compound 1-1, except that Compound a was changed to Compound h and Intermediate A was changed to Intermediate G in Preparation Example 1-1. (MS[M+H]$^+$=817)
Preparation Example 1-9: Synthesis of Compound 1-9
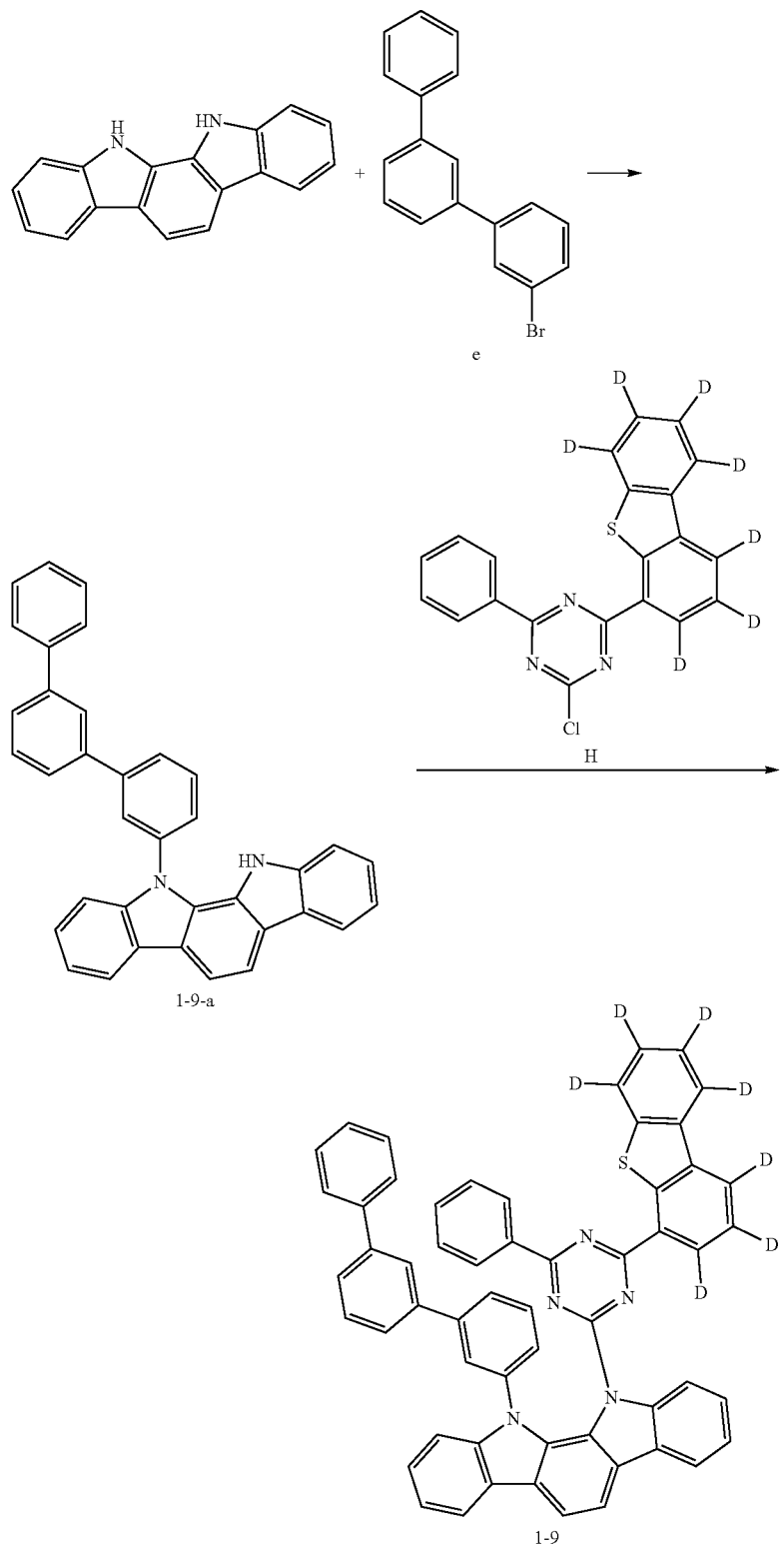

Compound 1-9 was prepared in the same manner as in the preparation method of Compound 1-1, except that Compound a was changed to Compound e and Intermediate A was changed to Intermediate H in Preparation Example 1-1.
MS[M+H]$^+$=830
Preparation Example 1-10: Synthesis of Compound 1-10
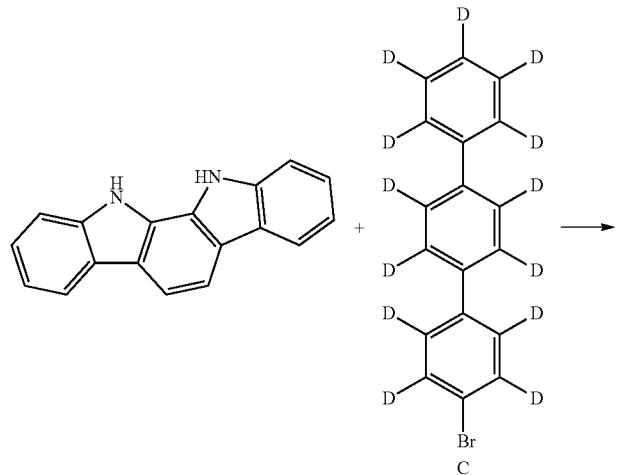
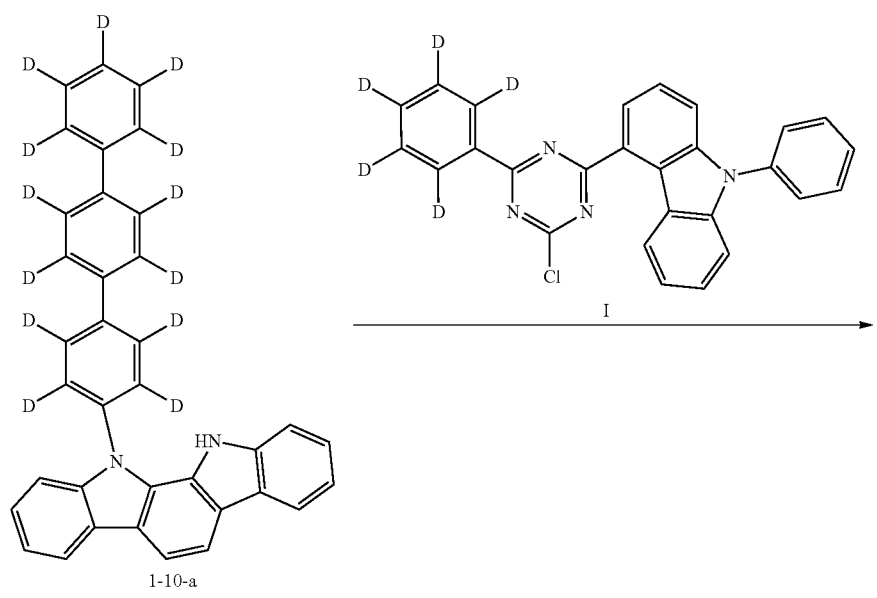

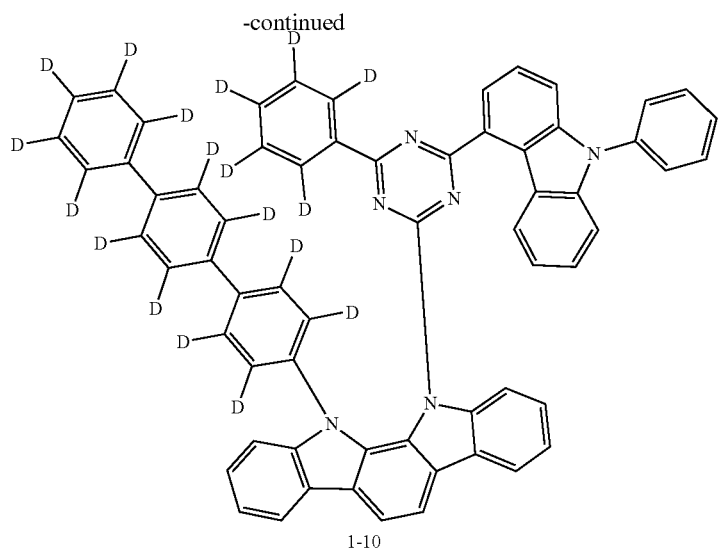
1-10
Compound 1-10 was prepared in the same manner as in the preparation method of Compound 1-1, except that Compound a was changed to Compound c and Intermediate A was changed to Intermediate I in Preparation Example 1-1.
MS[M+H]$^+$=900
Preparation Example 1-11: Synthesis of Compound 1-11
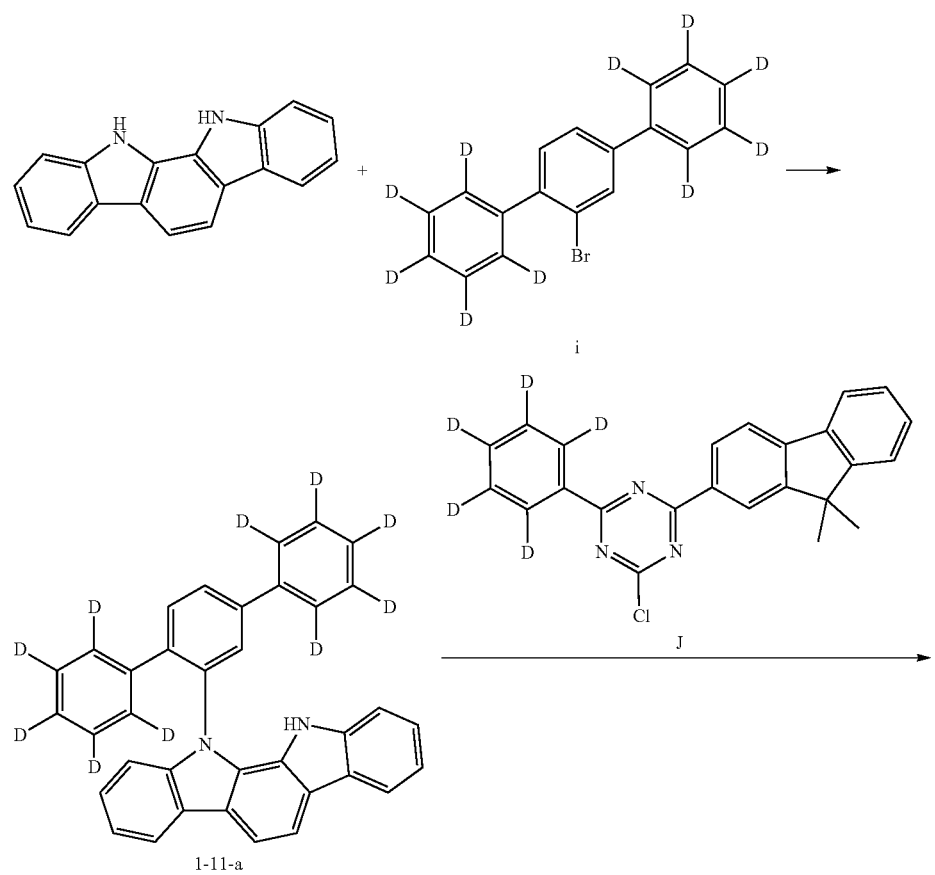

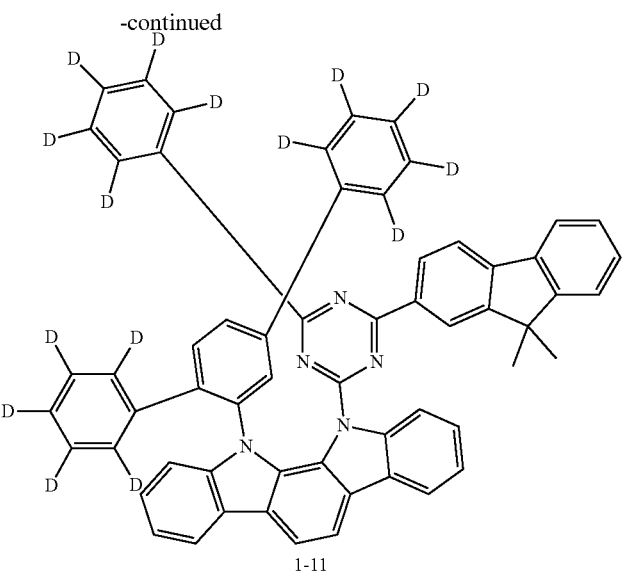

1-11

Compound 1-11 was prepared in the same manner as in the preparation method of Compound 1-1, except that Compound a was changed to Compound i and Intermediate A was changed to Intermediate J in Preparation Example 1-1.

MS[M+H]$^+$=843

Preparation Example 1-12: Synthesis of Compound 1-12

Step 1) Synthesis of Compound 1-12-a

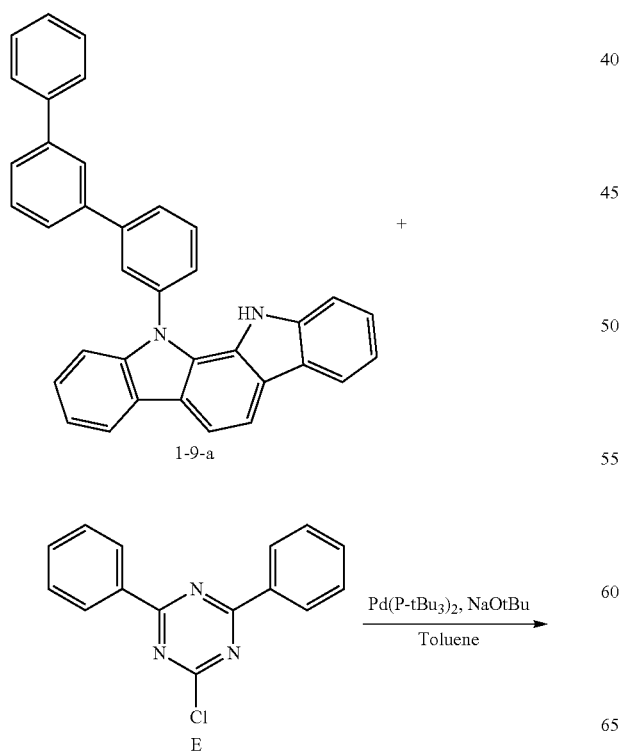

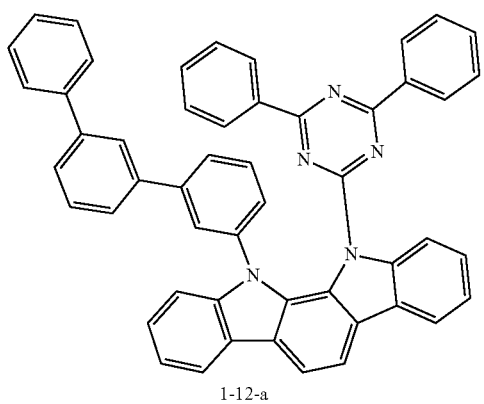

1-12-a

Compound 1-9-a (15.0 g, 31.0 mmol) and Compound E (9.1 g, 34 mmol) were added to 300 ml of toluene under a nitrogen atmosphere, and the mixture was stirred and refluxed. Then, sodium tert-butoxide (4.5 g, 46.4 mmol) and bis(tri-tert-butylphosphine)palladium(0) (0.5 g, 0.9 mmol) were added thereto. After 12 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 14.0 g (yield 63%) of Compound 1-12-a.

MS[M+H]$^+$=717

Step 2) Synthesis of Compound 1-12

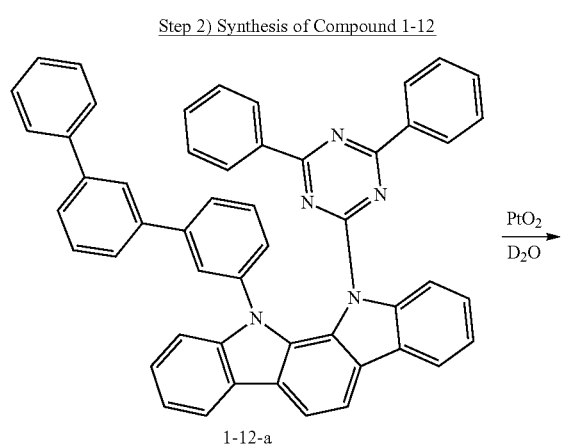

1-12-a

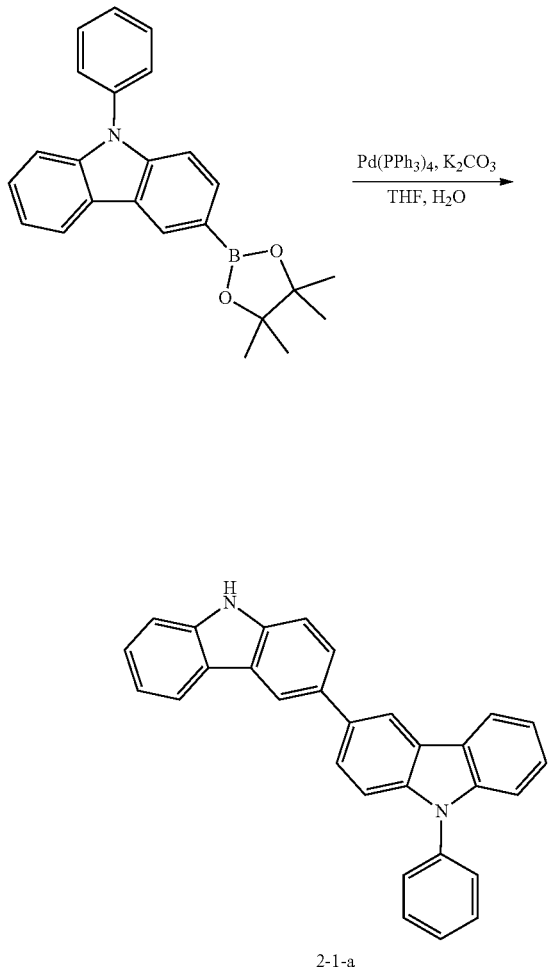

1-12

Compound 1-12-a (10.0 g, 14.0 mmol), PtO$_2$ (1.0 g, 4.2 mmol), and 70 ml of D$_2$O were placed in a shaker tube, and then the tube was sealed and heated at 250° C. and 600 psi for 12 hours. When the reaction was completed, chloroform was added, and the reaction solution was transferred to a separatory funnel for extraction. The extract was dried with MgSO$_4$, and concentrated. The sample was purified by silica gel column chromatography, and then 3.8 g (yield 36%) of Compound 1-12 was prepared through sublimation purification.

MS[M+H]$^+$=750

Preparation Example 2-1: Synthesis of Compound 2-1

Step 1) Synthesis of Compound 2-1-a

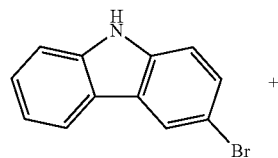

2-1-a 3-bromo-9H-carbazole (15.0 g, 60.9 mmol) and 9-phenyl-3-(4,4,5,5-tetramethyl-1,3,2-dioxaborolan-2-yl)-9H-carbazole (24.8 g, 67.0 mmol) were added to 300 ml of THF under a nitrogen atmosphere, and the mixture was stirred and refluxed. Then, potassium carbonate (33.7 g, 243.8 mmol) was dissolved in 101 ml of water, and then added thereto. Thereafter, it was stirred sufficiently, followed by adding tetrakis(triphenylphosphine)-palladium(0) (2.1 g, 1.8 mmol). After 10 hours of reaction, it was cooled to room temperature and the organic layer was separated from the water layer, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography to prepare 15.2 g (yield 61%) of Compound 2-1-a.

MS[M+H]$^+$=410

Step 2) Synthesis of Compound 2-1

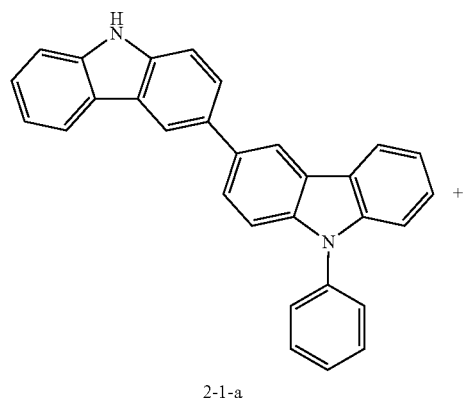

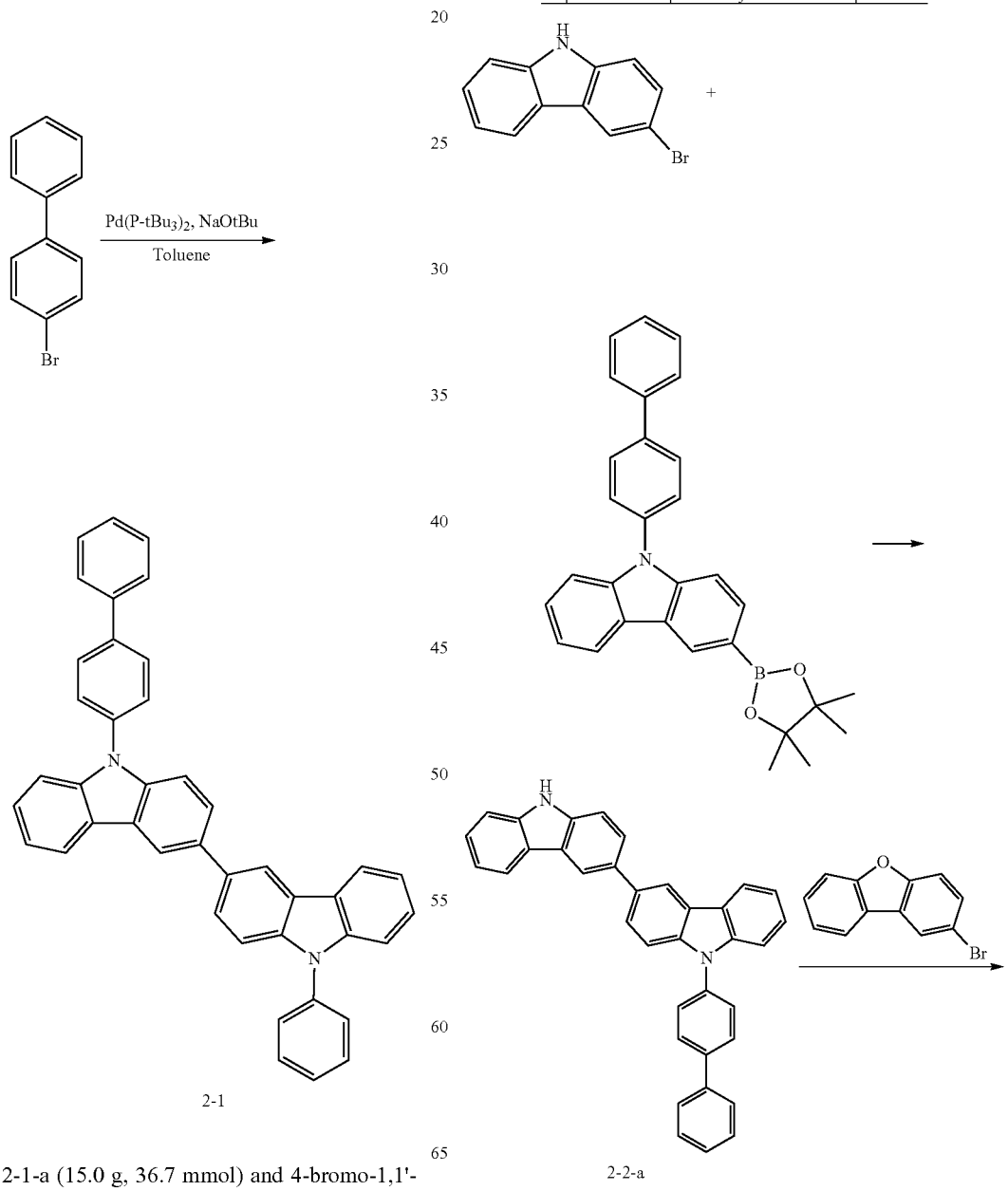

Compound 2-1-a (15.0 g, 36.7 mmol) and 4-bromo-1,1'-biphenyl (9.4 g, 40.4 mmol) were added to 300 ml of toluene under a nitrogen atmosphere, and the mixture was stirred and refluxed. Then, sodium tert-butoxide (5.3 g, 55.1 mmol) and bis(tri-tert-butylphosphine)palladium(0) (0.6 g, 1.1 mmol) were added thereto. After 10 hours of reaction, it was cooled to room temperature and the organic layer was separated using chloroform and water, and then the organic layer was distilled. Then, this was dissolved again in chloroform, and washed twice with water. Thereafter, the organic layer was separated, treated with anhydrous magnesium sulfate, stirred, then filtered, and the filtrate was distilled under reduced pressure. The concentrated compound was purified by silica gel column chromatography, and then 9.7 g (yield 47%) of Compound 2-1 was prepared through sublimation purification.

MS[M+H]$^+$=562

Preparation Example 2-2: Synthesis of Compound 2-2

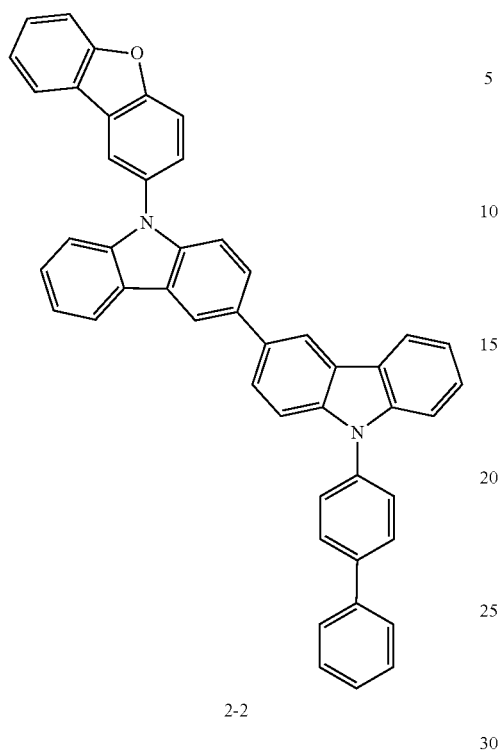
2-2
Compound 2-2 was prepared in the same manner as in the preparation method of Compound 2-1, except that 9-phenyl-3-(4,4,5,5-tetramethyl-1,3,2-dioxaborolan-2-yl)-9H-carbazole was changed to 9-([1,1'-biphenyl]-4-yl)-3-(4,4,5,5-tetramethyl-1,3,2-dioxaborolan-2-yl)-9H-carbazole and 4-bromo-1,1'-biphenyl was changed to 2-bromodibenzo[b,d]furan in Preparation Example 2-1.
MS[M+H]$^+$=652
Preparation Example 2-3: Synthesis of Compound 2-3
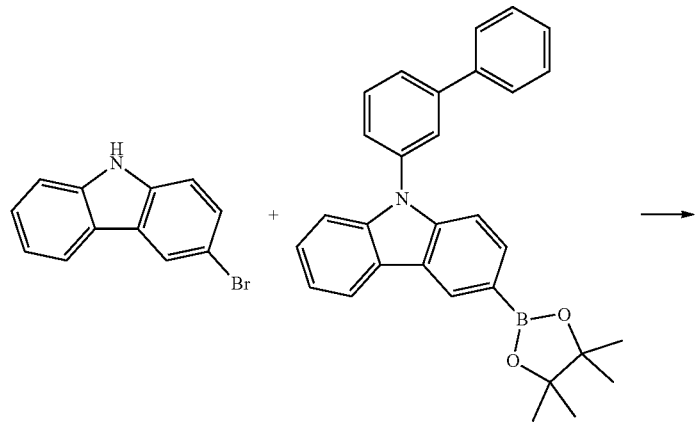

-continued

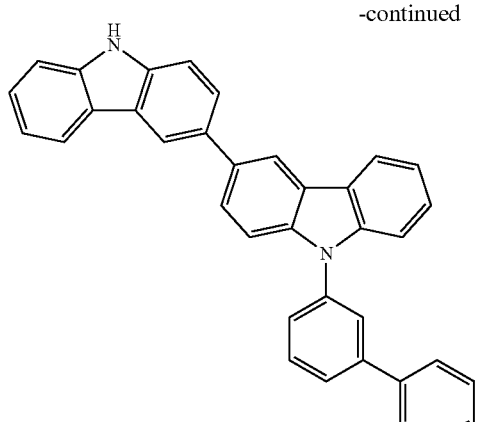

2-3-a

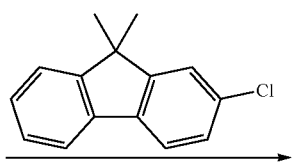

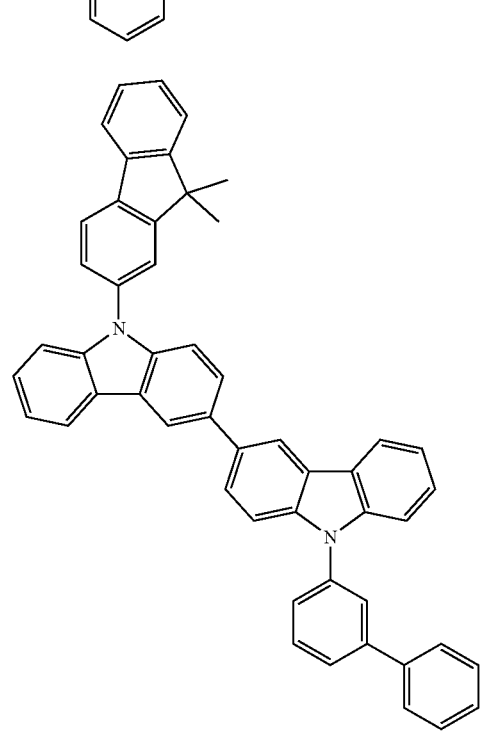

2-3

Compound 2-3 was prepared in the same manner as in the preparation method of Compound 2-1, except that 9-phenyl-3-(4,4,5,5-tetramethyl-1,3,2-dioxaborolan-2-yl)-9H-carbazole was changed to 9-([1,1'-biphenyl]-3-yl)-3-(4,4,5,5-tetramethyl-1,3,2-dioxaborolan-2-yl)-9H-carbazole and 4-bromo-1,1'-biphenyl was changed to 2-chloro-9,9-dimethyl-9H-fluorene in Preparation Example 2-1.

MS[M+H]$^+$=678

Example 1: Preparation of Organic Light Emitting Device

A glass substrate on which ITO (Indium Tin Oxide) was coated as a thin film to a thickness of 1400 Å was put into distilled water in which a detergent was dissolved, and ultrasonically cleaned. At this time, a product manufactured by Fischer Co. was used as the detergent, and distilled water filtered twice using a filter manufactured by Millipore Co. was used as the distilled water. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma and then transferred to a vacuum depositor.

95 wt % of the following compound HT-A and 5 wt % of the following compound PD were thermally vacuum-deposited on the prepared ITO transparent electrode to a thickness of 100 Å to form a hole injection layer. Then, only the following compound HT-A was deposited to a thickness of 1150 Å to form a hole transport layer. The following compound HT-B was thermally vacuum-deposited thereon to a thickness of 450 Å as an electron blocking layer.

Thereafter, host materials of Compound 1-1 prepared in the Preparation Example 1-1 and Compound 2-1 prepared in the Preparation Example 2-1, and a dopant material of the following compound GD were vacuum-deposited on the electron blocking layer at a weight ratio of 92:8 to form a light emitting layer. Herein, a weight ratio of the Compound 1-1 to the Compound 2-1 of the host materials was 30:70.

Then, the following compound ET-A was vacuum-deposited to a thickness of 50 Å as a hole blocking layer. Subsequently, the following compounds ET-B and Liq were thermally vacuum-deposited at a ratio 1:1 to a thickness of 300 Å as an electron transport layer, and then Yb was vacuum-deposited to a thickness of 10 Å as an electron injection layer.

Magnesium and silver were deposited on the electron injection layer at a ratio of 1:4 to a thickness of 150 Å to form a cathode, thereby manufacturing an organic light emitting device.

GD
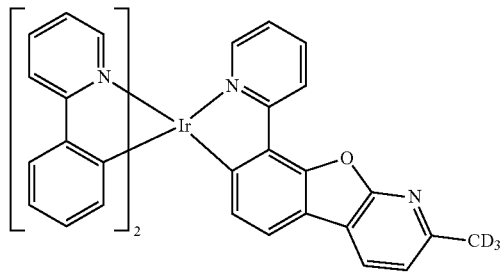

HT-A
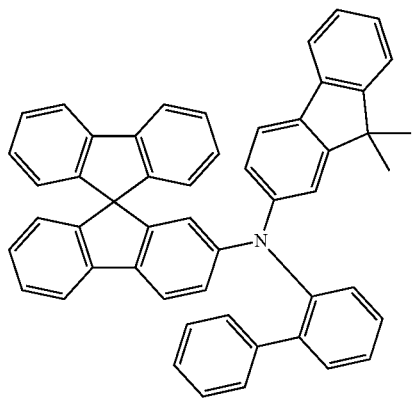

ET-A
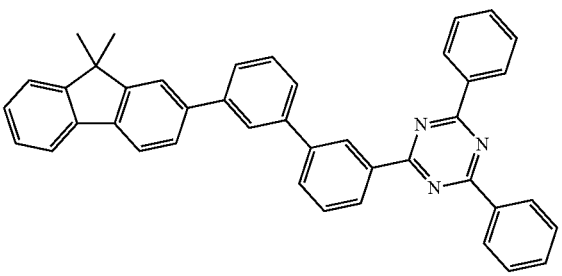

PD
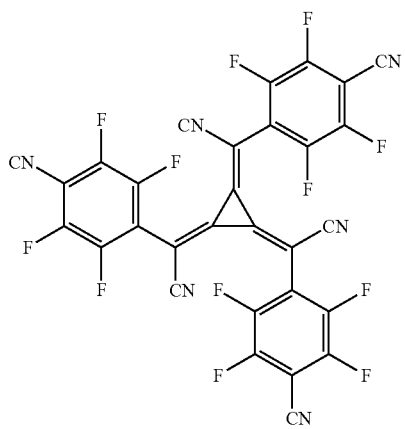

ET-B

Liq
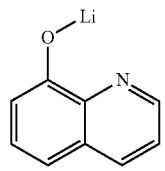

HT-B
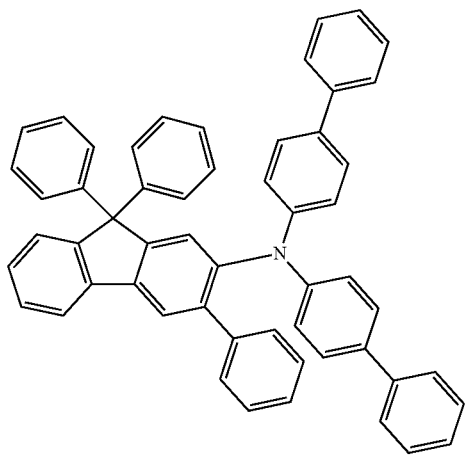

In the above process, the deposition rate of the organic material was maintained at 0.4 to 0.7 Å/sec, the deposition rate of magnesium and silver was maintained at 2 Å/sec, and the degree of vacuum during the deposition was maintained at $2\times10^{-7}$ to $5\times10^{-6}$ torr, thereby manufacturing an organic light emitting device.

Example 2 to Example 24 and Comparative Example 1 to Comparative Example 14

Organic light emitting devices of Examples 2 to 24 and Comparative Examples 1 to 14 were respectively manufactured in the same manner as in the Example 1, except that the host materials were changed as shown in Table 1 below. Herein, when a mixture of two types of compounds was used as the host, a weight ratio between the host compounds was described in parentheses.

The compounds used in the above Examples and Comparative Examples are as follows:
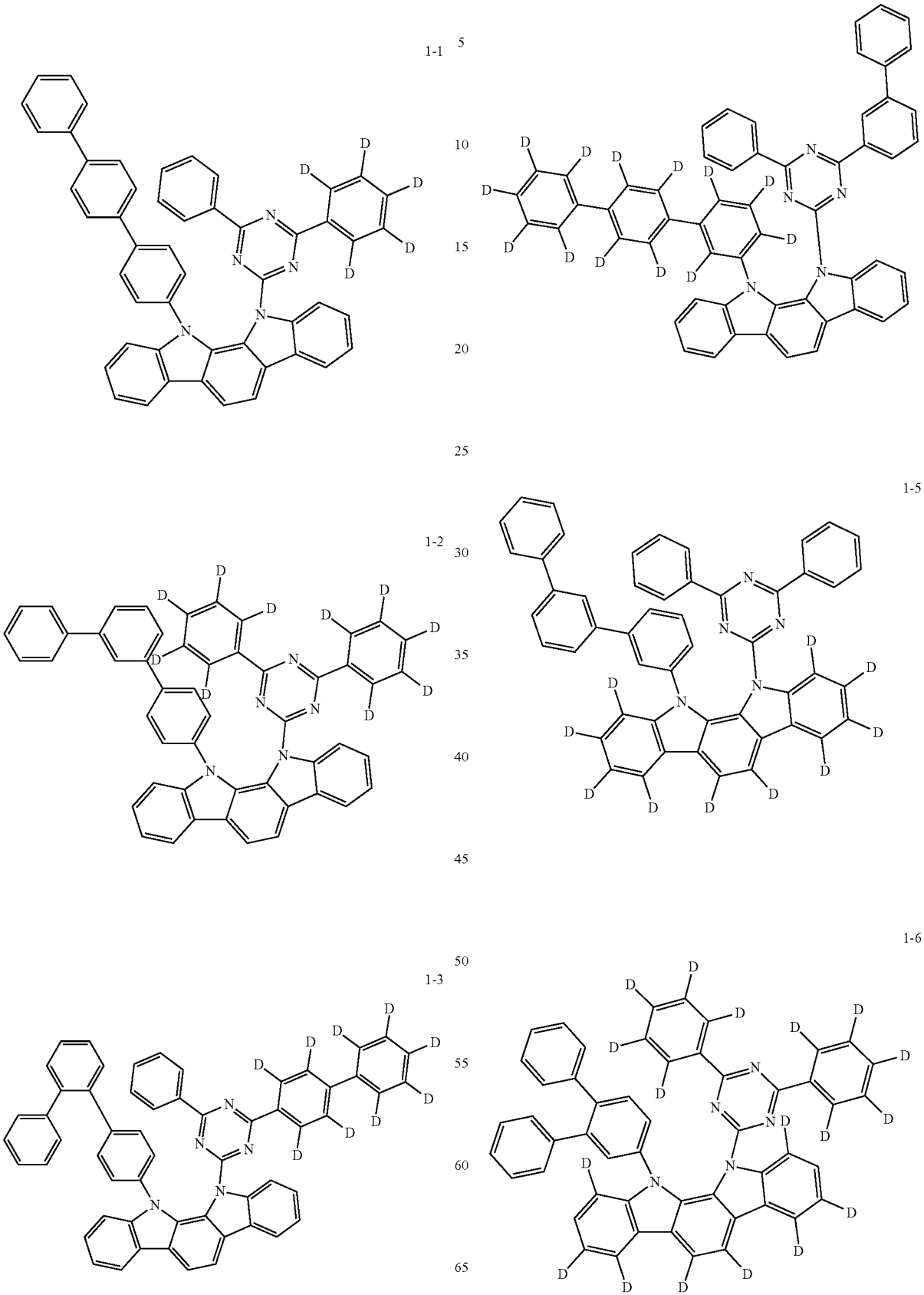

201
-continued
1-7
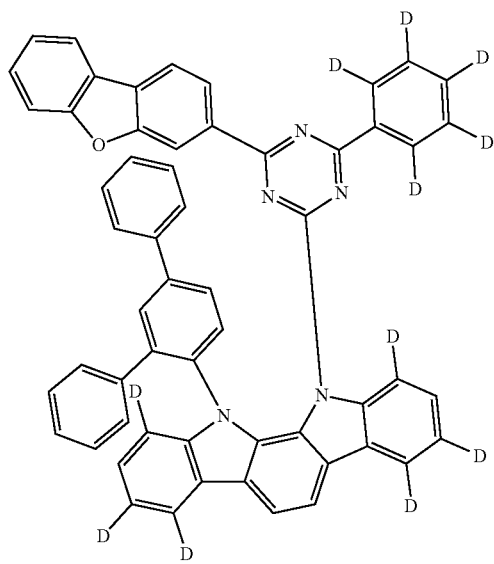
1-8
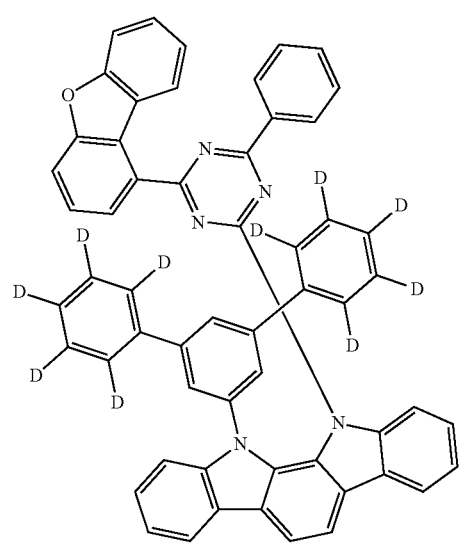
1-9
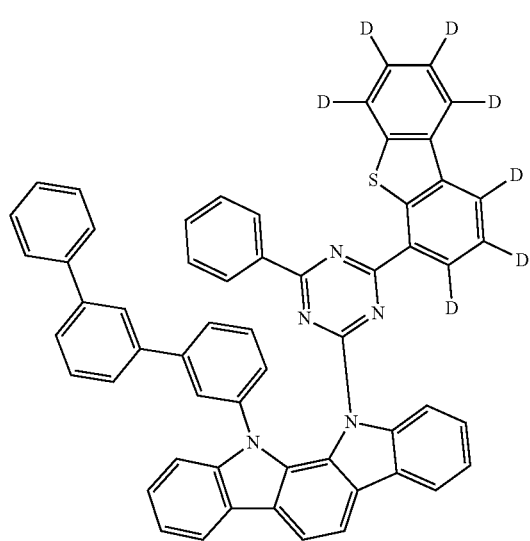
202
-continued
1-10
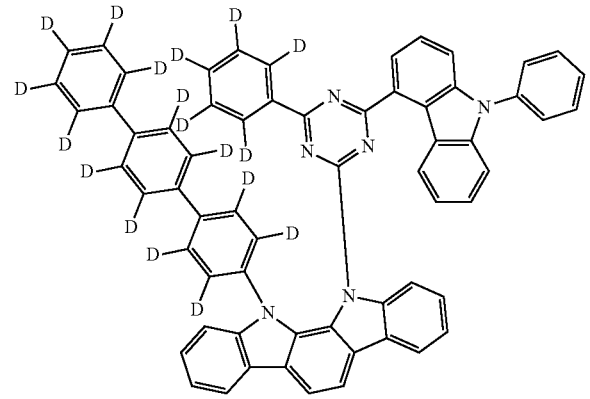
1-11
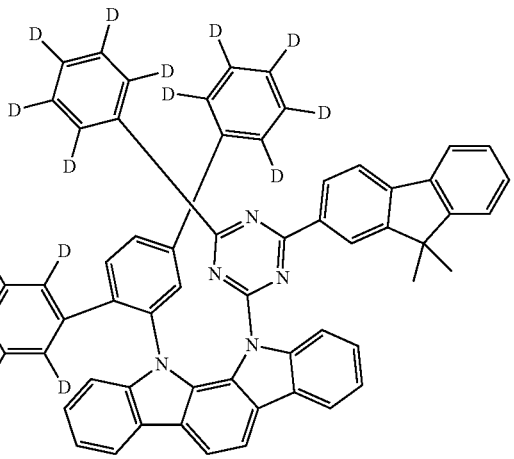
1-12
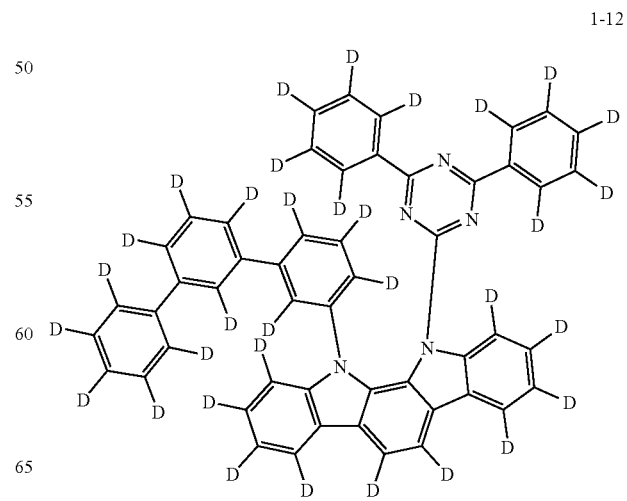

203
-continued
2-1
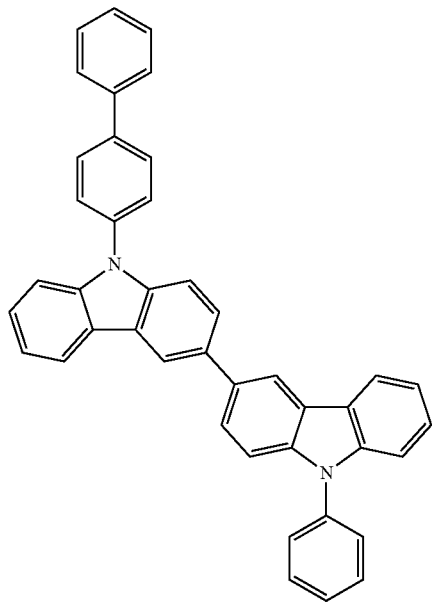
2-2
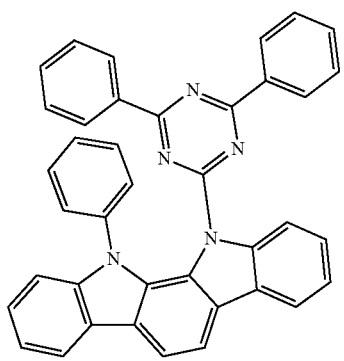
204
-continued
2-3
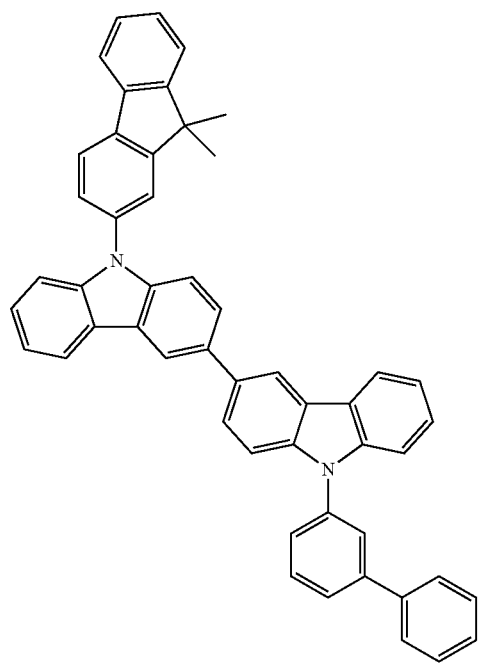
GH-A
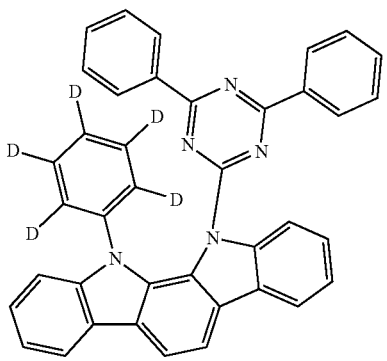
GH-B

GH-C

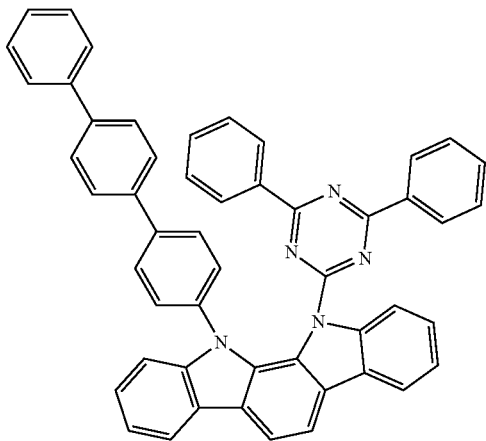

Experimental Example 1: Evaluation of Device Characteristics

The organic light emitting devices prepared in the above Examples 1 to 24 and Comparative Examples 1 to 14 were heat-treated in an oven at 120° C. for 30 minutes, and then taken out. Then, the voltage, efficiency, and lifespan (T95) were measured by applying a current, and the results are shown in Table 1 below. Herein, the voltage and efficiency were measured by applying a current density of 10 mA/cm$^2$, and T95 means the time taken (hr) until the initial luminance decreases to 95% at a current density of 20 mA/cm$^2$.

TABLE 1

| | | @ 10 mA/cm$^2$ | | @ 20 mA/cm$^2$ |
|---|---|---|---|---|
| | Host material | Voltage (V) | Efficiency (cd/A) | Lifespan (T95, hr) |
| Example 1 | Compound 1-1: Compound 2-1 (30:70) | 4.11 | 71.4 | 132 |
| Example 2 | Compound 1-2: Compound 2-1 (30:70) | 4.10 | 71.1 | 139 |
| Example 3 | Compound 1-3: Compound 2-1 (30:70) | 4.11 | 71.2 | 143 |
| Example 4 | Compound 1-4: Compound 2-1 (30:70) | 4.13 | 71.0 | 149 |
| Example 5 | Compound 1-5: Compound 2-1 (30:70) | 4.12 | 71.3 | 143 |
| Example 6 | Compound 1-6: Compound 2-1 (30:70) | 4.09 | 71.7 | 154 |
| Example 7 | Compound 1-7: Compound 2-1 (30:70) | 4.21 | 72.4 | 148 |
| Example 8 | Compound 1-8: Compound 2-1 (30:70) | 4.23 | 72.3 | 139 |
| Example 9 | Compound 1-9: Compound 2-1 (30:70) | 4.24 | 72.1 | 138 |
| Example 10 | Compound 1-10: Compound 2-1 (30:70) | 4.22 | 72.2 | 149 |
| Example 11 | Compound 1-11: Compound 2-1 (30:70) | 4.18 | 71.8 | 137 |
| Example 12 | Compound 1-12: Compound 2-1 (30:70) | 4.12 | 71.3 | 160 |
| Example 13 | Compound 1-1: Compound 2-2 (30:70) | 4.08 | 70.3 | 120 |
| Example 14 | Compound 1-3: Compound 2-2 (30:70) | 4.08 | 70.1 | 131 |
| Example 15 | Compound 1-5: Compound 2-2 (30:70) | 4.09 | 70.2 | 131 |
| Example 16 | Compound 1-7: Compound 2-2 (30:70) | 4.18 | 71.3 | 136 |
| Example 17 | Compound 1-9: Compound 2-2 (30:70) | 4.21 | 71.0 | 126 |
| Example 18 | Compound 1-11: Compound 2-2 (30:70) | 4.15 | 70.7 | 125 |
| Example 19 | Compound 1-2: Compound 2-3 (30:70) | 3.97 | 71.7 | 132 |
| Example 20 | Compound 1-4: Compound 2-3 (30:70) | 4.00 | 71.6 | 142 |
| Example 21 | Compound 1-6: Compound 2-3 (30:70) | 3.96 | 72.3 | 147 |
| Example 22 | Compound 1-8: Compound 2-3 (30:70) | 4.10 | 72.9 | 132 |
| Example 23 | Compound 1-10: Compound 2-3 (30:70) | 4.09 | 72.8 | 142 |
| Example 24 | Compound 1-12: Compound 2-3 (30:70) | 3.99 | 71.9 | 153 |
| Comparative Example 1 | Compound 1-1 | 5.70 | 58.5 | 72 |
| Comparative Example 2 | Compound 1-4 | 5.74 | 57.9 | 84 |
| Comparative Example 3 | Compound 1-7 | 5.90 | 59.6 | 86 |
| Comparative Example 4 | Compound 1-10 | 5.93 | 59.1 | 85 |
| Comparative Example 5 | GH-A | 6.32 | 38.1 | 29 |
| Comparative Example 6 | GH-B | 6.32 | 38.2 | 38 |
| Comparative Example 7 | GH-C | 5.70 | 58.4 | 46 |
| Comparative Example 8 | GH-A:Compound 2-1 (30:70) | 5.31 | 56.3 | 62 |
| Comparative Example 9 | GH-B:Compound 2-1 (30:70) | 5.32 | 56.3 | 79 |
| Comparative Example 10 | GH-C:Compound 2-1 (30:70) | 4.11 | 71.1 | 89 |
| Comparative Example 11 | GH-B:Compound 2-2 (30:70) | 5.28 | 55.0 | 68 |
| Comparative Example 12 | GH-B:Compound 2-3 (30:70) | 5.22 | 55.6 | 73 |
| Comparative Example 13 | GH-C:Compound 2-2 (30:70) | 4.08 | 70.0 | 79 |
| Comparative Example 14 | GH-C:Compound 2-3 (30:70) | 4.03 | 70.4 | 82 |

As shown in Table 1 above, the organic light emitting device of the Examples which simultaneously use the first compound of Chemical Formula 1 and the second compound of Chemical Formula 2 as the host materials in the light emitting layer exhibited equivalent or superior emission efficiency, low driving voltage and significantly improved lifespan characteristics, as compared with the organic light emitting devices of Comparative Examples which either employ only one of the compounds of Chemical Formulae 1 and 2, or do not employ both of them.

Specifically, referring to Comparative Examples 8, 9, 11 and 12, it can be seen that the device employing the first compound had improved characteristics in all of the driving voltage, light emitting efficiency, and lifespan as compared with the device employing the Compound GH-A and GH-B in which a terphenylyl group is not substituted on one of the N atoms of an indolocarbazole core. This is considered to be because the compound not including the terphenylyl group was damaged by heat during heat treatment, thereby having deteriorated device characteristics. In addition, referring to Comparative Examples 10, 13 and 14, the device employing the first compound exhibited significantly longer lifespan as compared with the device employing the Compound GH-C having a terphenylyl substituent but not substituted with deuterium. This is considered to be because the radical anion state of the host material was unstable when deuterium (D) was not included in the molecule, and thus the exciplex formed in the light emitting layer was in an unstable state.

Accordingly, when the first compound and the second compound are simultaneously employed as the host materials of the organic light emitting device, it was confirmed that the driving voltage, emission efficiency, and/or lifespan characteristics of the organic light emitting device can be improved. In consideration of the fact that the emission efficiency and lifespan characteristics of the organic light emitting device generally have a trade-off relationship with each other, it can be seen that the organic light emitting device employing the combination of the compounds of the present disclosure exhibits a significantly improved device characteristic as compared with the devices of Comparative Examples.

<Description of Symbols>

| | |
|---|---|
| 1: substrate | 2: Anode |
| 3: Light emitting layer | 4: Cathode |
| 5: Hole injection layer | 6: Hole transport layer |
| 7: Electron blocking layer | 8: Hole blocking layer |
| 9: Electron transport layer | 10: Electron injection layer |

The invention claimed is:

1. An organic light emitting device comprising:
an anode;
a cathode provided to face the anode; and
a light emitting layer provided between the anode and the cathode;
wherein the light emitting layer comprises a first compound of the following Chemical Formula 1 and a second compound of the following Chemical Formula 2:

<Chemical Formula 1>

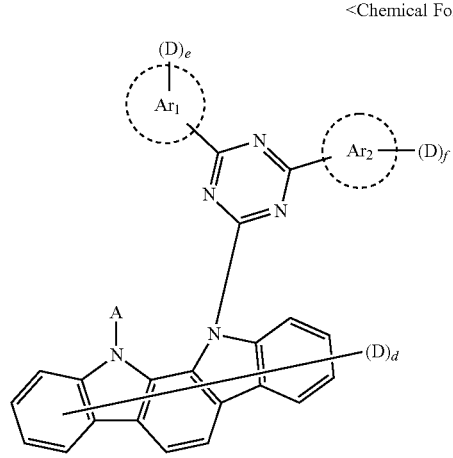

wherein in Chemical Formula 1:
A is the following Chemical Formula 1a or 1b:

<Chemical Formula 1a>

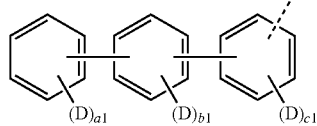

-continued

<Chemical Formula 1b>

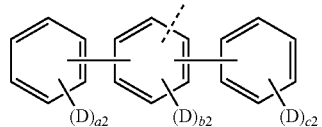

wherein in Chemical Formulae 1a and 1b:

a1, a2 and c2 are each independently an integer of 0 to 5;

b1 and c1 are each independently an integer of 0 to 4;

b2 is an integer of 0 to 3; and $Ar_1$ and $Ar_2$ are each independently a $C_{6-60}$ aromatic ring or a $C_{2-60}$ heteroaromatic ring containing at least one heteroatom of N, O and S;

wherein $Ar_1$ and $Ar_2$ are unsubstituted, or substituted with at least one substituent selected from the group consisting of $C_{1-60}$ alkyl, $C_{6-60}$ aryl, and $C_{2-60}$ heteroaryl containing at least one heteroatom of N, O and S;

D is deuterium; and d, e and f are each independently an integer of 0 to 10, provided that a1+b1+c1+d+e+f is 1 or more; or a2+b2+c2+d+e+f is 1 or more;

<Chemical Formula 2>

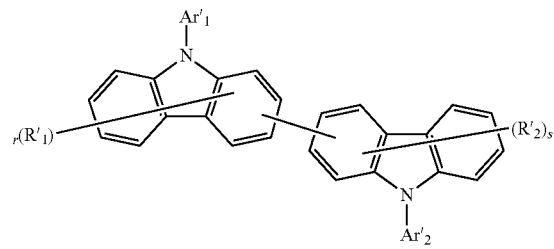

wherein in Chemical Formula 2:

$Ar'_1$ and $Ar'_2$ are each independently substituted or unsubstituted $C_{6-60}$ aryl or substituted or unsubstituted $C_{2-60}$ heteroaryl containing at least one heteroatom of N, O and S;

$R'_1$ and $R'_2$ are each independently hydrogen, deuterium, $C_{1-60}$ alkyl, $C_{6-60}$ aryl; or $C_{2-60}$ heteroaryl containing at least one heteroatom of N, O and S; and r and s are each independently an integer of 0 to 7.

2. The organic light emitting device of claim 1, wherein the first compound is the following Chemical Formula 1A or 1B;

<Chemical Formula 1A>

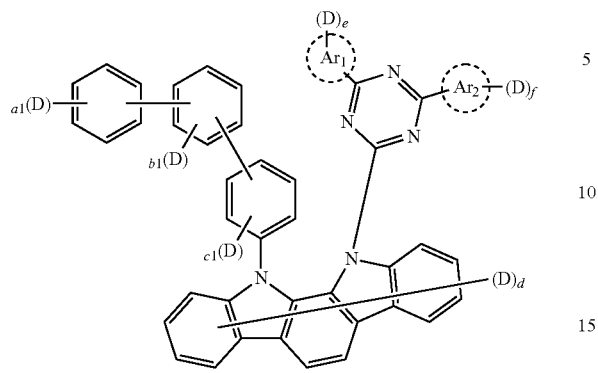

wherein in Chemical Formula 1A:
Ar$_1$ and Ar$_2$ are each independently a benzene ring, a biphenyl ring, a terphenyl ring, a fluorene ring, a carbazole ring, or a dibenzothiophenyl ring,
wherein Ar$_1$ and Ar$_2$ are unsubstituted, or substituted with 1 or 2 substituents selected from the group consisting of C$_{1-10}$ alkyl and C$_{6-20}$ aryl;
a1+b1+c1+d+e+f is 1 to 43; and
a1, b1, c1, d, e, and f are as defined in claim 1;

<Chemical Formula 1B>

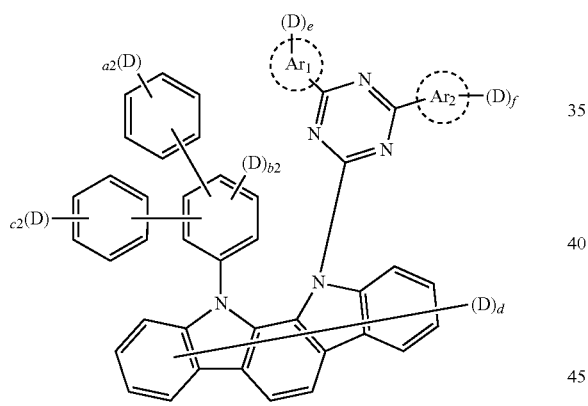

wherein in Chemical Formula 1B:
Ar$_1$ and Ar$_2$ are each independently a benzene ring, a biphenyl ring, a terphenyl ring, a fluorene ring, a carbazole ring, or a dibenzothiophenyl ring,
wherein Ar$_1$ and Ar$_2$ are unsubstituted, or substituted with 1 or 2 substituents selected from the group consisting of C$_{1-10}$ alkyl and C$_{6-20}$ aryl;
a2+b2+c2+d+e+f is 1 to 43; and
a2, b2, c2, d, e, and f are as defined in claim 1.

3. The organic light emitting device of claim 1, wherein Ar$_1$ is a benzene ring, and Ar$_2$-(D)$_f$ is any one selected from the group consisting of the following:

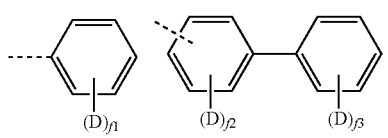

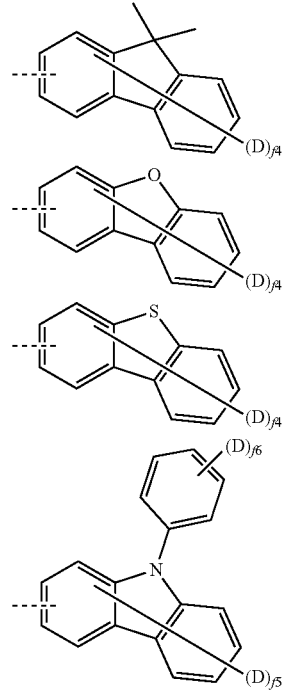

wherein in the above:
f1 is an integer of 0 to 5;
f2 is an integer of 0 to 4;
f3 is an integer of 0 to 5;
f4 is an integer of 0 to 7;
f5 is an integer of 0 to 7; and
f6 is an integer of 0 to 5.

4. The organic light emitting device of claim 1, wherein A is any one of Chemical Formulae 1a-1 to 1a-9 and Chemical Formulae 1b-1 to 1b-6:

1a-1

1a-2

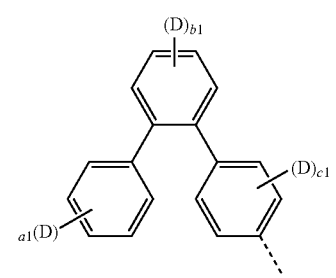
1a-3
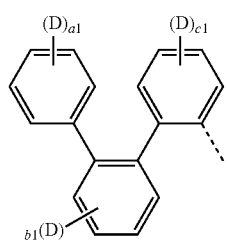
1a-9
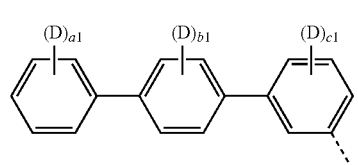
1a-4
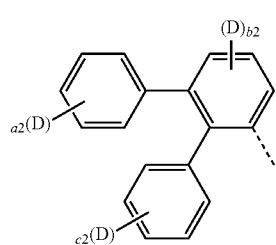
1b-1
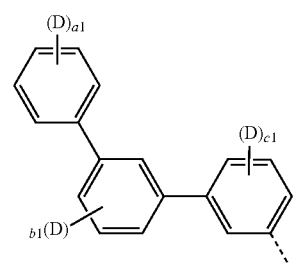
1a-5
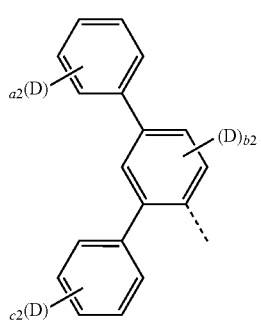
1b-2
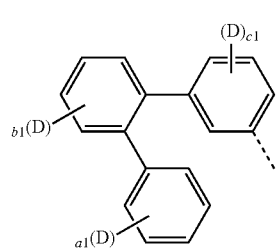
1a-6
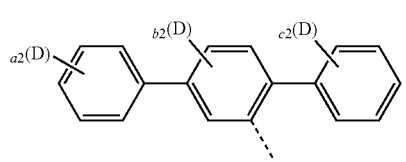
1b-3
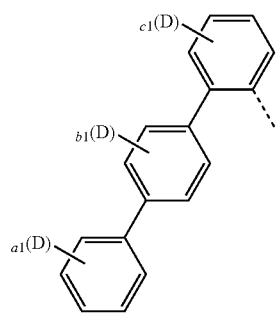
1a-7
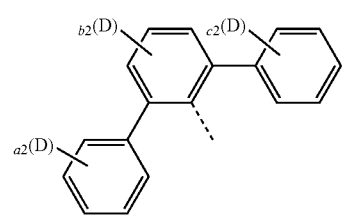
1b-4
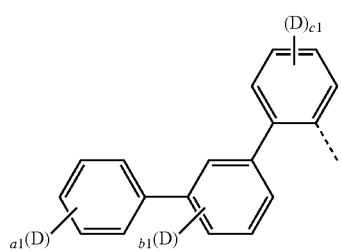
1a-8
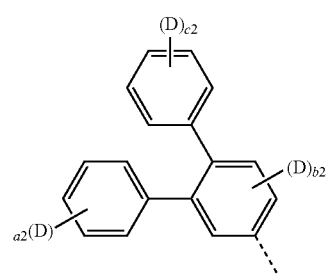
1b-5

1b-6
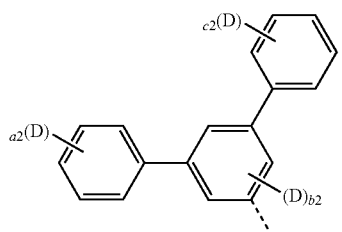
wherein in Chemical Formulae 1a-1 to 1a-9 and Chemical Formulae 1b-1 to 1b-6;
a1, b1, c1, a2, b2, c2, d, e, and f are as defined in claim 1.
5. The organic light emitting device of claim 1, wherein the first compound is any one compound selected from the group consisting of the following compounds:
H1-1-1
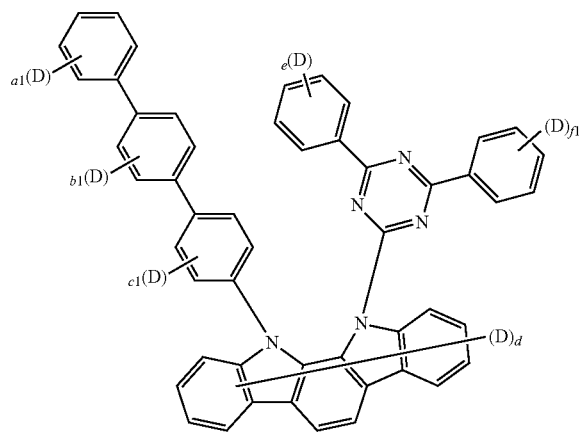
H1-1-2
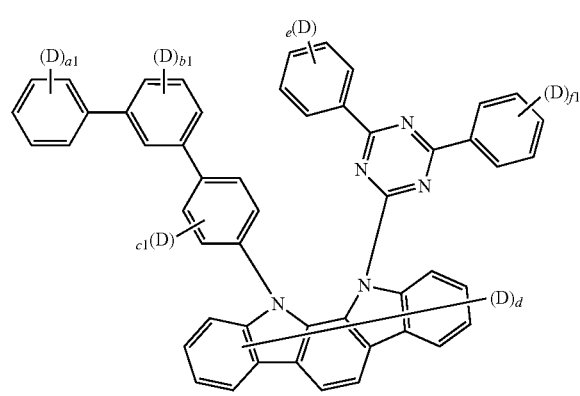
H1-1-3
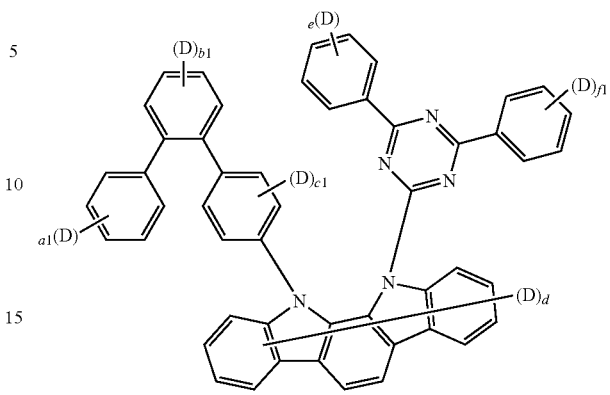
H1-1-4
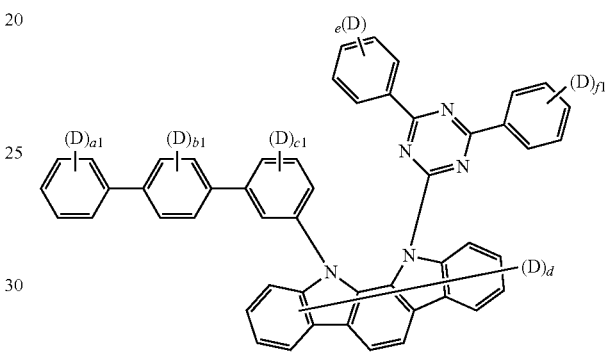
H1-1-5
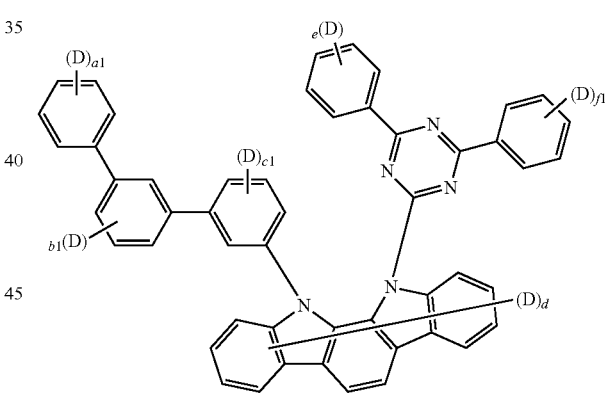
H1-1-6
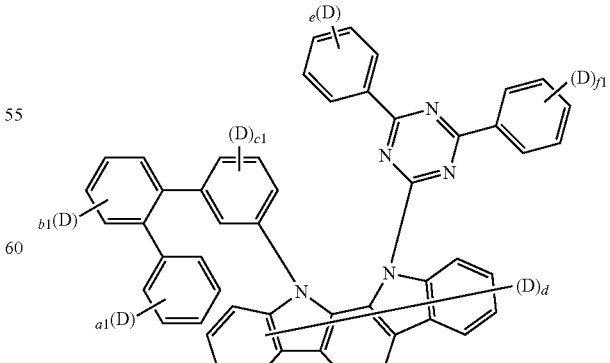

H1-1-7
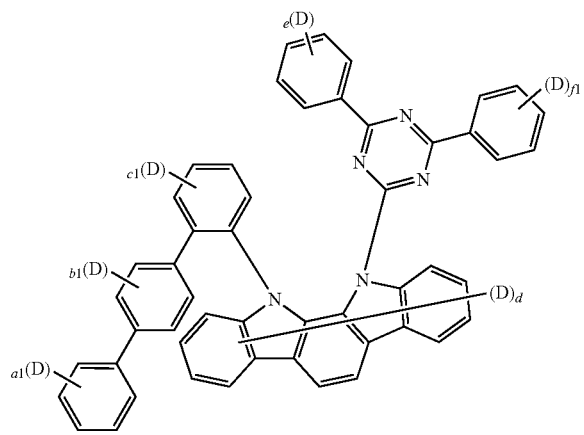
H1-1-8
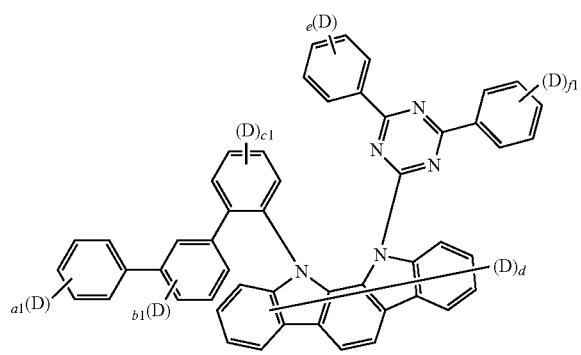
H1-1-9
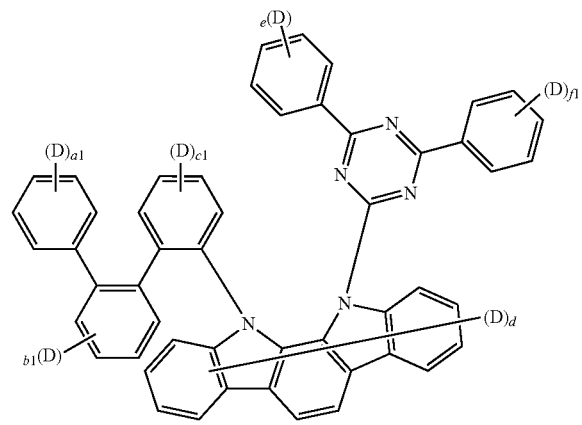
H1-1-10
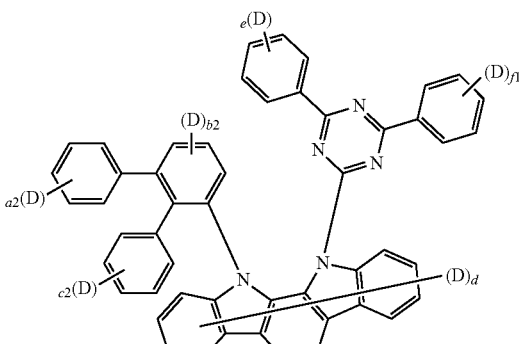
H1-1-11
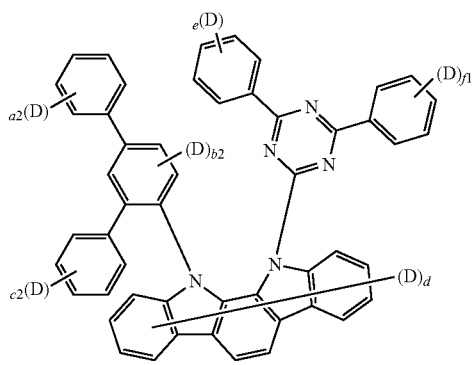
H1-1-12
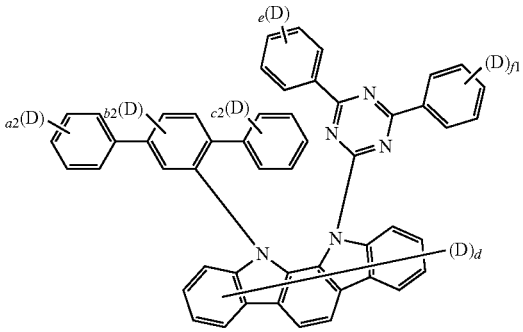
H1-1-13
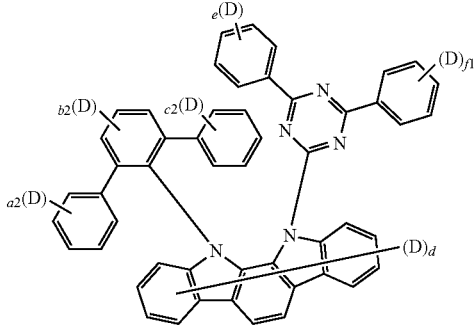
wherein in Chemical Formulae H1-1-1 to H1-1-9:
a1, b1, c1, and d are as defined in Chemical Formula 1,
e and f1 are each independently an integer of 0 to 5,
provided that a1+b1+c1+d+e+f1 is 1 to 33;

H1-1-14
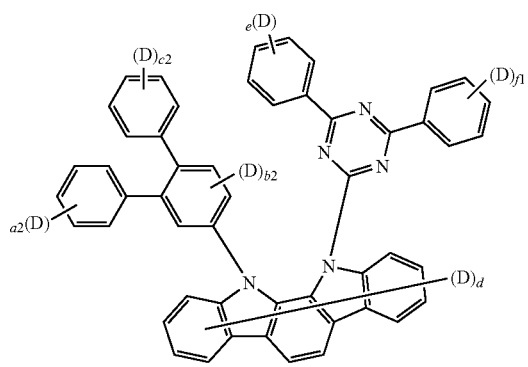
H1-1-15
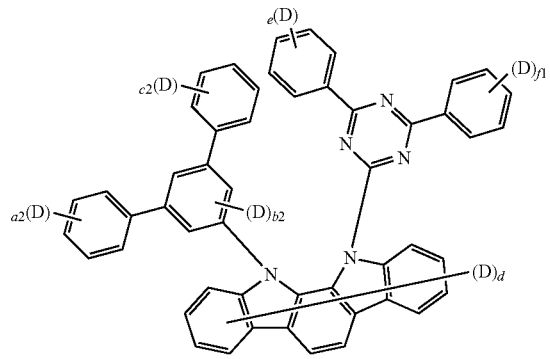
wherein in Chemical Formulae H1-1-10 to H1-1-15:
a2, b2, c2, and d are as defined in Chemical Formula 1, and
e and f1 are each independently an integer of 0 to 5,
provided that a2+b2+c2+d+e+f1 is 1 to 33;
H1-2-1
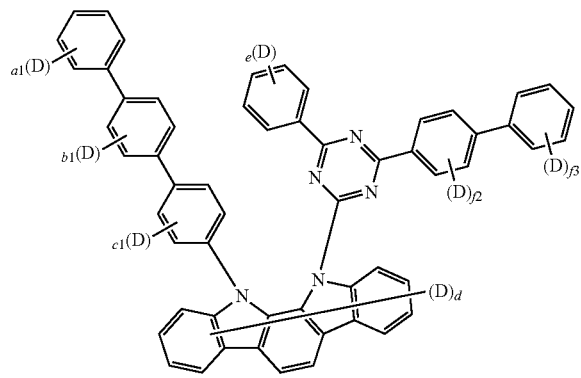
H1-2-2
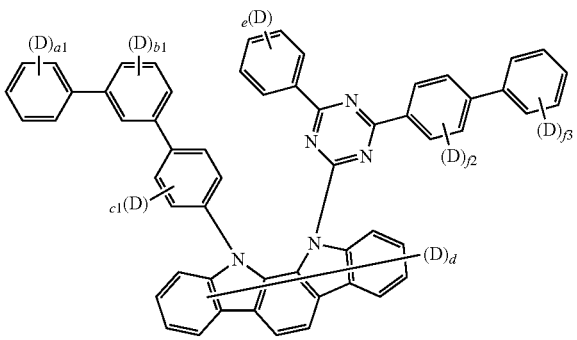
H1-2-3
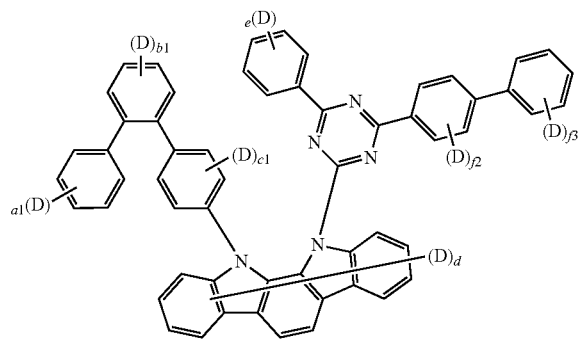

-continued
H1-2-4
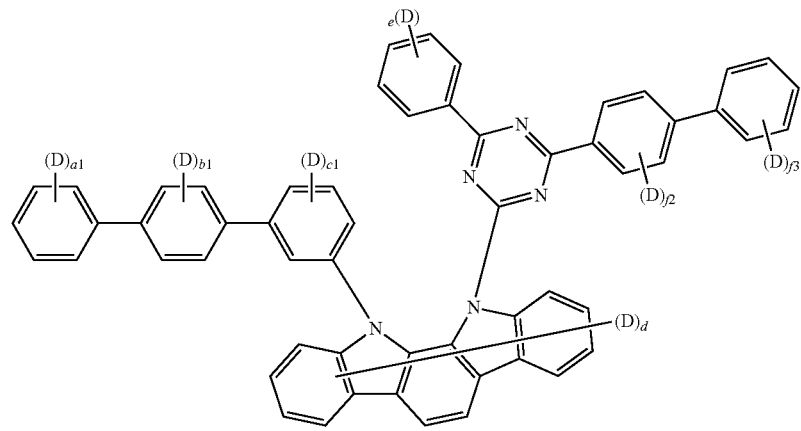
H1-2-5
H1-2-6
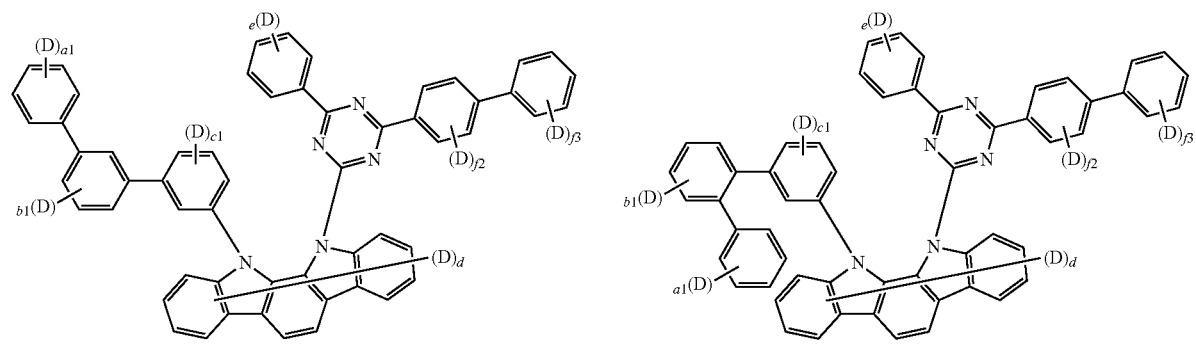
H1-2-7
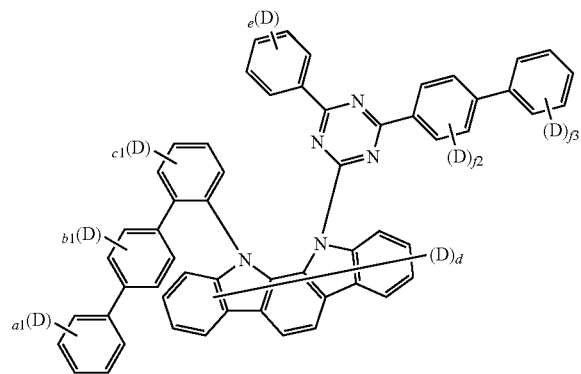
H1-2-8
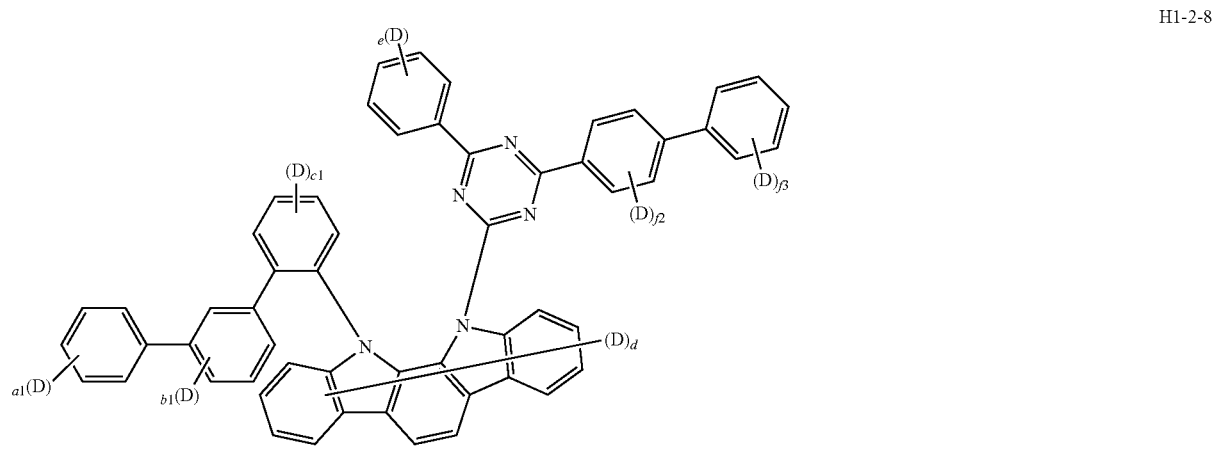

-continued
H1-2-9
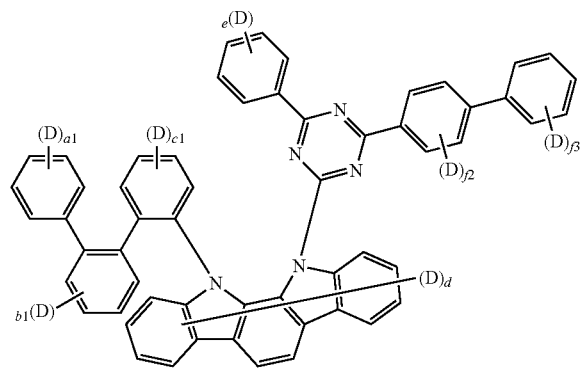
H1-3-1
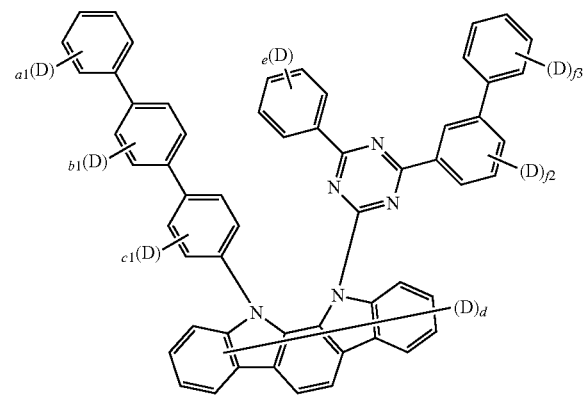
H1-3-2
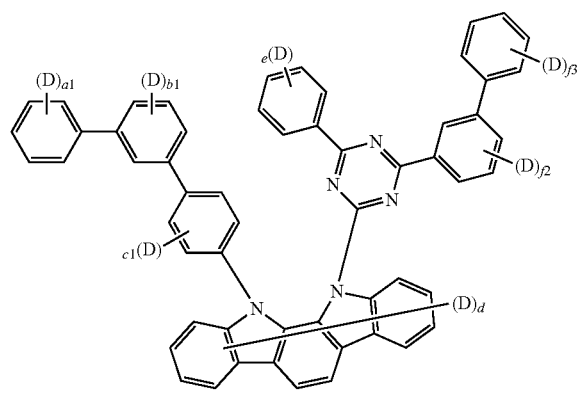
H1-3-3
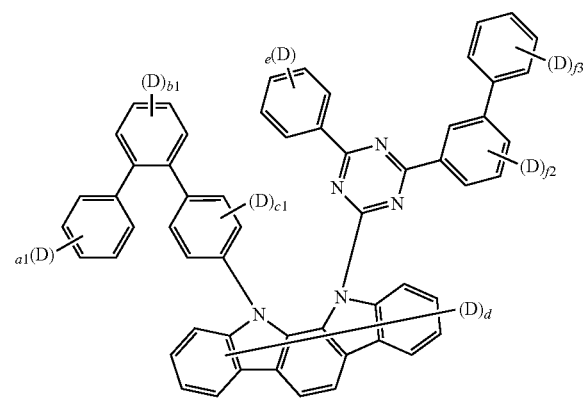
H1-3-4
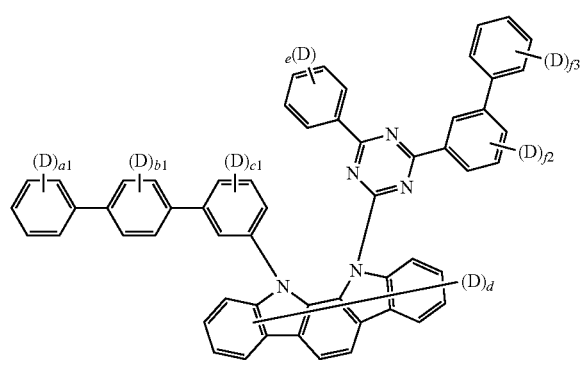
H1-3-5
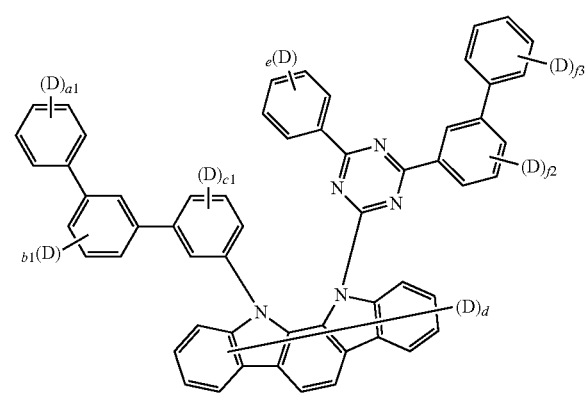

H1-3-6
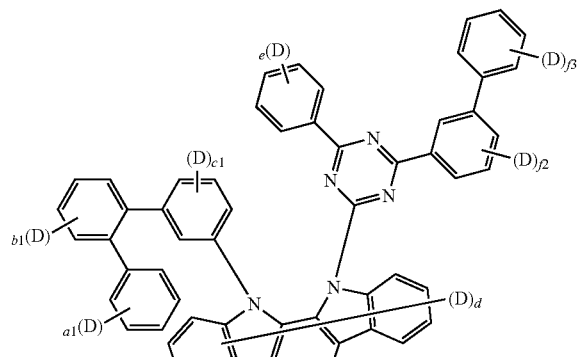
H1-3-7
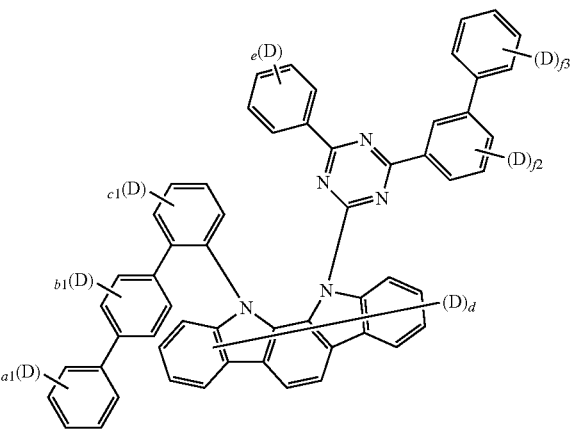
H1-3-8
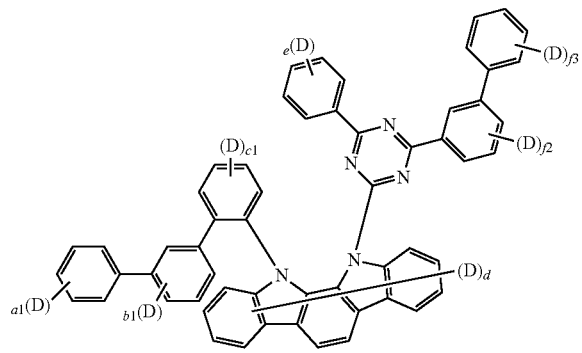
H1-3-9
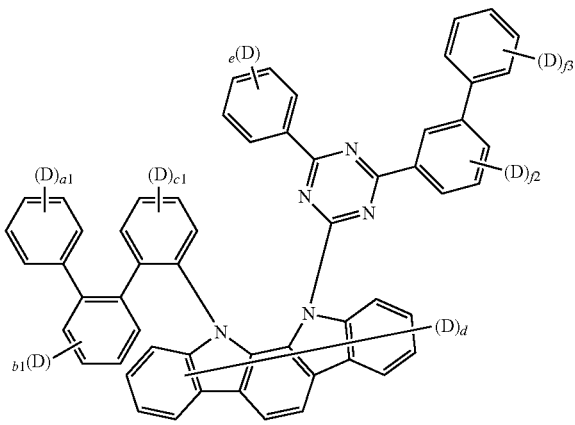
wherein in Chemical Formulae H1-2-1 to H1-2-9 and H1-3-1 to H1-3-9:
a1, b1, c1, and d are as defined in Chemical Formula 1,
e is an integer of 0 to 5,
f2 is an integer of 0 to 4,
f3 is an integer of 0 to 5, and
a1+b1+c1+d+e+f2+f3 is 1 to 37;
-continued
H1-2-10
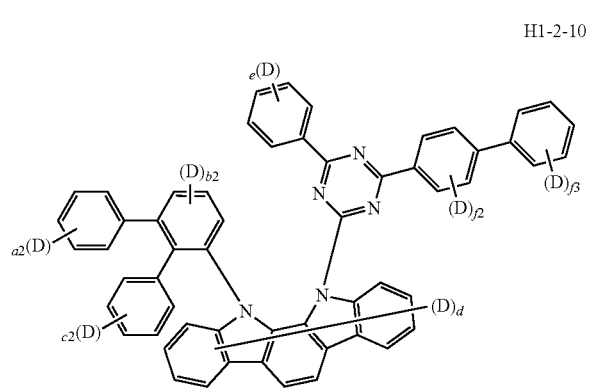
H1-2-11
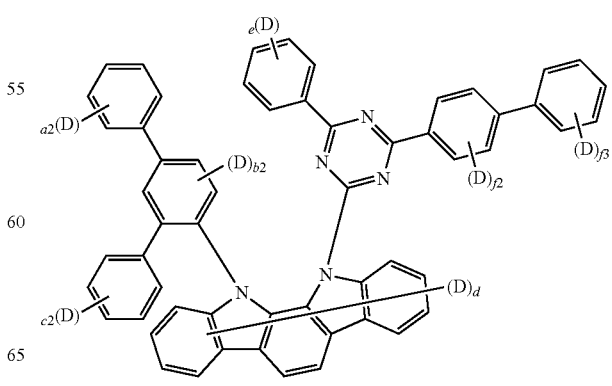

H1-2-12
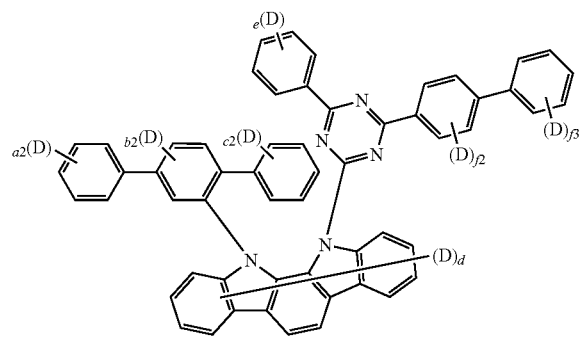
H1-2-13
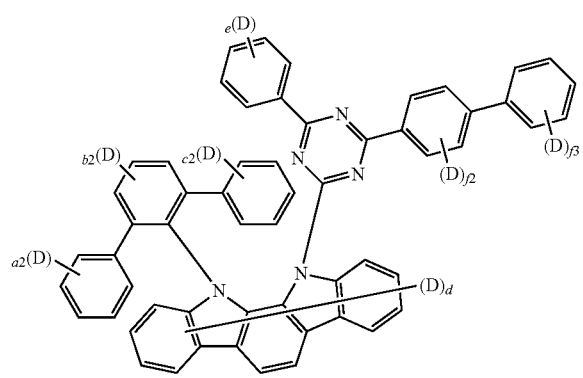
H1-2-14
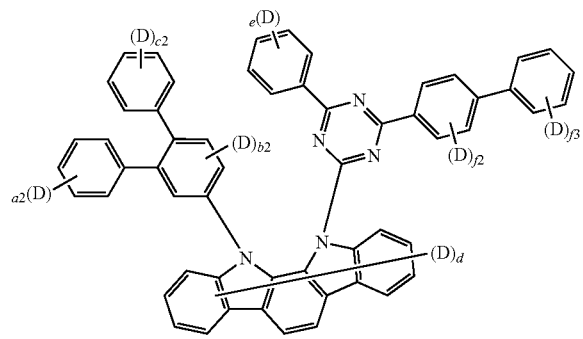
H1-2-15
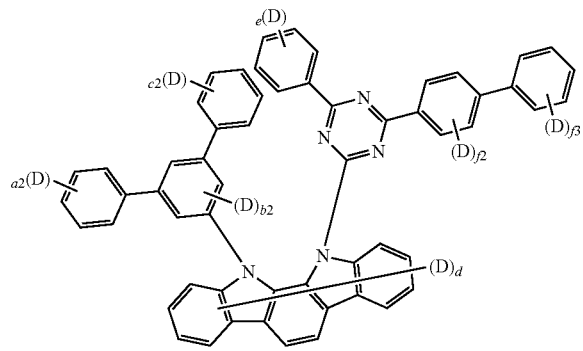
H1-3-10
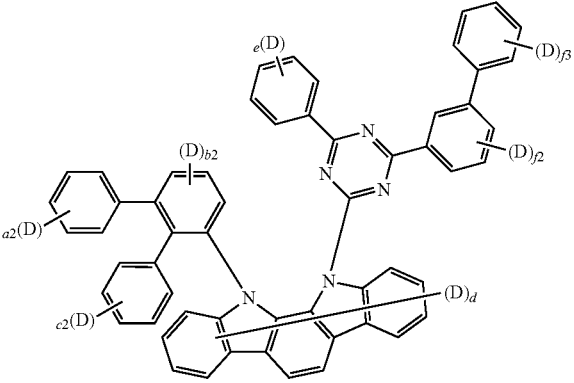
H1-3-11
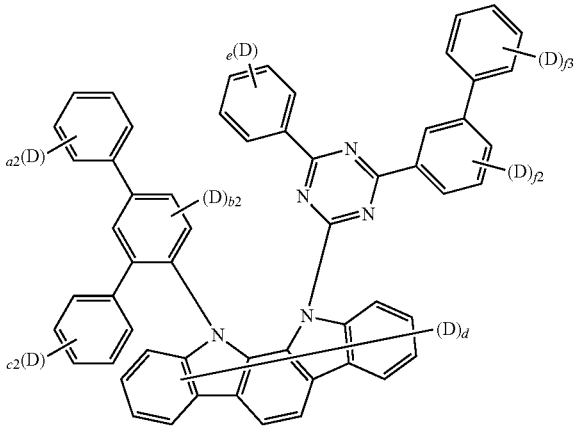
H1-3-12
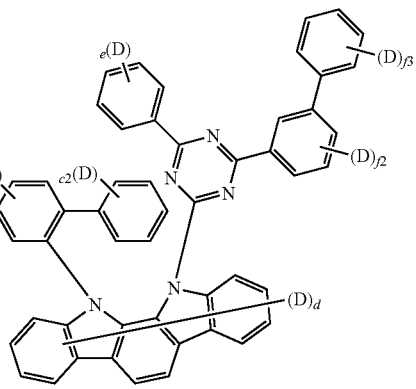

H1-3-13
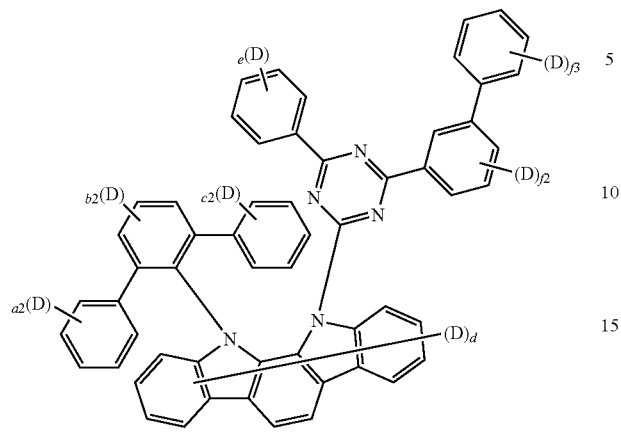
H1-3-14
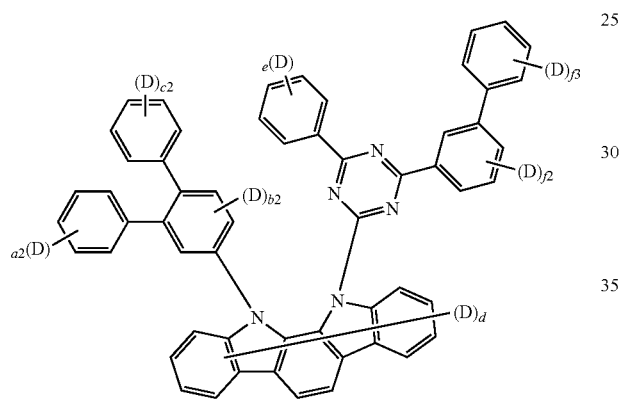
H1-3-15
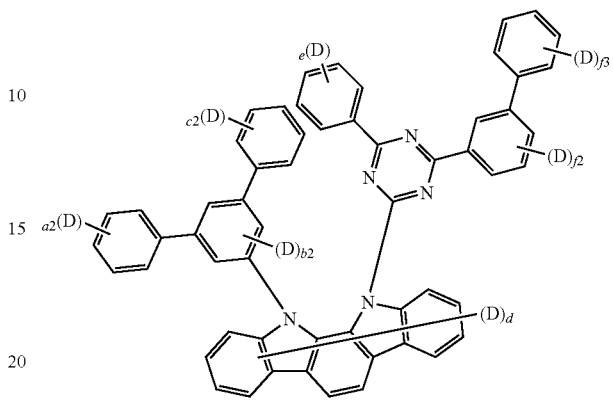
wherein in Chemical Formulae H1-2-10 to H1-2-15 and H1-3-10 to H1-3-15;
a2, b2, c2, and d are as defined in Chemical Formula 1,
e is an integer of 0 to 5,
f2 is an integer of 0 to 4,
f3 is an integer of 0 to 5, and
a2+b2+c2+d+e+f2+f3 is 1 to 37;
H1-4-1
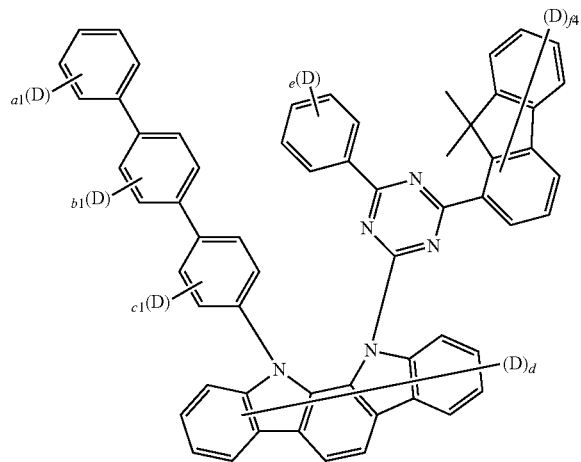
H1-4-2
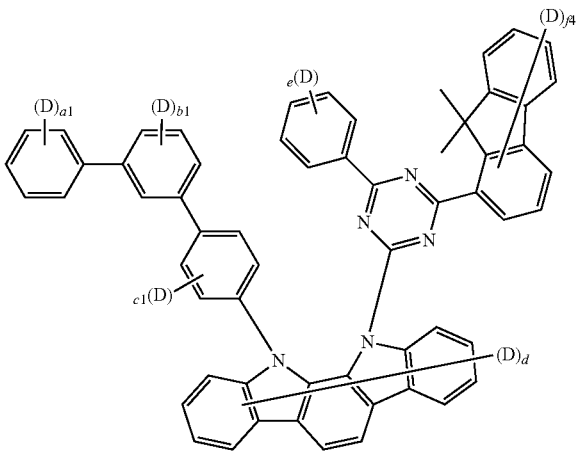

-continued
H1-4-3
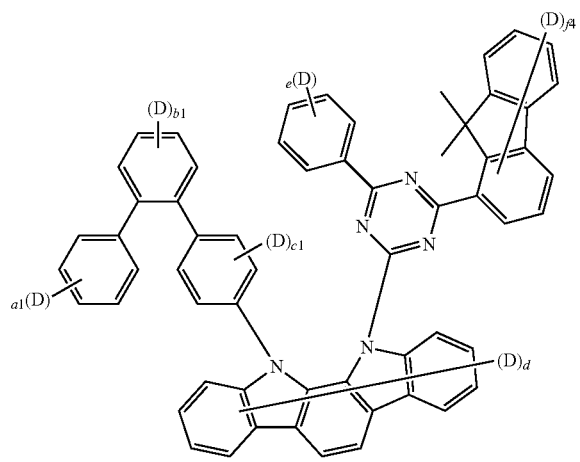
H1-4-4
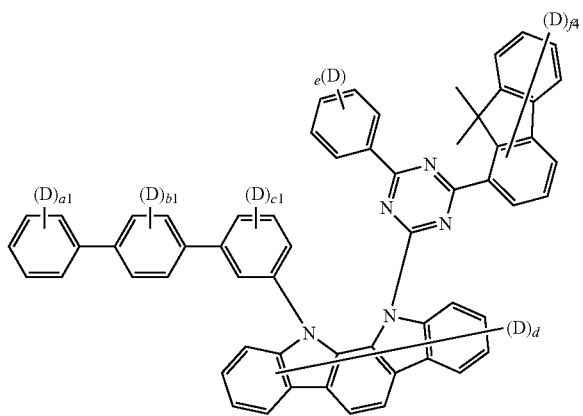
H1-4-5
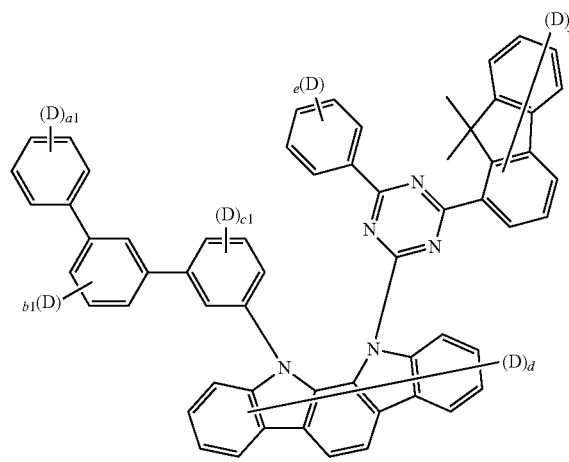
H1-4-6
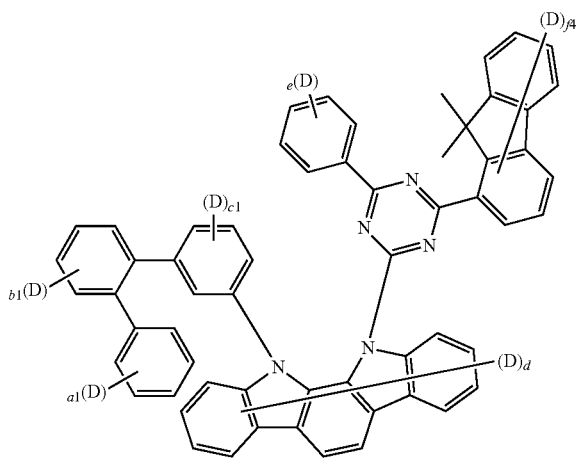
H1-4-7
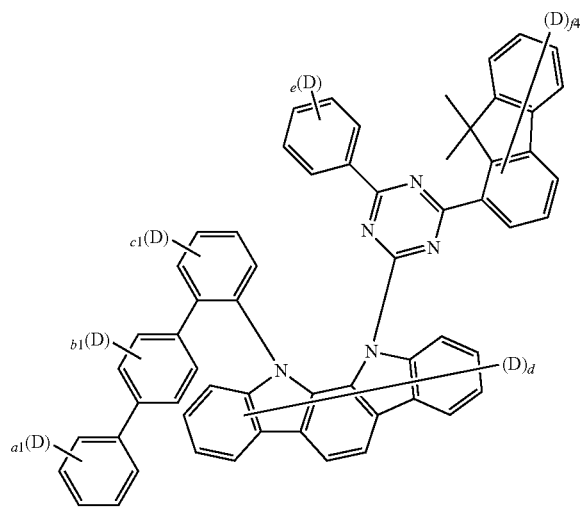
H1-4-8
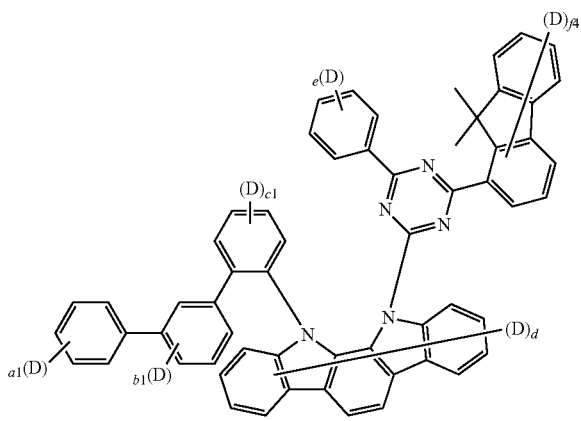

-continued
H1-4-9
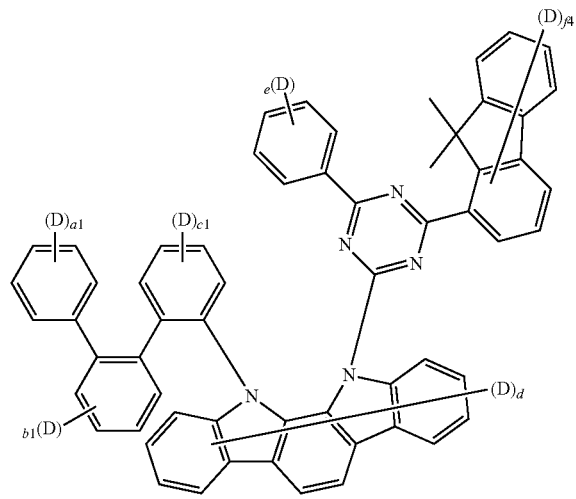
H1-5-1
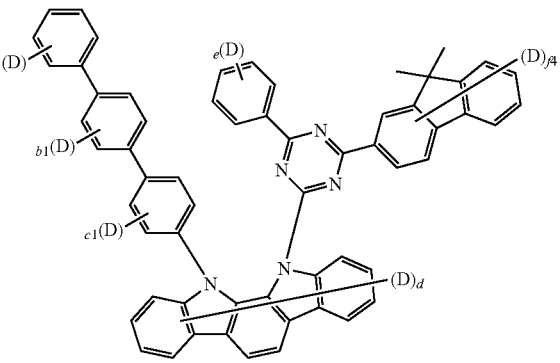
H1-5-2
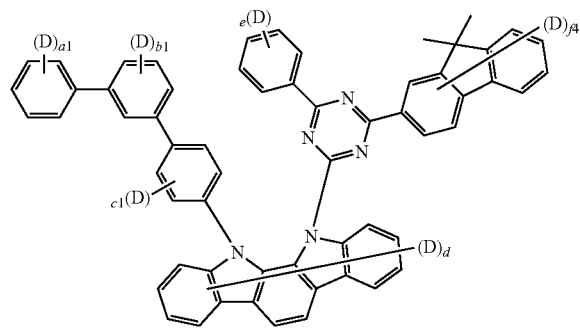
H1-5-3
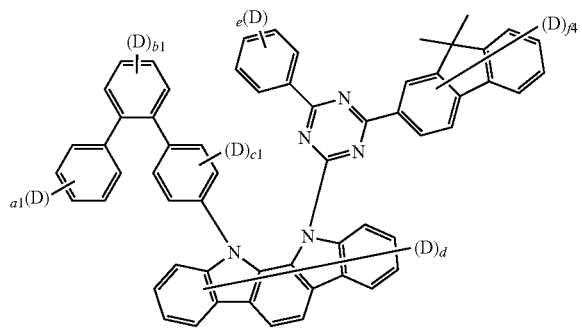
H1-5-4
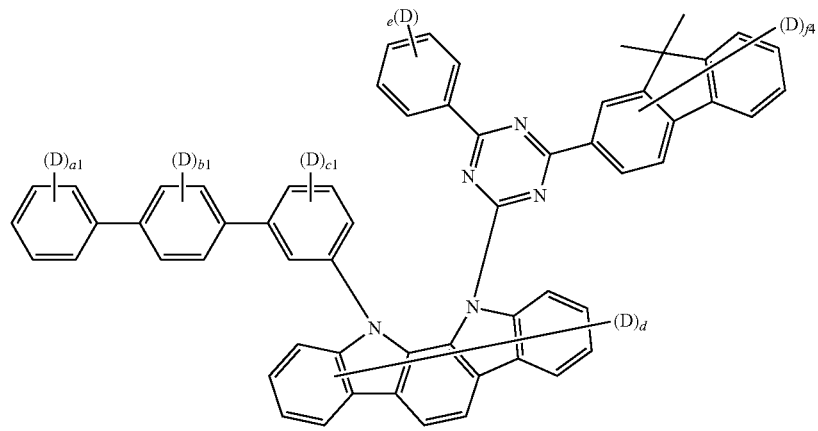
H1-5-5
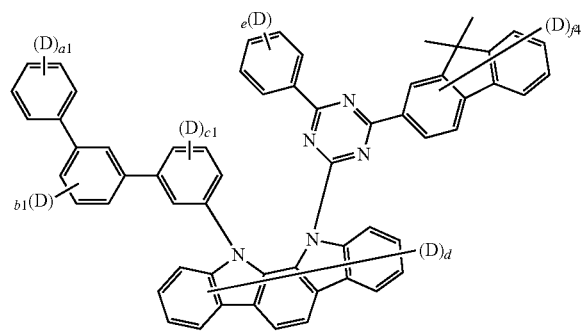
H1-5-6
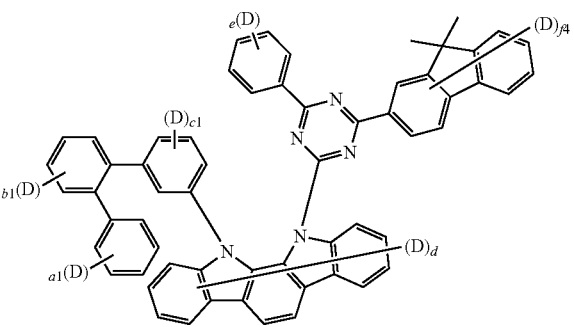

H1-5-7
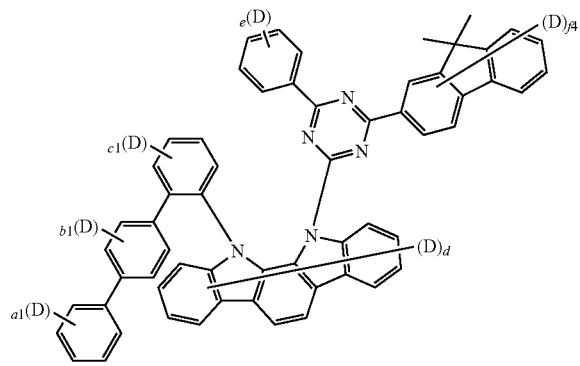
H1-5-8
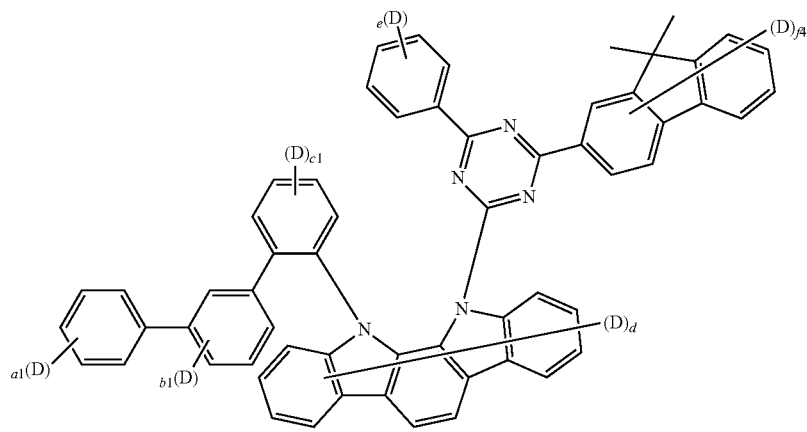
H1-5-9
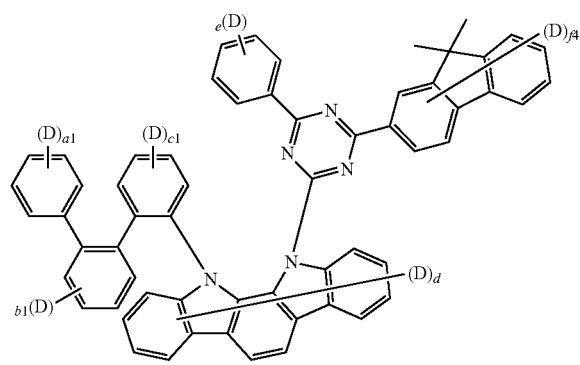
H1-6-1
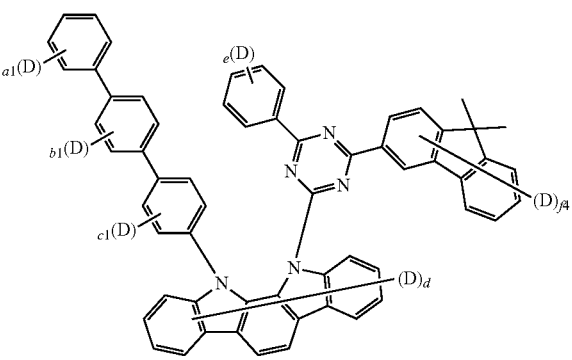
H1-6-2
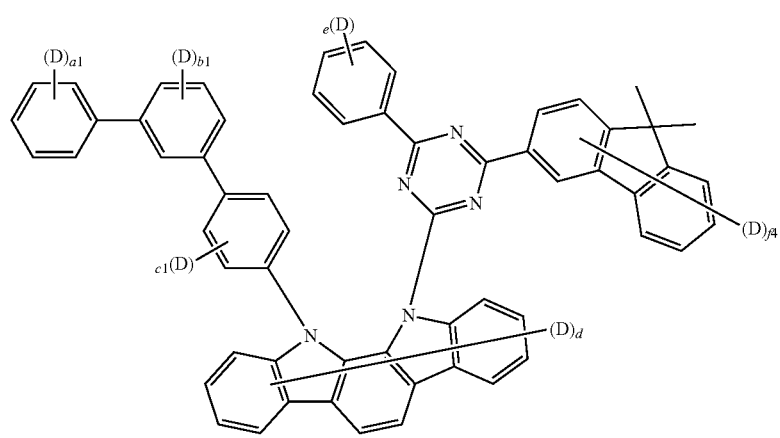

-continued
H1-6-3
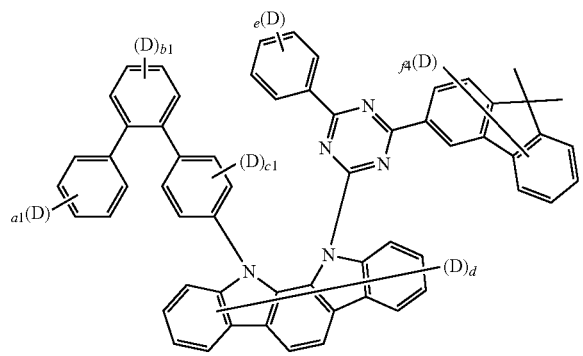
H1-6-4
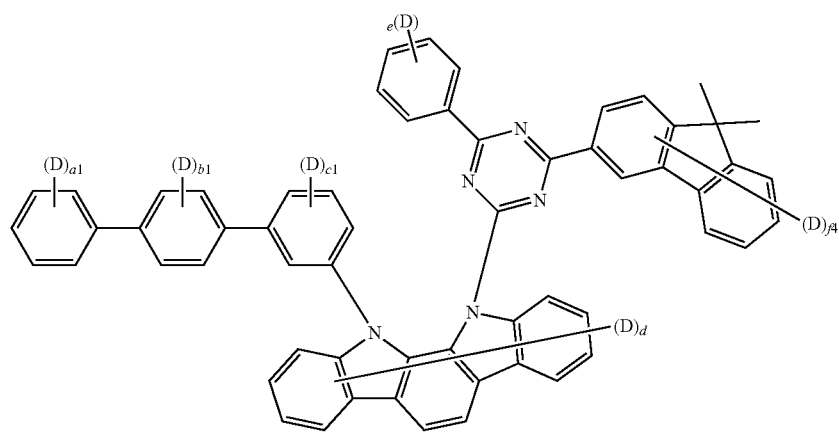
H1-6-5
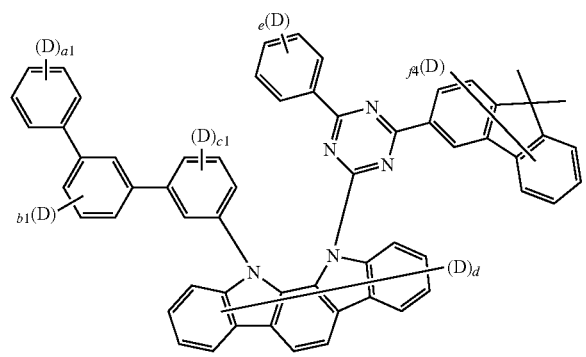
H1-6-6
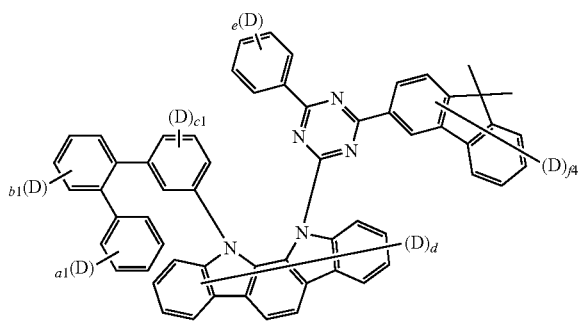
H1-6-7
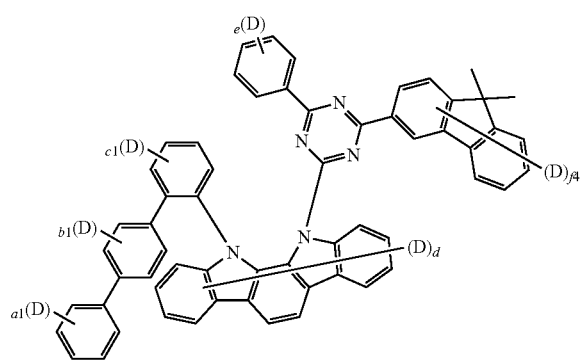

-continued
H1-6-8
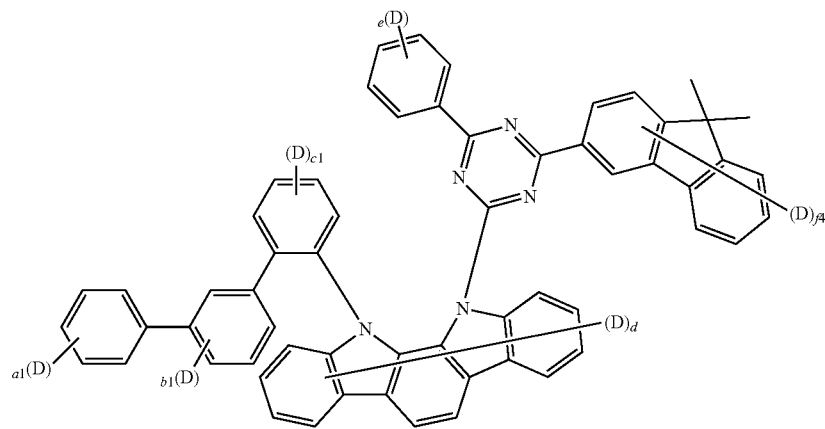
H1-6-9
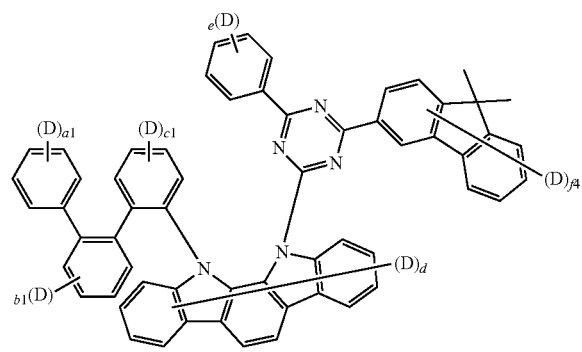
H1-7-1
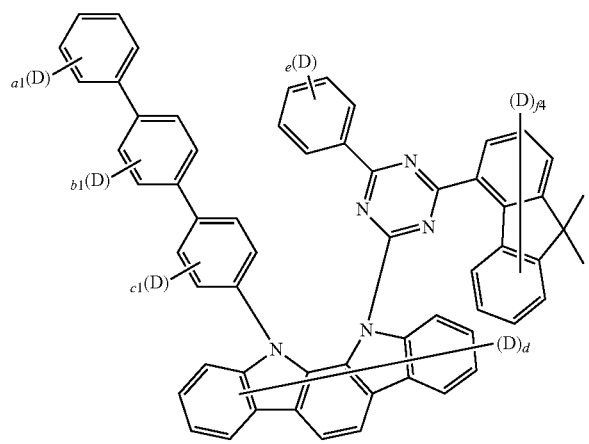
H1-7-2
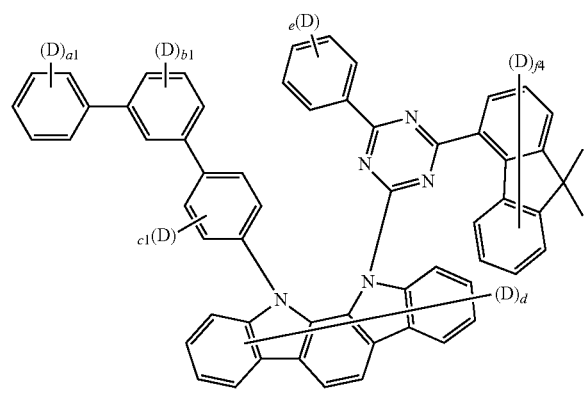
H1-7-3
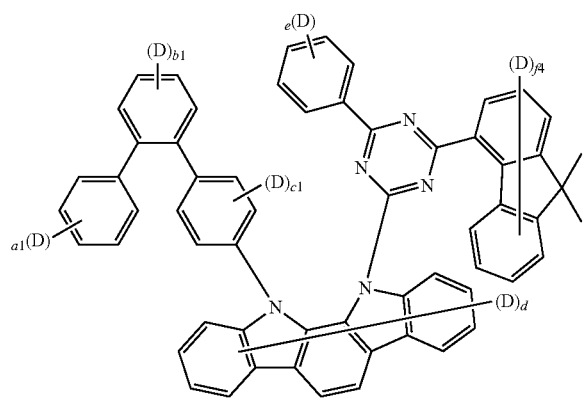

-continued
H1-7-4
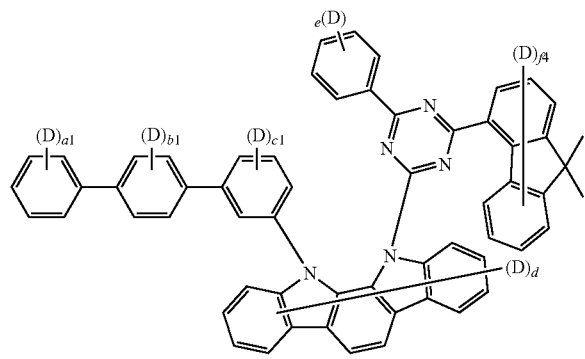
H1-7-5
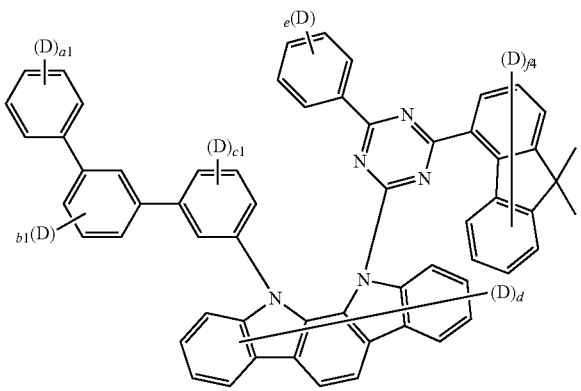
H1-7-6
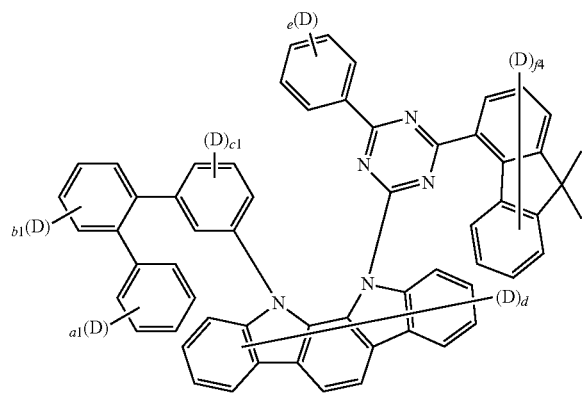
H1-7-7
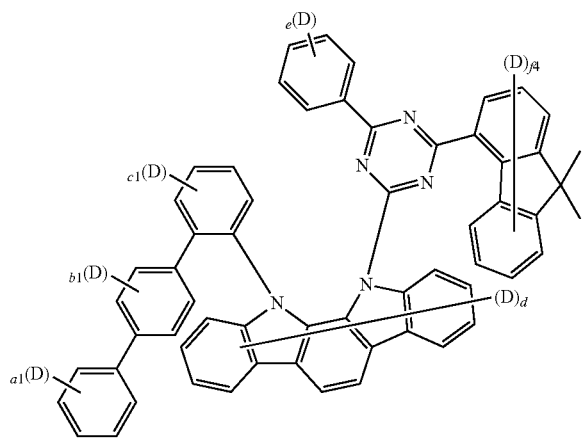
H1-7-8
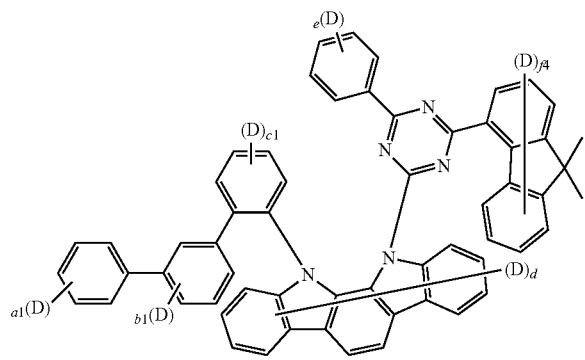
H1-7-9
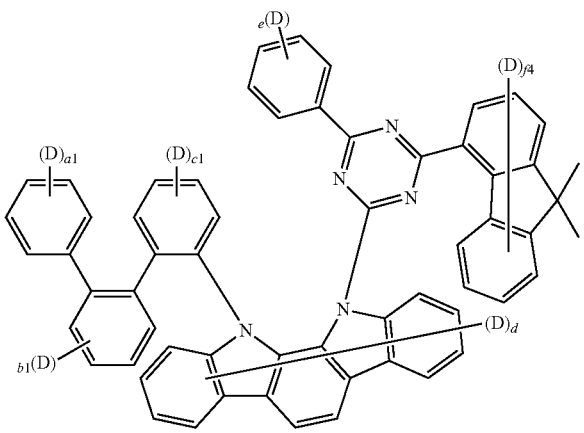

-continued
H1-8-1
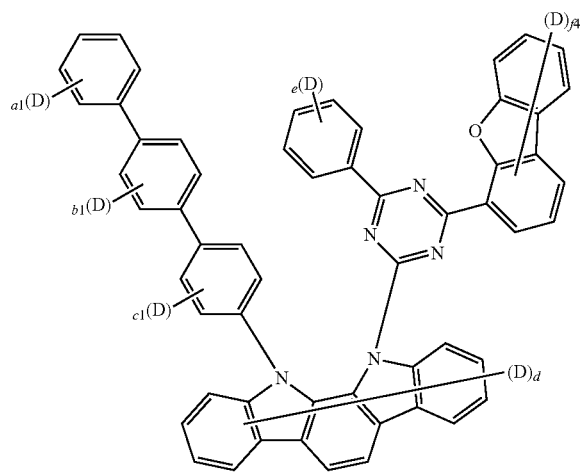
H1-8-2
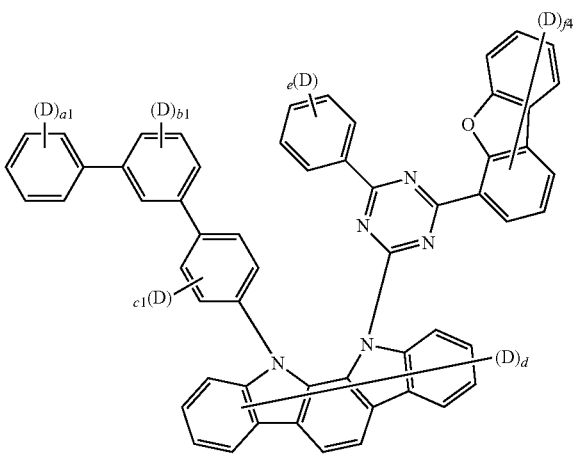
H1-8-3
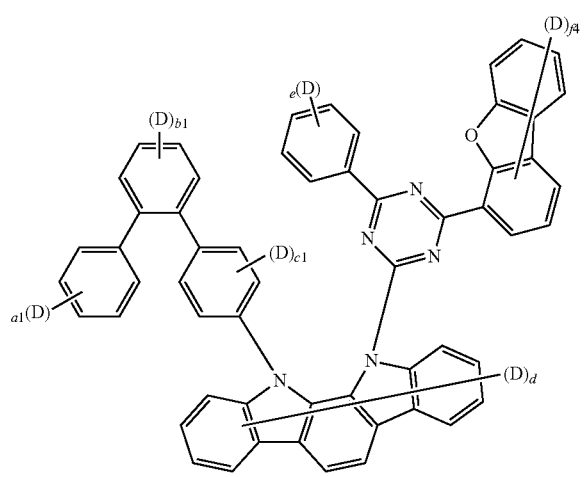
H1-8-4
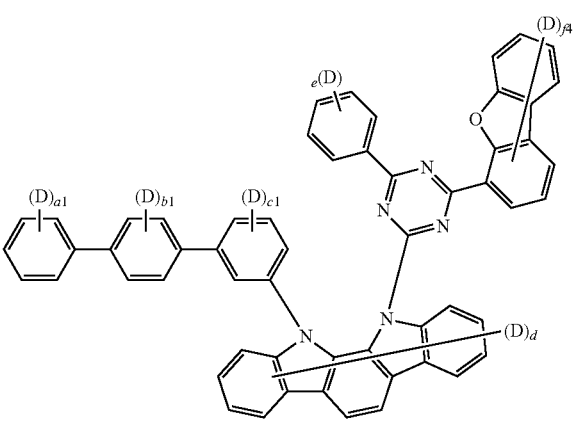
H1-8-5
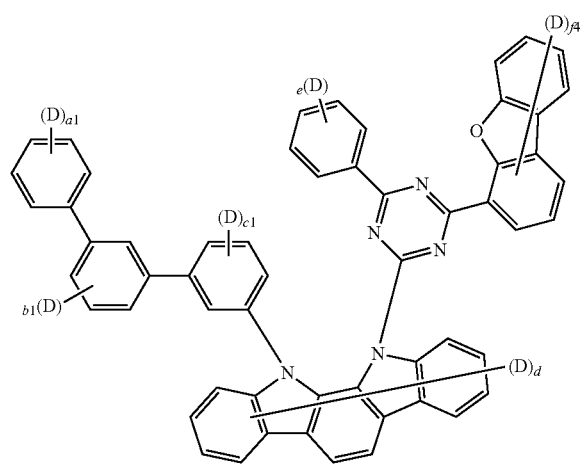
H1-8-6
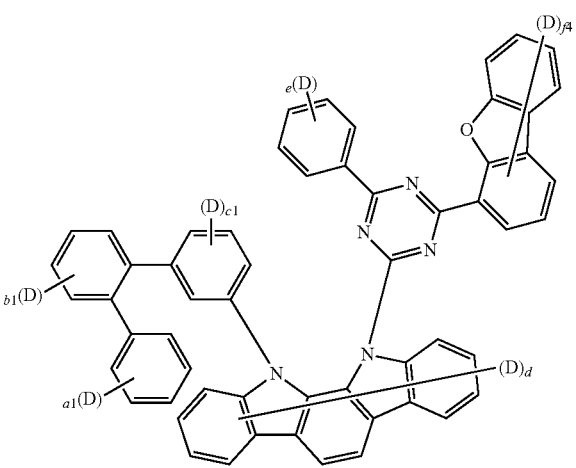

-continued
H1-8-7
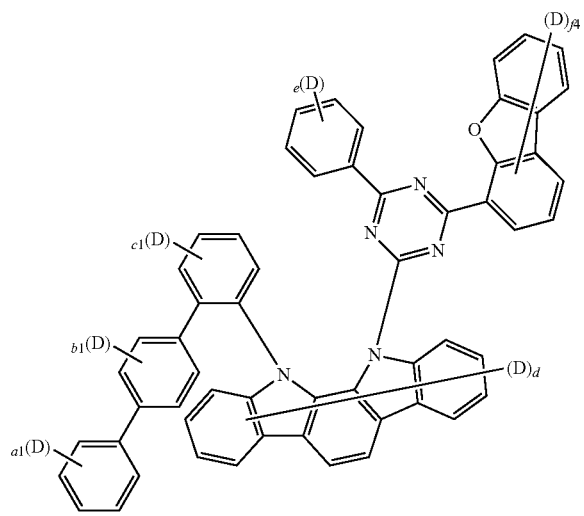
H1-8-8
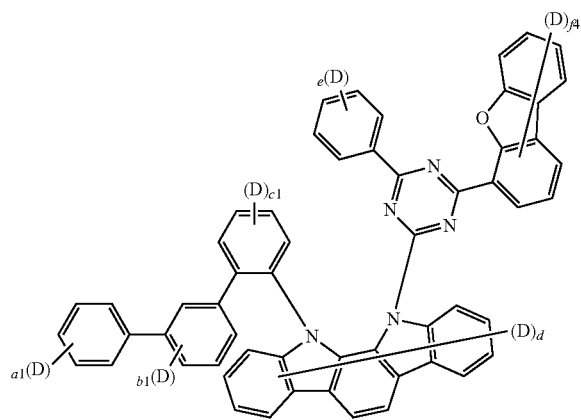
H1-8-9
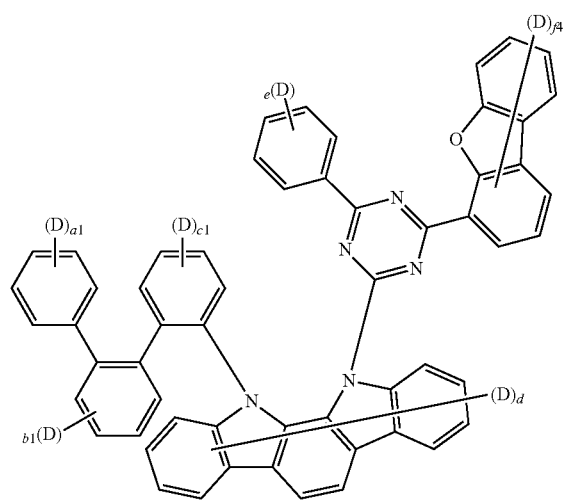
H1-9-1
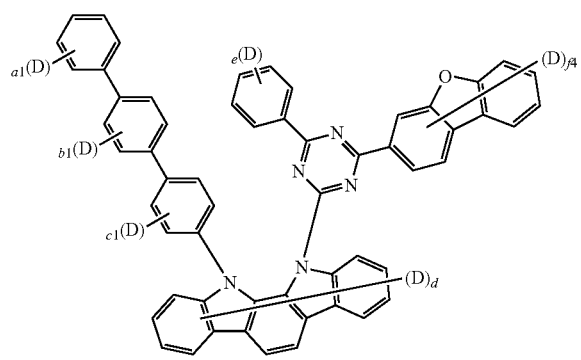
H1-9-2
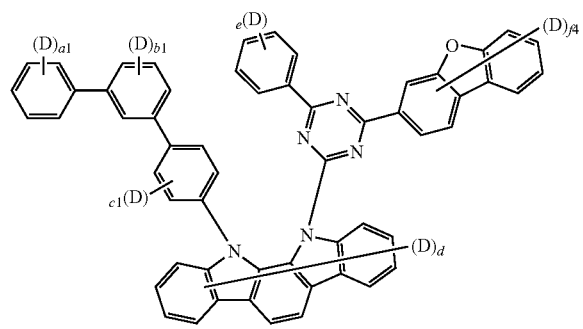
H1-9-3
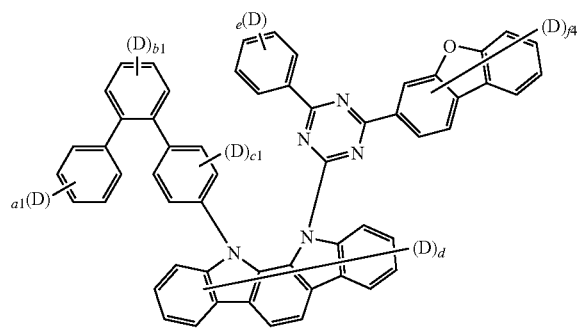

-continued
H1-9-4
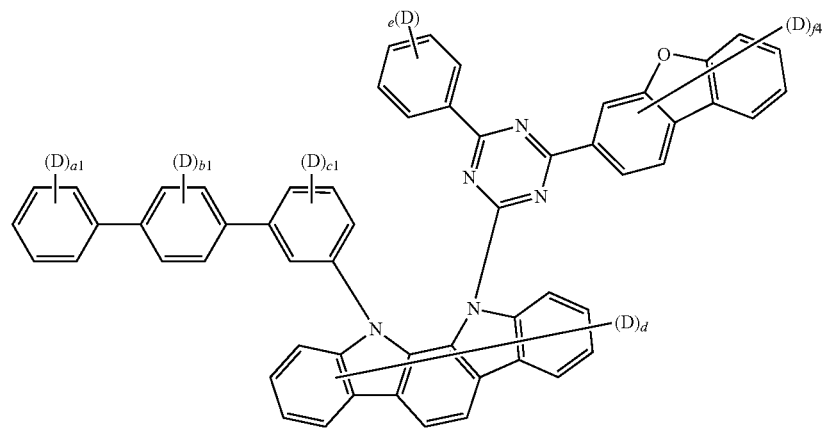
H1-9-5
H1-9-6
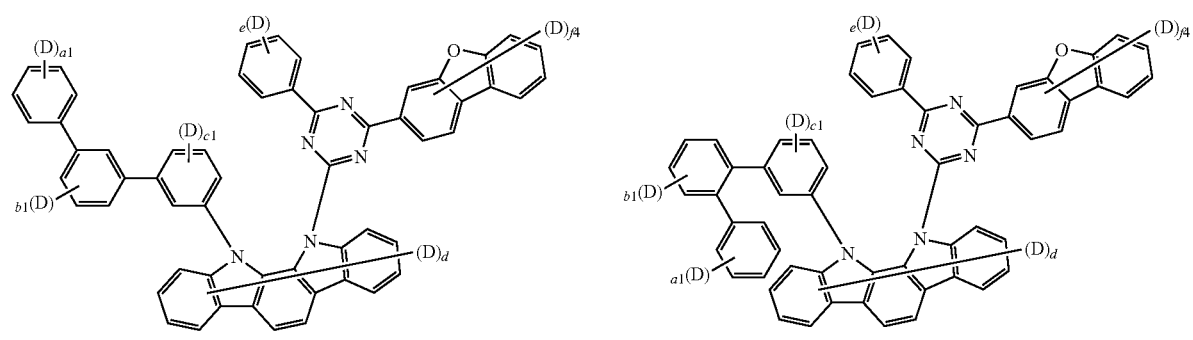
H1-9-7
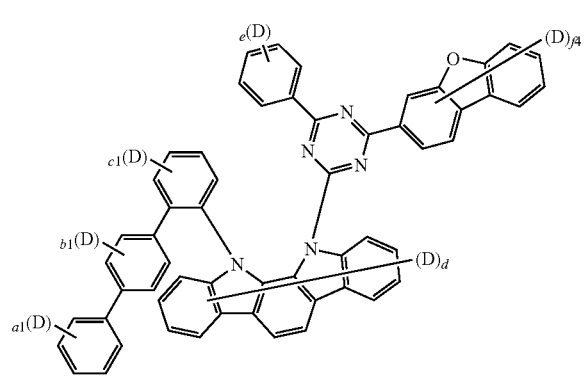
H1-9-8
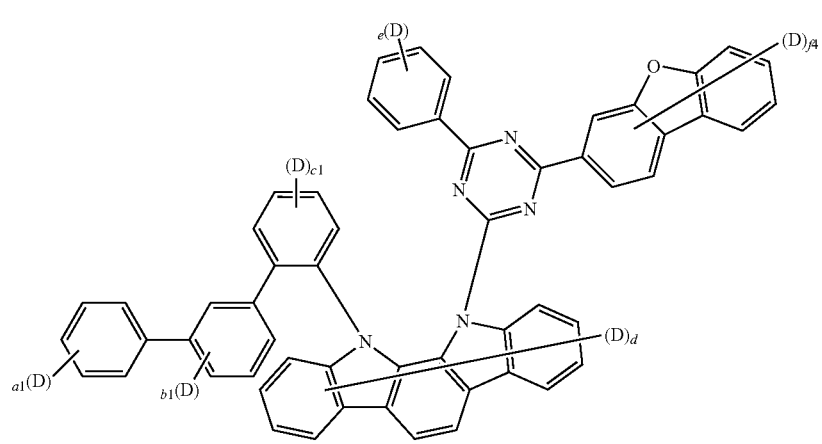

-continued
H1-9-9
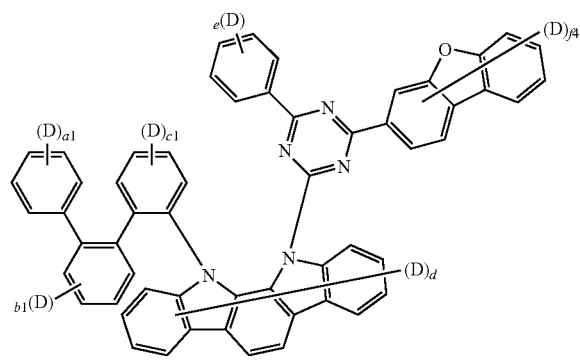
H1-10-1
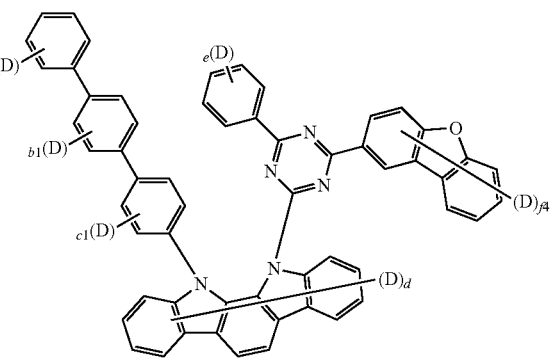
H1-10-2
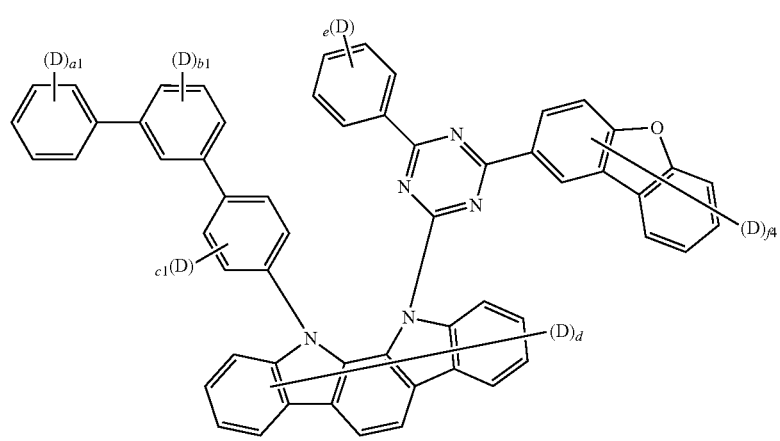
H1-10-3
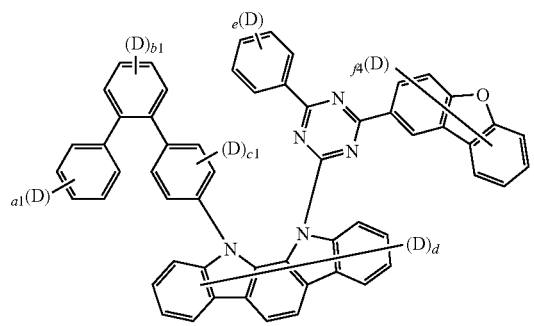
H1-10-4
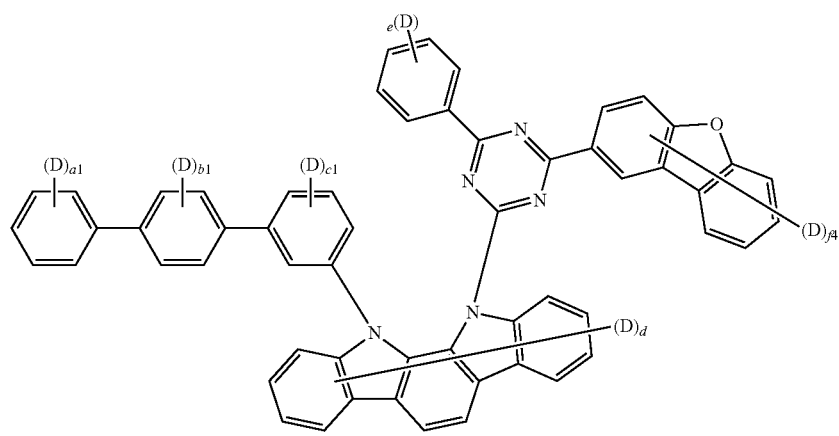

H1-10-5
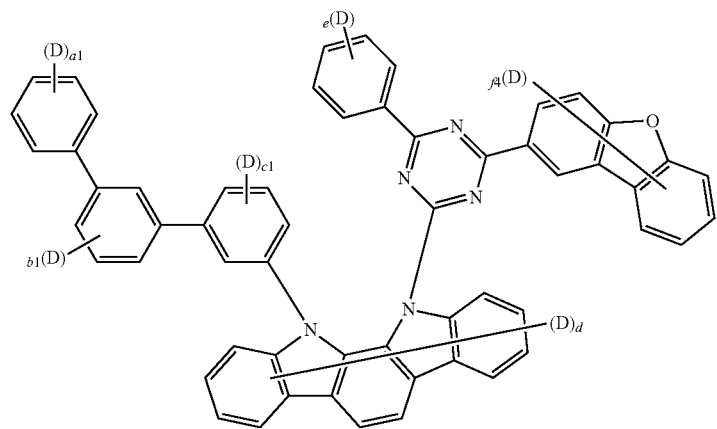
H1-10-6
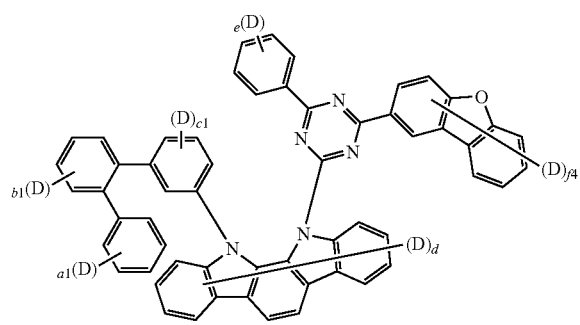
H1-10-7
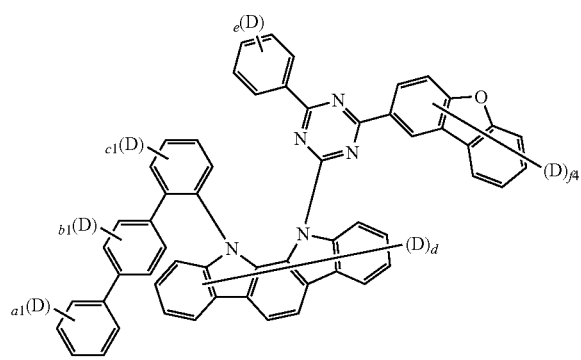
H1-10-8
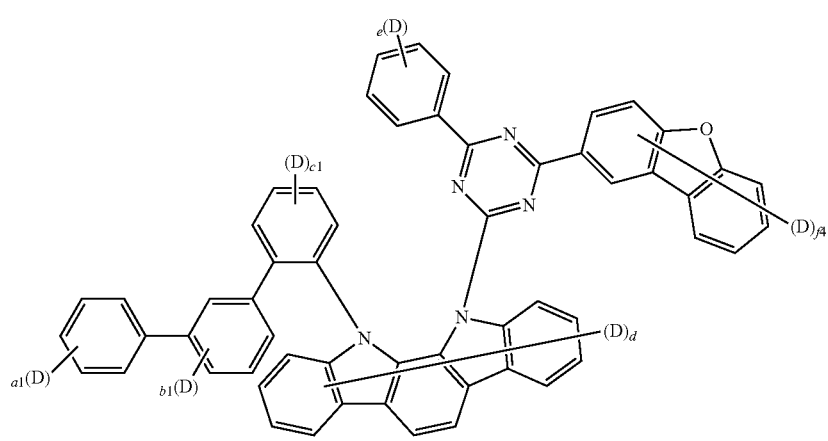

-continued
H1-10-9
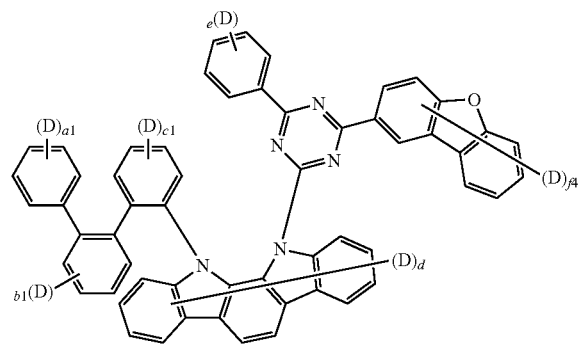
H1-11-1
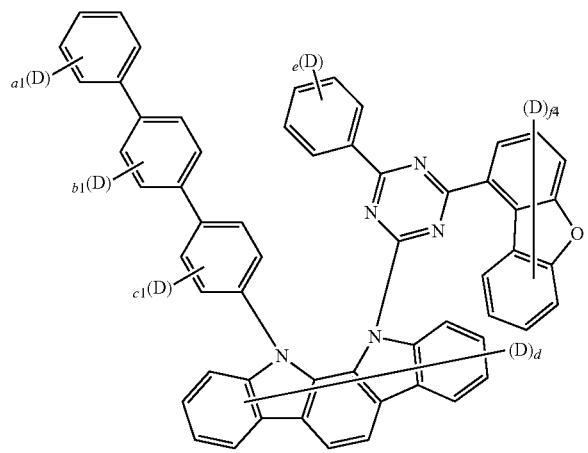
H1-11-2
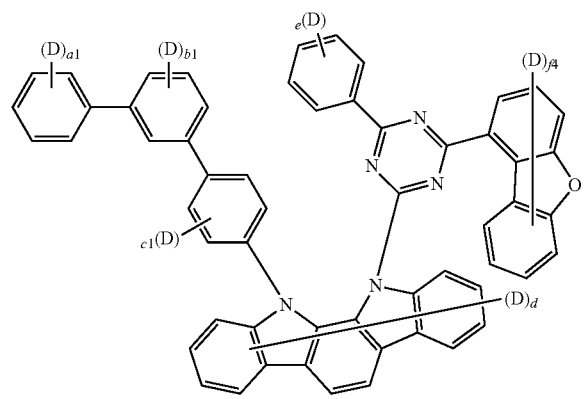
H1-11-3
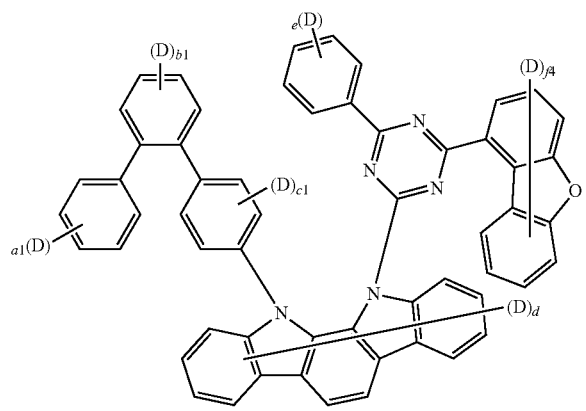
H1-11-4
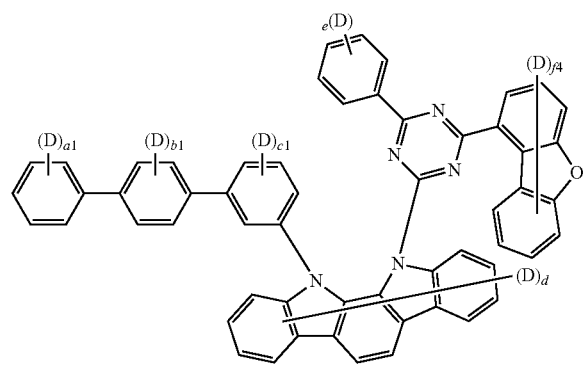
H1-11-5
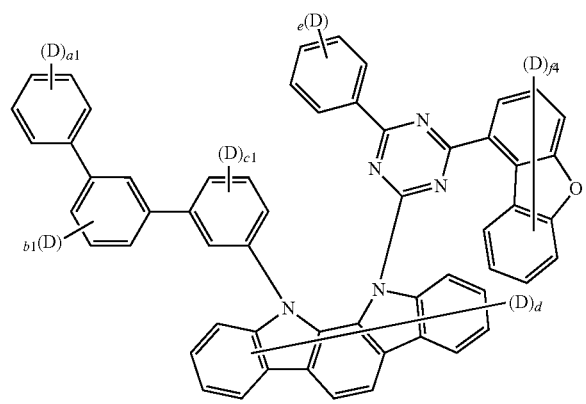

-continued
H1-11-6
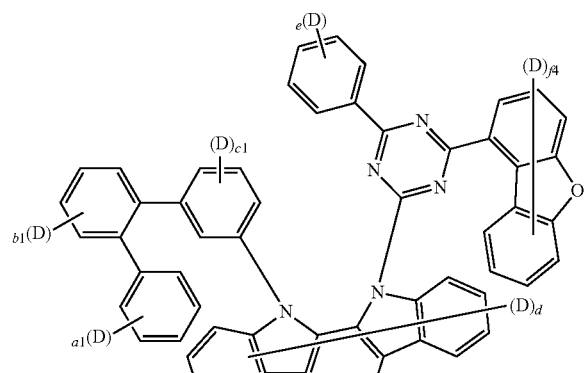
H1-11-7
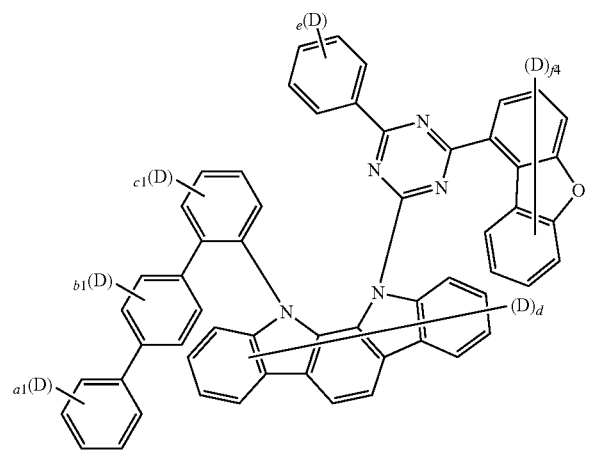
H1-11-8
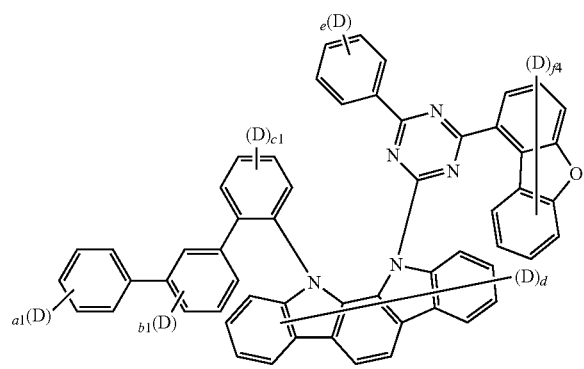
H1-11-9
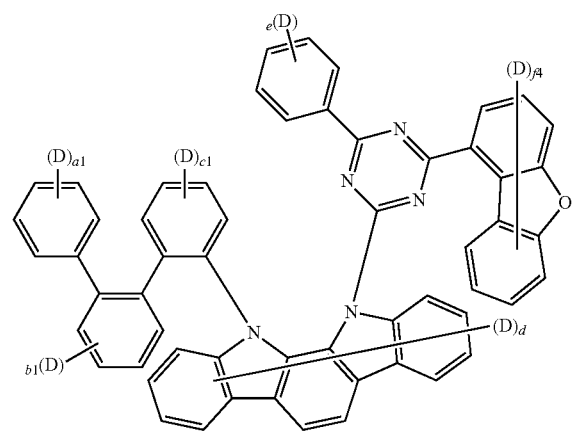
H1-12-1
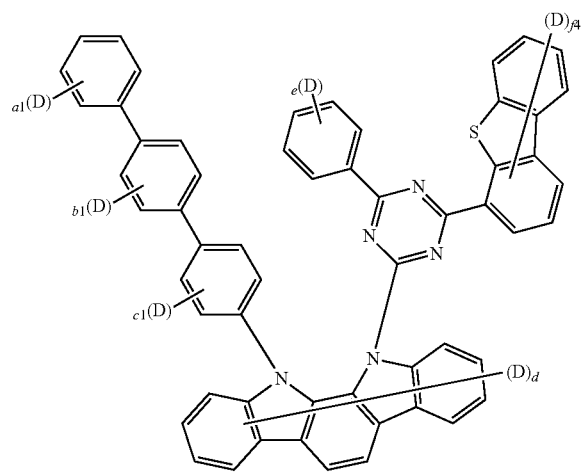
H1-12-2
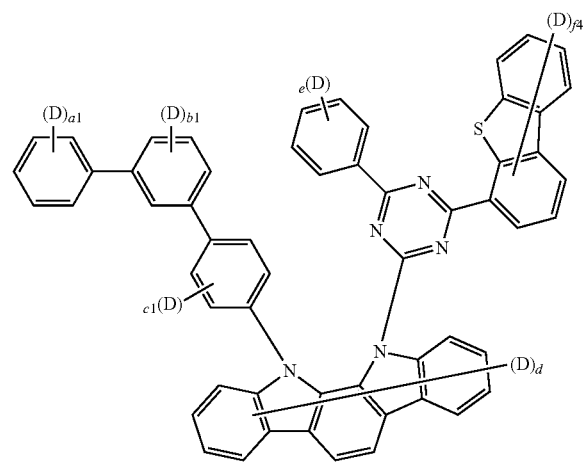

-continued
H1-12-3
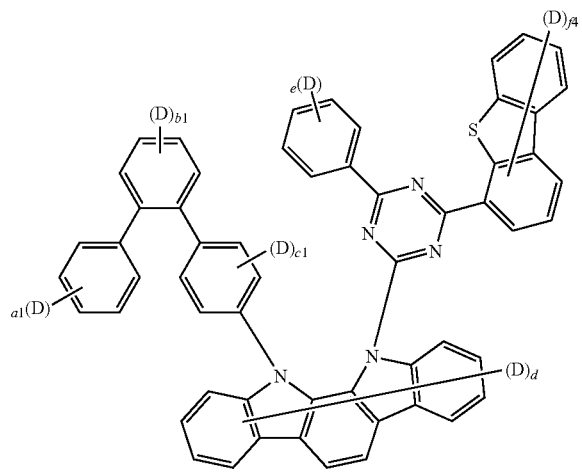
H1-12-4
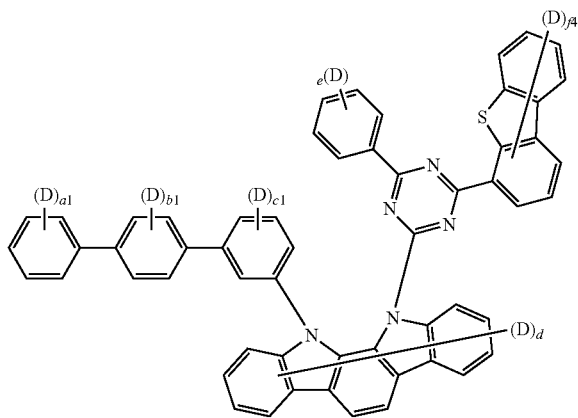
H1-12-5
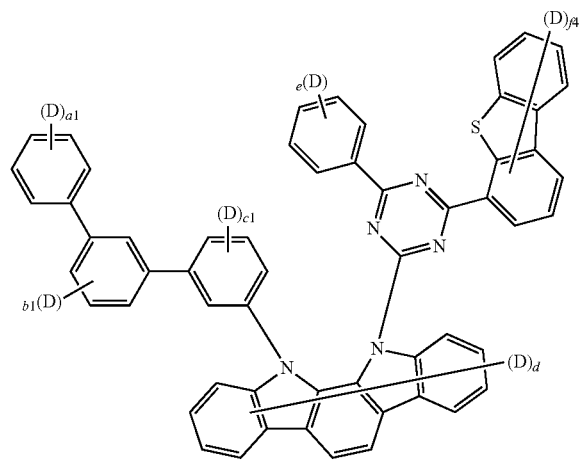
H1-12-6
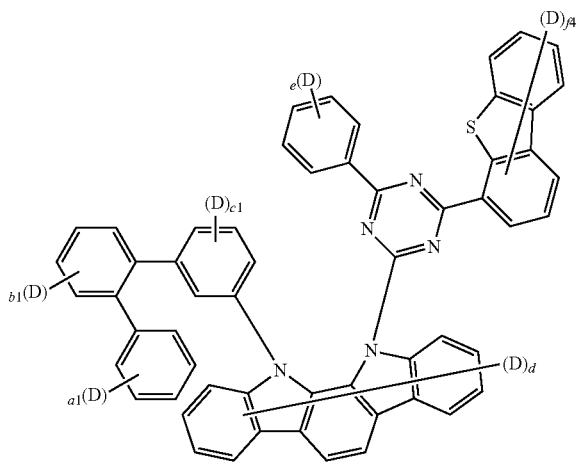
H1-12-7
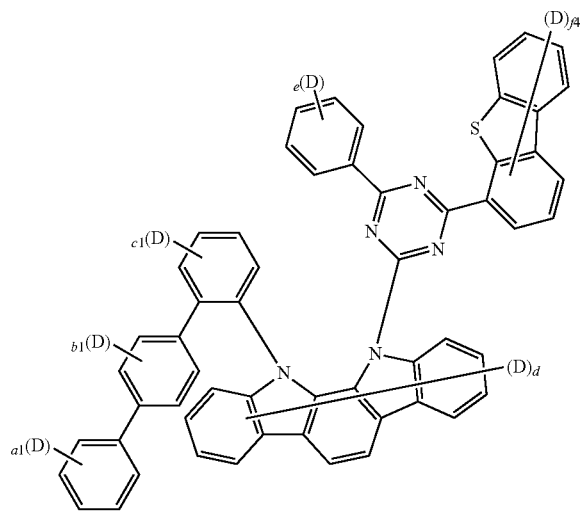
H1-12-8
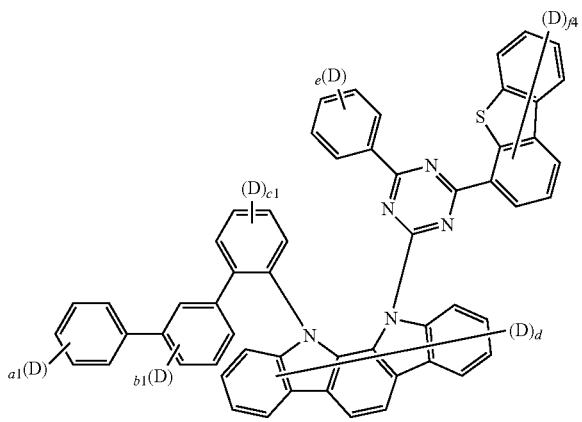

-continued
H1-12-9
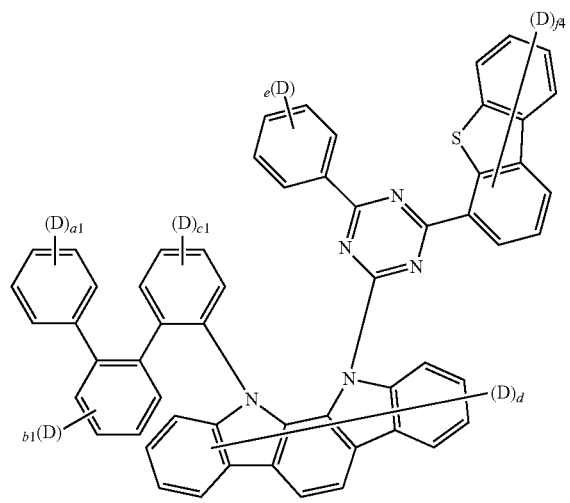
H1-13-1
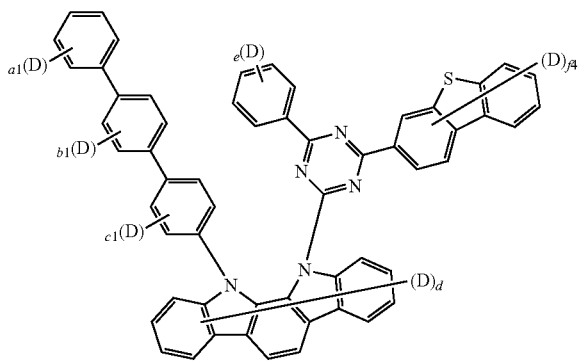
H1-13-2
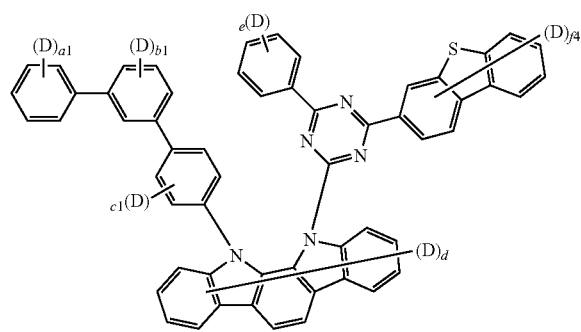
H1-13-3
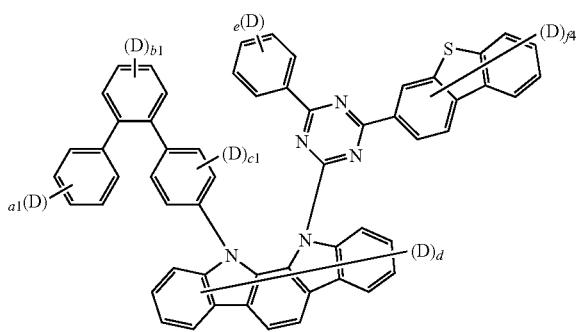
H1-13-4
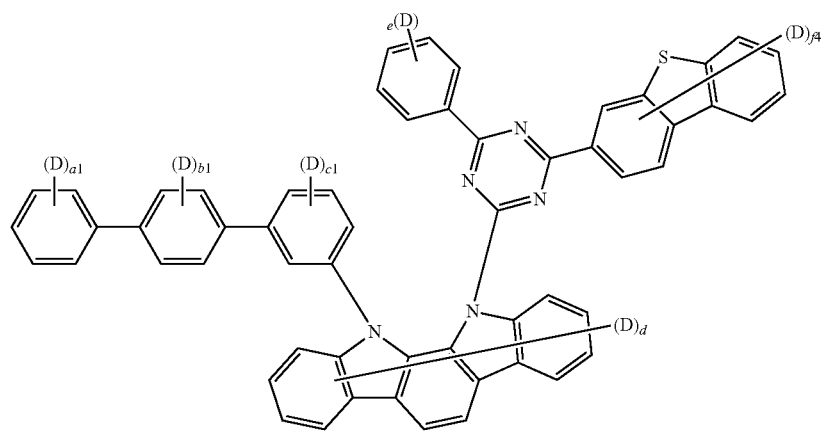
H1-13-5
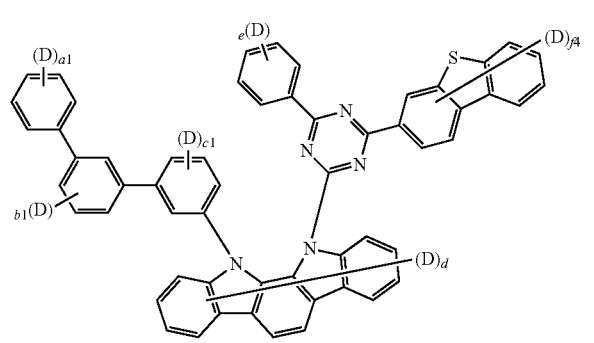
H1-13-6
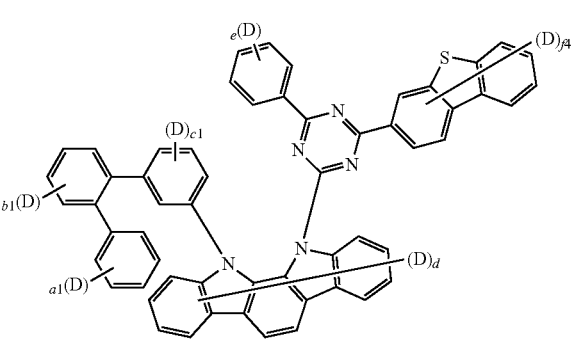

-continued
H1-13-7
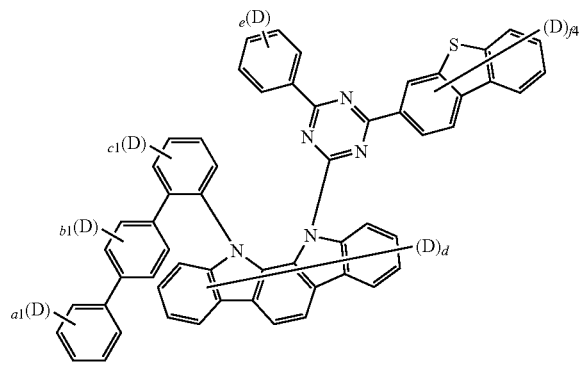
H1-13-8
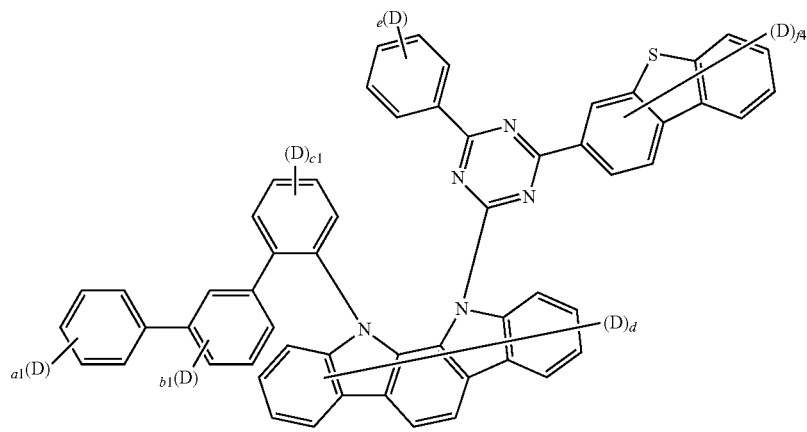
H1-13-9
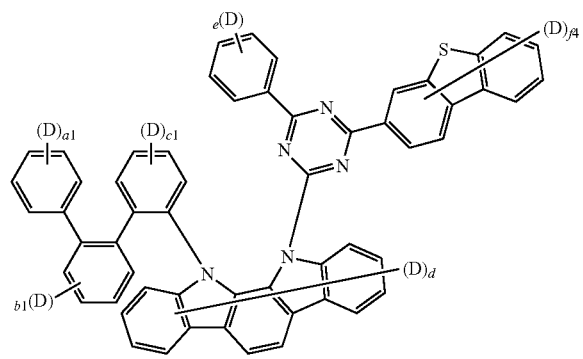
H1-14-1
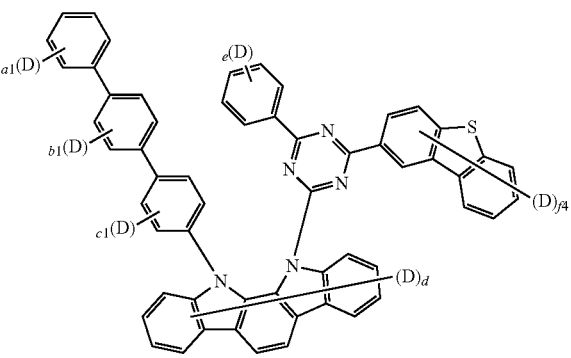
H1-14-2
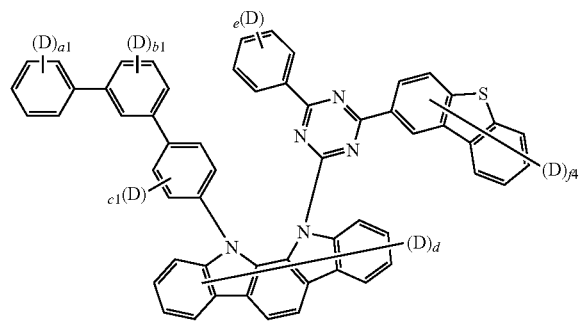
H1-14-3
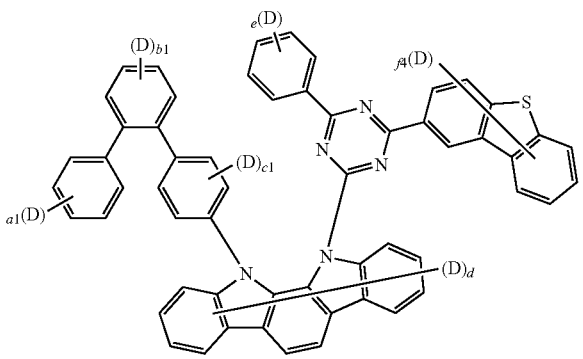

-continued
H1-14-4
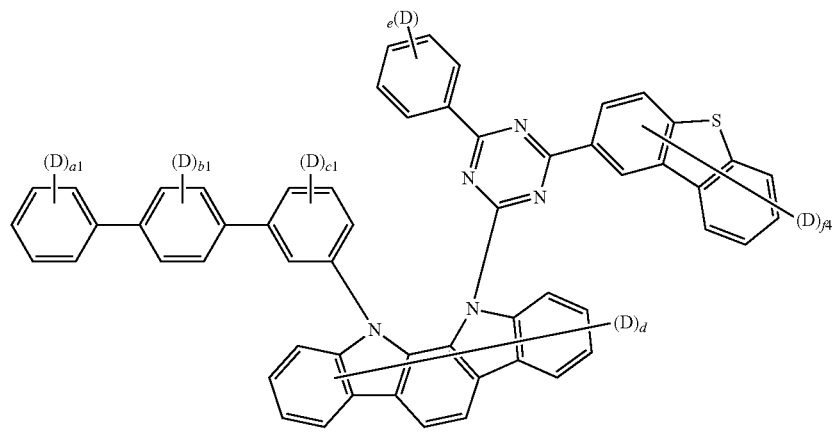
H1-14-5
H1-14-6
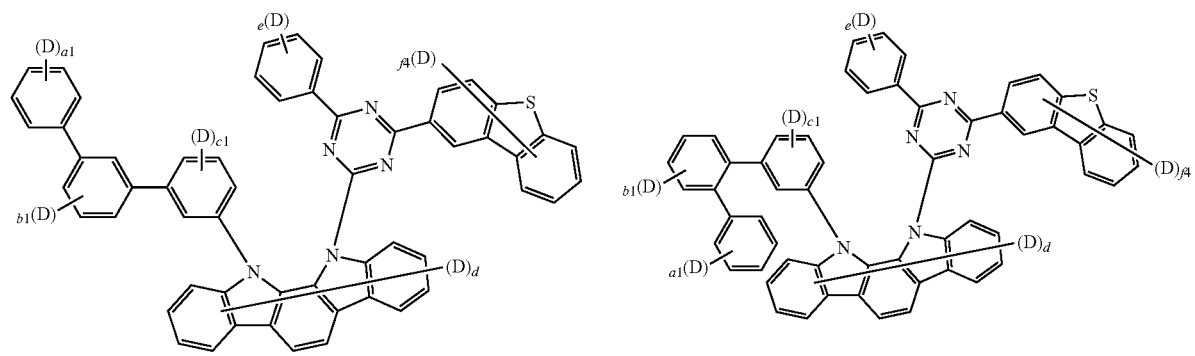
H1-14-7
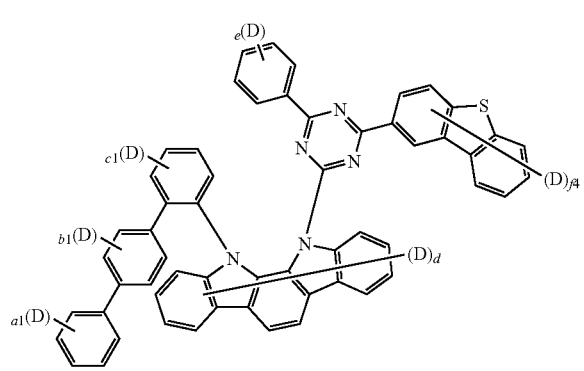
H1-14-8
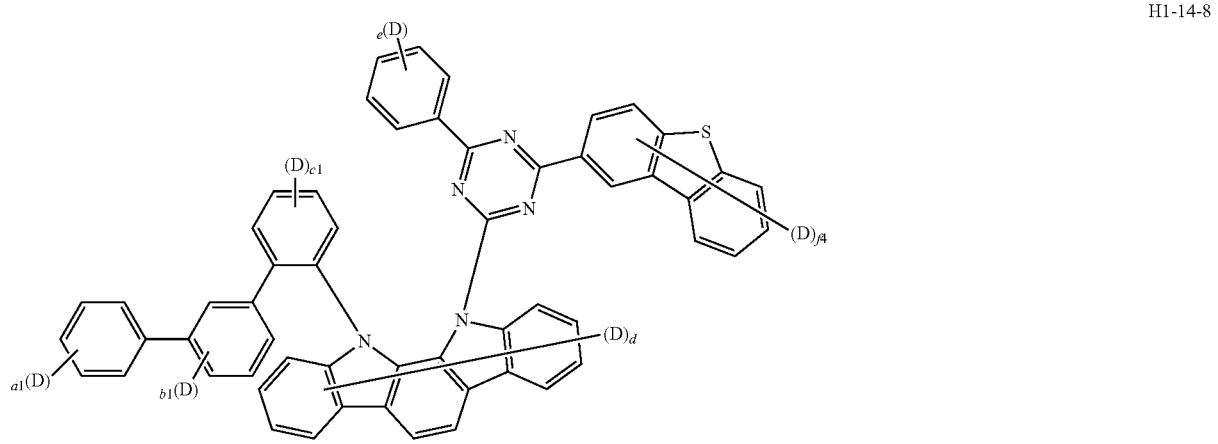

-continued
H1-14-9
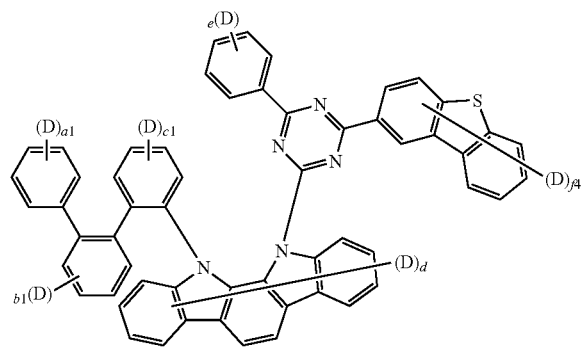
H1-15-1
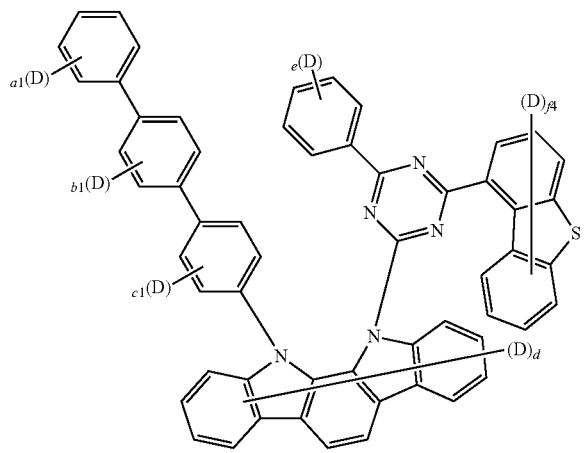
H1-15-2
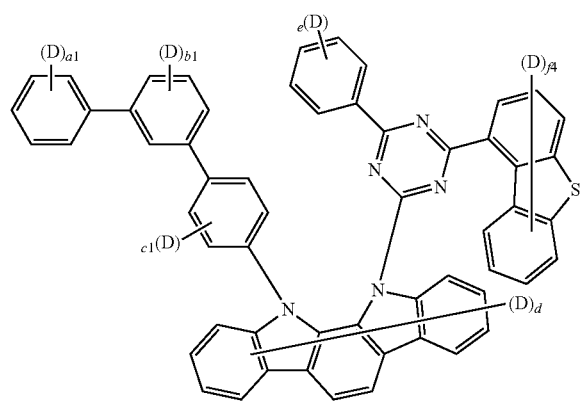
H1-15-3
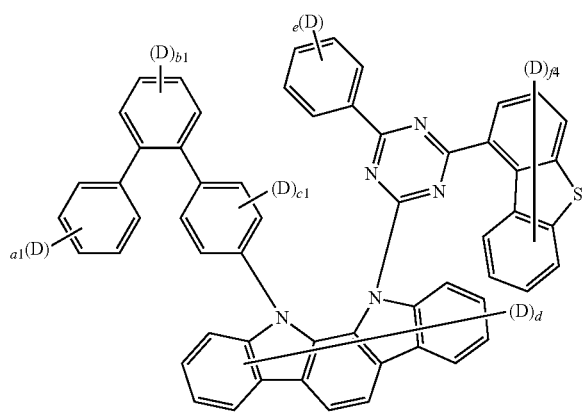
H1-15-4
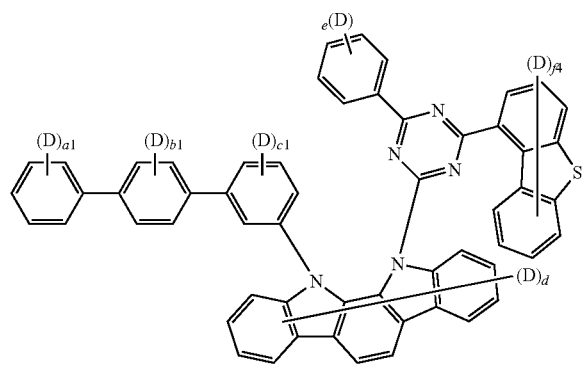
H1-15-5
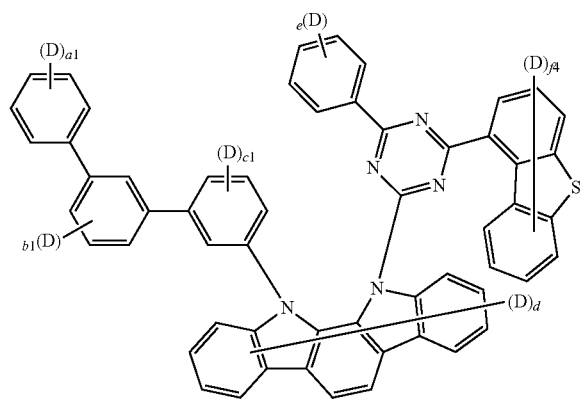

-continued
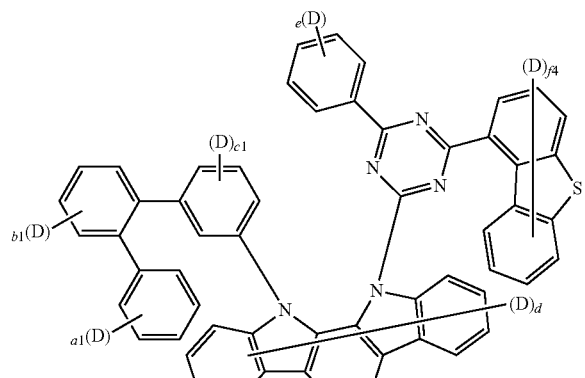
H1-15-6
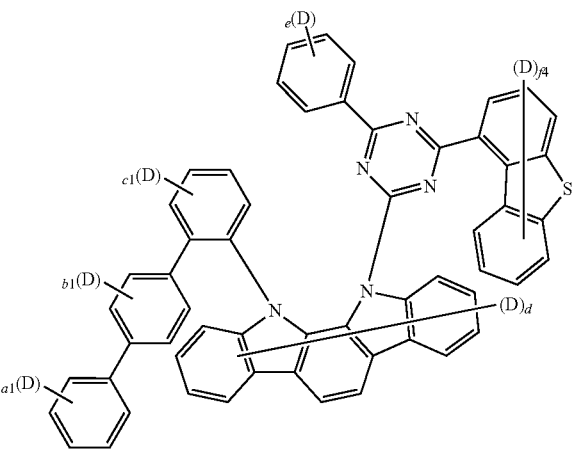
H1-15-7
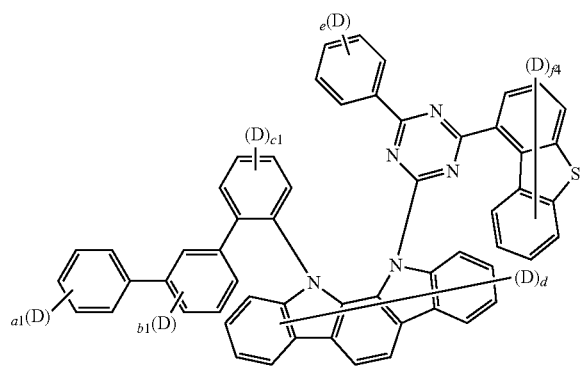
H1-15-8
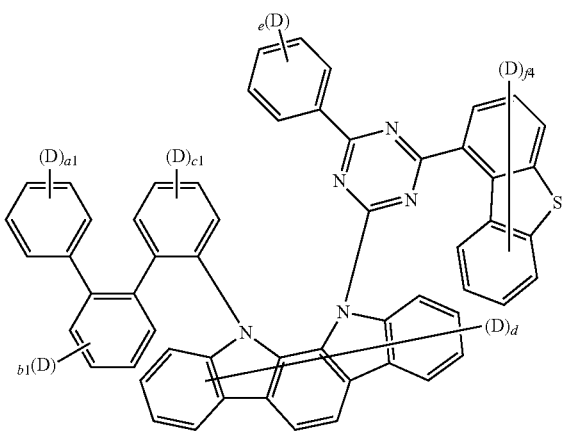
H1-15-9
wherein in Chemical Formulae H1-4-1 to H1-4-9, H1-5-1 to H1-5-9, H1-6-1 to H1-6-9, H1-7-1 to H1-7-9, H1-8-1 to H1-8-9, H1-9-1 to H1-9-9, H1-10-1 to H1-10-9, H1-11-1 to H1-11-9, H1-12-1 to H1-12-9, H1-13-1 to H1-13-9, H1-14-1 to H1-14-9, and H1-15-1 to H1-15-9:
a1, b1, c1, and d are as defined in Chemical Formula 1,
e is an integer of 0 to 5,
f4 is an integer of 0 to 7, and
a1+b1+c1+d+e+f4 is 1 to 35;
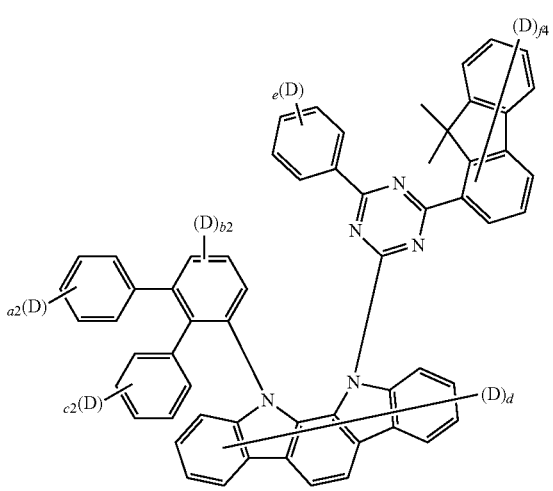
H1-4-10

-continued
H1-4-11
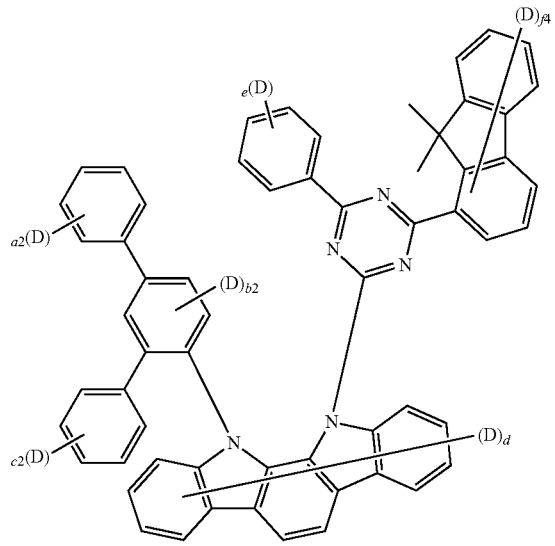
H1-4-12
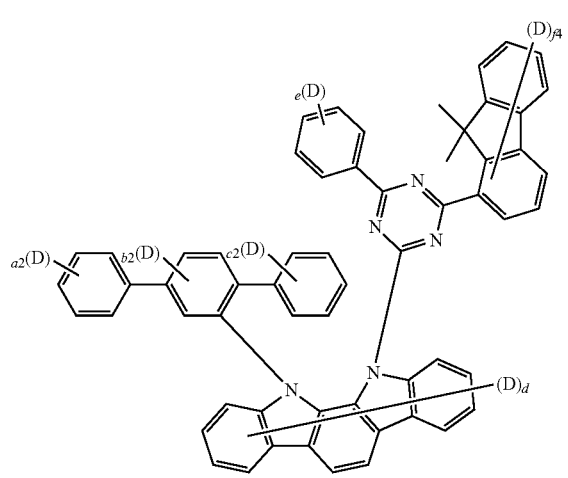
H1-4-13
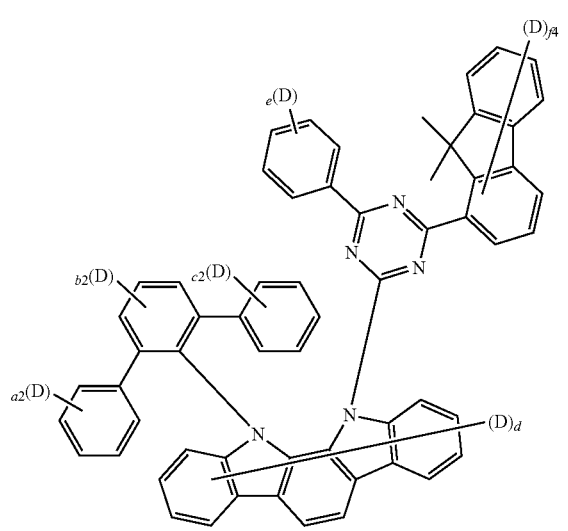

-continued
H1-4-14
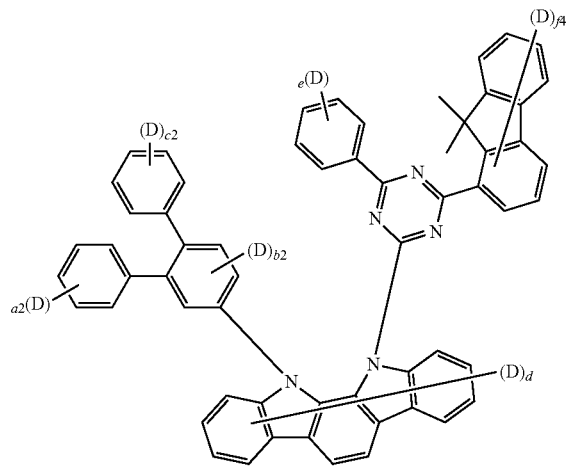
H1-4-15
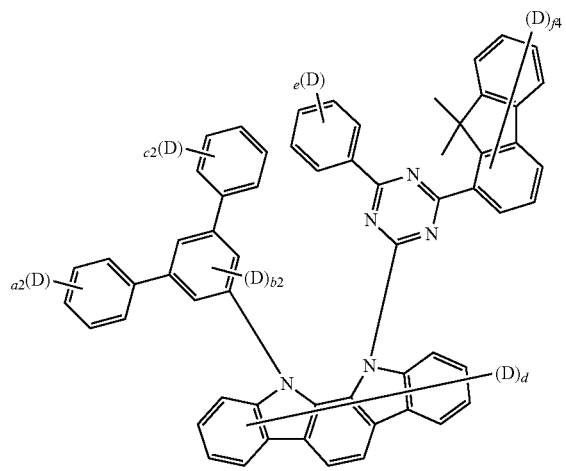
H1-5-10
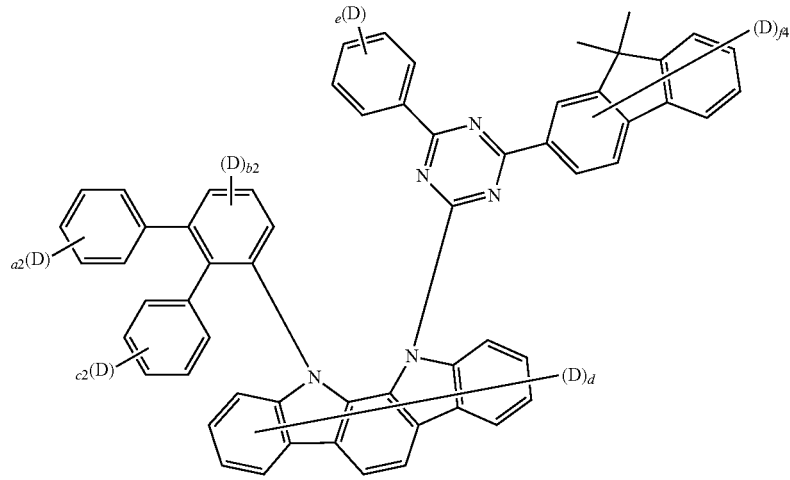

-continued
H1-5-11
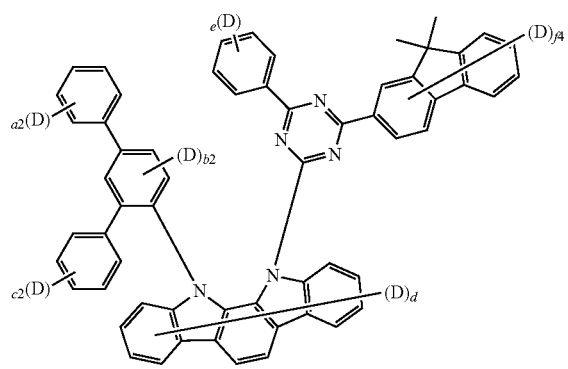
H1-5-12
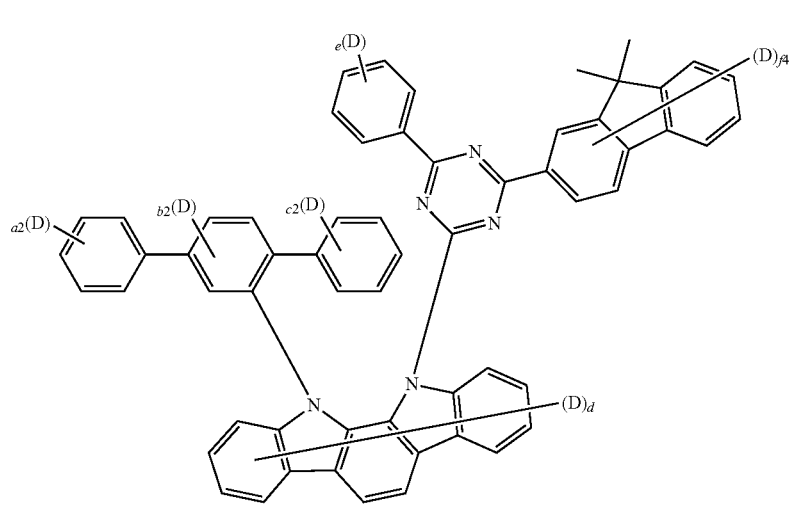
H1-5-13
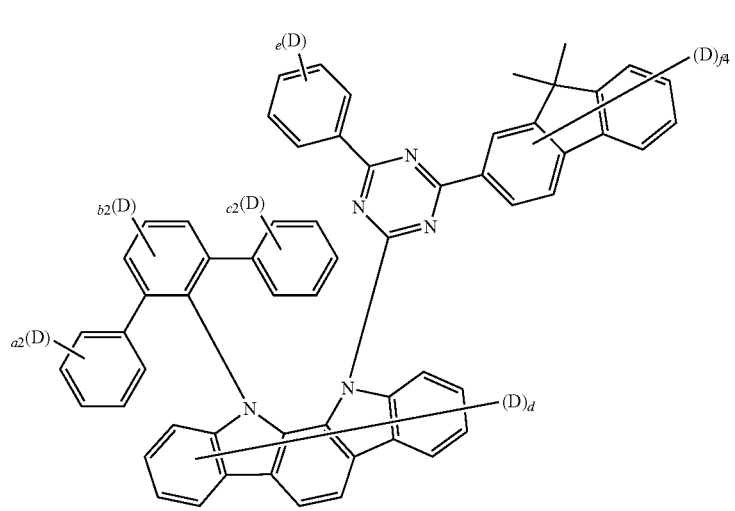

-continued
H1-5-14
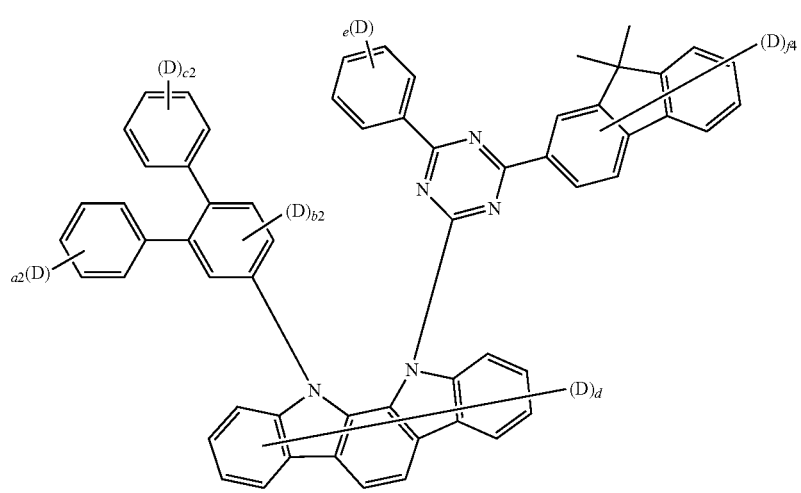
H1-5-15
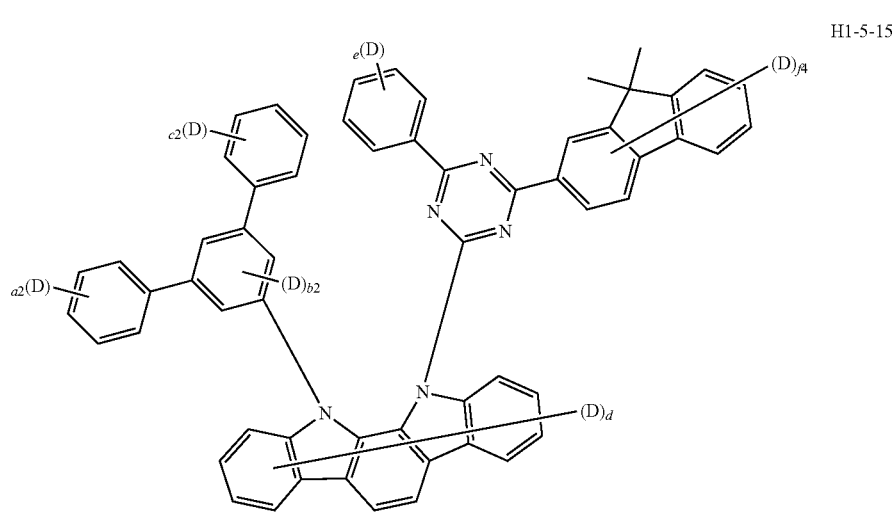
H1-6-10
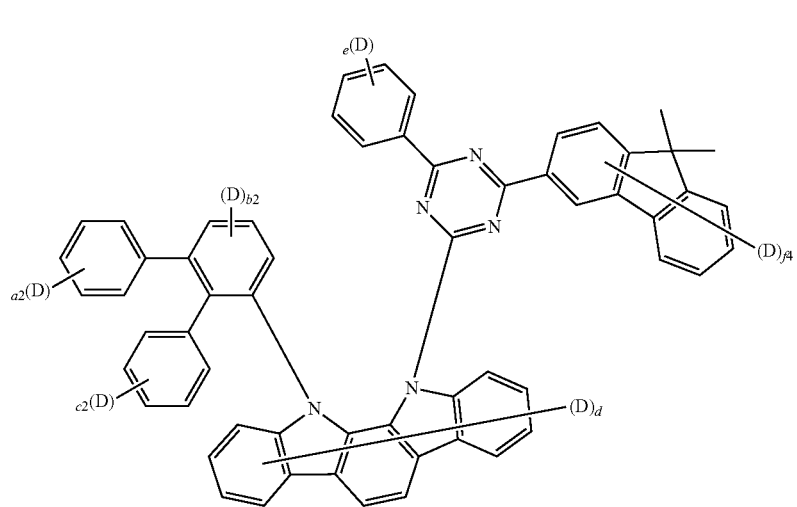

H1-6-11
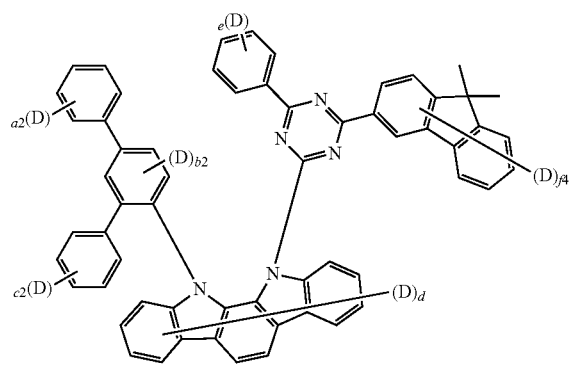
H1-6-12
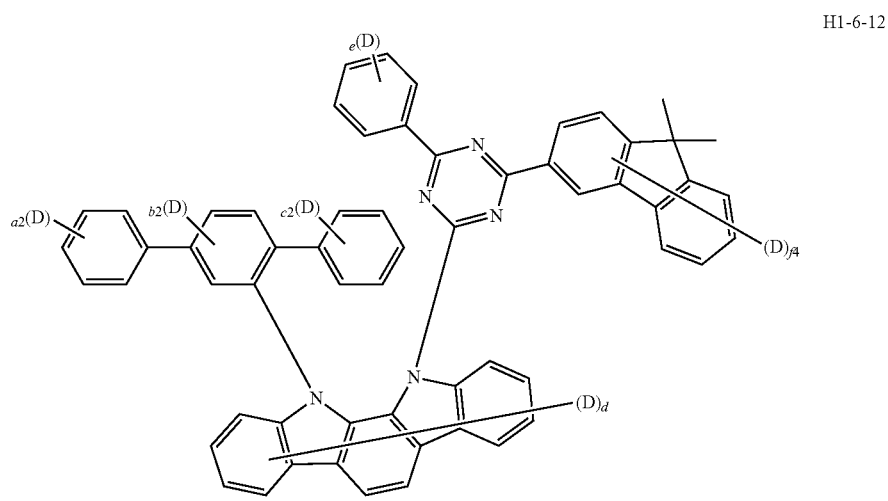
H1-6-13
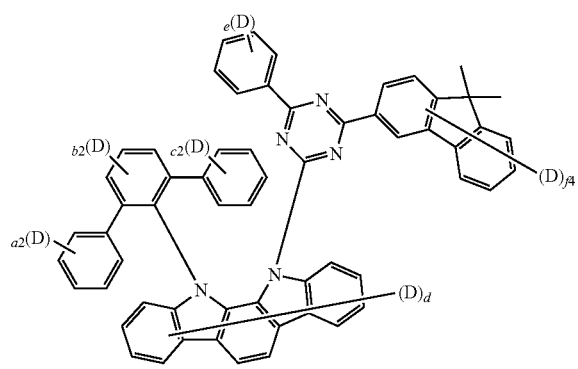
H1-6-14
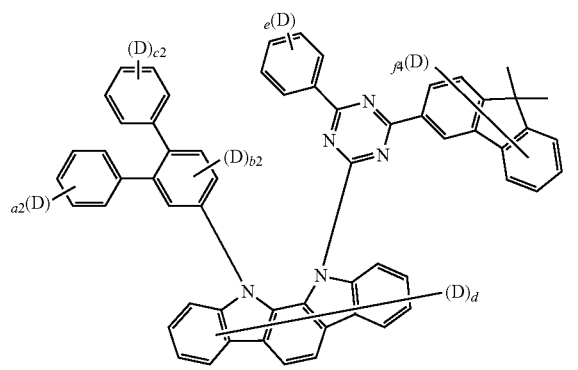

-continued
H1-6-15
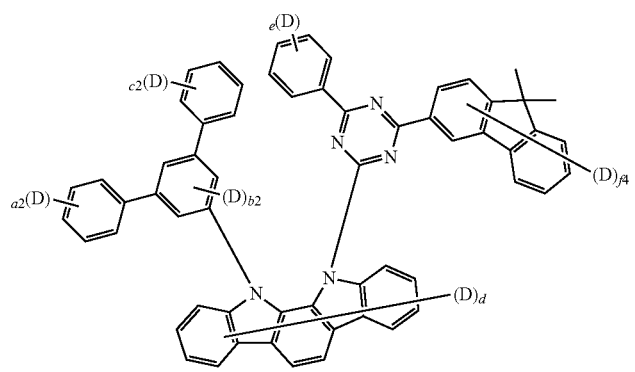
H1-7-10
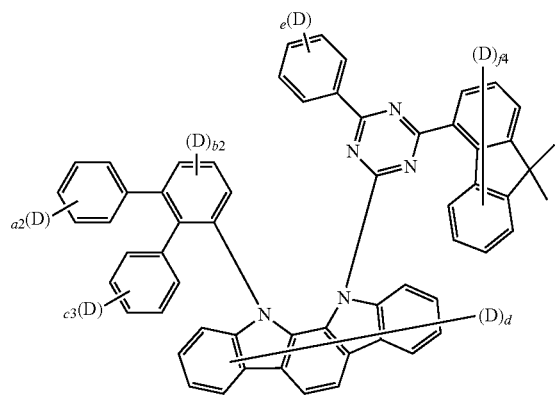
H1-7-11
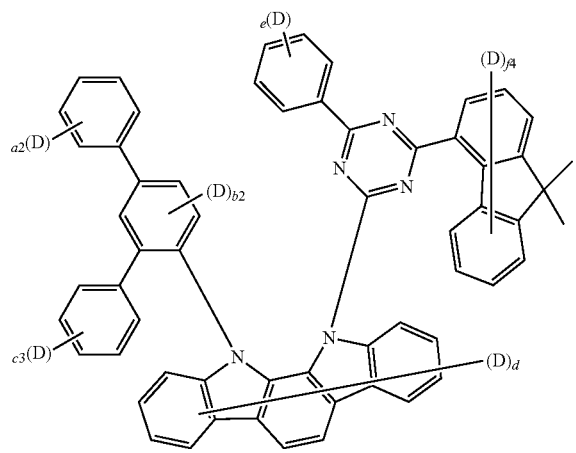
H1-7-12
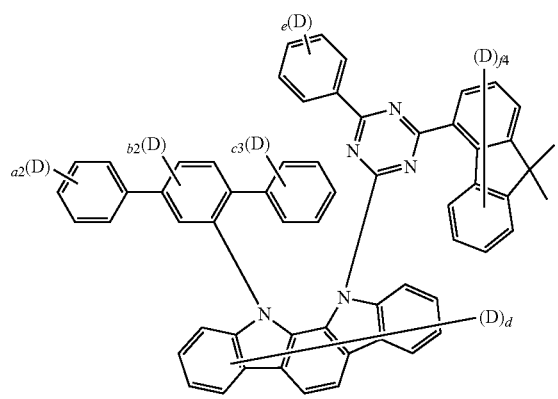

-continued
H1-7-13
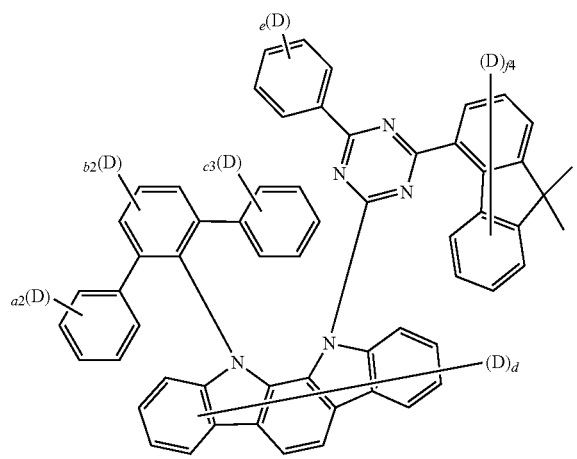
H1-7-14
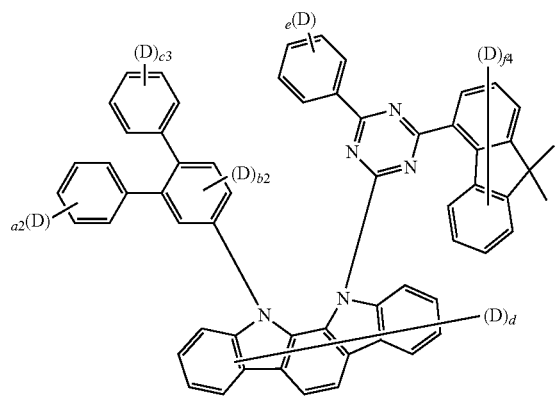
H1-7-15
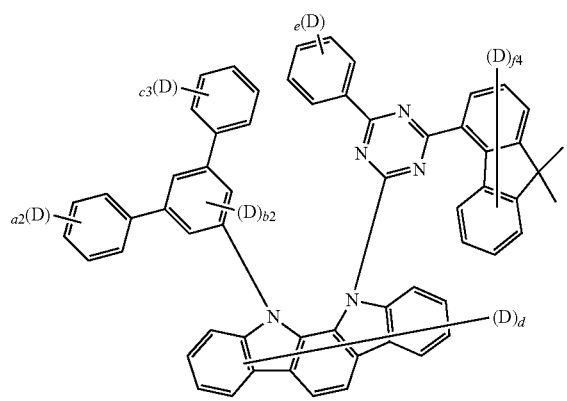

-continued
H1-8-10
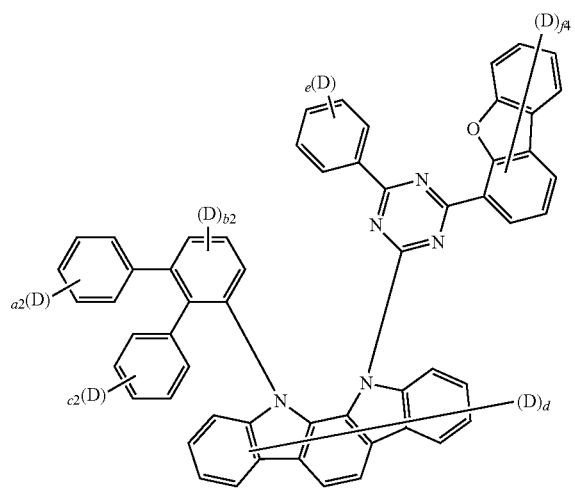
H1-8-11
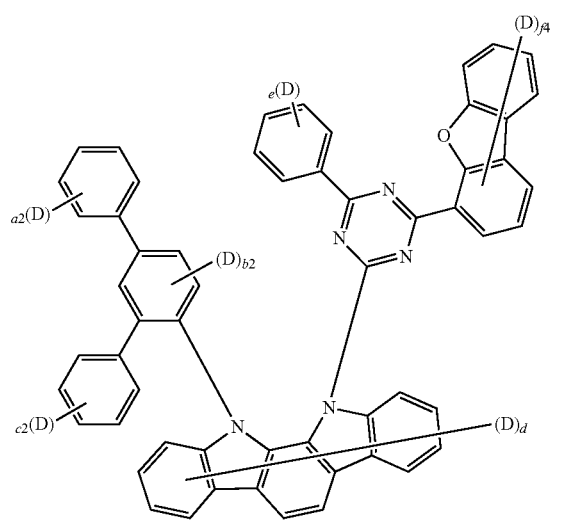
H1-8-12
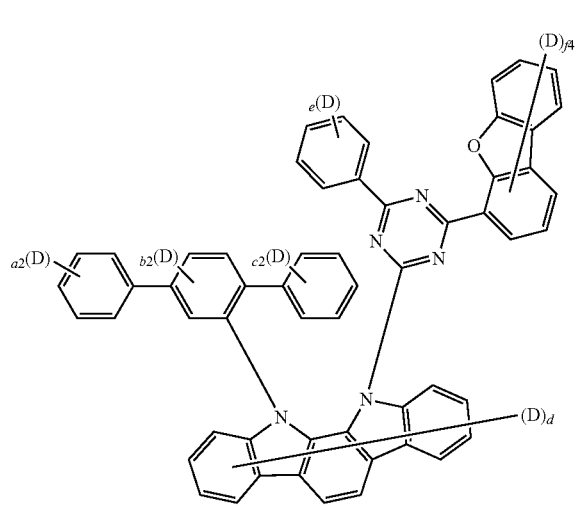

-continued
H1-8-13
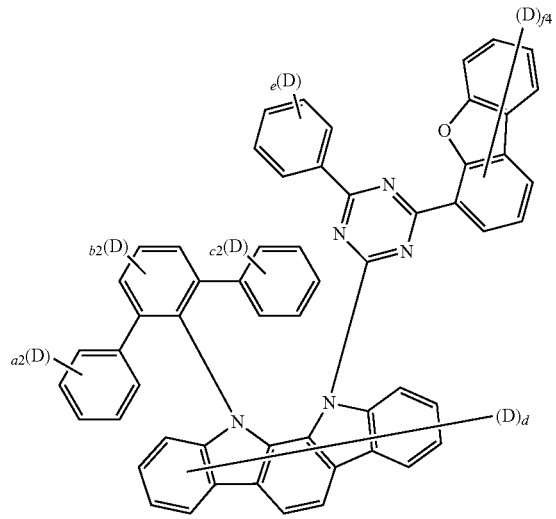
H1-8-14
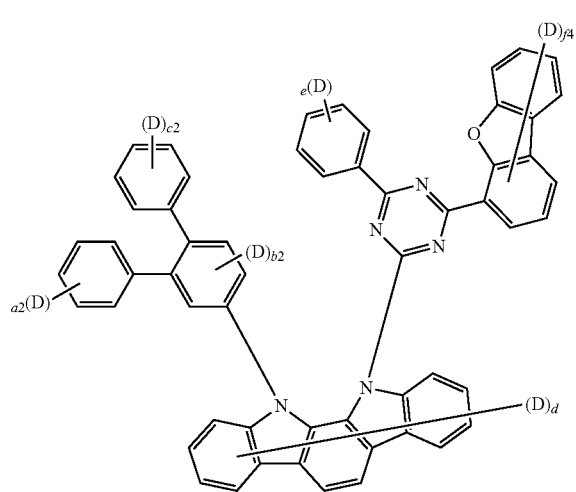
H1-8-15
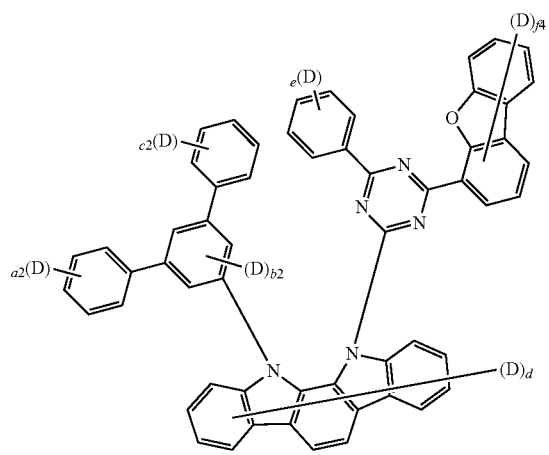

-continued
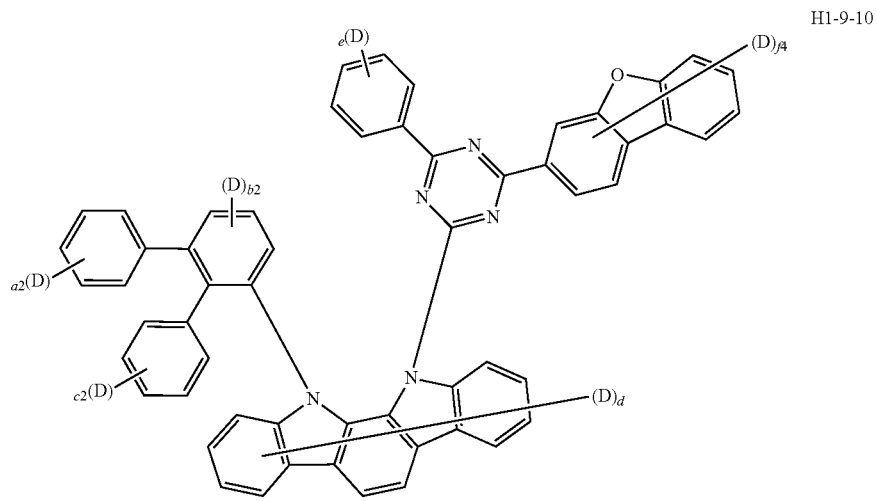
H1-9-10
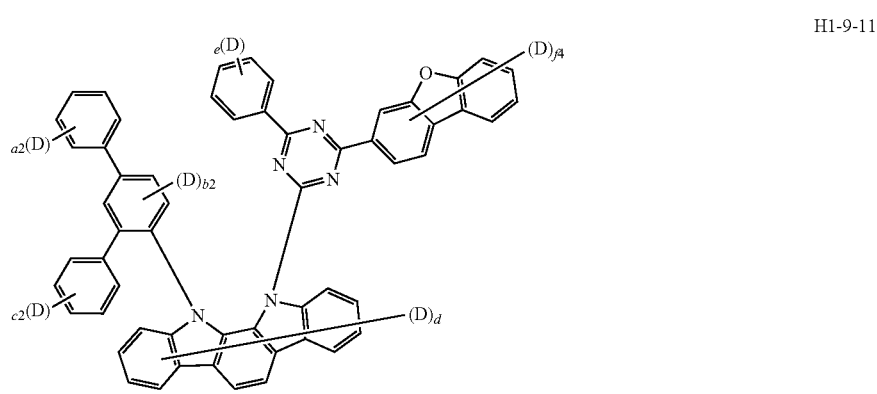
H1-9-11
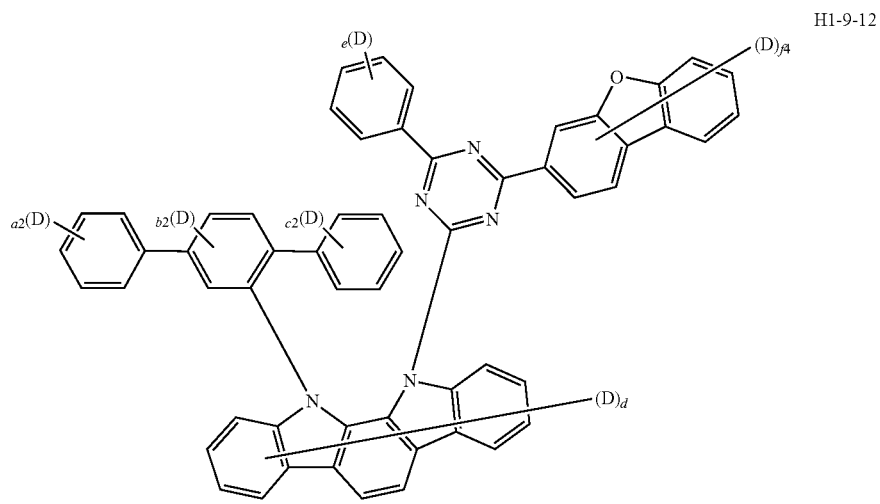
H1-9-12

-continued
H1-9-13
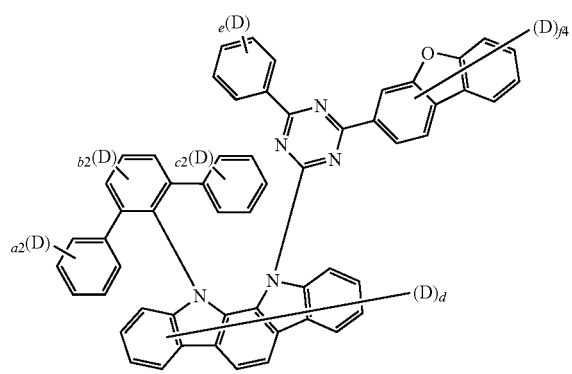
H1-9-14
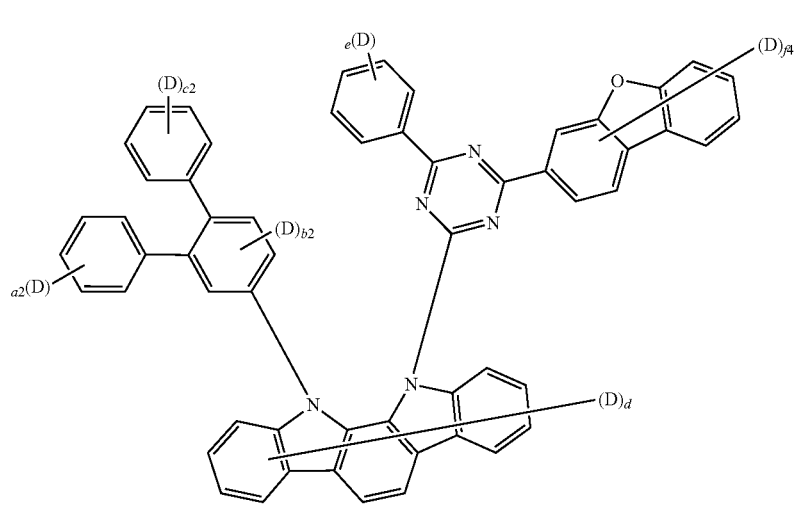
H1-9-15
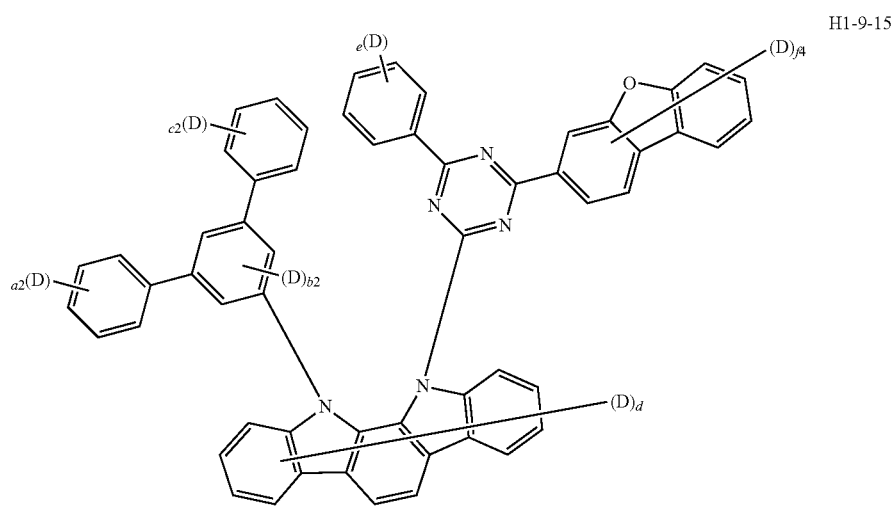

-continued
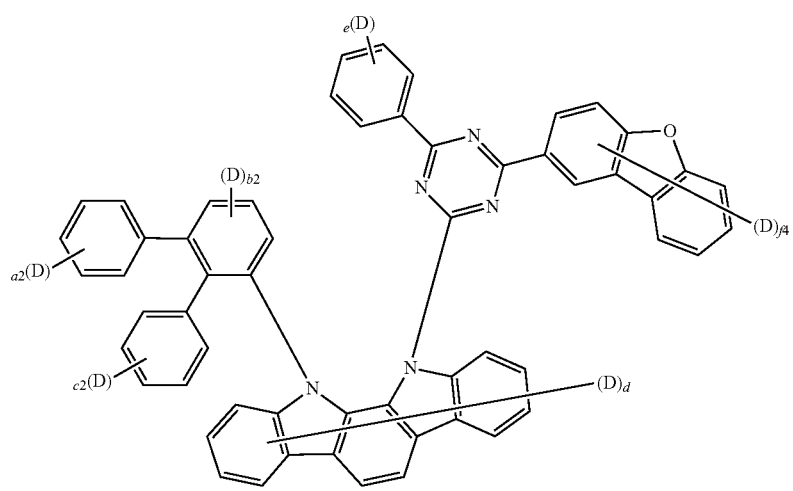
H1-10-10
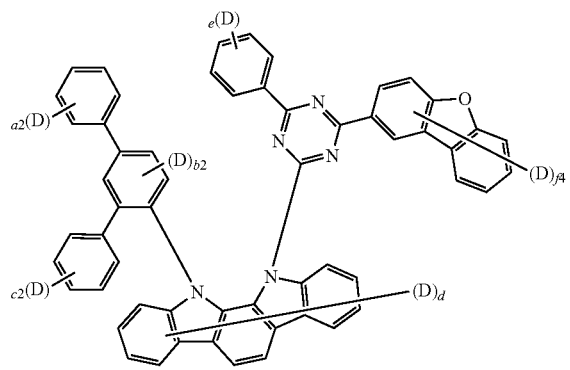
H1-10-11
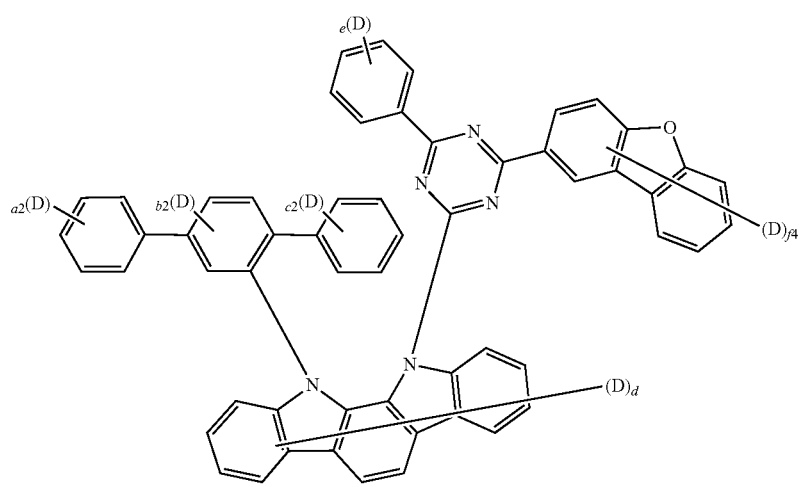
H1-10-12

H1-10-13
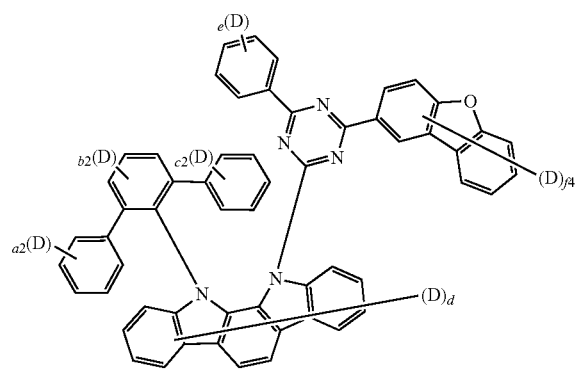
H1-10-14
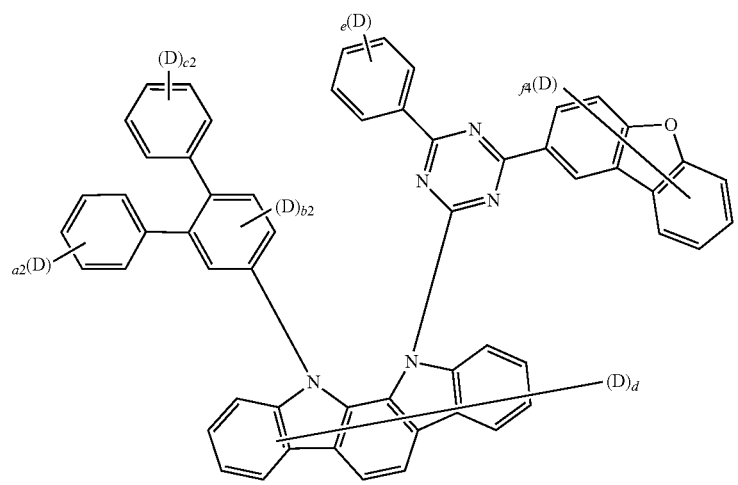
H1-10-15
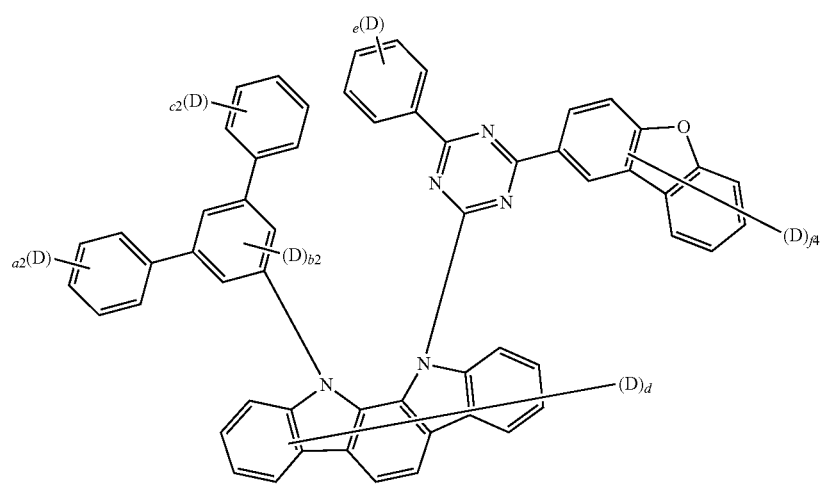

-continued
H1-11-10
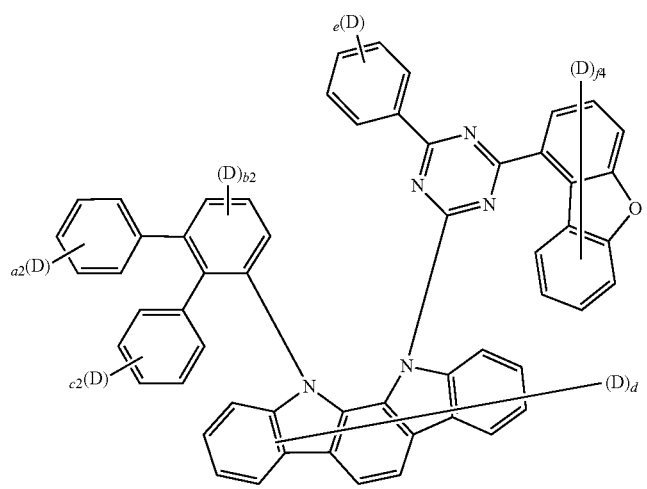
H1-11-11
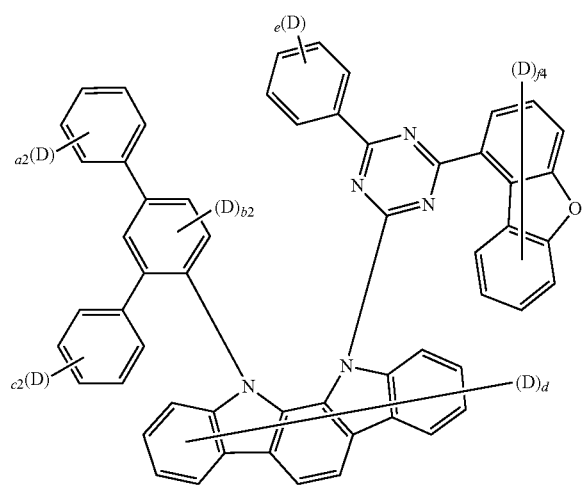
H1-11-12
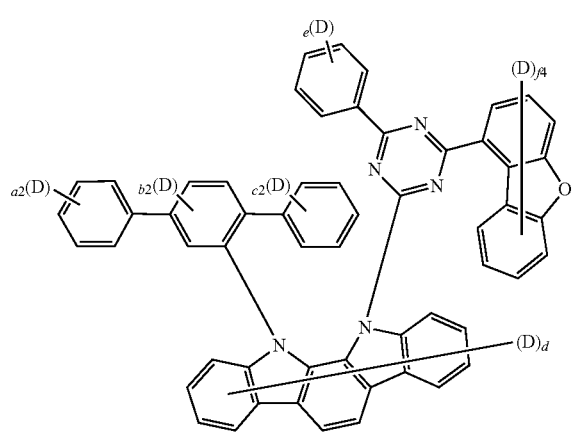

-continued
H1-11-13
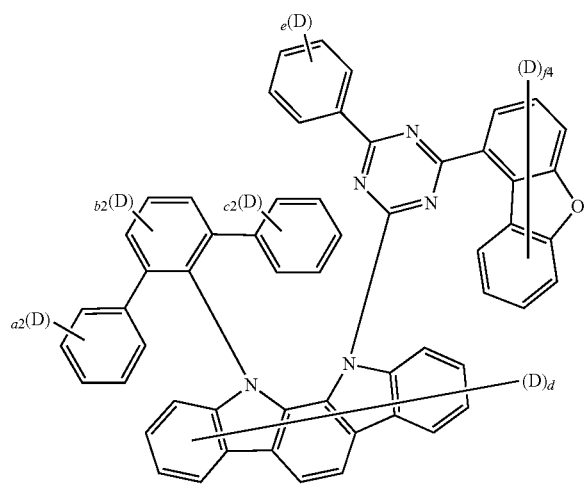
H1-11-14
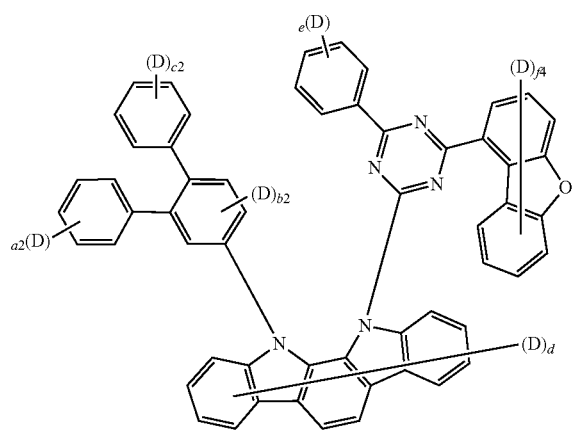
H1-11-15
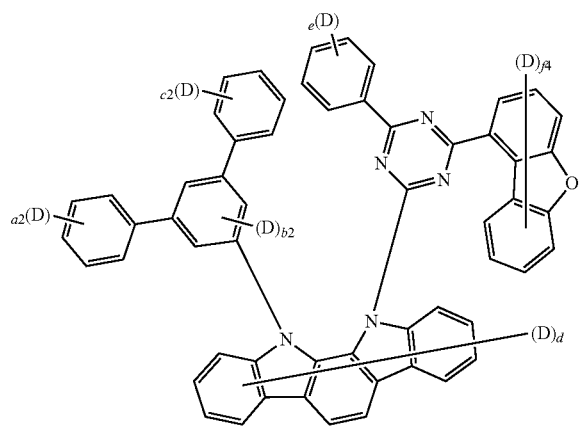

-continued
H1-12-10
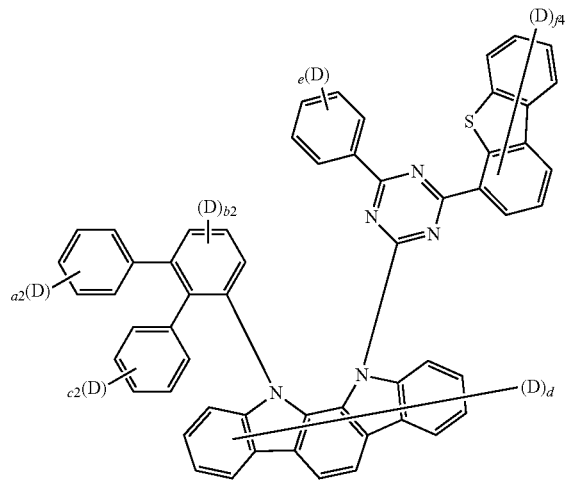
H1-12-11
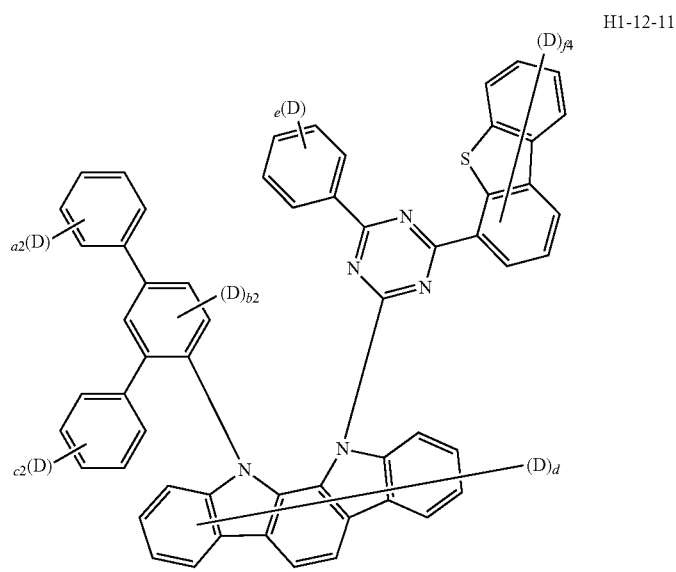
H1-12-12
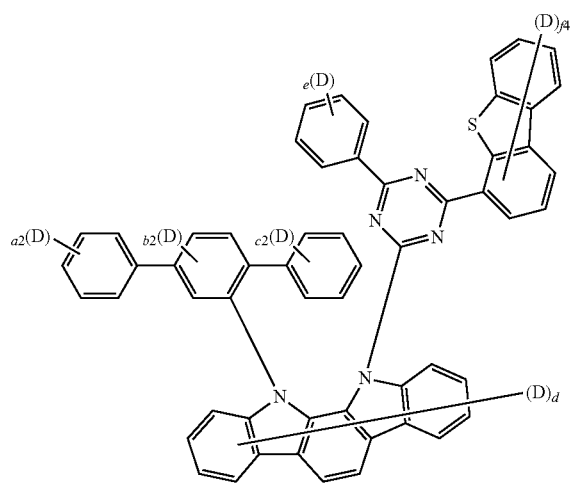

-continued
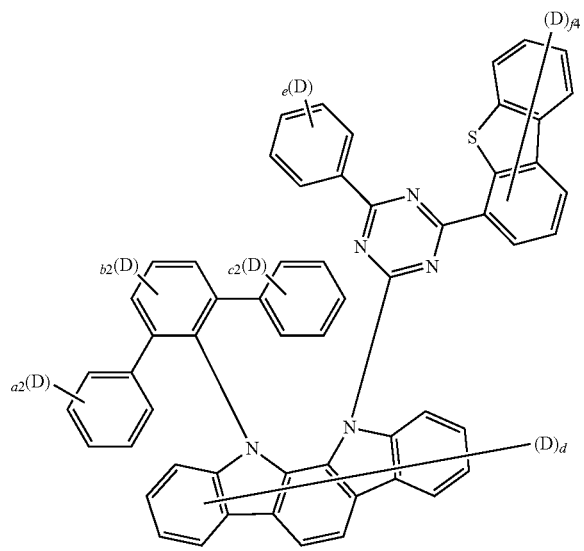
H1-12-13
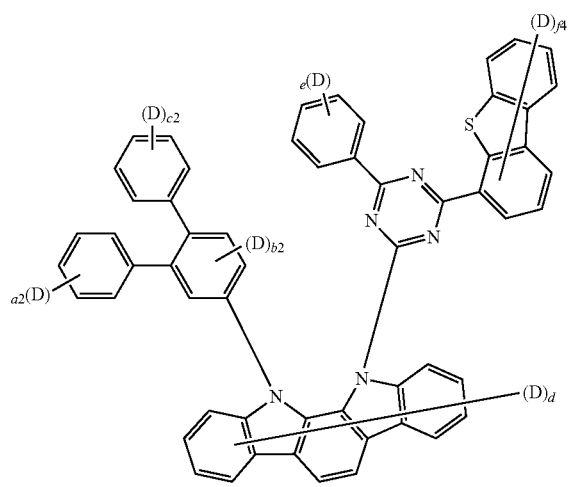
H1-12-14
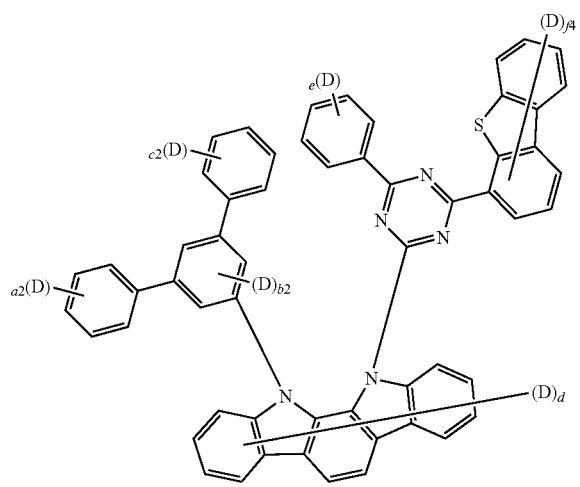
H1-12-15

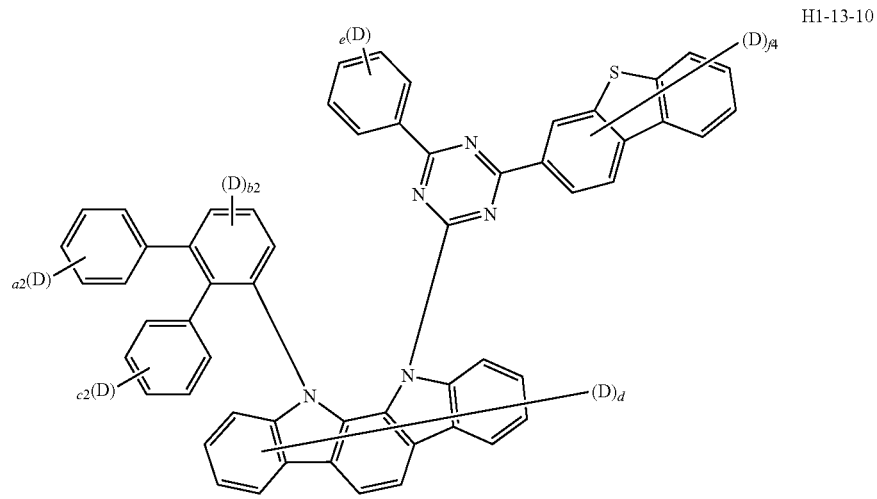
H1-13-10
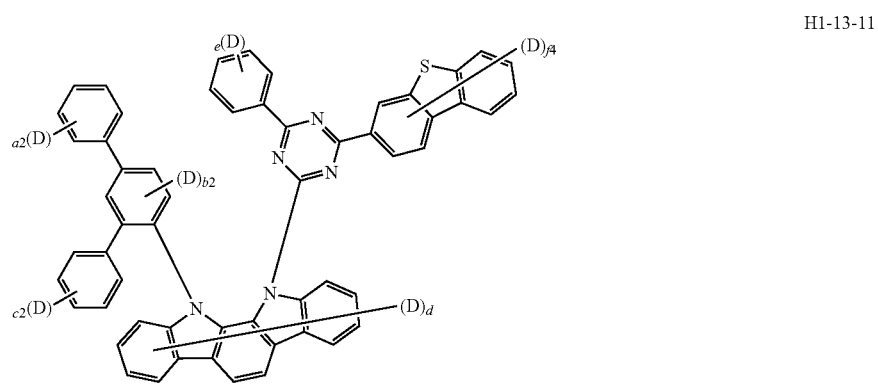
H1-13-11
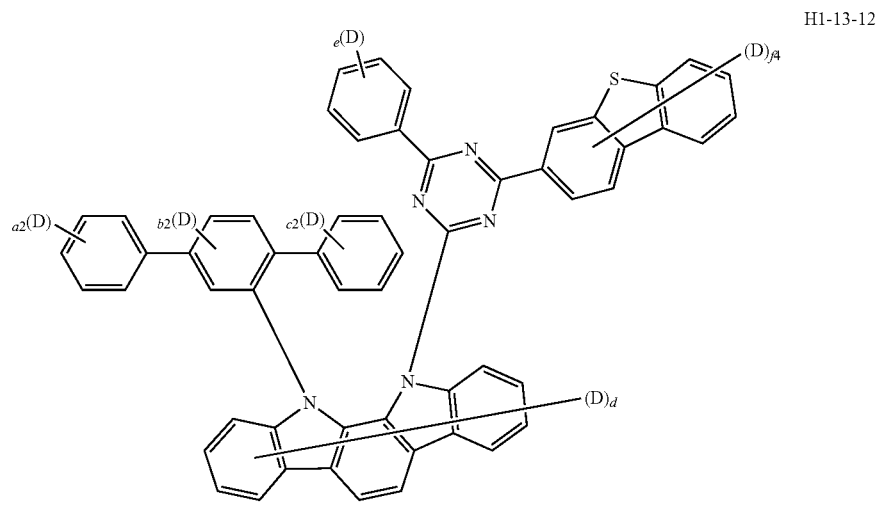
H1-13-12

-continued
H1-13-13
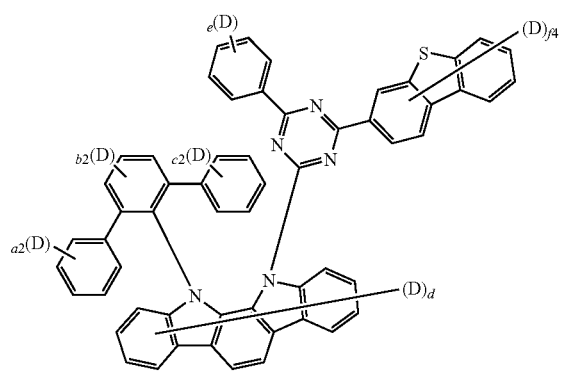
H1-13-14
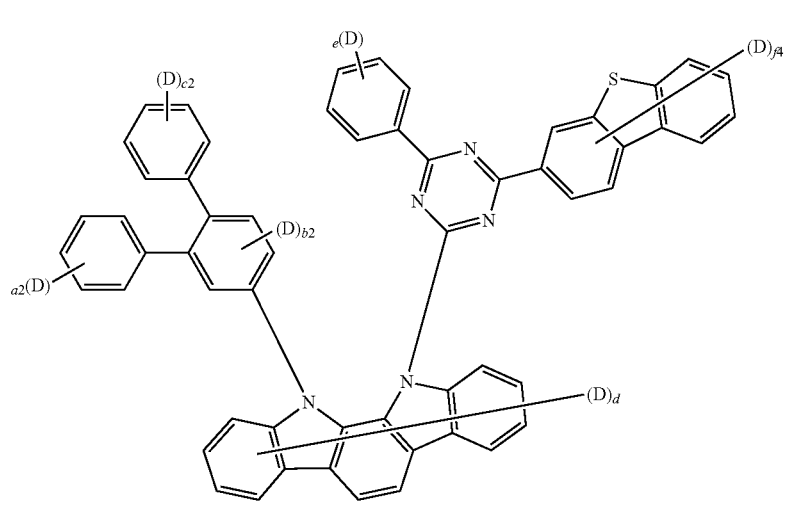
H1-13-15
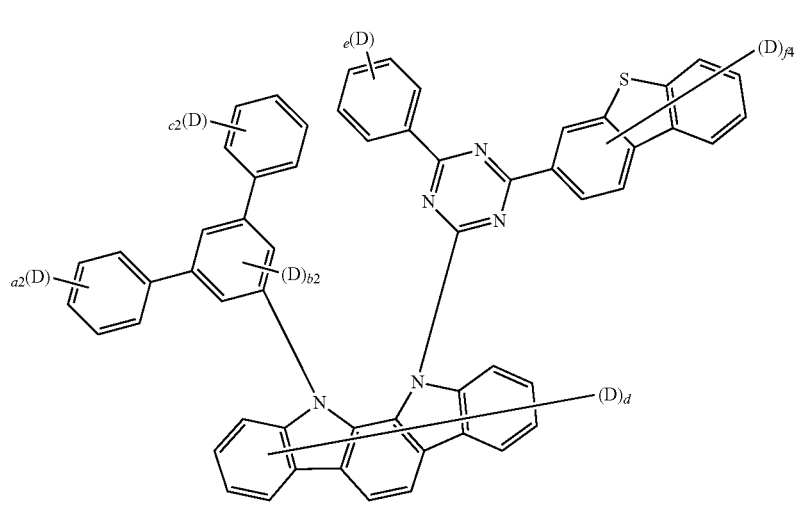

-continued
H1-14-10
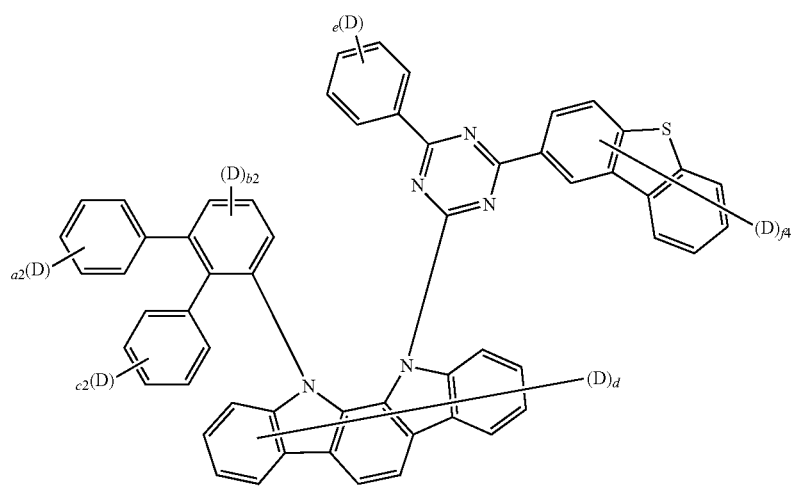
H1-14-11
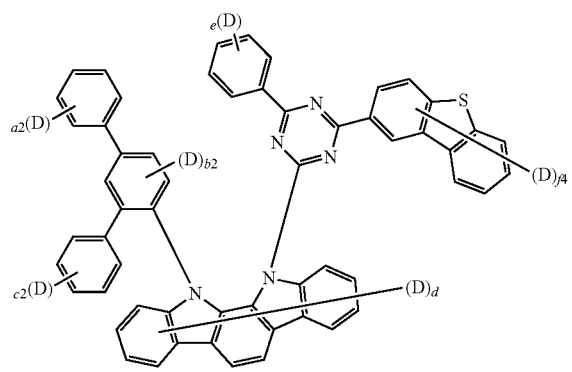
H1-14-12
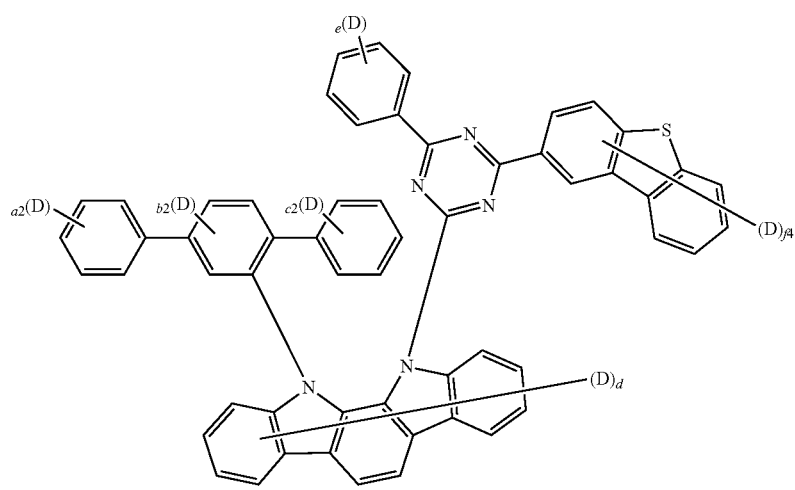

H1-14-13
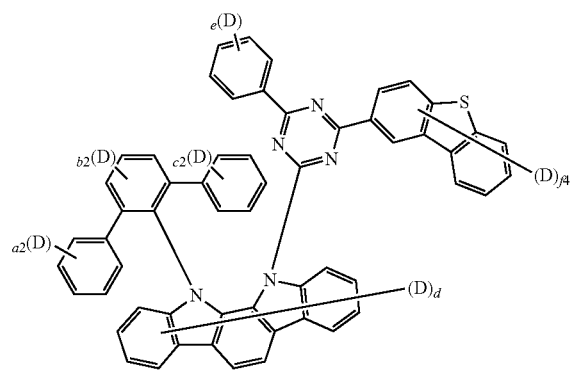
H1-14-14
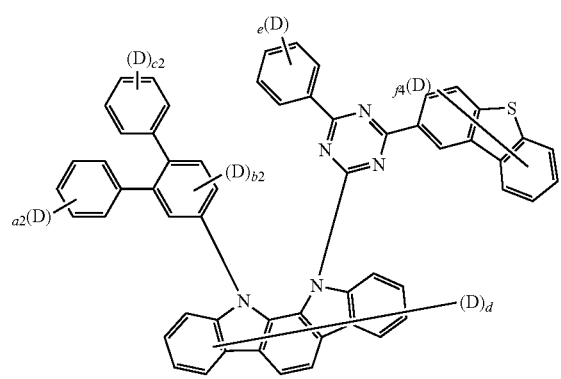
H1-14-15
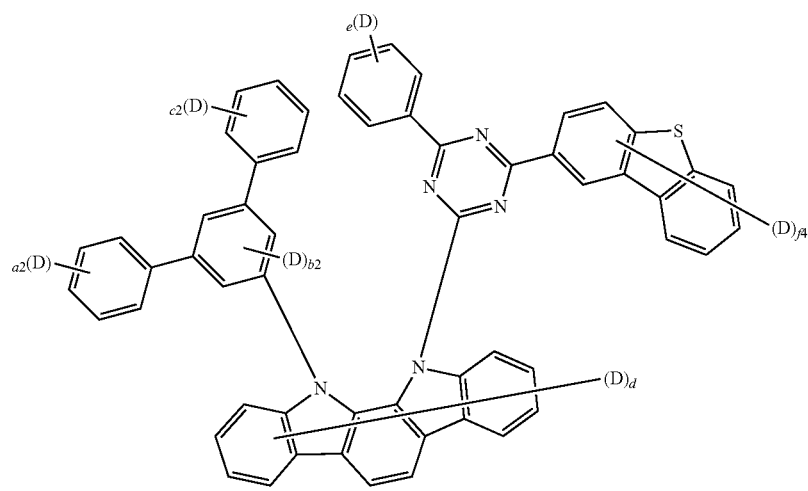

H1-15-10
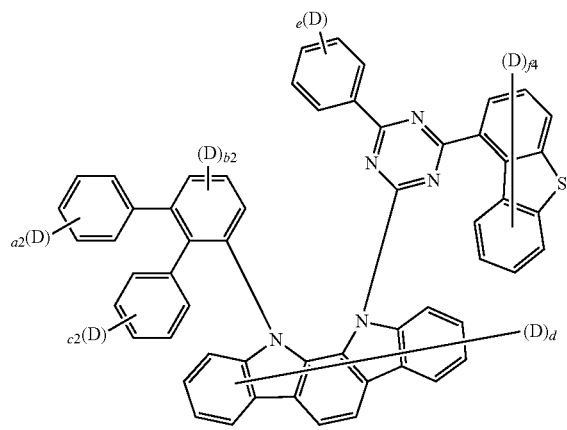
H1-15-11
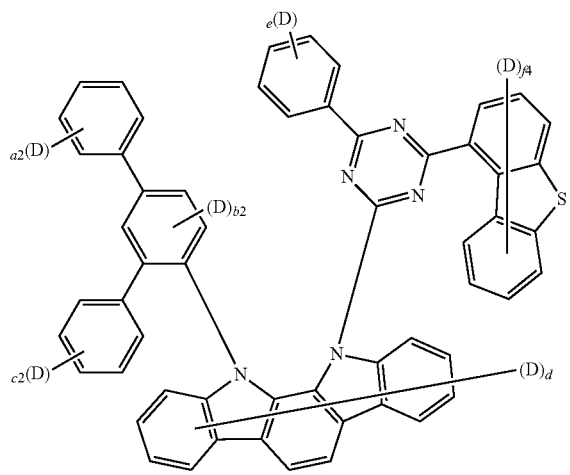
H1-15-12
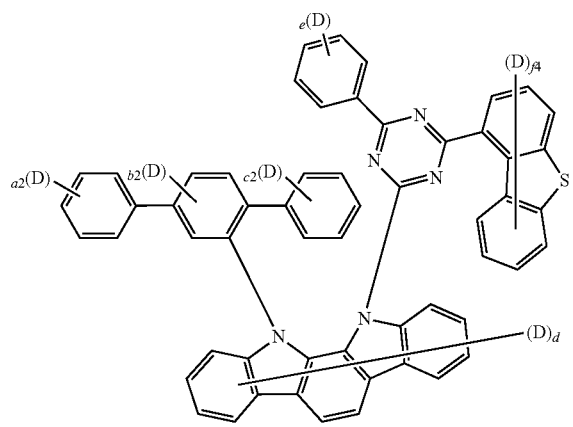
H1-15-13
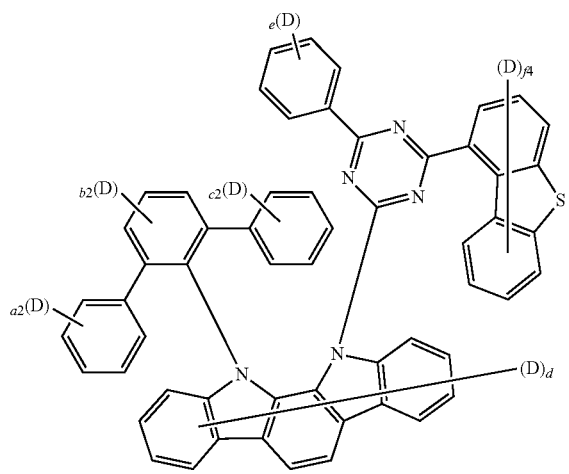
H1-15-14
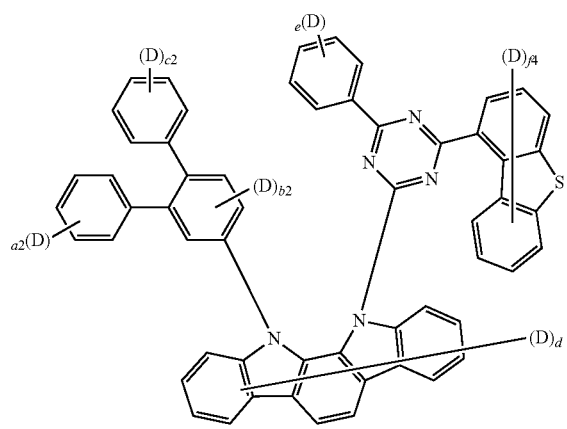
H1-15-15
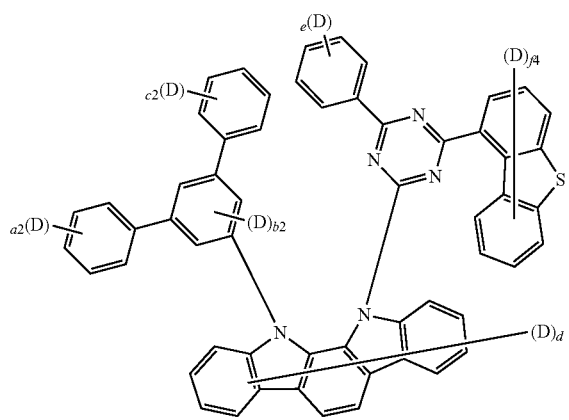
wherein in Chemical Formulae H1-4-10 to H1-4-15, H1-5-10 to H1-5-15, H1-6-10 to H1-6-15, H1-7-10 to H1-7-15, H1-8-10 to H1-8-15, H1-9-10 to H1-9-15, H1-10-10 to H1-10-15, H1-11-10 to H1-11-15, H1-12-10 to H1-12-15, H1-13-10 to H1-13-15, H1-14-10 to H1-14-15, and H1-15-10 to H1-15-15:
a2, b2, c2, and d are as defined in Chemical Formula 1,
e is an integer of 0 to 5,
f4 is an integer of 0 to 7, and
a2+b2+c2+d+e+f4 is 1 to 35;

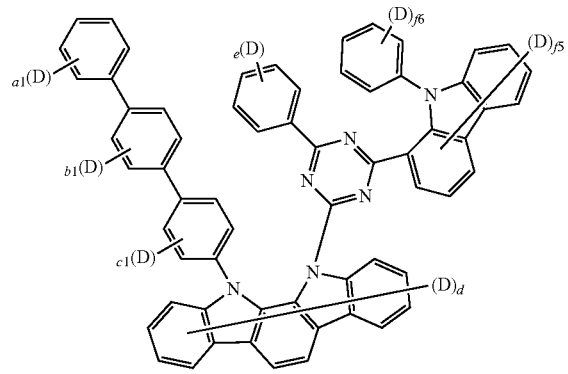
H1-16-1
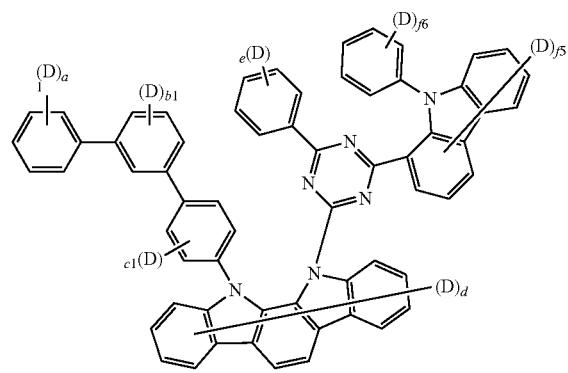
H1-16-2
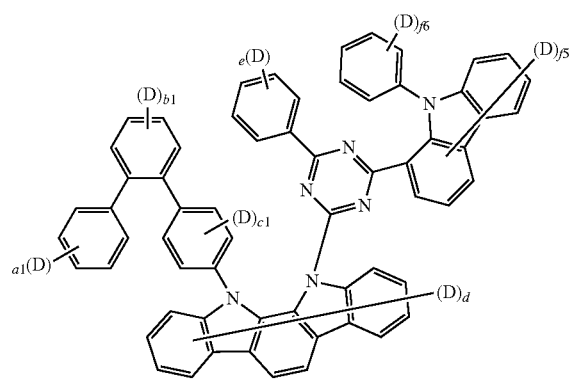
H1-16-3
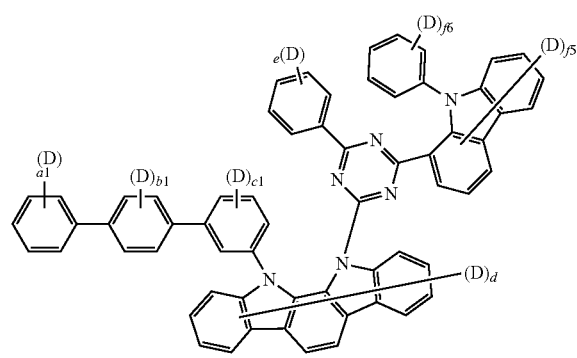
H1-16-4

-continued
H1-16-5
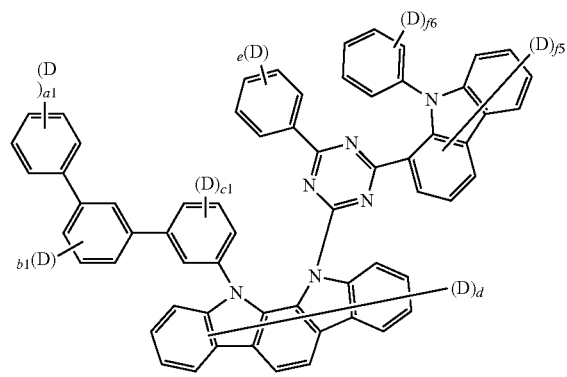
H1-16-6
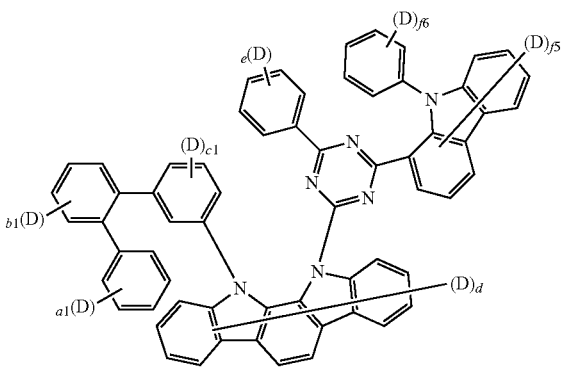
H1-16-7
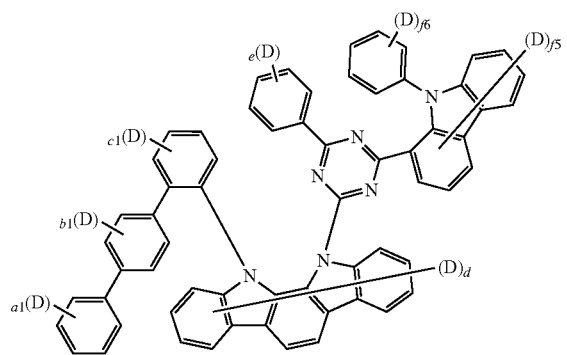
H1-16-8
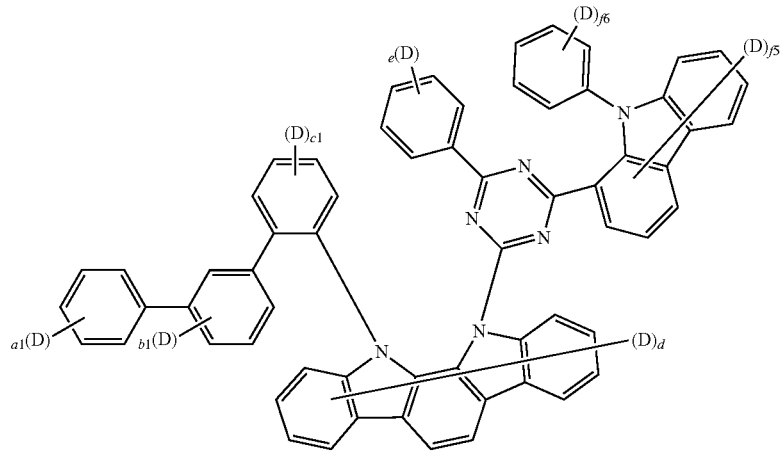
H1-16-9
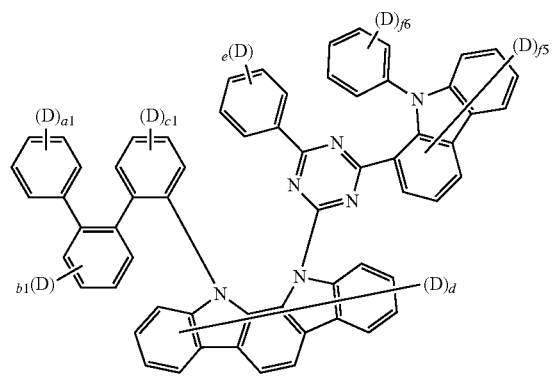

-continued
H1-17-1
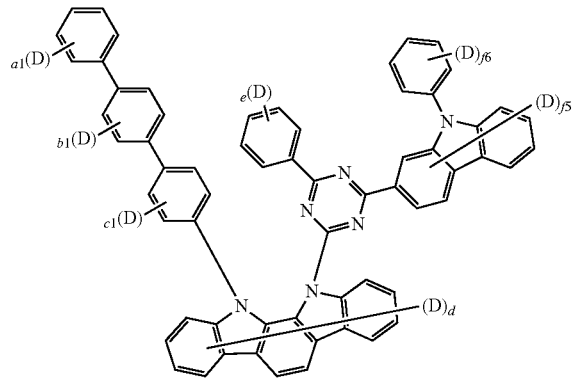
H1-17-2
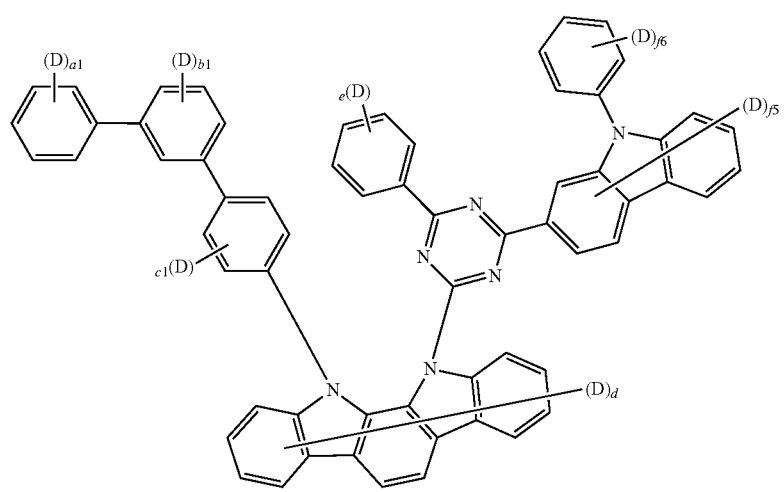
H1-17-3
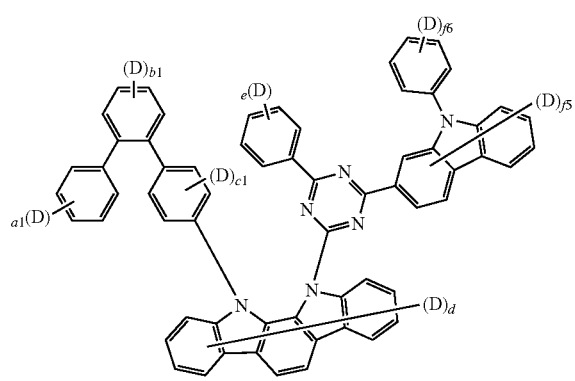

-continued
H1-17-4
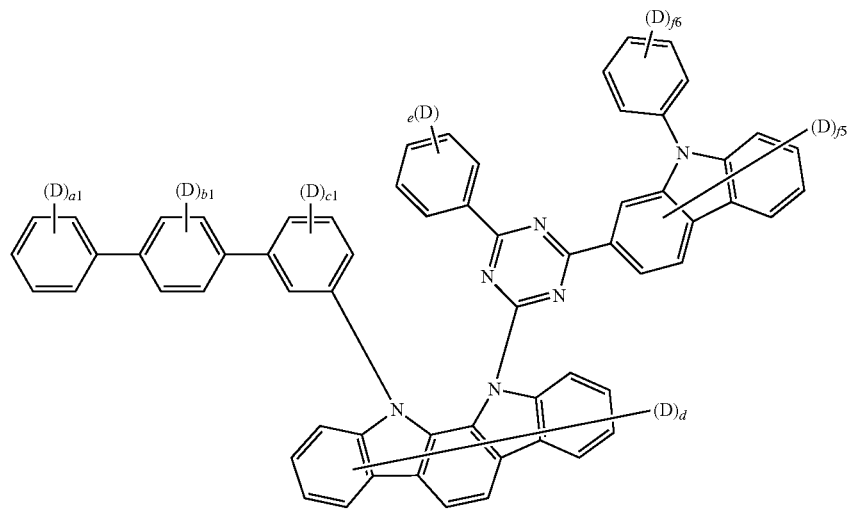
H1-17-5
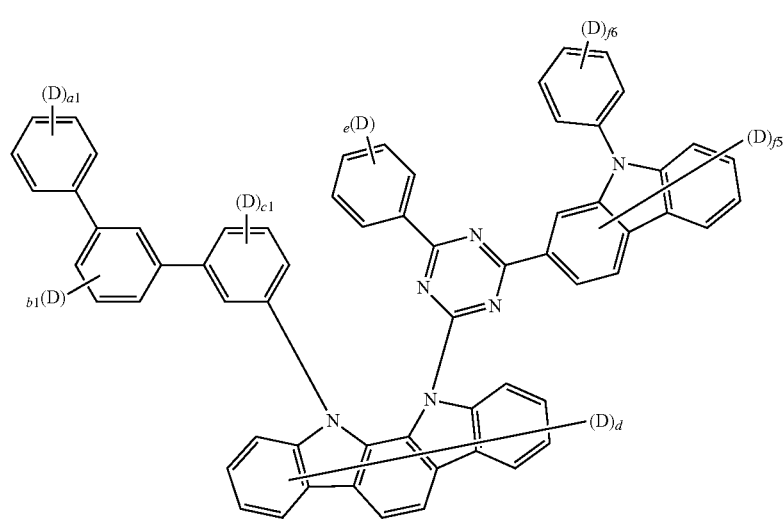
H1-17-6
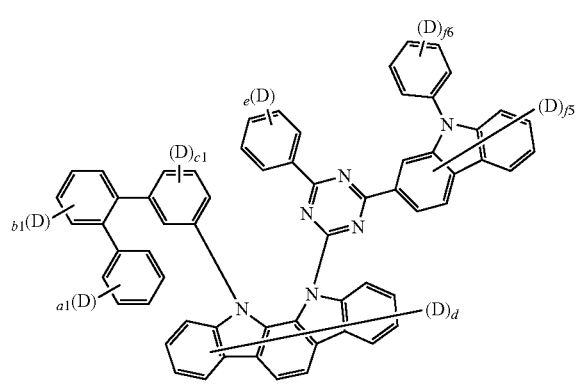

-continued
H1-17-7
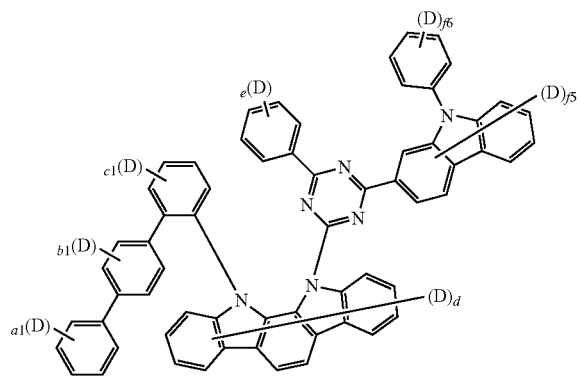
H1-17-8
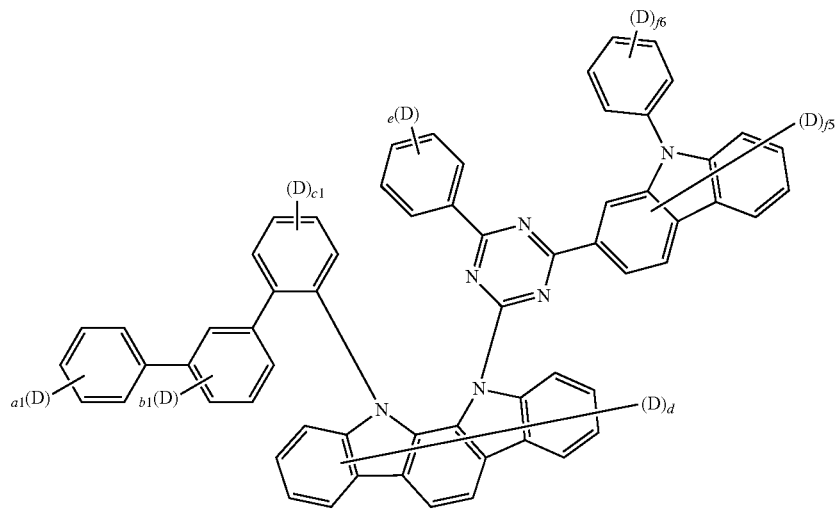
H1-17-9
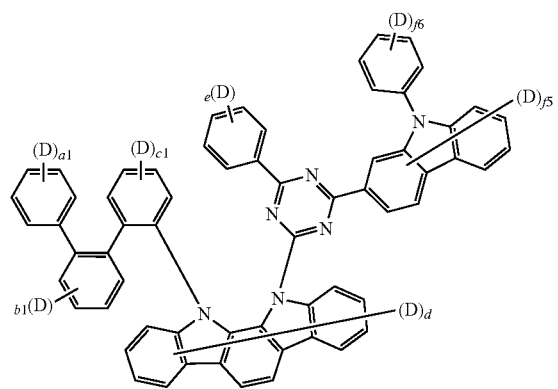

-continued
H1-18-1
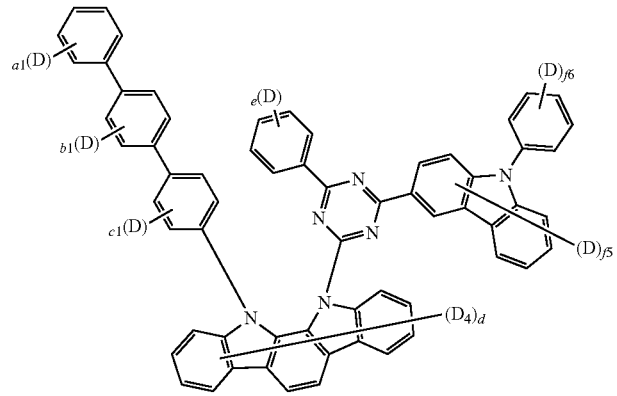
H1-18-2
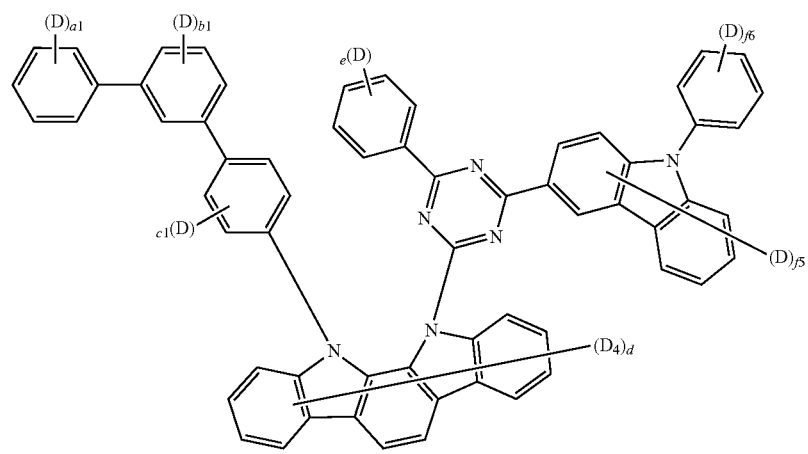
H1-18-3
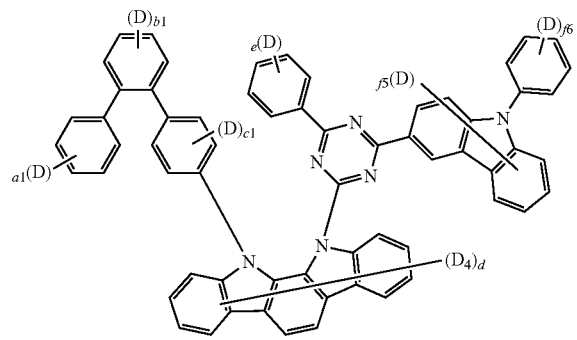
H1-18-4
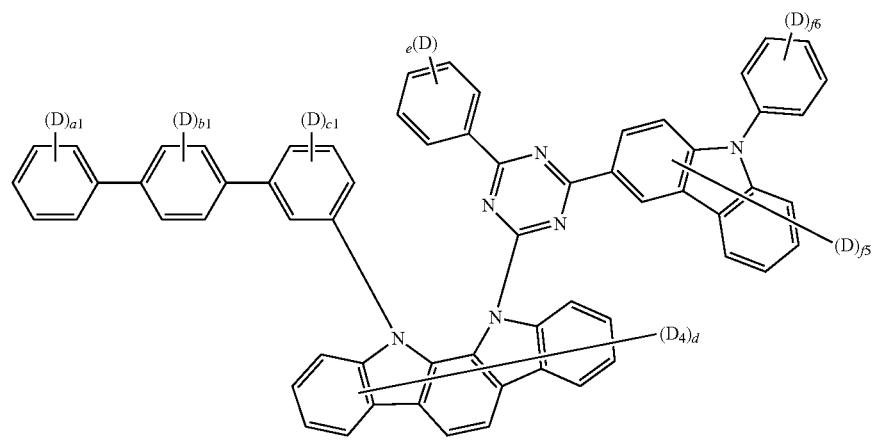

H1-18-5
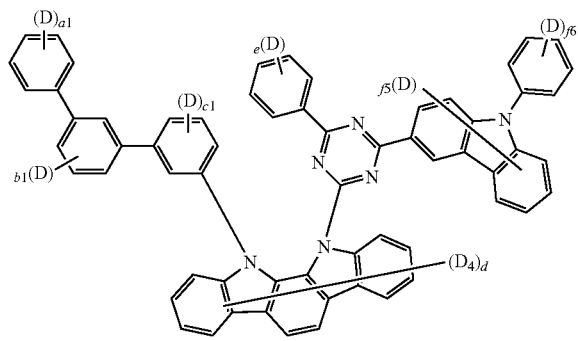
H1-18-6
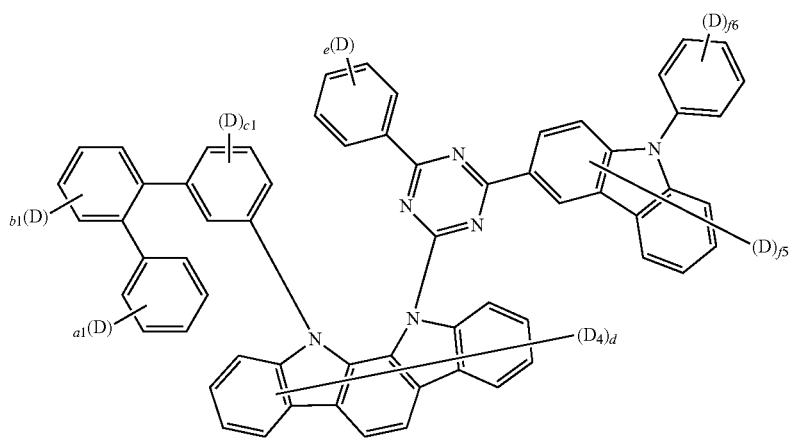
H1-18-7
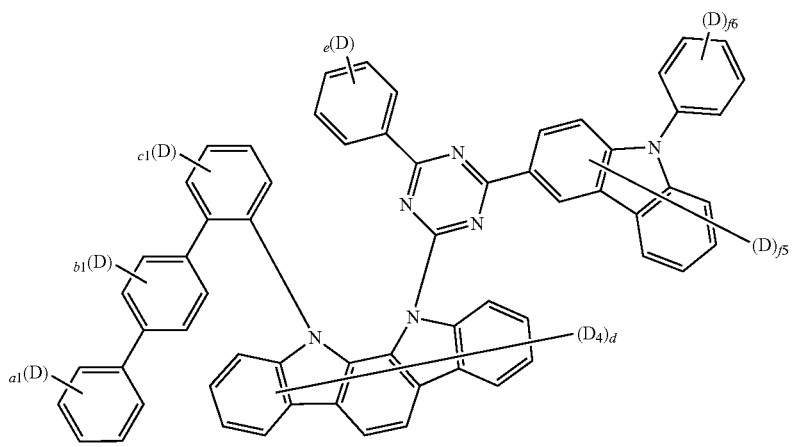
H1-18-8
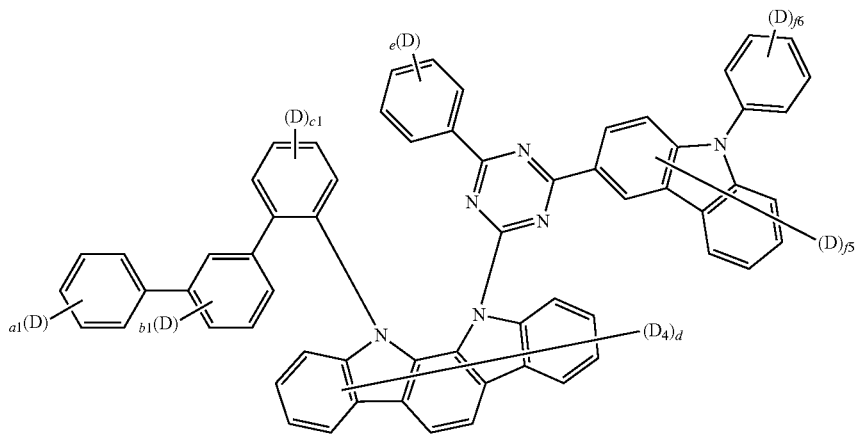

H1-18-9
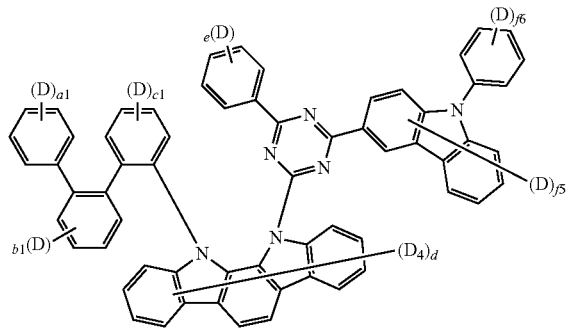
H1-19-1
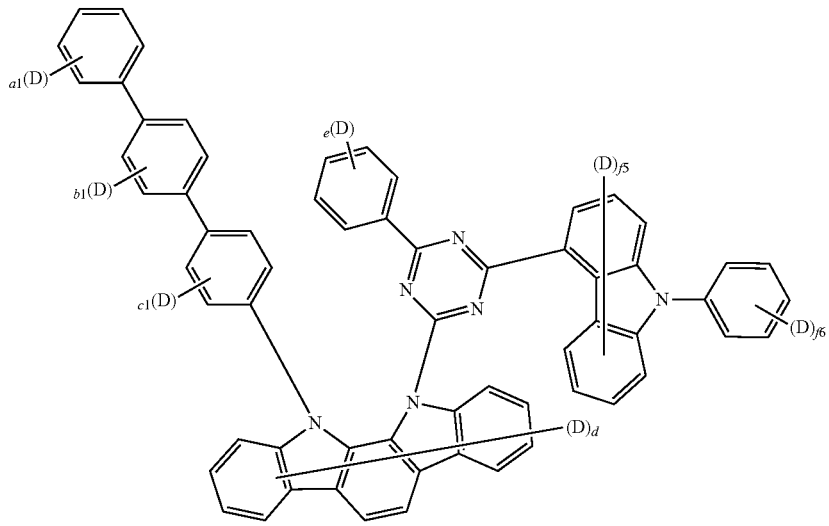
H1-19-2
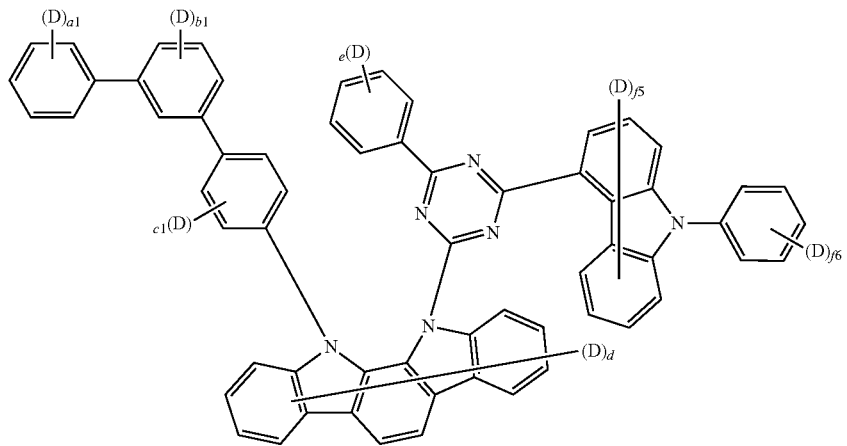

H1-19-3
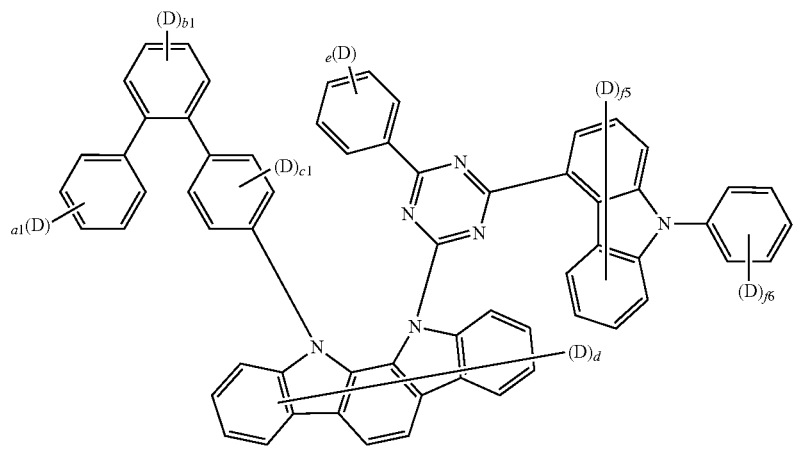
H1-19-4
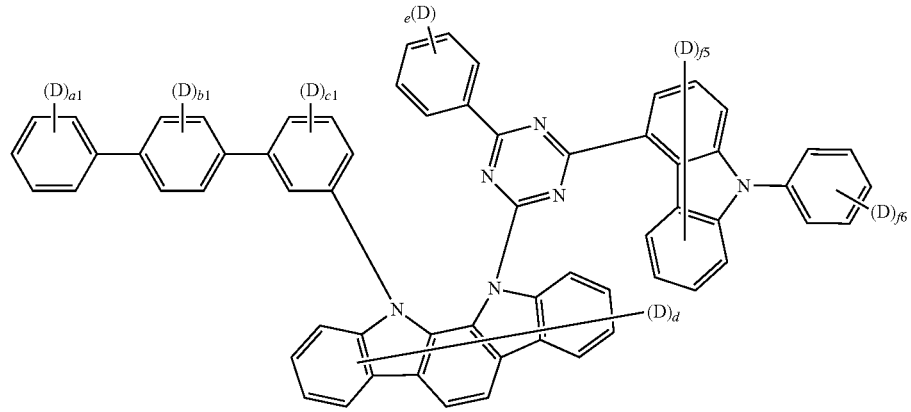
H1-19-5
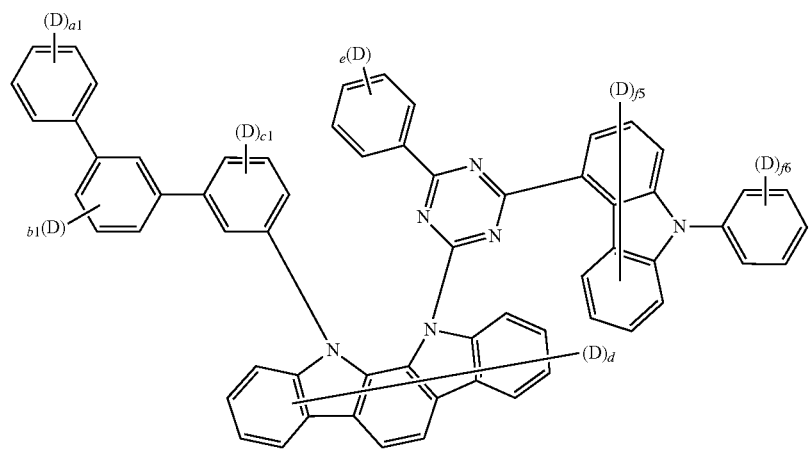

H1-19-6
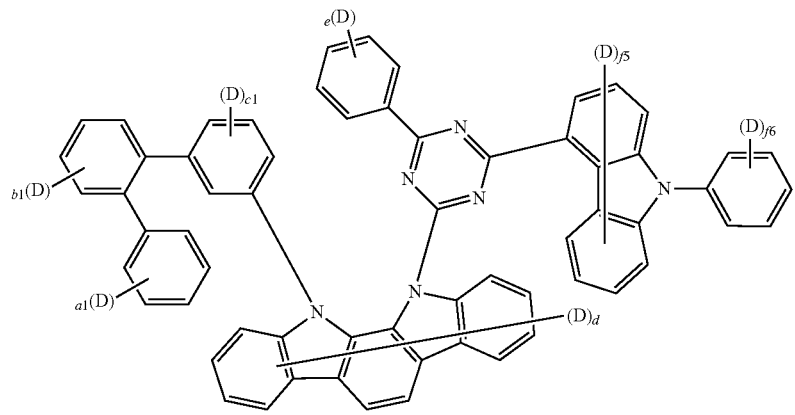
H1-19-7
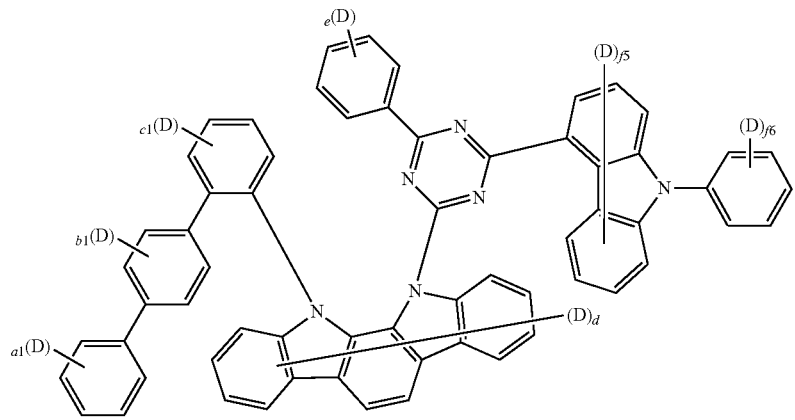
H1-19-8
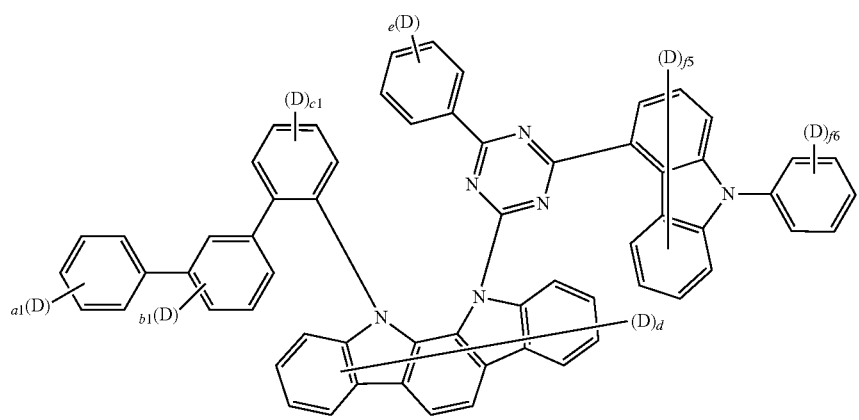
H1-19-9
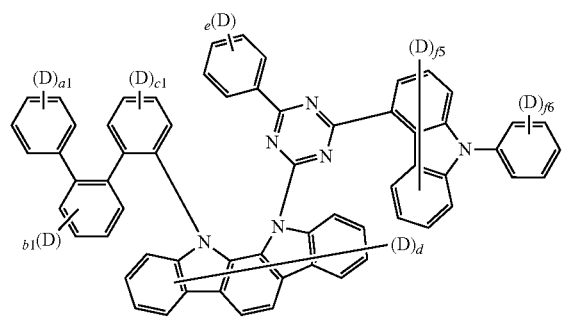

wherein in Chemical Formulae H1-16-1 to H1-16-9, H1-17-1 to H1-17-9, H1-18-1 to H1-18-9, and H1-19-1 to H1-19-9:
a1, b1, c1, and d are as defined in Chemical Formula 1,
e is an integer of 0 to 5,
f5 is an integer of 0 to 7,
f6 is an integer of 0 to 5, and
a1+b1+c1+d+e+f5+f6 is 1 to 40;
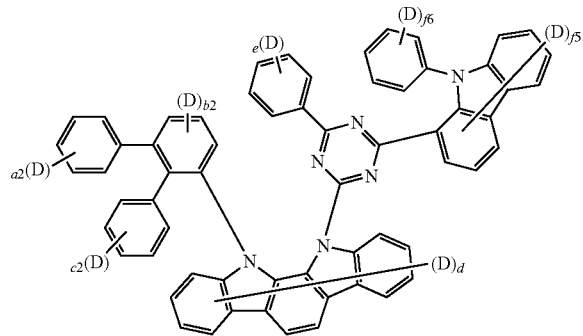
H1-16-10
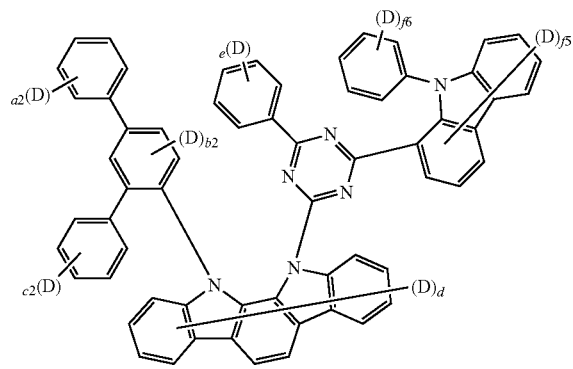
H1-16-11
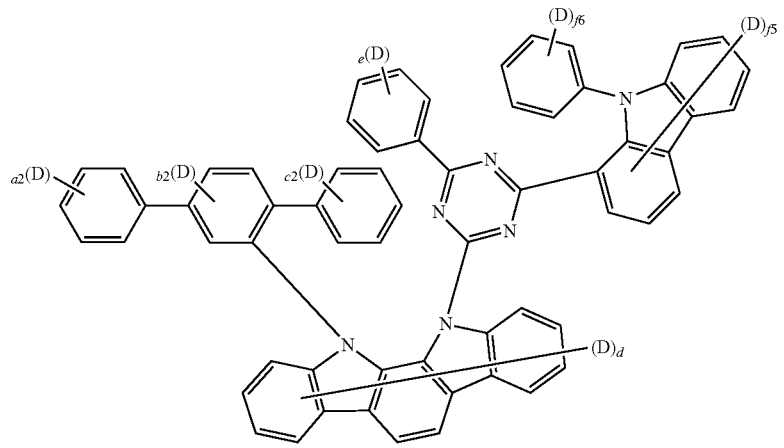
H1-16-12

-continued
H1-16-13
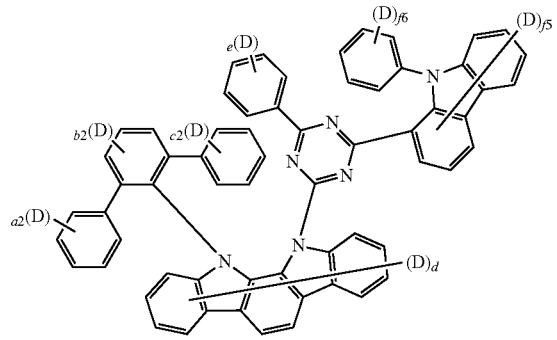
H1-16-14
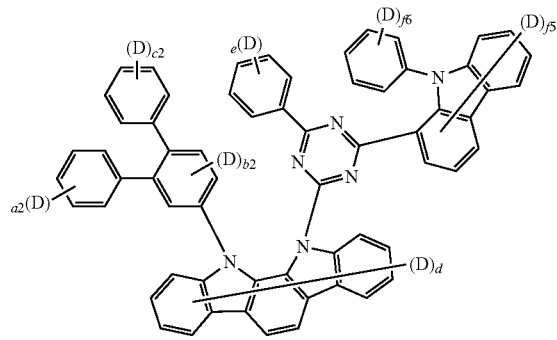
H1-16-15
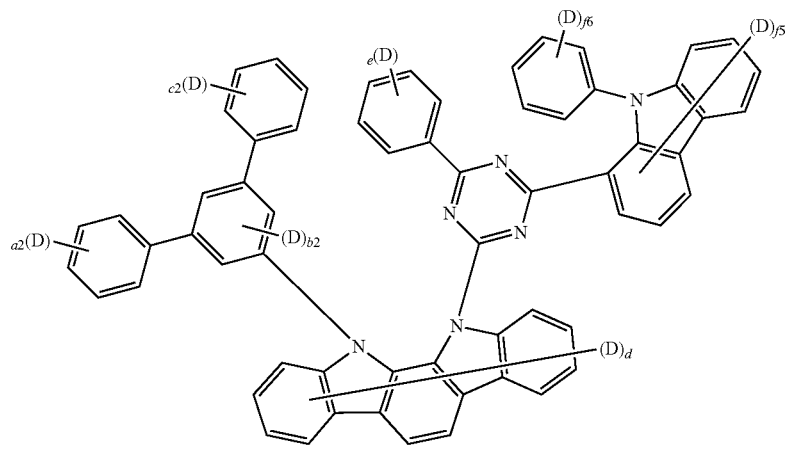
H1-17-10
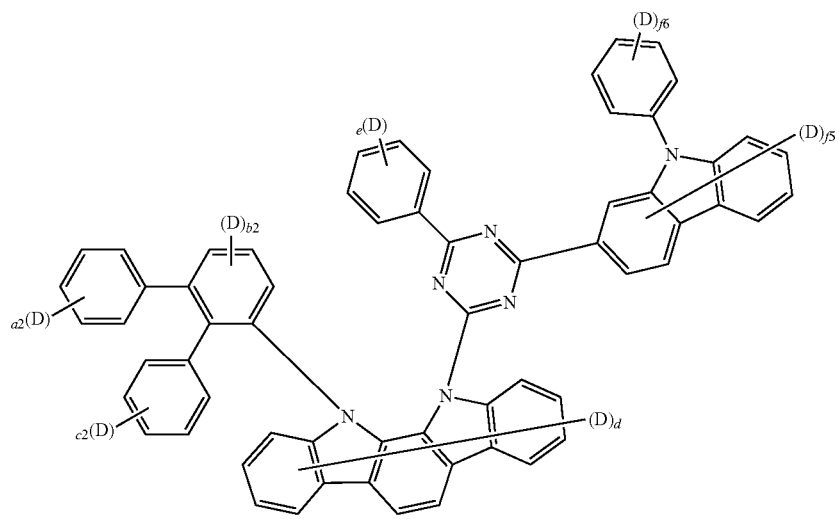

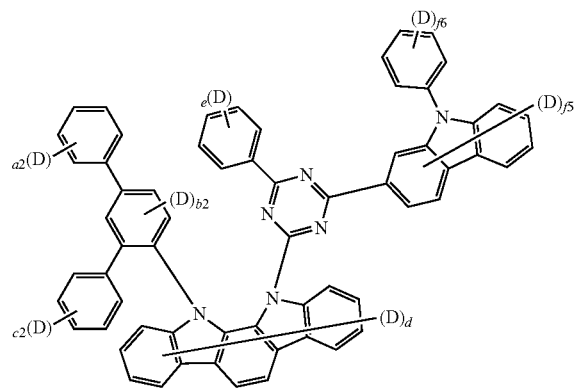
H1-17-11
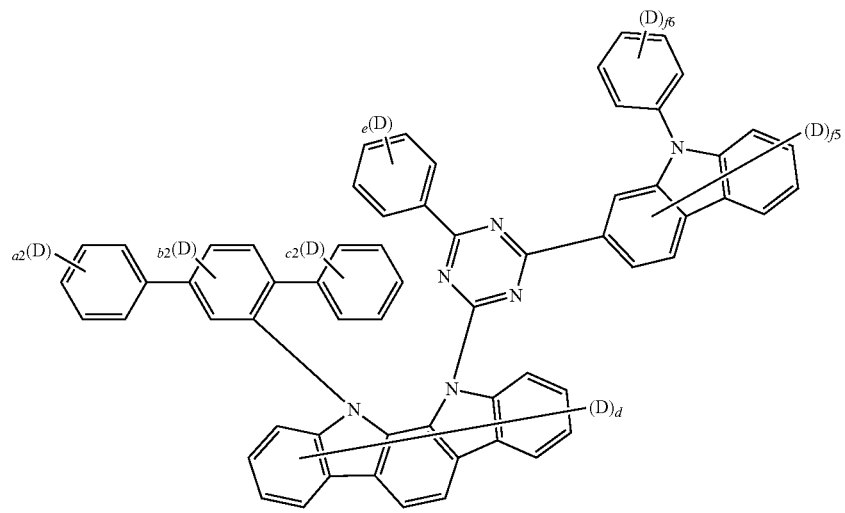
H1-17-12
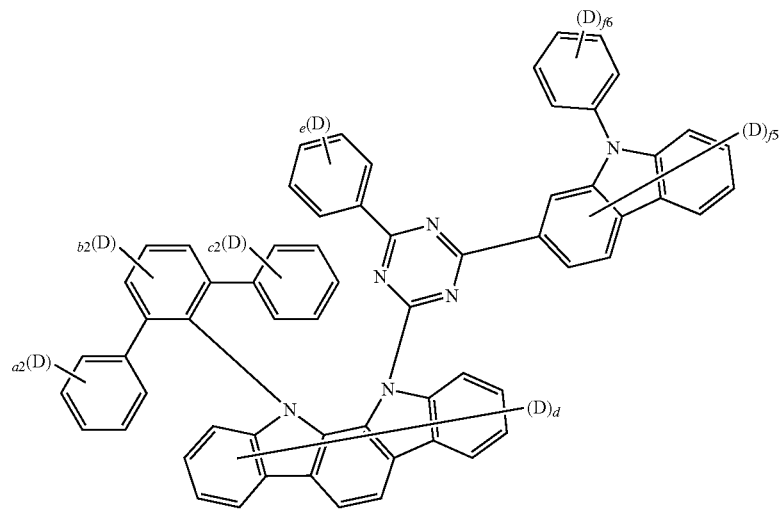
H1-17-13

H1-17-14
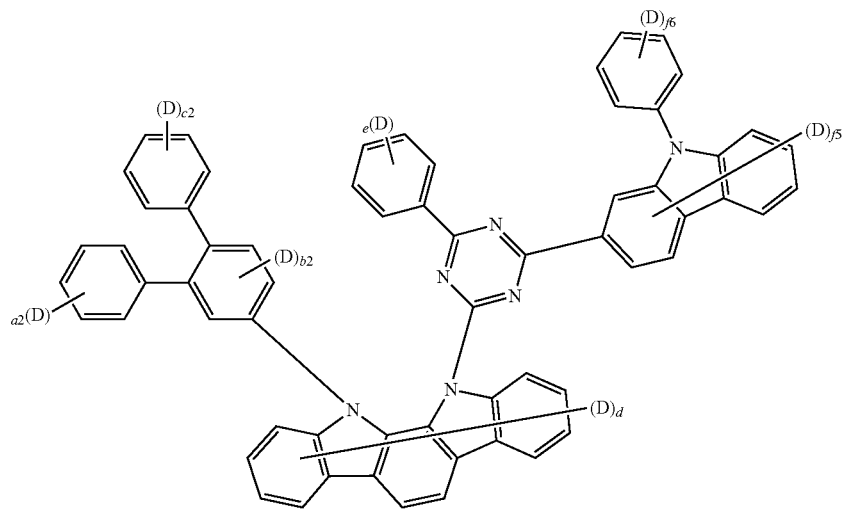
H1-17-15
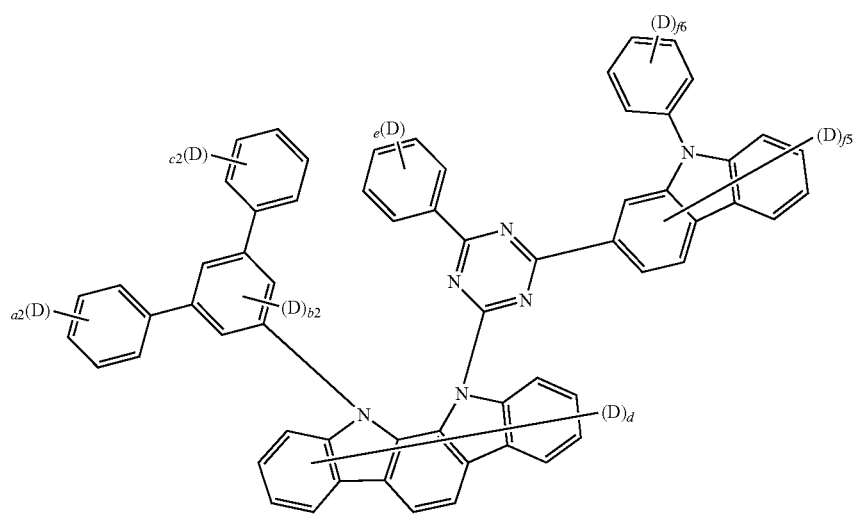
H1-18-10
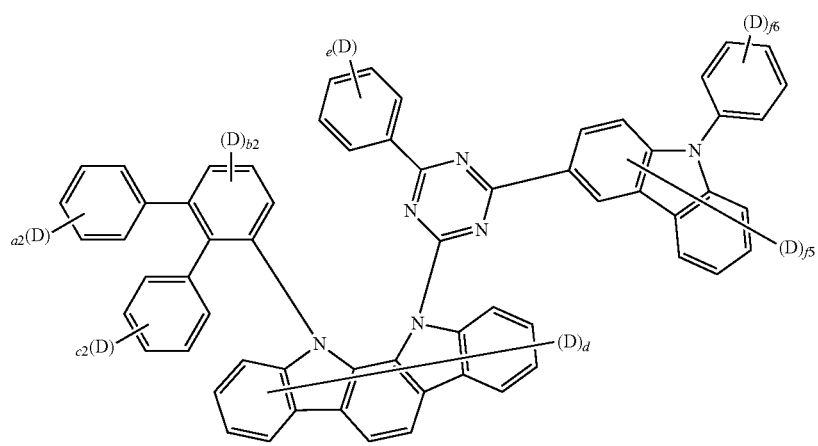

H1-18-11
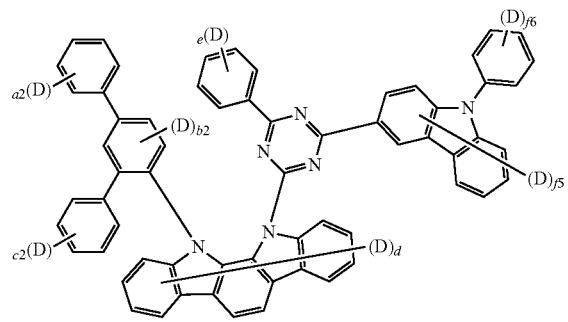
H1-18-12
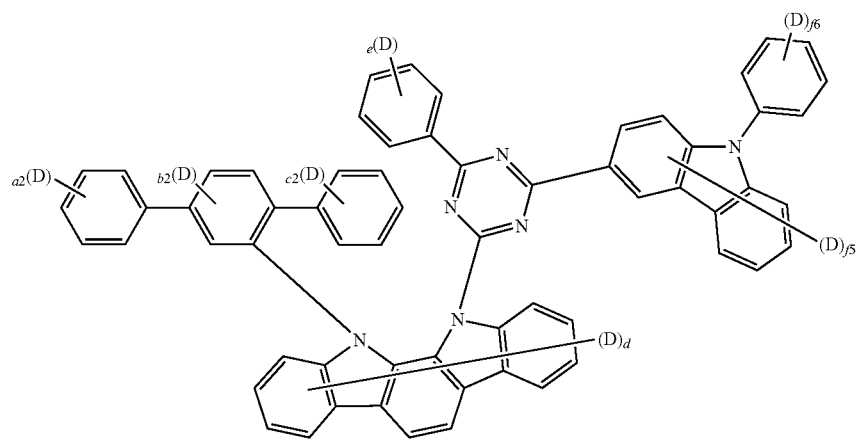
H1-18-13
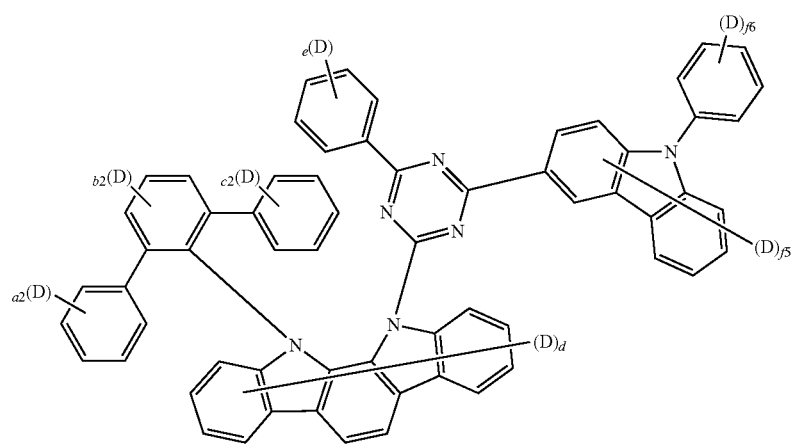
H1-18-14
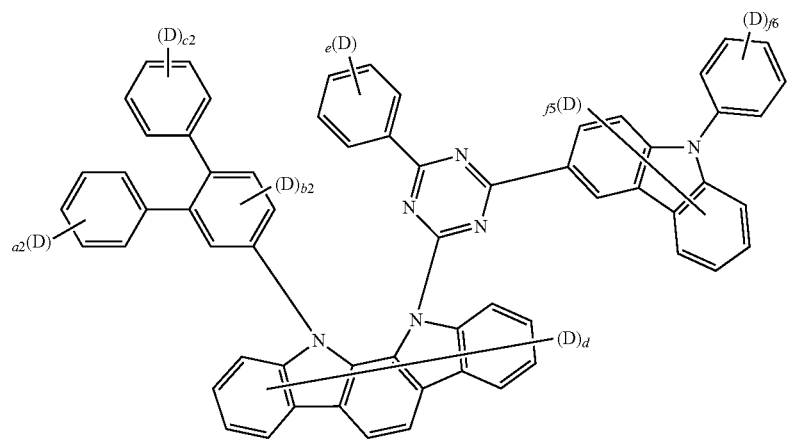

H1-18-15
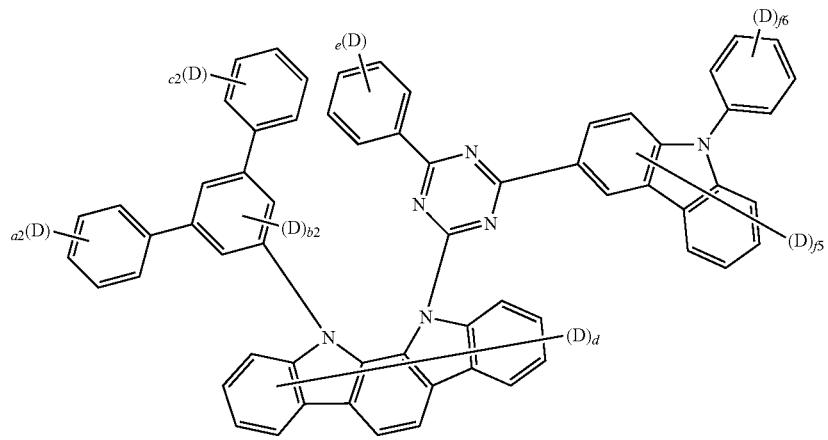
H1-19-10
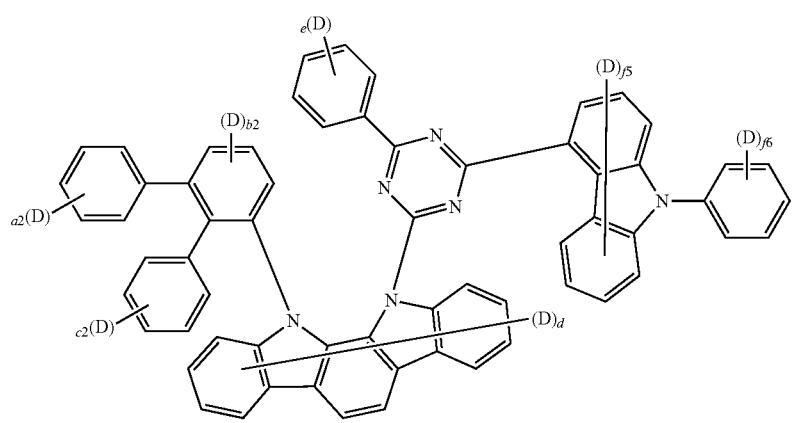
H1-19-11
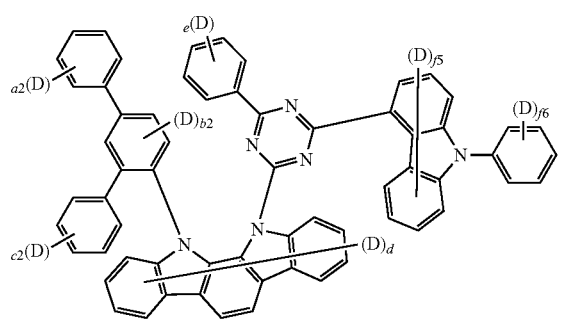
H1-19-12
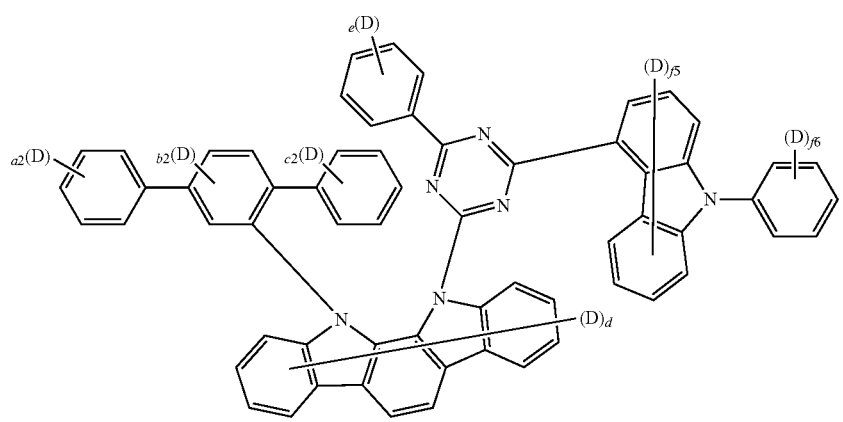

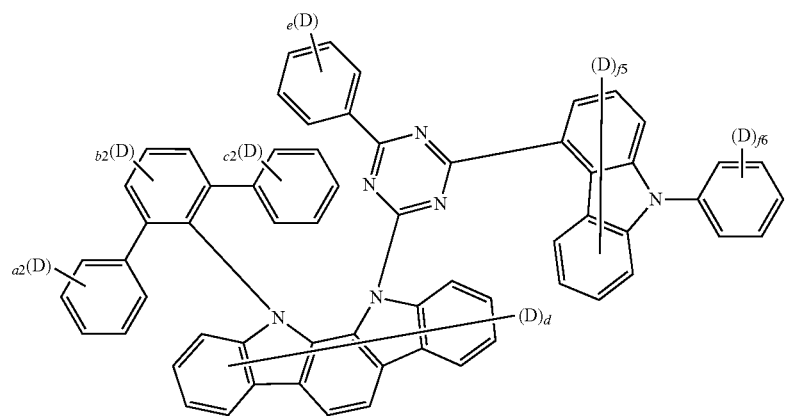
H1-19-13
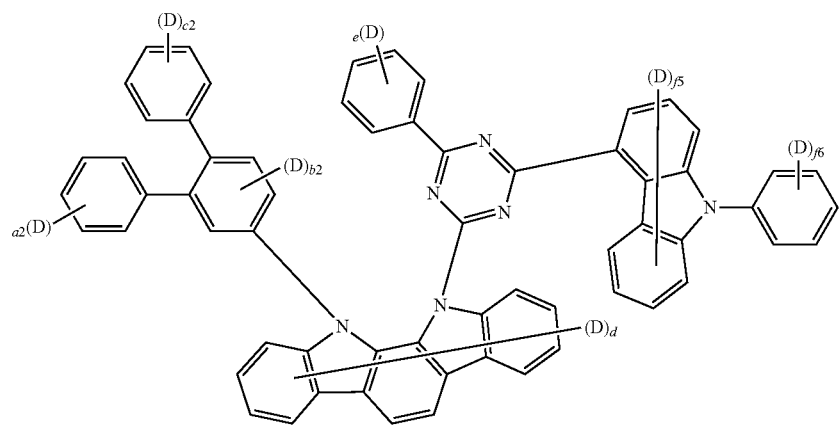
H1-19-14
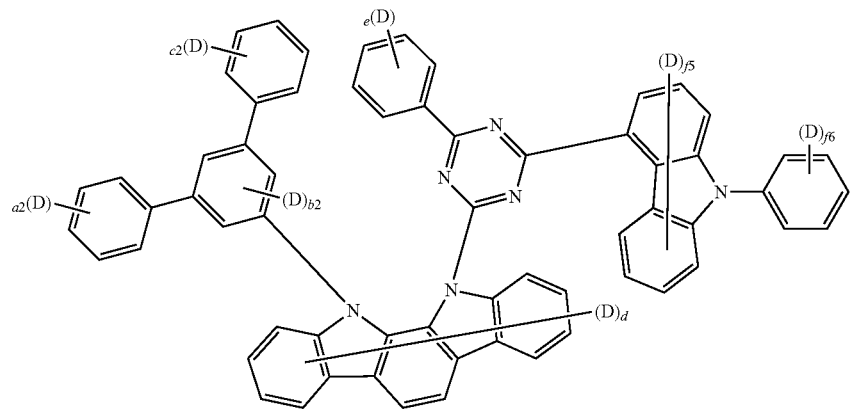
H1-19-15 wherein in Chemical Formulae H1-16-10 to H1-16-15, H1-17-10 to H1-17-15, H1-18-10 to H1-18-15, and H1-19-10 to H1-19-15:

a2, b2, c2, and d are as defined in Chemical Formula 1, e is an integer of 0 to 5, f5 is an integer of 0 to 7, f6 is an integer of 0 to 5, and a2+b2+c2+d+e+f5+f6 is 1 to 40.

6. The organic light emitting device of claim 1, wherein the second compound is the following Chemical Formula 2':

<Chemical Formula 2'>

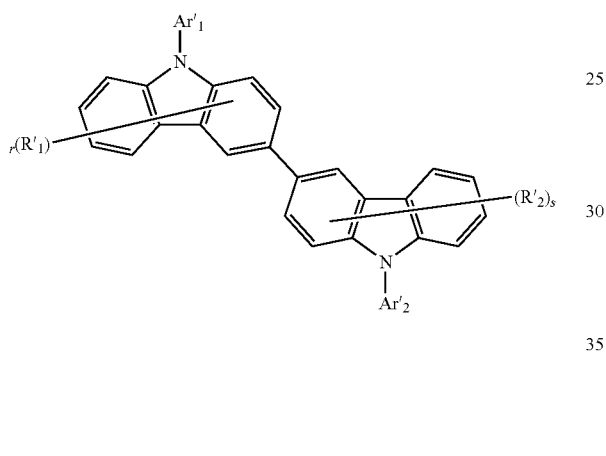

wherein in Chemical Formula 2':

Ar'$_1$, Ar'$_2$, R'$_1$, R'$_2$, r, and s are as defined in claim 1.

7. The organic light emitting device of claim 1, wherein Ar'$_1$ and Ar'$_2$ are each independently phenyl, biphenylyl, terphenylyl, naphthyl, dibenzofuranyl, or dibenzothiophenyl; and Ar'$_1$ is unsubstituted, or substituted with at least one substituent selected from the group consisting of deuterium and $C_{6-20}$ aryl.

8. The organic light emitting device of claim 1, wherein at least one of Ar'$_1$ and Ar'$_2$ is phenyl or biphenylyl.

9. The organic light emitting device of claim 1, wherein R'$_1$ and R'$_2$ are each independently hydrogen, deuterium, or phenyl.

10. The organic light emitting device of claim 1, wherein r+s is 0 or 1.

11. The organic light emitting device of claim 1, wherein the second compound is any one compound selected from the group consisting of the following compounds:

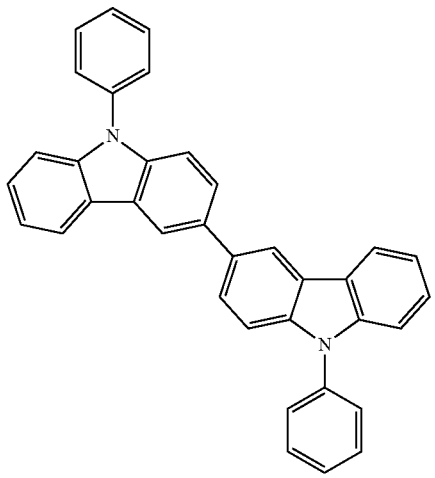

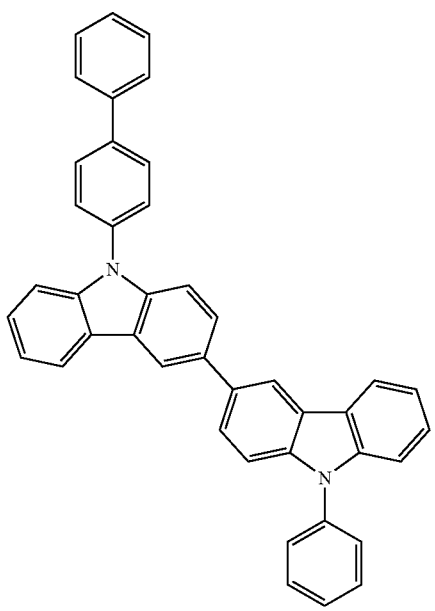

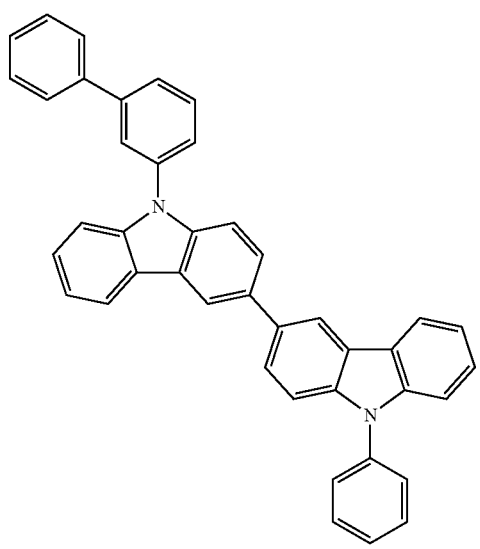

347
-continued
348
-continued
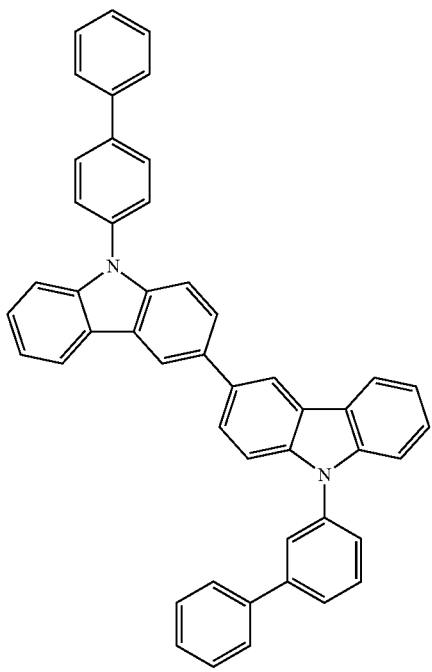
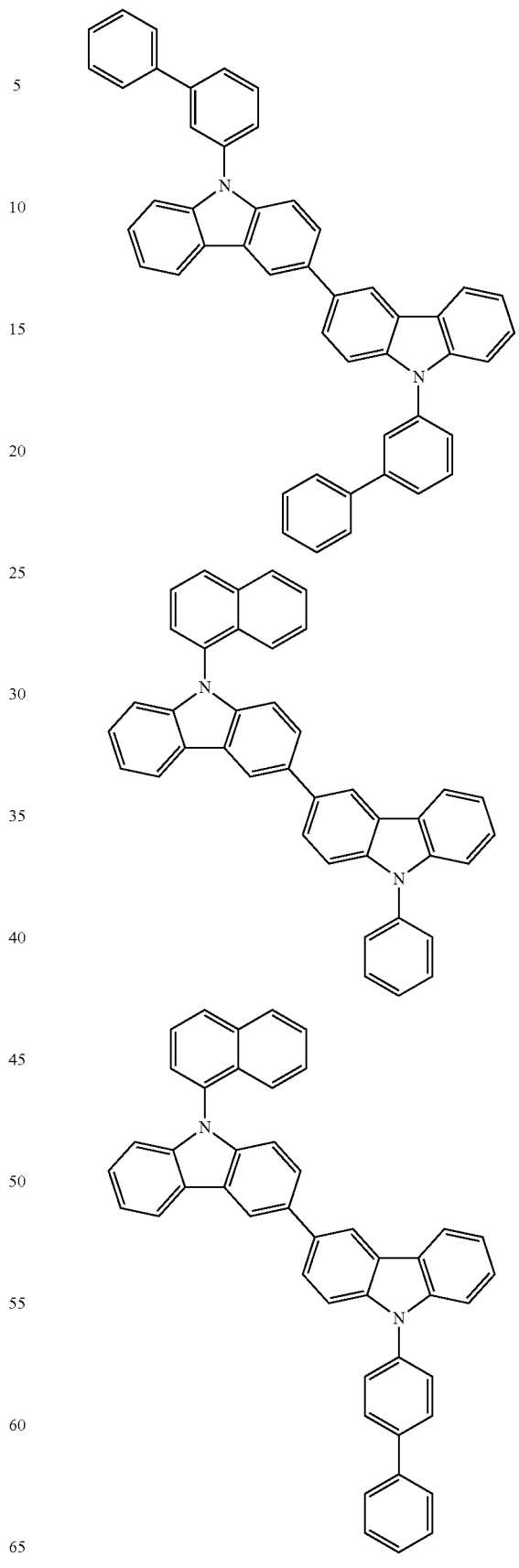

349
-continued
350
-continued
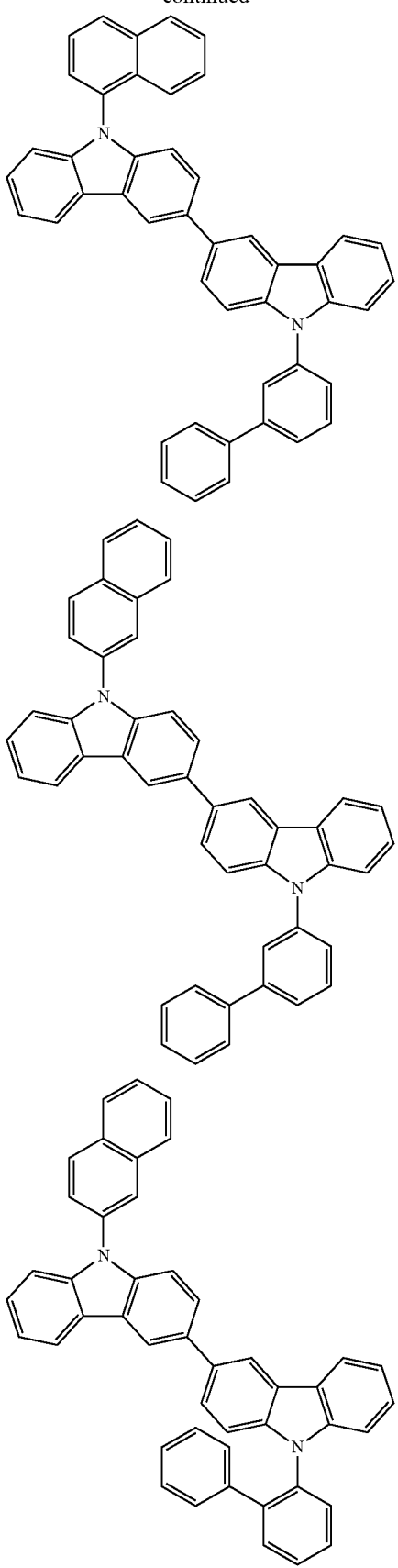
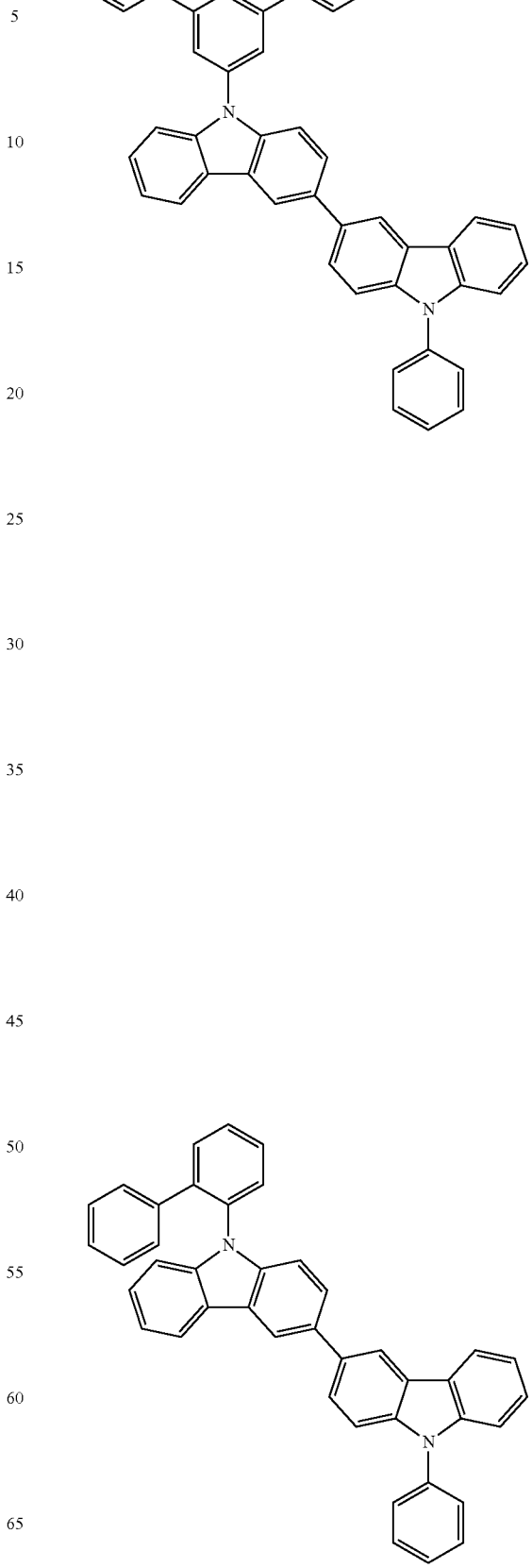

351
-continued
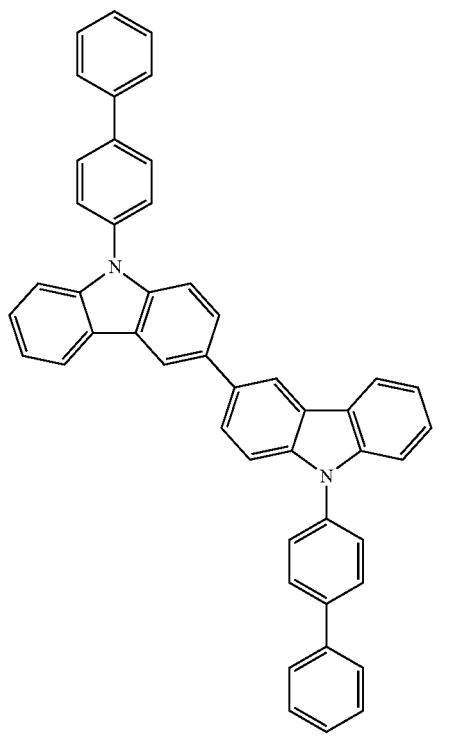
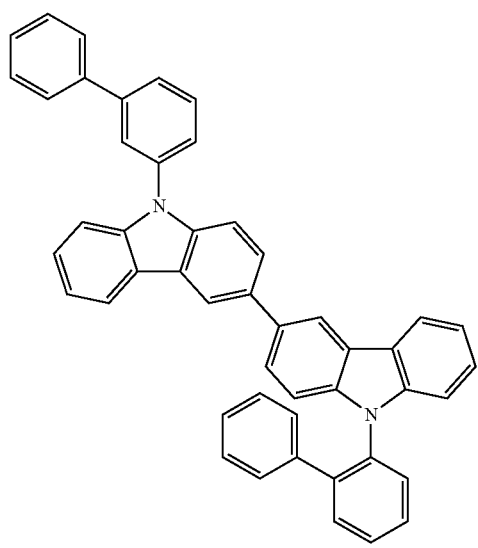
352
-continued
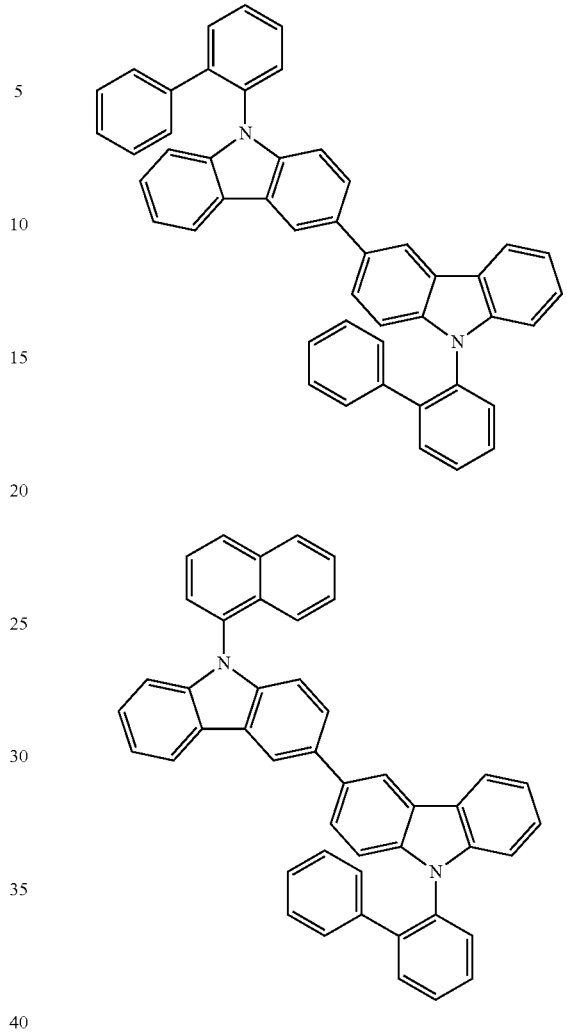
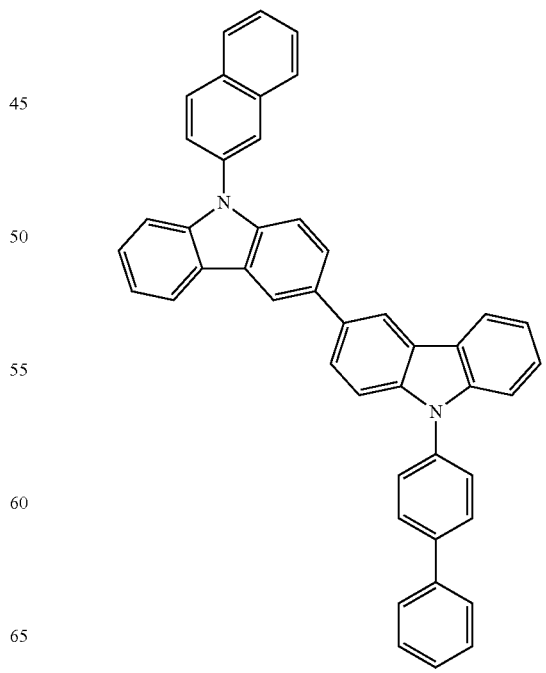

353
-continued
354
-continued
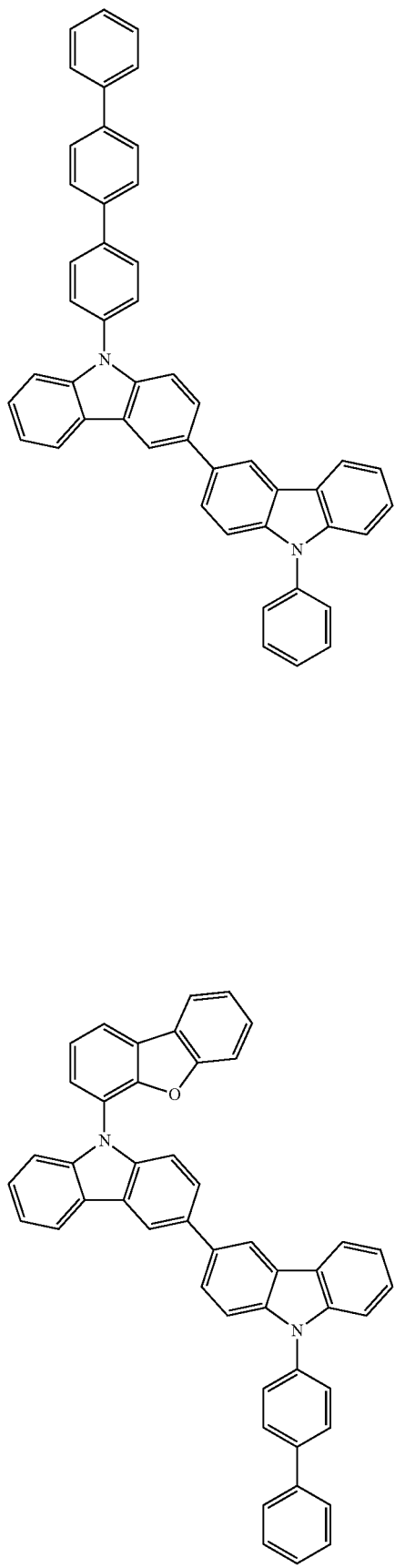
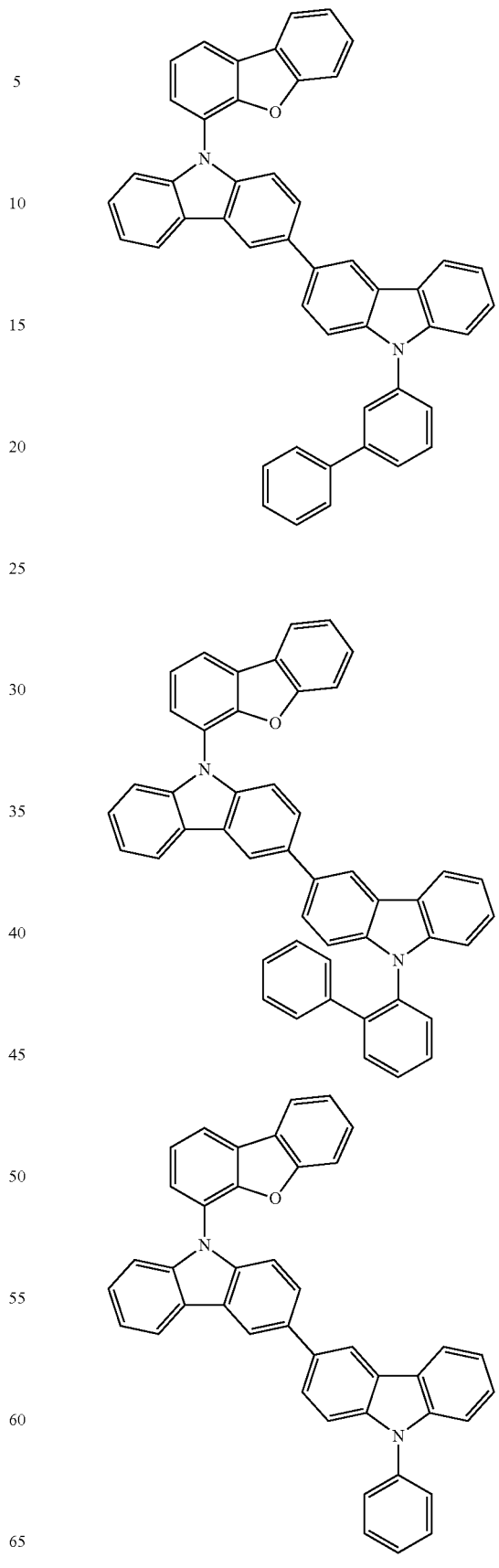

355
-continued
356
-continued
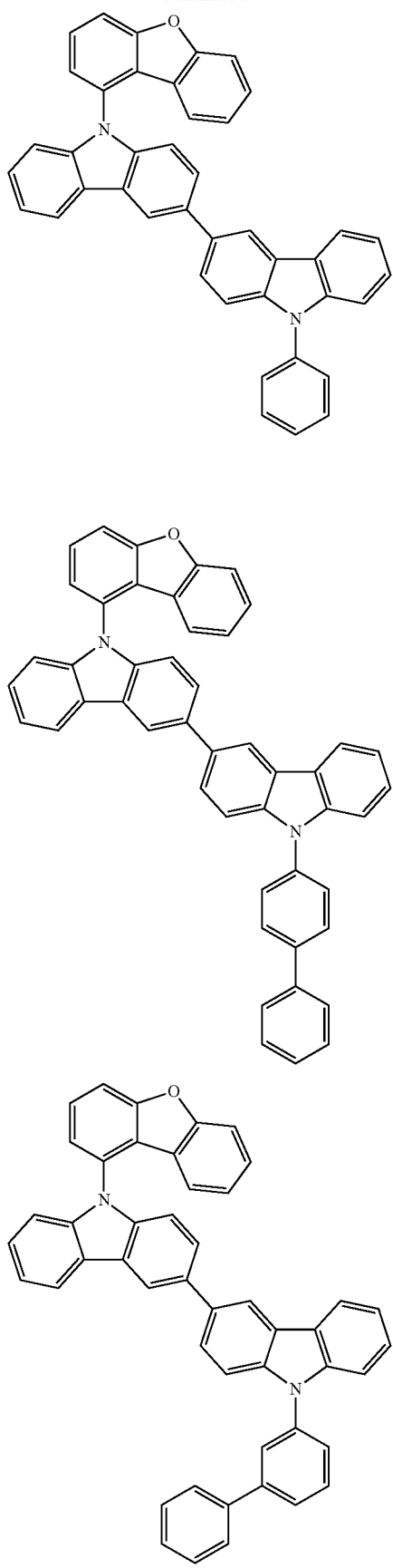
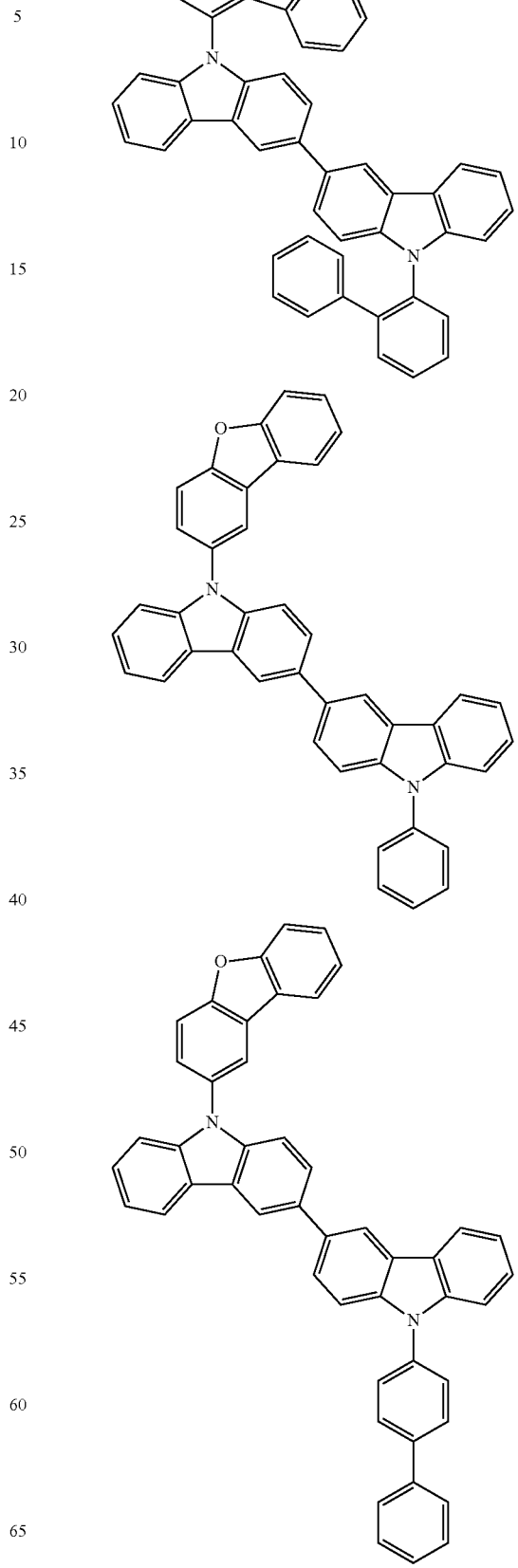

357
-continued
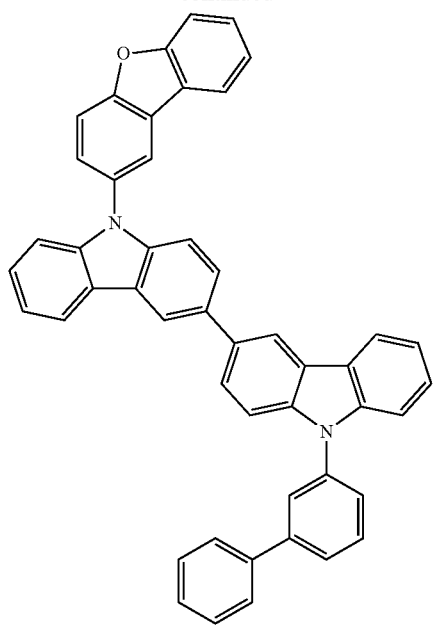
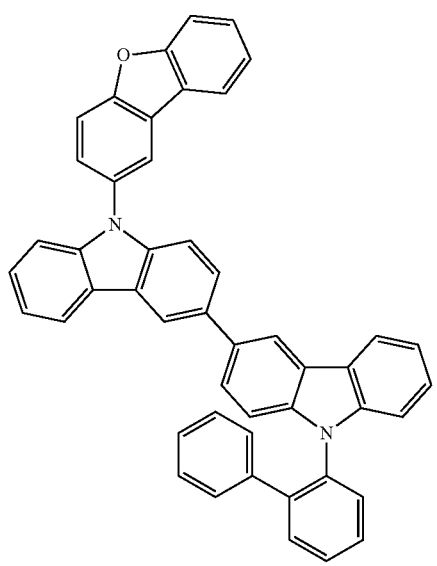
358
-continued
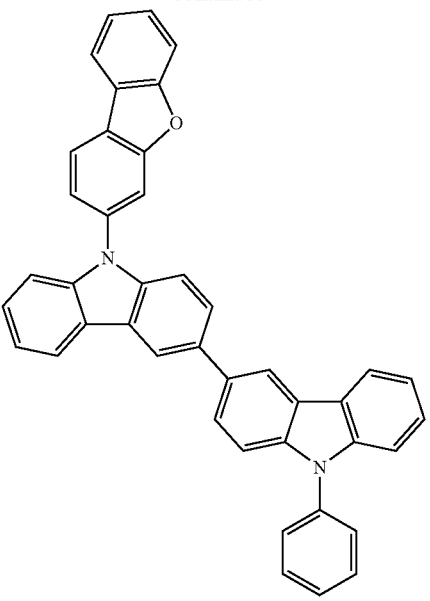
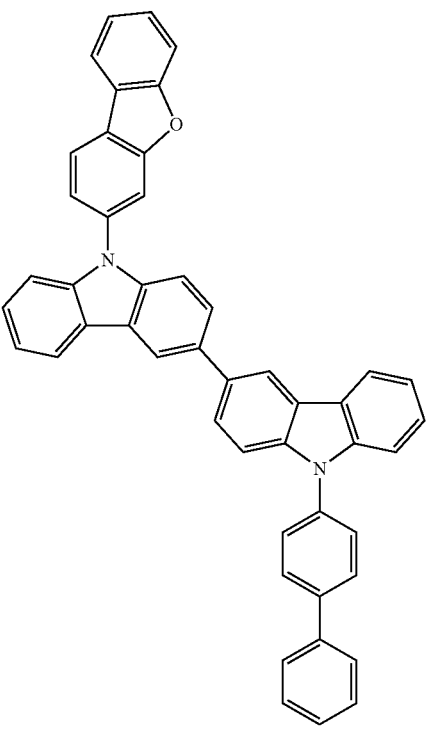

359
-continued
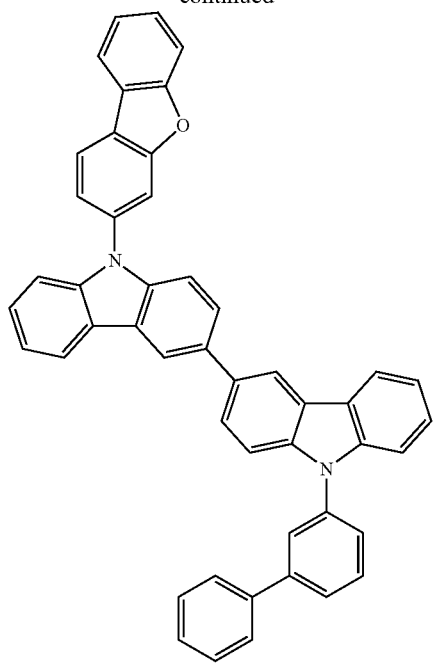
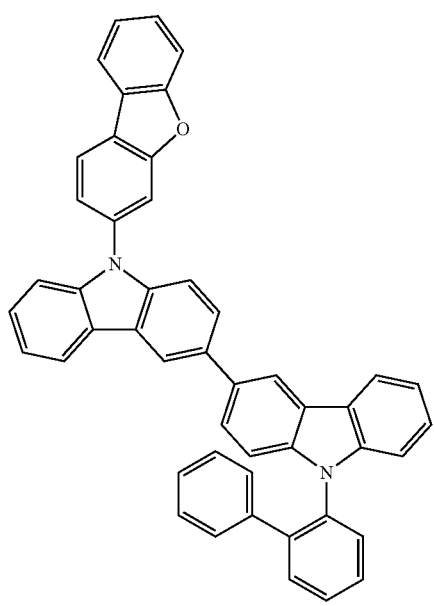
360
-continued
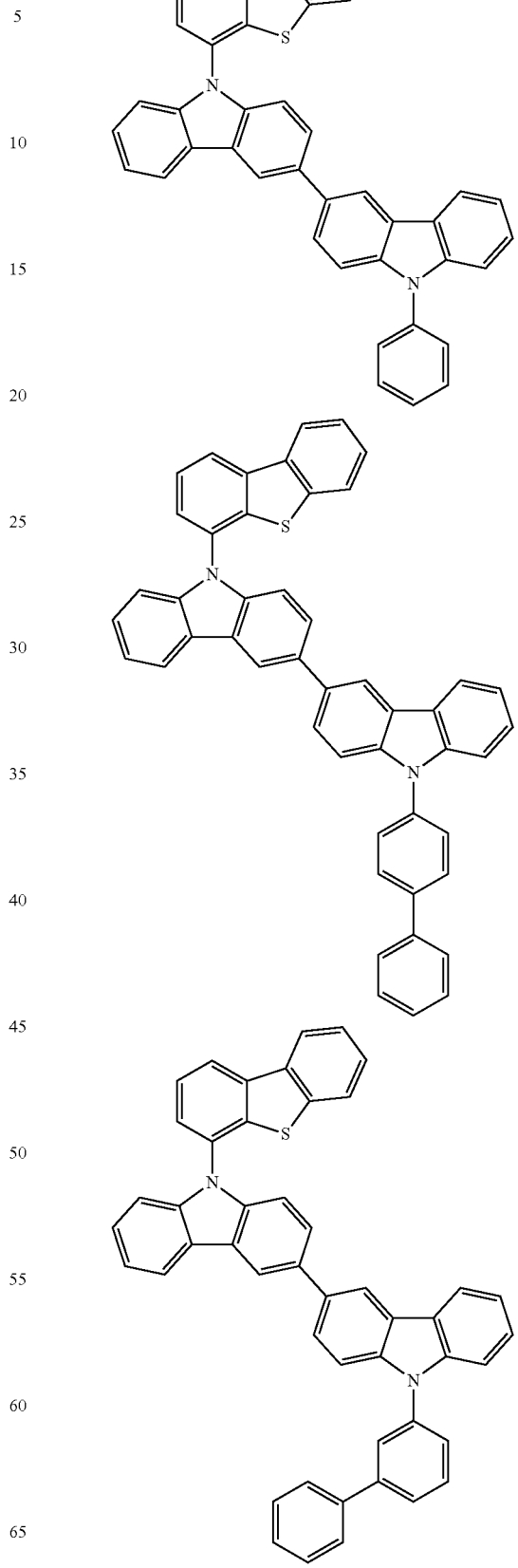

361
-continued
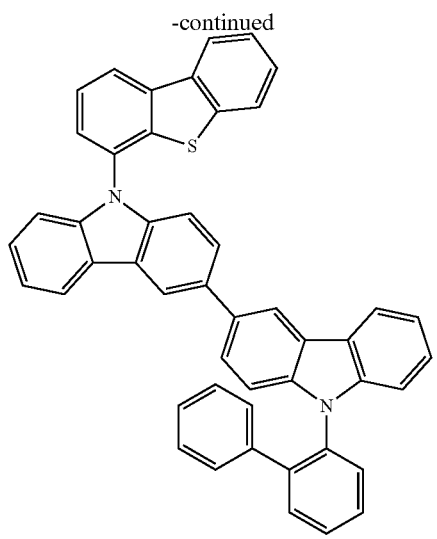
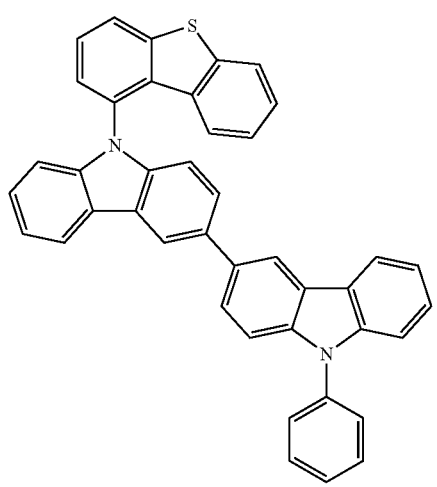
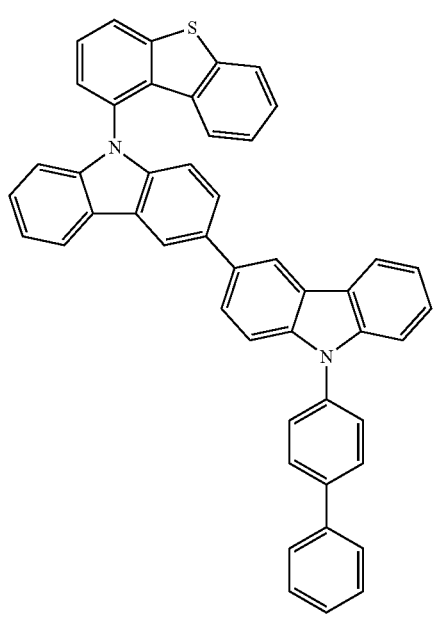
362
-continued
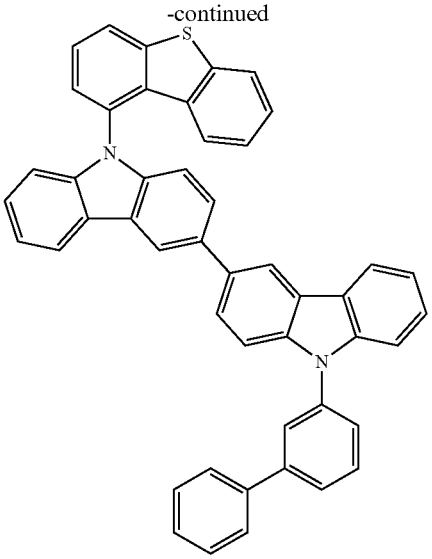
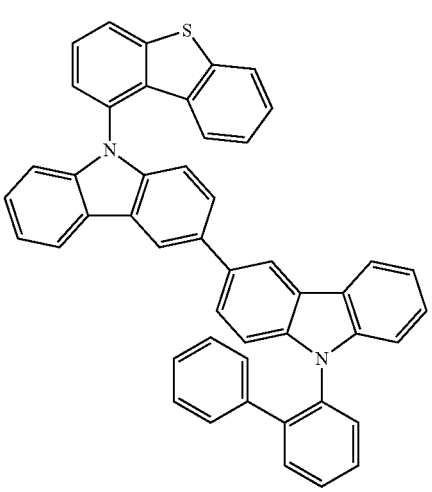
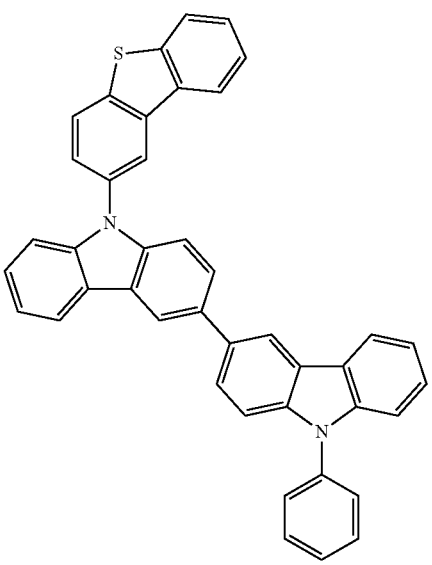

363
-continued
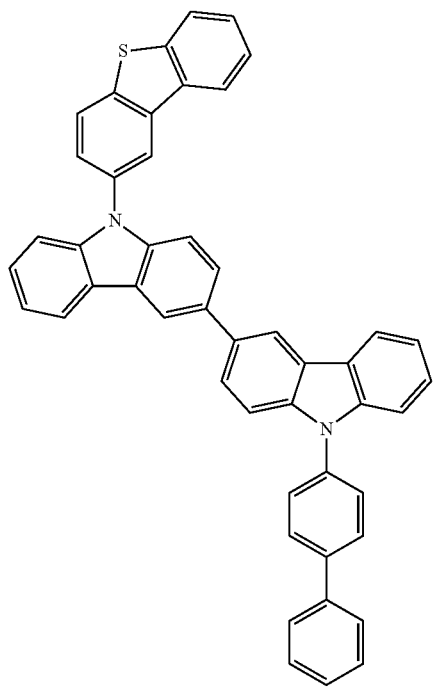
364
-continued
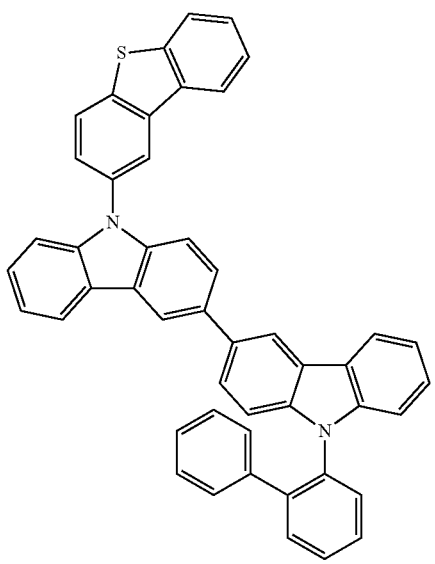
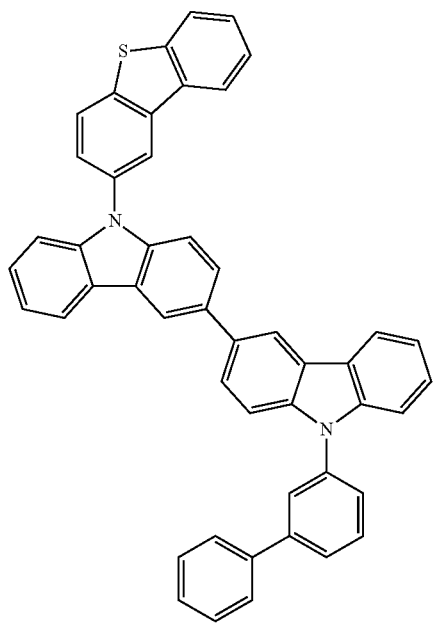
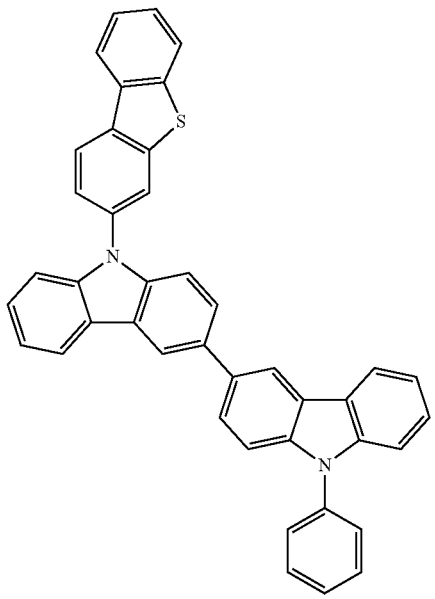

365
-continued
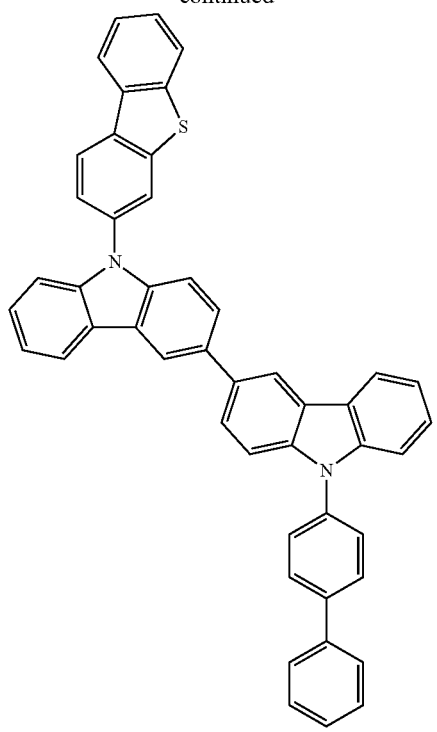
366
-continued
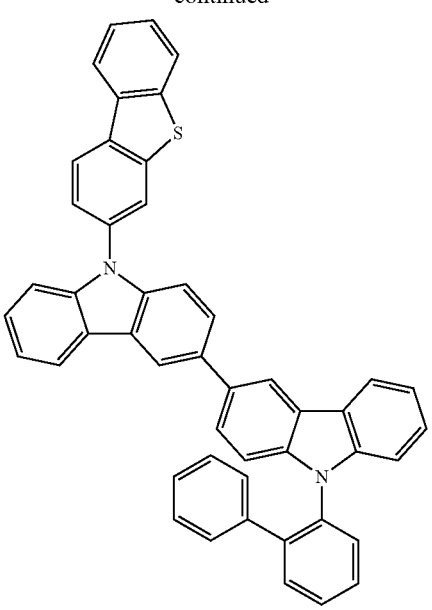
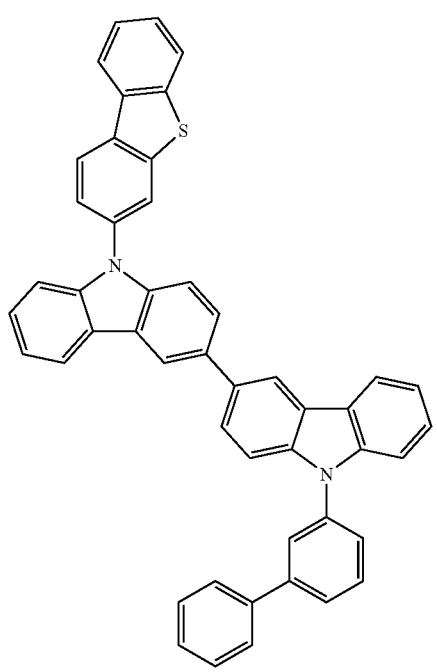
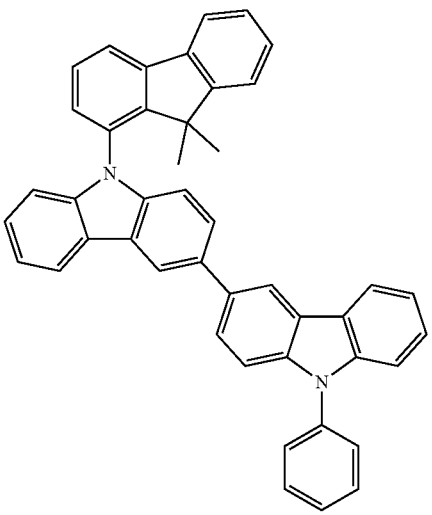

367
-continued
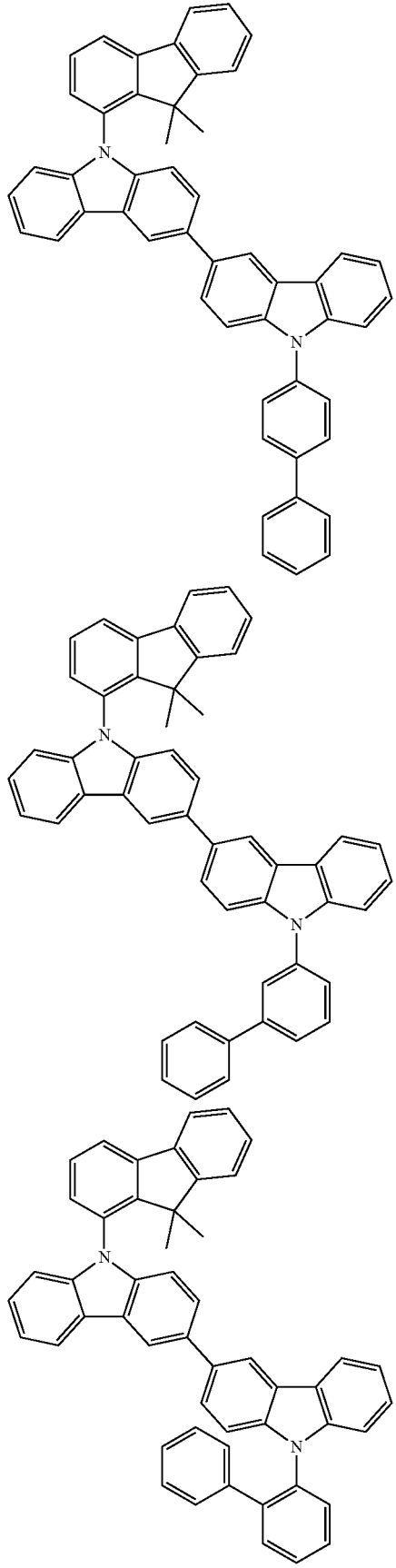
368
-continued
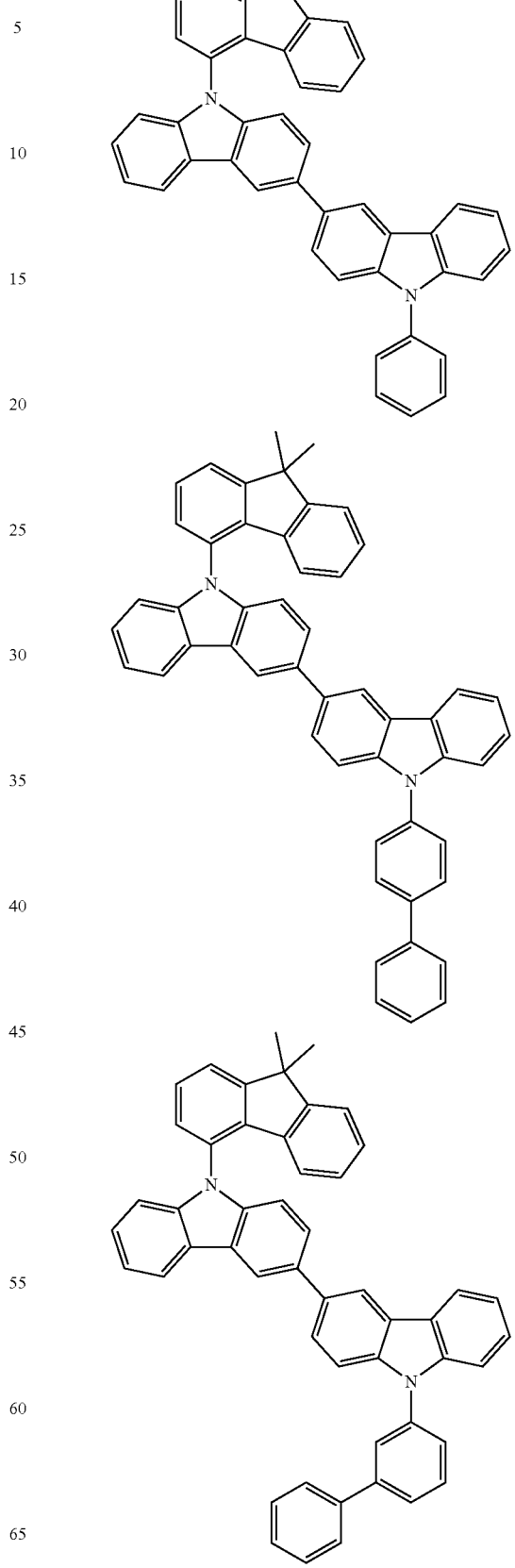

369
-continued
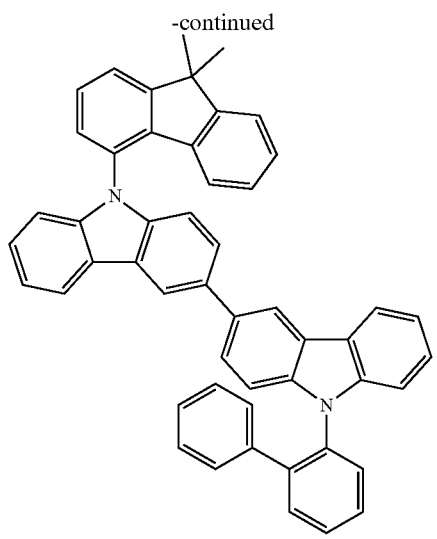
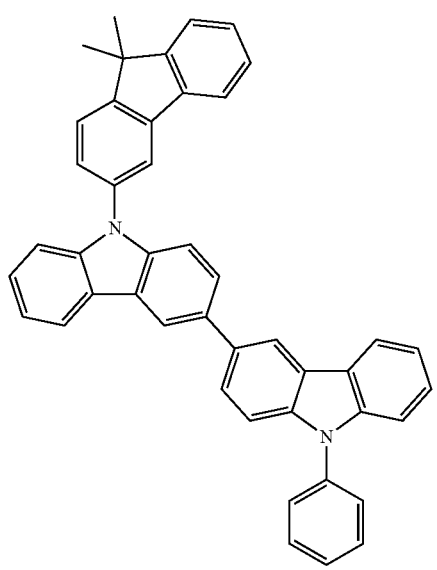
370
-continued
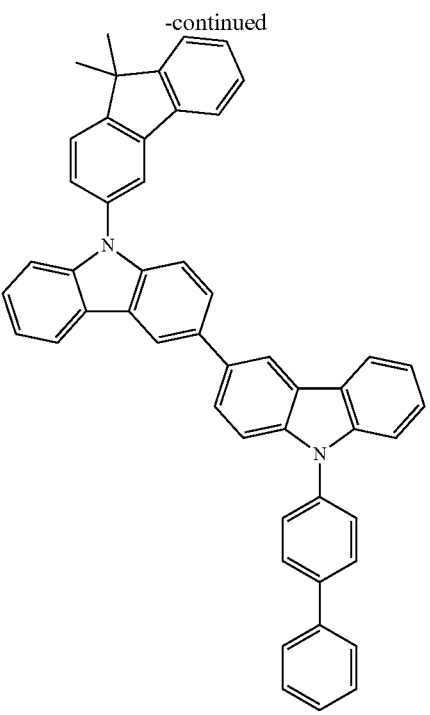
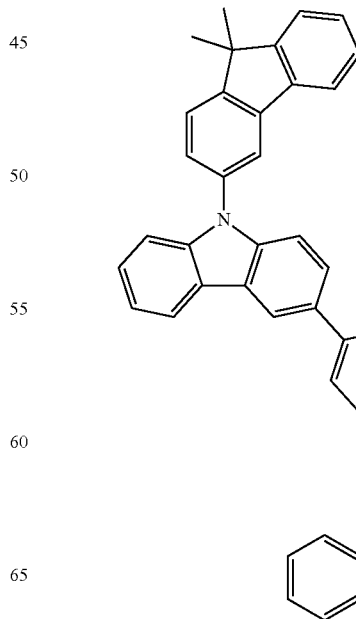

371
-continued
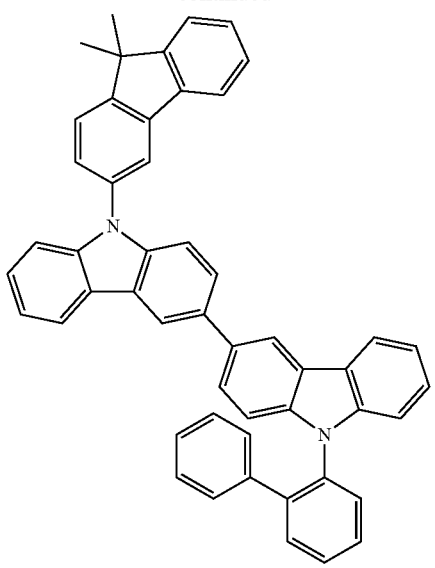
372
-continued
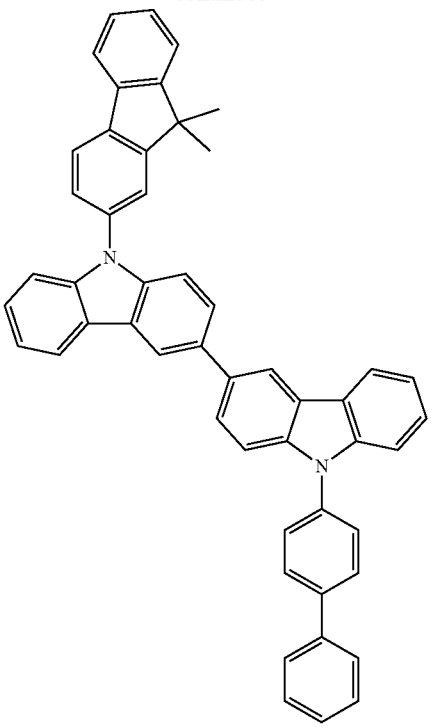
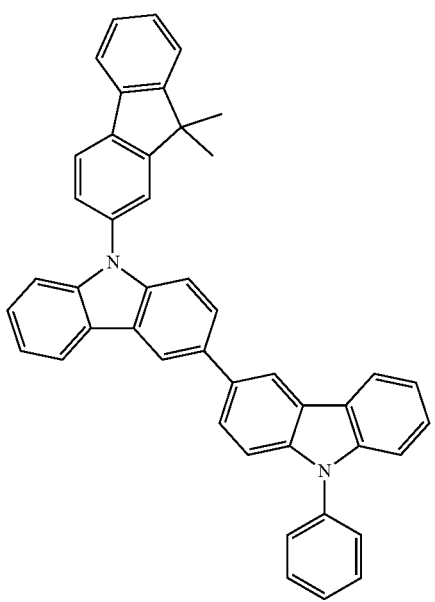
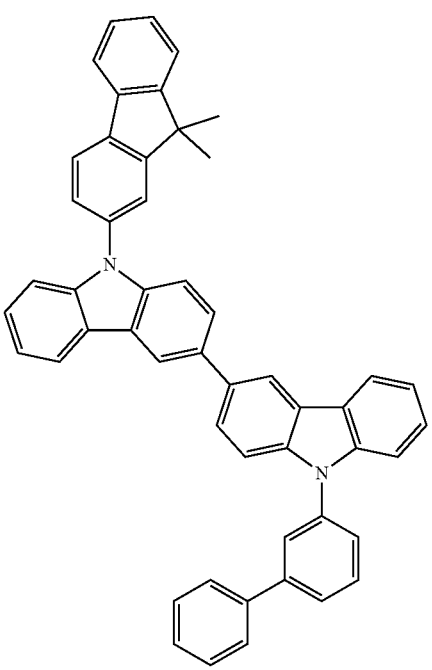

373
-continued
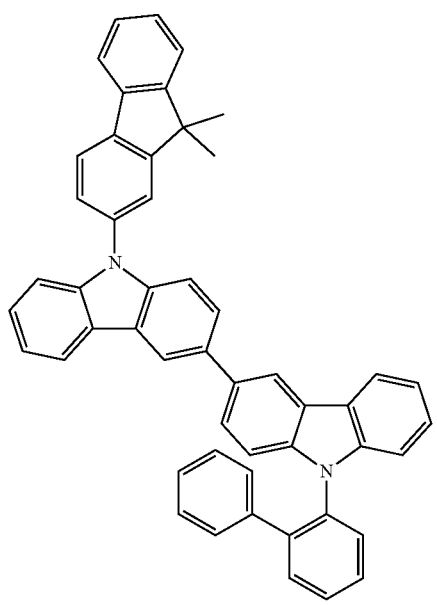
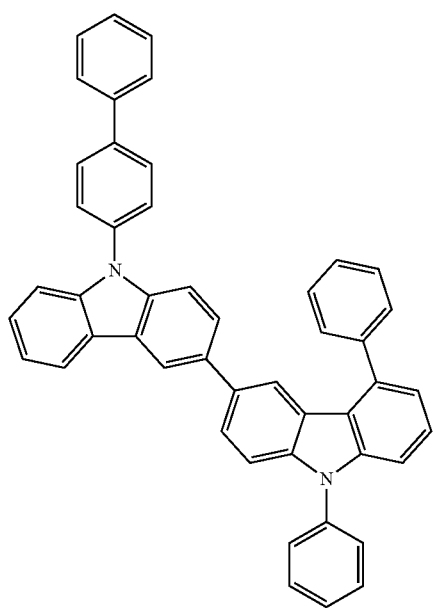
374
-continued
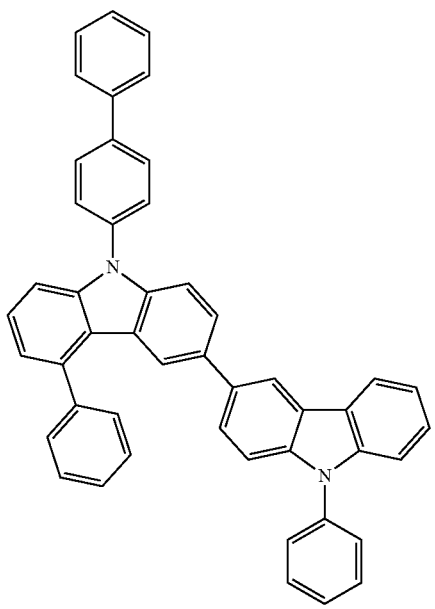
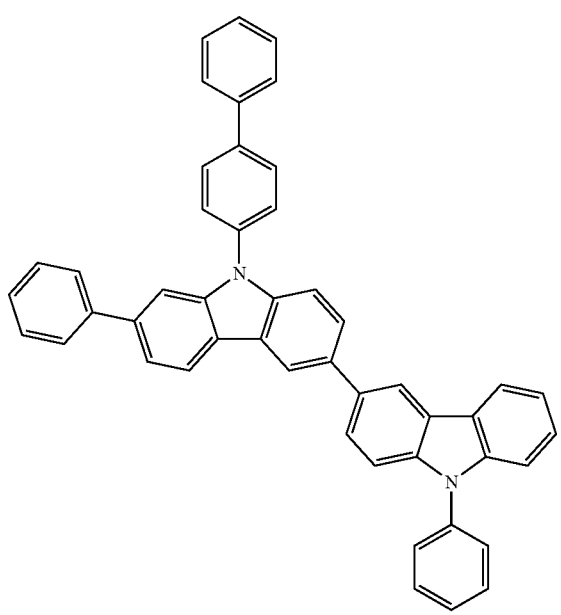

375
-continued
376
-continued
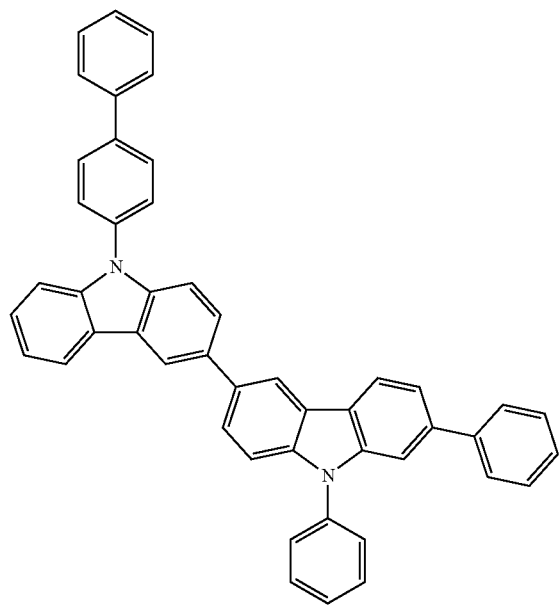
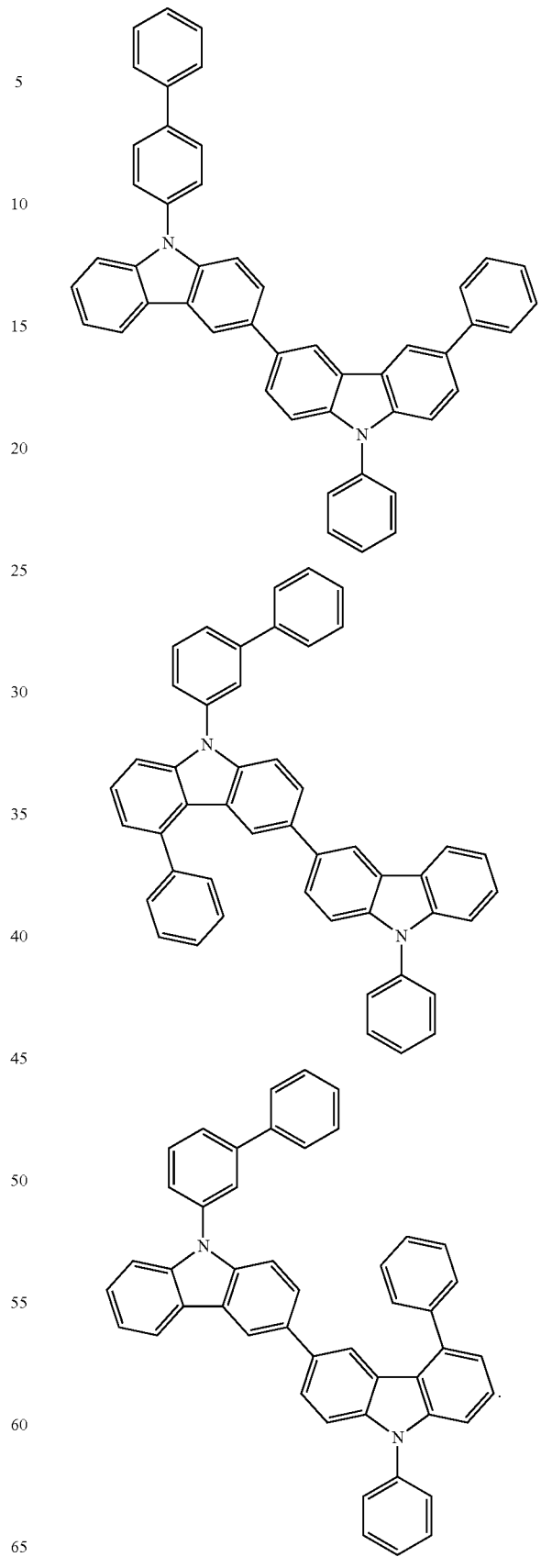

12. The organic light emitting device of claim 1, wherein the first compound and the second compound are included in the light emitting layer in a weight ratio of 10:90 to 90:10.

* * * * *